(12) United States Patent
Loqué et al.

(10) Patent No.: US 11,085,048 B2
(45) Date of Patent: Aug. 10, 2021

(54) LIGNIFICATION REDUCTION IN PLANTS

(71) Applicant: The Regents of the University of California, Oakland, CA (US)

(72) Inventors: Dominique Loqué, Albany, CA (US); Aymerick Guillaume Eudes, Emeryville, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/396,580

(22) Filed: Apr. 26, 2019

(65) Prior Publication Data

US 2019/0300895 A1    Oct. 3, 2019

Related U.S. Application Data

(63) Continuation of application No. 14/232,018, filed as application No. PCT/US2012/046764 on Jul. 13, 2012.

(60) Provisional application No. 61/507,484, filed on Jul. 13, 2011.

(51) Int. Cl.
    *C12N 15/82*    (2006.01)
    *C12N 9/88*    (2006.01)

(52) U.S. Cl.
    CPC ........... *C12N 15/8255* (2013.01); *C12N 9/88* (2013.01)

(58) Field of Classification Search
None
See application file for complete search history.

(56) References Cited

U.S. PATENT DOCUMENTS

| | | | |
|---|---|---|---|
| 7,238,512 B2 * | 7/2007 | Meyer | C12N 9/88 435/183 |
| 2005/0086712 A1 | 4/2005 | Meyer et al. | |
| 2007/0076159 A1 | 4/2007 | Lee et al. | |
| 2008/0076159 A1 | 3/2008 | Baez-Vasquez et al. | |

FOREIGN PATENT DOCUMENTS

WO    WO 9735999 A2    10/1997

OTHER PUBLICATIONS

Mayer et al.; "Rerouting the Plant Phenylpropanoid Pathway by Expression of a Novel Bacterial Enoyl-CoA Hydratase/Lyase"; *The Plant Cell.* 13:1669-1682 (2001).

Merali et al.; "Metabolic diversion of the phenylpropanoid pathway causes cell wall and morphological changes in transgenic tobacco stems"; *Planta.* 225:1165-1178 (2007).

Mitra et al.; 4-Hydroxycinnamoyl-CoA hydratase/lyase, an enzyme of phenylpropanoid cleavage from *Pseudomonas*, causes formation of $C_6$-$C_1$ acid and alcohol glucose conjugates when expressed in hairy roots of *Datura stramonium* L.; *Planta.* 215: 79-89 (2002).

McQualter et al.; "Initial evaluation of sugarcane as a production platform for p-hydroxybenzoic acid"; *Plant Biotechnology Journal.* 3:29-41 (2005).

Rahman et al.; "HCHL expression in hairy roots of *Beta vulgaris* yields a high of p-hydroxybenzoic acid (pHBA) glucose ester, and linkage of pHBA into cell walls"; *Bioresource Technology*; 100:4836-4842 (2009).

International Search Report and Written Opinion from PCT/US2012/046764, dated Sep. 21, 2012.

Hisano, "Genetic modification of lignin biosynthesis for improved biofuel production," In Vitro Cell. Dev. Biol. Plant (2009) 45:306-313.

Kim et al., "A 20 nucleotide upstream element is essential for the nopaline synthase (nos) promoter activity," Plant Molecular Biology, 1994, vol. 24 pp. 105-117.

Brown (2006), Dissertation, University of California, Davis.

Ngo et al., "Computational Complexity, Protein Structure Prediction, and the Levinthal Paradox," in The Protein Folding Problem and Tertiary Structure Prediction, 1994, Merz et al. (ed.), Birkhauser, Boston, MA, pp. 491-495.

Guo et al, "Protein tolerance to random amino acid change," 2004, Proc. Natl. Acad. Sci. USA vol. 101 pp. 9205-9210.

Kajita et al, "Generation of transgenic hybrid aspen that express a bacterial gene for feruloyl-CoA hydratase/lyase (FerB), which is involved in lignin degradation in *Sphingomonas paucimobilis* SYK-6," Journal of Wood Science, Jun. 2004, vol. 50, Issue 3, pp. 275-280).

Duncan et al, "Increased Saccharification Yields from Aspen Biomass Upon Treatment with Enzymatically Generated Peracetic Acid," Appl Biochem Biotechnol, 2010, 160:1637-1652.

Stewart et al., "The Effects on Lignin Structure of Overexpression of Ferulate 5-Hydroxylase in Hybrid Poplar," Plant Physiology, Jun. 2009, vol. 150, pp. 621-635.

Friedberg, "Automated protein function prediction-the genomic challenge," Briefings in Bioinformatics, 2006, vol. 7, No. 3, pp. 225-242.

\* cited by examiner

*Primary Examiner* — Brent T Page

(74) *Attorney, Agent, or Firm* — Kilpatrick Townsend & Stockton, LLP

(57) ABSTRACT

The present invention provides an expression cassette containing a polynucleotide coding sequence for a hydroxycinnamoyl-CoA hydratase-lyase (HCHL), which is operably linked to a heterologous promoter. Also provided are methods of engineering plants that have reduced lignification, as well as cells, plant parts, and plant tissues from such engineered plants.

8 Claims, 20 Drawing Sheets

Specification includes a Sequence Listing.

```
Majority                                              XXXXXXXXMSKYXXXXEG
                                                              |
                                                              10
                                                              |

Sagittula_stellata_E-37_1-285                         MTATEATLPANDPDLSGD
Saccharopolyspora_erythraea_NRRL_2338_1  MSTPTTDPGTTTTP
Solibacter_usitatus_Ellin6076_1-278                         MDQ     E
Ralstonia_solanacearum_GMI1000_1-277                        MAT     EG
Xanthomonas_albilineans_1-276                               MSNYQD
Acinetobacter_baumannii_ATCC_17978_1-27  MKMS               Y       EN
Acinetobacter_sp._ADP1_1-277             MT                 YDK
Chromohalobacter_salexigens_DSM_3043_1-                     MSDYTN
Burkholderia_cenocepacia_AU_1054_1-276                      MSKYDN
Burkholderia_ambifaria_MC40-6_1-276                         MSKYDN
Burkholderia_cepacia_AMMD_1-276                             MSKYDN
Burkholderia_thailandensis_MSMB43_1-276                     MSKYDN
Burkholderia_ubonensis_Bu_1-276                             MSKY    EN
Azotobacter_vinelandii_AvOP_1-276                           MNKY    EG
Pseudomonas_putida_KT2440_1-276                             MSKY    EG
Pseudomonas_fluorescens_SBW25_1-276                         MSNY    EG
Pseudomonas_syringae_1-276                                  MSKY    EG
Ralstonia_eutropha_JMP134_1-277                             MANY    EG
Burkholderia_glumae_BGR1_1-275                        MS    Y       EG
Burkholderia_phytofirmans_PsJN_1-275                  MS    Y       EG
Burkholderia_mallei_ATCC_23344_1-275                  MS    Y       EG
Burkholderia_pseudomallei_Pasteur_1-275  MS                 Y       EG
Burkholderia_multivorans_ATCC_17616_1-2  MS                 Y       EG
Burkholderia_vietnamiensis_G4_1-275                   MG    Y       EG
Sphingobium_japonicum_UT26S_1-283                           MSEYLTEGPD
Xanthomonas_axonopodis_1-275                                MNEHDV
Xanthomonas_campestris_ATCC_33913_1-275                     MNEHDV
Azospirillum_sp._B510_1-281              MTQQQAAART                 G
Agrobacterium_vitis_S4_1-277                                MTVA    EK
Rhizobium_etli_Brasil_5_1-267
Rhizobium_leguminosarum_bv._trifolii_WS  MT                         ED
```

```
AKLDQAQLRDPEGGREQGLKQFLDDKSIKPGLQAYKRXXXX
        260       270       280       290

AKGDQTVFVDKEKGREQGLKQFLDDKTYRPGLGAYKR            296
AKLEQSQFLDAERGREKGMAQFLDDKSYRPGLSAYSTD           296
AKLDQALHRDPEDARAEGMKQFLDEKSIKPGLQSYKRS           296
AKVDQSNHRDPEKGRQFLKQFLDDKTIKPGLQTYKRA            296
AKVDQSNHRDPEKGRQQGLKQFLDDKIIKPGLQTYKR            296
AKLDQCIHRDTENGPQEGLKQFLDEKSIKPGLQSYKRTG          296
AKLDQCNHRDTEGGRQFGLKQFLDDKSIKPGLQSYKRTG          296
AKLDQAQLDPEHGREQGLKQFLDDKSIKPGLESYRR             296
AKLDQAQLRDPERGREQGLKQFLDDKTIKPGLQAYKR            296
AKLDQAQLRDPERGREQGLKQFLDDKAIKPGLQAYKR            296
AKLDQAQLRDPERGREQGLKQFLDDKAIKPGLQAYKR            296
AKLDQAQLRDPERGREQGLKQFLDDKAIKPGLQAYKR            296
AKLDQSRLLDEGGREKGMRQFLDEKSIKPGLQAYKR             296
AKLDQSRLLDTTGGREQGMKQFLDDKSIKPGLQAYKR            296
AKLDQSRLLDTEGGREQGMKQFLDDKSIKPGLQAYKR            296
AKLDQSRLLDKEGGREQGMKQFLDDKSIKPGLEAYKR            296
AKLDQAQLRDPEHGREQGLKQFLDDKSIKPGLQAYKRA           296
AKLDQANYRDKEGGREKGLKQFLDDKSIKPGLQAYKR            296
AKLDQAQLRDPEGGREQGLKQFLDDKAIKPGLQTYKR            296
AKLDQAQLRDPEHGREQGLKQFLDDKTIKPGLQAYRR            296
AKLDQAQLRDPEHGREQGLKQFLDDKTIKPGLQAYRR            296
AKLDQANYRDPEGGREQGLKQFLDEKSIKPGLQAYKR            296
AKLDQANYRDPEGGREQGLKQFLDDKSIKPGLQAYKR            296
AKGAQTRVADKTDGRNEGITQFLDEKSYKPGLEGYRRDK          296
RMQEAANSFDNNARKEGIRQFIDEKSYKPGLGEYDLSKHSA        296
RMQEAANSFDNNARKEGIRQFIDEKRYKPGLGAYEPDAGTN        296
VRQESLNYLDKSEGRKQGIKQFIDDKTYRPGLGAYKR            296
AKLEQMLLDKTRGRDEGLKQFLDDKTYRPGLGAYKRK            296
AKLEQMLFLDKTKGRDEGLKQFLDDKTYQPGLGAYKRGR          296
AKLEQMLFLDKTKGRDEGLKQFLDDKTYQPGLGAYKRGR          296
```

FIG. 8F

LIGNIFICATION REDUCTION IN PLANTS

CROSS-REFERENCE TO RELATED APPLICATIONS

This application is a continuation of U.S. application Ser. No. 14/232,018, filed Apr. 17, 2014 which is the U.S. National Stage of International Application No. PCT/US2012/046764, filed Jul. 13, 2012 which claims benefit of U.S. provisional application No. 61/507,484, filed Jul. 13, 2011, each of which application is herein incorporated by reference.

STATEMENT AS TO RIGHTS TO INVENTIONS MADE UNDER FEDERALLY SPONSORED RESEARCH AND DEVELOPMENT

This invention was made with government support under Contract No. DE-AC02-05CH11231 awarded by the U.S. Department of Energy. The government has certain rights in this invention.

REFERENCE TO A "SEQUENCE LISTING" SUBMITTED AS AN ASCII TEXT FILE VIA EFS-WEB

This application contains a Sequence Listing file named 077429_1137486_SL.TXT, created on Apr. 25, 2019 and containing 170,590 bytes, which has been filed electronically in ASCII format. The material contained in this text file is hereby incorporated by reference in its entirety.

BACKGROUND OF THE INVENTION

Lignocellulosic plant biomass is utilized as a renewable feedstock in various agro-industrial activities. Lignin is an aromatic and hydrophobic branched polymer incrusted within biomass that negatively affects extraction and hydrolysis of polysaccharides during industrial processes. Engineering the monomer composition of lignin offers attractive potential for reducing its recalcitrance. The present invention offers a new strategy developed in *Arabidopsis* for the overproduction of rare lignin monomers, which incorporate as end-groups in the polymer and reduce lignin chain extension. Biosynthesis of these 'lignification stoppers' is achieved by expressing a bacterial hydroxycinnamoyl-CoA hydratase-lyase (HCHL) in lignifying tissues of *Arabidopsis* inflorescence stems. HCHL cleaves the propanoid side chain of hydroxycinnamoyl-CoA lignin precursors to produce the corresponding hydroxybenzaldehydes. Stems from plants that express HCHL accumulate higher amount of hydroxybenzaldehyde and hydroxybenzoate derivates compared to wild type plants. Part of these $C_6C_1$ phenolics are alcohol-extractable from plant tissues and are released from extract-free cell walls upon mild alkaline hydrolysis. Engineered plants with intermediate HCHL activity level show no reduction of total lignin, sugar content and biomass yield compared to wild type plants. However, cell wall characterization by 2D-NMR reveals the presence of new molecules in the aromatic region and the analysis of lignin isolated from these plants revealed an increased amount of $C_6C_1$ phenolic end-groups and a reduced molecular mass distribution. In addition, these engineered lines show saccharification improvement of pretreated cell wall biomass. Enhancing the incorporation of $C_6C_1$ phenolic end-groups in lignin represents a promising strategy to alter lignin structure and reduce cell wall recalcitrance to enzymatic hydrolysis.

BRIEF SUMMARY OF THE INVENTION

In the first aspect, the present invention provides an isolated expression cassette comprising a polynucleotide sequence encoding a hydroxycinnamoyl-CoA hydratase-lyase (HCHL) and a heterologous promoter, and the promoter is operably linked to the polynucleotide sequence. In some embodiments, the HCHL is *Pseudomonas fluorescens* HCHL, which has the amino acid sequence set forth in SEQ ID NO:1. In some embodiments, the promoter used in this expression cassette is a secondary cell wall specific promoter, such as pIRX5, which is within the polynucleotide sequence set forth in SEQ ID NO:3.

In a second aspect, the present invention provides a method for engineering a plant having reduced lignification. The method includes these steps: (1) introducing the expression cassette described herein into the plant; and (2) culturing the plant under conditions under which the HCHL is expressed, thereby reducing lignification in the plant. In some embodiments, the plant is selected from the group consisting of *Arabidopsis*, poplar, *Eucalyptus*, rice, corn, switchgrass, sorghum, millet, *Miscanthus*, sugarcane, pine, alfalfa, wheat, soy, barley, turfgrass, tobacco, hemp, bamboo, rape, sunflower, willow, and *Brachypodium*.

In a third aspect, the present invention provides a plant that is engineered by the methods described herein, and a plant cell from such a plant, a seed, flower, leaf, or fruit from such a plant, a plant cell that contains the expression cassette described herein, and biomass comprising plant tissue from the plant or part of the plant described herein. Thus, the invention provides an engineered plant comprising a heterologous hydroxycinnamoyl-CoA hydratase-lyase (HCHL) operably linked to a promoter. In some embodiments, the polynucleotide encoding the heterologous HCHL is integrated into a plant genome. In some embodiments, the promoter is heterologous to the plant. In some embodiments, the promoter is an endogenous promoter. In some embodiment, the promoter is a secondary cell wall-specific promoter, such as an IRX5 promoter. In some embodiments, the HCHL is *Pseudomonas fluorescens* HCHL. The plant may be a monocot or a dicot. In some embodiments, the plant is selected from the group consisting of *Arabidopsis*, poplar, *Eucalyptus*, rice, corn, switchgrass, sorghum, millet, *Miscanthus*, sugarcane, pine, alfalfa, wheat, soy, barley, turfgrass, tobacco, hemp, bamboo, rape, sunflower, willow, and *Brachypodium*.

In further aspects, the invention provide methods of using an engineered plant of the invention, or parts of the plant, or plant biomass comprising material from the plant. In some embodiments, plant material is used in a saccharification reaction, e.g., enzymatic saccharification, to generate soluble sugars at an increased level of efficiency as compared to wild-type plants that have not been modified to express HCHL. In some embodiments, the plants, parts of plants, or plant biomass material are used to increase biomass yield or simplify downstream processing for wood industries (such as paper, pulping, and construction) as compared to wild-type plants. In some embodiments, the plants, parts of plants, or plant biomass material are used to increase the quality of wood for construction purposes. In some embodiments the plants, parts of plants, or plant biomass material can be used in a combustion reaction, gasification, pyrolysis, or polysaccharide hydrolysis (enzymatic or chemical). In some embodiments, the plants, plant parts, or plant biomass material are used as forage that is more readily digested compared to wild-type plants.

BRIEF DESCRIPTION OF THE DRAWINGS

FIG. 8A-8F. Alignment of amino acid sequences of *Pseudomonas fluorecsens* HCHL and other homologous proteins (SEQ ID NOS:4-32, 62 and 34). Majority=SEQ ID NO:63.

DETAILED DESCRIPTION OF THE INVENTION

I. Definitions

Figure 1:
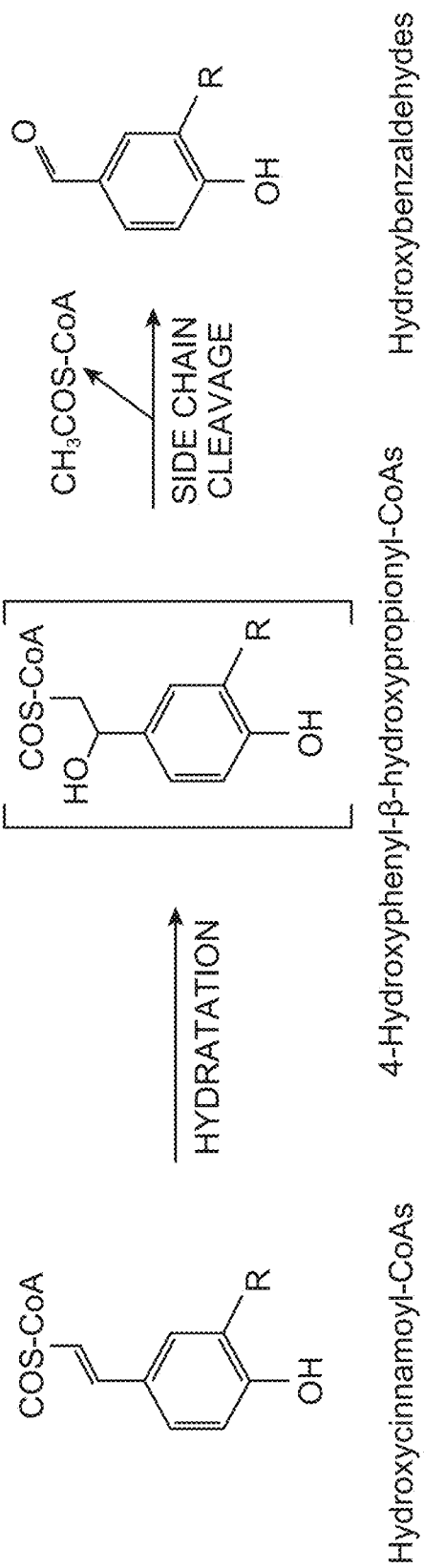
FIG. 1 HCHL-mediated conversion of hydroxycinnamoyl-CoAs into hydroxybenzaldehydes. HCHL performs the hydration and cleavage of hydroxycinnamoyl-CoAs (R=H, coumaroyl-CoA; R=OH, caffeoyl-CoA; R=OCH$_3$, feruloyl-CoA) to produce hydroxybenzaldehydes (R=H, 4-hydroxybenzaldehyde; R=OH, 3,4-dihydroxybenzaldehyde; R=OCH$_3$, 4-hydroxy-3-methoxybenzaldehyde) and acetyl-CoA via the formation of the corresponding reaction intermediates 4-hydroxyphenyl-β-hydroxypropionyl-CoAs.

As used herein, the term "hydroxycinnamoyl-CoA hydratase-lyase" or "HCHL" refers to an enzyme that catalyzes the hydratation of the double bond of lignin precursor p-coumaroyl-CoA, caffeoyl-CoA, or feruloyl-CoA thioester, which is followed by a retro aldol cleavage reaction to produce a corresponding $C_6C_1$ hydroxylbenzaldehyde and acetyl-CoA. A typical HCHL within the meaning of this invention is an HCHL from bacterium *Pseudomonas fluorescens* (EC 4.2.1.101—trans-feruloyl-CoA hydratase), which has the amino acid sequence set forth as SEQ ID NO:1 (GenBank Accession No. CAA73502), encoded by cDNA sequence set forth in GenBank Accession No. Y13067.1 or by a codon-optimized polynucleotide sequence set forth in SEQ ID NO:2 (synthesized by GenScript, Piscatway, N.J.). In this application, the term HCHL includes polymorphic variants, alleles, mutants, and interspecies homologs to the *Pseudomonas fluorescens* HCHL, some examples of which are provided in FIG. 8A-8F. A nucleic acid that encodes an HCHL refers to a gene, pre-mRNA, mRNA, and the like, including nucleic acids encoding polymorphic variants, alleles, mutants, and interspecies homologs of the particular sequences described herein. Thus, an HCHL nucleic acid (1) has a polynucleotide sequence that has greater than about 50% nucleotide sequence identity, 55%, 60%, 65%, 70%, 75%, 80%, 85%, 90%, preferably 91%, 92%, 93%, 94%, 95%, 96%, 97%, 98% or 99% or higher nucleotide sequence identity, preferably over a region of at least about 10, 15, 20, 25, 50, 100, 200, 500 or more nucleotides or over the length of the entire polynucleotide, to a polynucleotide sequence encoding SEQ ID NO:1 (e.g., SEQ ID NO:2 or the polynucleotide sequence set forth in Y13067.1); or (2) encodes a polypeptide having an amino acid sequence that has greater than about 50% amino acid sequence identity, 55%, 60%, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200 or more amino acids or over the length of the entire polypeptide, to a polypeptide having the amino acid sequence set forth in SEQ ID NO:1 or to any one of the amino acid sequences shown in FIG. 8A-8F (SEQ ID NOS:4-34 and 62). The enzymatic activity of an HCHL within the meaning of this application can be verified by functional assays known in the art or described in the example section of this application, for its ability to convert any one of lignin precursors p-coumaroyl-CoA, caffeoyl-CoA, and feruloyl-CoA thioester to a corresponding $C_6C_1$ hydroxylbenzaldehyde and acetyl-CoA.

The term "substantially localized," when used in the context of describing a plant expressing an exogenous HCHL that is substantially localized to a particular tissue, refers to the enzymatic activity and modified monolignols produced therefore in substantially higher amounts in the particular cell or tissue type of interest as compared to other cell or tissue types. In some embodiments, the presence of HCHL and modified monolignols is substantially localized to the secondary cell wall of a plant cell and in the stem of a plant.

The terms "polynucleotide" and "nucleic acid" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "substantially identical," used in the context of two nucleic acids or polypeptides, refers to a sequence that has at least 50% sequence identity with a reference sequence. Percent identity can be any integer from 50% to 100%. Some embodiments include at least: 50%, 55%, 60%, 65%, 70%, 75%, 80%, 85%, 90%, 91%, 92%, 93%, 94%, 95%, 96%, 97%, 98%, or 99%, compared to a reference sequence using the programs described herein; preferably BLAST using standard parameters, as described below. For example, an HCHL may have an amino acid sequence that is at least 50%, 55%, 60%, 65%, 70%, 75%, 80%, 85%, 90%, 91%, 92%, 93%, 94%, 95%, 96%, 97%, 98%, or 99% identical to SEQ ID NO:1, the amino acid sequence of *Pseudomonas fluorescens* HCHL.

Two nucleic acid sequences or polypeptide sequences are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

Nucleic acid or protein sequences that are substantially identical to a reference sequence include "conservatively modified variants." With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, *Proteins* (1984)).

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. For example, stringent conditions for hybridization, such as RNA-DNA hybridizations in a blotting technique are those which include at least one wash in 0.2×SSC at 55° C. for 20 minutes, or equivalent conditions.

The term "promoter," refers to a polynucleotide sequence capable of driving transcription of a DNA sequence in a cell. Thus, promoters used in the polynucleotide constructs of the invention include cis- and trans-acting transcriptional control elements, translational control elements (5'UTR: untranslated region) and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic or exonic sequence, which are involved in transcriptional regulation. These cis-acting sequences typically interact with proteins or other biomolecules to carry out (turn on/off, regulate, modulate, etc.) gene transcription. Promoters are located 5' to the transcribed gene, and as used herein, include the sequence 5' from the translation start codon (i.e., including the 5' untranslated region of the mRNA, typically comprising 50-200 bp). Most often the core promoter sequences lie within 1-3 kb of the translation start site, more often within 1 kbp and often within 500 bp of the translation start site. By convention, the promoter sequence is usually provided as the sequence on the coding strand of the gene it controls.

A "constitutive promoter" is one that is capable of initiating transcription in nearly all cell types, whereas a "cell type-specific promoter" initiates transcription only in one or a few particular cell types or groups of cells forming a tissue. In some embodiments, the promoter is secondary cell wall specific. Secondary cell wall is mainly composed of cellulose, hemicellulose, and lignin and is deposited in some, but not all, tissues of a plant, such as woody tissue. As used herein, a "secondary cell wall specific" promoter refers to a promoter that initiates higher levels of transcription in cell types that have secondary cell walls, e.g., lignified tissues such as vessels and fibers, which may be found in wood and bark cells of a tree, as well as other parts of plants such as the leaf stalk. In some embodiments, a promoter is secondary cell wall specific if the transcription levels initiated by the promoter in secondary cell walls are at least 3-fold, 4-fold, 5-fold, 6-fold, 7-fold, 8-fold, 9-fold, 10-fold, 50-fold, 100-fold, 500-fold, 1000-fold higher or more as compared to the transcription levels initiated by the promoter in other tissues, resulting in the encoded protein substantially localized in plant cells that possess secondary cell wall, e.g., the stem of a plant. Non-limiting examples of secondary cell wall specific promoters include the promoters directing expression of genes IRX1, IRX3, IRX5, IRX7, IRX8, IRX9, IRX10, IRX14, NST1, NST2, NST3, MYB46, MYB58, MYB63, MYB83, MYB85, MYB103, PAL1, PAL2, C3H, CcOAMT, CCR1, F5H, LAC4, LAC17, CADc, and CADd. See, e.g., Turner et al 1997; Meyer et al 1998; Jones et al 2001; Franke et al 2002; Ha et al 2002; Rohde et al 2004; Chen et al 2005; Stobout et al 2005; Brown et al 2005; Mitsuda et al 2005; Zhong et al 2006; Mitsuda et al 2007; Zhong et al 2007a, 2007b; Zhou et al 2009; Brown et al 2009; McCarthy et al 2009; Ko et al 2009; Wu et al 2010; Berthet et al 2011. In some embodiments, the promoter is substantially identical to the native promoter sequence directing expression of the IRX5 gene (see, e.g., the promoter and transcriptional regulatory elements for IRX5 are contained in SEQ ID NO:3). Some of the above mentioned secondary cell wall promoter sequences can be found within the polynucleotide sequences provided herein as SEQ ID NOs:36-61. A promoter originated from one plant species may be used to direct gene expression in another plant species.

A polynucleotide is "heterologous" to an organism or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety).

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" refers to a nucleic acid construct that, when introduced into a host cell, results in transcription and/or translation of an RNA or polypeptide, respectively. Antisense or sense constructs that are not or cannot be translated are expressly included by this definition. In the case of both expression of transgenes and suppression of endogenous genes (e.g., by antisense, RNAi, or sense suppression) one of skill will recognize that the inserted polynucleotide sequence need not be identical, but may be only substantially identical to a sequence of the gene from which it was derived. As explained herein, these substantially identical variants are specifically covered by reference to a specific nucleic acid sequence. One example of an expression cassette is a polynucleotide construct that comprises a polynucleotide sequence encoding a HCHL protein operably linked to a promoter that is heterologous to the plant cell into which the expression cassette may be introduced. In some embodiments, an expression cassette comprises a polynucleotide sequence encoding a HCHL protein that is targeted to a position in the genome of a plant such that expression of the HCHL polynucleotide sequence is driven by a promoter that is present in the plant.

The term "plant," as used herein, refers to whole plants and includes plants of a variety of a ploidy levels, including aneuploid, polyploid, diploid and haploid. The term "plant part," as used herein, refers to shoot vegetative organs and/or structures (e.g., leaves, stems and tubers), branches, roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, and plant tissue (e.g., vascular tissue, ground tissue, and the like), as well as individual plant cells, groups of plant cells (e.g., cultured plant cells), protoplasts, plant extracts, and seeds.

The class of plants that can be used in the methods of the invention is generally as broad as the class of higher and lower plants amenable to transformation techniques, including angiosperms (monocotyledonous and dicotyledonous plants), gymnosperms, ferns, and multicellular algae.

The term "biomass," as used herein, refers to plant material that is processed to provide a product, e.g., a biofuel such as ethanol, or livestock feed, or a cellulose for paper and pulp industry products. Such plant material can include whole plants, or parts of plants, e.g., stems, leaves, branches, shoots, roots, tubers, and the like.

The term "reduced lignification" encompasses both reduced size of a lignin polymer, e.g., a shorter lignin polymer chain due to a smaller number of monolignols being incorporated into the polymer, a reduced degree of branching of the lignin polymer or a reduced space filling (also called a reduced pervaded volume). Typically, a reduced lignin polymer can be shown by detecting a decrease in it molecular weight or a decrease in the number of monolignols by at least 2%, 5%, 10%, 20%, 25%, 30%, 40%, 50%, or more, when compared to the average lignin molecule in a control plant. Methods for detecting reduced lignification are described in detail in the example section of this application.

As used herein and in the appended claims, the singular "a", "an" and "the" include the plural reference unless the context clearly dictates otherwise. Thus, for example, reference to a "plant cell" includes a plurality of such plant cells.

II. Introduction

Plant cell walls are constituted by a polysaccharidic network of cellulose microfibrils and hemicellulose embedded in an aromatic polymer known as lignin. This ramified polymer is mainly composed of three phenylpropanoid-derived phenolics (i.e., monolignols) named p-coumaryl, coniferyl, and sinapyl alcohols which represent the p-hydroxyphenyl (H), guaiacyl (G) and syringyl (S) lignin units (Boerjan et al., 2003). Monolignols have a $C_6C_3$ carbon skeleton which consists of a phenyl ring ($C_6$) and a propane ($C_3$) side chain. Lignin is crucial for the development of terrestrial plants as it confers recalcitrance to plant cell walls. It also provides mechanical strength for upright growth, confers hydrophobicity to vessels that transport water, and acts as a physical barrier against pathogens that degrade cell walls (Boudet, 2007). Notably, lignin content and composition are finely regulated in response to environmental biotic and abiotic stresses (Moura et al., 2010).

Economically, lignocellulosic biomass from plant cell walls is widely used as raw material for the production of pulp in paper industry and as ruminant livestock feed. Plant feedstocks also represent a source of fermentable sugars for the production of synthetic molecules such as pharmaceuticals and transportation fuels using engineered microorganisms (Keasling, 2010). However, negative correlations exist between lignin content in plant biomass and pulp yield, forage digestibility, or polysaccharides enzymatic hydrolysis (de Vrije et al., 2002; Reddy et al., 2005; Dien et al., 2006; Chen and Dixon, 2007; Dien et al., 2009; Taboada et al., 2010; Elissetche et al., 2011; Studer et al., 2011). Consequently, reducing lignin recalcitrance in plant feedstocks is a major focus of interest, especially in the lignocellulosic biofuels field for which efficient enzymatic conversion of polysaccharides into monosaccharides is crucial to achieve economically and environmentally sustainable production (Carroll and Somerville, 2009).

Lignin biosynthesis is well characterized and well conserved across land plants (Weng and Chapple 2010). Genetic modifications such as silencing of genes involved in particular steps of this pathway or its regulation have been employed to reduce lignin content (Simmons et al., 2010; Umezawa, 2010) but this approach often results in undesired phenotypes such as dwarfism, sterility, reduction of plant biomass, and increased susceptibly to environmental stress and pathogens (Bonawitz and Chapple, 2010). These pleiotropic effects are generally the consequences of a loss of secondary cell wall integrity, accumulation of toxic intermediates, constitutive activation of defense responses, or depletion of other phenylpropanoid-derived metabolites which are essential for plant development and defense (Li et al., 2008; Naoumkina et al., 2010, Gallego-Giraldo et al., 2011). Alternatively, changing the recalcitrant structure and physico-chemical properties of lignin can be achieved by modifying its monomer composition. For example, incorporation of coniferyl ferulate into lignin improves enzymatic degradation of cell wall polysaccharides (Grabber et al., 2008). Recently, it has been demonstrated that enrichment in 5-hydroxy-G units and reduction in S units in lignin contribute to enhanced saccharification efficiencies without affecting drastically biomass yields and lignin content (Weng et al., 2010; Dien et al., 2011; Fu et al., 2011).

In this study, as an alternative strategy to reduce lignin recalcitrance, the inventors developed a dominant approach that uses precursors derived from the lignin biosynthetic pathways to enhance production of non-conventional monolignols, namely $C_6C_1$ phenolics. These phenol units lack propane side chain and thus have different polymerization properties compared to classic $C_6C_3$ monolignols. Such $C_6C_1$ phenolics are usually found in trace amount in some lignins and form the so-called 'benzyl end-groups' (Kim et al., 2000; Ralph et al., 2001; Kim et al., 2003; Morreel et al., 2004; Ralph et al., 2008; Kim and Ralph, 2010). The inventors considered increasing $C_6C_1$ end-group phenolics in lignin to reduce its polymerization degree and native branched structure. For this purpose, a hydroxycinnamoyl-CoA hydratase-lyase (HCHL, EC 4.2.2.101/EC 4.1.2.41) from *Pseudomonas fluorescens* was expressed in stems of *Arabidopsis*. HCHL is an enzyme that catalyzes the hydratation of the double bond of the lignin precursor p-coumaroyl-CoA, caffeoyl-CoA, and feruloyl-CoA thioesters, followed by a retro aldol cleavage reaction that produces the corresponding $C_6C_1$ hydroxybenzaldehydes and acetyl-CoA (FIG. 1; Mitra et al., 1999). The promoter of a secondary cell wall cellulose synthase gene (Cesa4/IRX5) was used to restrict HCHL expression in lignified tissues of the stem (xylem and interfascicular fibers) and prevent depletion of hydroxycinnamoyl-CoAs in other tissues in which they are precursors of hydroxycinnamate conjugates and other derivates involved in plant defense and development (Gou et al., 2009; Luo et al., 2009; Buer et al., 2010; Milkowski and Strack, 2010). The data disclosed herein show that HCHL expression driven by the IRX5 promoter results for some lines in no significant changes in lignin content, plant development and biomass yields. It has also been demonstrated that $C_6C_1$ phenolics accumulate as end-groups in the lignin of HCHL transgenics, which reduces lignin size and renders cell walls less recalcitrant to enzymatic hydrolysis.

III. Plants Having Reduced Lignification

A. Modification of Expression of an HCHL Enzyme

In one aspect, the present invention provides a method for engineering a plant having reduced lignification. This method includes these steps: first, introducing into the plant an expression cassette comprising a polynucleotide sequence encoding an HCHL enzyme and a promoter, with the coding sequence and the promoter being in an operably linked arrangement; and second, culturing the plant under conditions permissible for the expression of a functional HCHL to produce $C_6C_1$ phenolics, which can be polymerized with other monolignols and thereby reducing lignification in the plant.

In particular, the present invention provides methods of engineering a plant having modified lignin polymers, which may have reduced size, molecular weight, and/or altered (especially reduced or less extensive) branching, that are substantially localized to the lignified tissue of the plant. This is achieved by first introducing into the plant an expression cassette as described above but in particular having a secondary cell wall specific promoter, and then culturing the plant under conditions in which the functional HCHL enzyme is expressed. This enzyme converts various hydroxycinnamoyl-coA into their respective hydroxybenzaldehydes that can be either directly incorporated or further modified (e.g., oxidation or reduction of the aldehyde group) by native enzymes prior to their incorporation into the lignin polymer by polymerization with native monolignols.

The expression cassette as described herein, when introduced into a plant, does not necessarily modify the lignin content. Vessel stays intact indicating that the lignin cell wall structure is still robust to prevent vessel collapse, but the lignin composition and properties are modified to a level that its recalcitrance is reduce.

One of skill in the art will understand that the HCHL that is introduced into the plant by an expression cassette described herein does not have to be identical to the *Pseudomonas fluorescens* HCHL, which was used in the experiments detailed in the example section of this disclosure. In some embodiments, the HCHL that is introduced into the plant by an expression cassette is substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to the *Pseudomonas fluorescens* HCHL. For example, a variant HCHL will have at least 80%, 85%, 90%, or 95% sequence identity in its amino acid residues as compared to SEQ ID NO:1, especially within one or more of the 8 highly conserved regions (shown in the 8 boxes in FIG. 8A-F).

1. Hydroxycinnamoyl-CoA Hydratase-Lyase (HCHL)

In some embodiments, the expression cassette of this invention comprises a polynucleotide encoding an enzyme that produces modified monoligols that can cause reduced lignification. An example of such an enzyme is the *Pseudomonas fluorescens* HCHL, having the amino acid sequence set forth in SEQ ID NO:1. Additional examples of such HCHL suitable for use in the present invention include those shown in FIG. 8A-8F Also appropriate for use in the present invention are variants HCHL, which may be naturally occurring or recombinantly engineered, provided the variants possess (1) substantially amino acid sequence identity to an exemplary HCHL (e.g., SEQ ID NO:1) and (2) the enzymatic activity to convert at least one lignin precursor p-coumaroyl-CoA, caffeoyl-CoA, or feruloyl-CoA thioester into a corresponding $C_6C_1$ hydroxylbenzaldehyde, as determined by an HCHL enzymatic assay known in the art by way of various scientific publications or described herein.

Examples of naturally occurring HCHL that can be used to practice the present invention includes, p-hydroxycinnamoyl CoA hydratase/lyase (HCHL), Enoyl-CoA hydratase/isomerase (ECH), Feruloyl-CoA hydratase/lyase (FCA, FerA), as well as those named in FIG. 8A-8F, the amino acid sequences for which are provided in SEQ ID NOS:4-34 and 62.

2. Secondary Cell Wall-Specific Promoters

In some embodiments, the polynucleotide encoding the HCHL is operably linked to a secondary cell wall-specific promoter. The secondary cell wall-specific promoter is heterologous to the polynucleotide encoding the HCHL, in other words, the promoter and the HCHL coding sequence are derived from two different species. A promoter is suitable for use as a secondary cell wall-specific promoter if the promoter is expressed strongly in the secondary cell wall, e.g., in vessel and fiber cells of the plant, but is expressed at a much lower level or not expressed in cells without the secondary cell wall.

In some embodiments, the promoter is substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to the native promoter of a gene encoding a secondary cell wall cellulose synthase Cesa4/IRX5, polynucleotide sequence set forth in Genebank Accession No. AF458083_1 and SEQ ID NO:35, and the promoter pIRX5 is contained in SEQ ID NO:3.

In some embodiments, the secondary cell wall-specific promoter comprises SEQ ID NO:3. In some embodiments, the secondary cell wall-specific promoter comprises a subsequence of SEQ ID NO:3 or a variant thereof. In some embodiments, the secondary cell wall-specific promoter comprises a subsequence of SEQ ID NO:3 comprising about 50 to about 1000 or more contiguous nucleotides of SEQ ID NO:3. In some embodiments, the secondary cell wall-specific promoter comprises a subsequence of SEQ ID NO:3 comprising 50 to 1000, 50 to 900, 50 to 800, 50 to 700, 50 to 600, 50 to 500, 50 to 400, 50 to 300, 50 to 200, 50 to 100; 75 to 1000, 75 to 900, 75 to 800, 75 to 700, 75 to 600, 75 to 500, 75 to 400, 75 to 300, 75 to 200; 100 to 1000, 100 to 900, 100 to 800, 100 to 700, 100 to 600, 100 to 500, 100 to 400, 100 to 300, or 100 to 200 contiguous nucleotides of SEQ ID NO:3.

Secondary cell wall-specific promoters are also described in the art. See, for example, Mitsuda et al 2005 Plant Cell; Mitsuda et al 2007 Plant Cell; Zhou et al 2009 plant cell; Ohtani et al 2011 Plant Journal. They are contained the polynucleotide sequences provided in this application as SEQ ID NOS:36-61.

It will be appreciated by one of skill in the art that a promoter region can tolerate considerable variation without diminution of activity. Thus, in some embodiments, the secondary cell wall-specific promoter is substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to SEQ ID NO:3. The effectiveness of a secondary cell wall-specific promoter may be confirmed by an reporter gene (e.g., β-glucuronidase or GUS) assay known in the art or as described in the example section of this application.

B. Preparation of Recombinant Expression Vectors

Once the promoter sequence and the coding sequence for the gene of interest (e.g., a *Pseudomonas fluorescens* HCHL or any other HCHL as shown in FIG. 8A-8F) are obtained, the sequences can be used to prepare an expression cassette for expressing the gene of interest in a transgenic plant. Typically, plant transformation vectors include one or more cloned plant coding sequences (genomic or cDNA) under the transcriptional control of 5' and 3' regulatory sequences and a selectable marker. Such plant transformation vectors may also contain a promoter (e.g., a secondary cell wall-specific promoter as described herein), a transcription initiation start site, an RNA processing signal (such as intron splice sites), a transcription termination site, and/or a polyadenylation signal.

The plant expression vectors may include RNA processing signals that may be positioned within, upstream, or downstream of the coding sequence. In addition, the expression vectors may include regulatory sequences taken from the 3'-untranslated region of plant genes, e.g., a 3' terminator region to increase mRNA stability of the mRNA, such as the PI-II terminator region of potato or the octopine or nopaline synthase 3' terminator regions.

Plant expression vectors routinely also include selectable marker genes to allow for the ready selection of transformants. Such genes include those encoding antibiotic resistance genes (e.g., resistance to hygromycin, kanamycin, bleomycin, G418, streptomycin or spectinomycin), herbicide resistance genes (e.g., phosphinothricin acetyltransferase), and genes encoding positive selection enzymes (e.g. mannose isomerase).

Once an expression cassette comprising a polynucleotide encoding the HCHL and operably linked to a promoter (especially a secondary cell wall specific promoter) has been constructed, standard techniques may be used to introduce the polynucleotide into a plant in order to express the HCHL and effectuate reduced lignification. See, e.g., protocols described in Ammirato et al. (1984) Handbook of Plant Cell Culture-Crop Species. Macmillan Publ. Co. Shimamoto et al. (1989) Nature 338:274-276; Fromm et al. (1990) Bio/Technology 8:833-839; and Vasil et al. (1990) Bio/Technology 8:429-434.

Transformation and regeneration of plants is known in the art, and the selection of the most appropriate transformation technique will be determined by the practitioner. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumeficiens* mediated transformation. Transformation means introducing a nucleotide sequence in a plant in a manner to cause stable or transient expression of the sequence. Examples of these methods in various plants include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042.

Following transformation, plants can be selected using a selectable marker incorporated into the transformation vector. Typically, such a marker will confer antibiotic or herbicide resistance on the transformed plants or the ability to grow on a specific substrate, and selection of transformants can be accomplished by exposing the plants to appropriate concentrations of the antibiotic, herbicide, or substrate.

The polynucleotide sequence coding for an HCHL, as well as the polynucleotide sequence comprising a promoter (e.g., a secondary cell wall-specific promoter), can be obtained according to any method known in the art. Such methods can involve amplification reactions such as polymerase chain reaction (PCR) and other hybridization-based reactions or can be directly synthesized.

C. Plants in which Lignification can be Reduced

An expression cassette comprising a polynucleotide encoding an HCHL operably linked to a promoter, especially a secondary cell wall specific promoter, as described herein, can be expressed in various kinds of plants. The plant may be a monocotyledonous plant or a dicotyledonous plant. In some embodiments of the invention, the plant is a green field plant. In some embodiments, the plant is a gymnosperm or conifer.

In some embodiments, the plant is a plant that is suitable for generating biomass. Examples of suitable plants include, but are not limited to, *Arabidopsis*, poplar, *Eucalyptus*, rice, corn, switchgrass, sorghum, millet, *Miscanthus*, sugarcane, pine, alfalfa, wheat, soy, barley, turfgrass, tobacco, hemp, bamboo, rape, sunflower, willow, *Jatropha*, and *Brachypodium*.

In some embodiments, the plant into which the expression cassette of this invention is introduced is the same species of plant as the one from which the promoter is derived. In some embodiments, the plant into which the expression cassette is introduced is a different species of plant from the plant species the promoter is derived from.

D. Screening for Plants Having Reduced Lignification

After transformed plants are selected, the plants or parts of the plants may be evaluated to determine whether expression of the exogenous HCHL can be detected, e.g., by evaluating the level of RNA or protein, by measuring enzymatic activity of the HCHL, as well as by evaluating the size, molecular weight, content, or degree of branching in the lignin molecules found in the plants. These analyses can be performed using any number of methods known in the art.

In some embodiments, plants are screened by evaluating the level of RNA or protein. Methods of measuring RNA expression are known in the art and include, for example, PCR, northern analysis, reverse-transcriptase polymerase chain reaction (RT-PCR), and microarrays. Methods of measuring protein levels are also known in the art and include, for example, mass spectroscopy or antibody-based techniques such as ELISA, Western blotting, flow cytometry, immunofluorescence, and immunohistochemistry.

In some embodiments, plants are screened by assessing HCHL activity, and also by evaluating lignin size and composition. The enzymatic assays for HCHL are well known in the art and are described in this application. Lignin molecules can be assessed, for example, by nuclear magnetic resonance (NMR), spectrophotometry, microscopy, klason lignin assays, acetyl-bromide reagent or by histochemical staining (e.g., with phloroglucinol).

IV. Methods of Using Plants Having Reduced Lignification

Plants, parts of plants, or plant biomass material from plants having reduced lignification due to the expression of an exogenous HCHL in the secondary cell wall can be used for a variety of methods. In some embodiments, the plants, parts of plants, or plant biomass material generate less recalcitrant biomass for use in a conversion reaction as compared to wild-type plants. In some embodiments, the plants, parts of plants, or plant biomass material are used in a saccharification reaction, e.g., enzymatic saccharification, to generate soluble sugars at an increased level of efficiency as compared to wild-type plants. In some embodiments, the plants, parts of plants, or plant biomass material are used to increase biomass yield or simplify downstream processing for wood industries (such as paper, pulping, and construction) as compared to wild-type plants. In some embodiments, the plants, parts of plants, or plant biomass material are used to increase the quality of wood for construction purposes. In some embodiments the plants, parts of plants, or plant biomass material can be used in a combustion reaction, gasification, pyrolysis, or polysaccharide hydrolysis (enzymatic or chemical). In further embodiments, the plants, parts of plants, or plant biomass is used as a forage crop and exhibit improved digestibility compared to wild-type plants.

Methods of conversion, for example biomass gasification, are known in the art. Briefly, in gasification plants or plant biomass material (e.g., leaves and stems) are ground into small particles and enter the gasifier along with a controlled amount of air or oxygen and steam. The heat and pressure of the reaction break apart the chemical bonds of the biomass, forming syngas, which is subsequently cleaned to remove impurities such as sulfur, mercury, particulates, and trace materials. Syngas can then be converted to products such as ethanol or other biofuels.

Methods of enzymatic saccharification are also known in the art. Briefly, plants or plant biomass material (e.g., leaves and stems) are optionally pre-treated with hot water, dilute alkaline, AFEX (Ammonia Fiber Explosion), ionic liquid or dilute acid, followed by enzymatic saccharification using a mixture of cell wall hydrolytic enzymes (such as hemicellulases, cellulases and beta-glucosidases) in buffer and incubation of the plants or plant biomass material with the enzymatic mixture. Following incubation, the yield of the saccharification reaction can be readily determined by measuring the amount of reducing sugar released, using a standard method for sugar detection, e.g. the dinitrosalicylic acid method well known to those skilled in the art. Plants engineered in accordance with the invention provide a higher saccharification efficiency as compared to wild-type plants, while the plants growth, development, or disease resistance is not negatively impacted.

Sugars generated from a saccharification reaction using plant biomass of the invention can be used for producing any product for which the sugars can serve as a carbon source. Examples of products include, but are not limited to, alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); vitamins (e.g., riboflavin, B12, beta-carotene), fatty acids and fatty acid derivatives (as described, e.g., in PCT/US2008/068833); isoprenyl alkanoates (as described, e.g., PCT/US2008/068756, methyl butenol (as described, e.g., PCT/US2008/068831; fatty acid esters (as described, e.g., in PCT/US2010/033299), isoprenoid-based alternative diesel fuels (as described, e.g., in PCT/US2011/059784; a polyketide synthesized by a polyketide synthase, such as a diacid (see, e.g., PCT/US2011/061900), biofuels (see, e.g., PCT/US2009/042132) and alpha-olefins (see, e.g., PCT/US2011/053787).

EXAMPLES

The following examples are provided to illustrate but not to limit the claimed invention.

Example 1: Expression of Bacterial HCHL in *Arabidopsis*

1. Materials and Methods
Plant Material and Growth Conditions
*Arabidopsis thaliana* (ecotype Columbia, Col-0) seeds were germinated directly on soil. Growing conditions were 14 h of light per day at 100 μmol $m^{-2}$ $s^{-1}$, 22° C., 55% humidity. Selection of T1 and T2 homozygote transgenic plants was made on solid Murashige and Skoog vitamin medium (PhytoTechnology Laboratories) supplemented with 1% sucrose, 1.5% agar (Sigma-Aldrich) adjusted to pH 5.6-5.8, and containing 50 μg $mL^{-1}$ kanamycin.

Chemicals

4-Hydroxybenzoic acid, 3,4-dihydroxybenzoic acid, vanillic acid, 4-hydroxybenzaldehyde, vanillin, 5-hydroxyvanillin, 4-hydroxybenzyl alcohol, vanillyl alcohol, and 1-methyl-2-pyrrolidinone were purchased from Sigma-Aldrich. Vanillic acid, syringic acid, 3,4-dihydroxybenzaldehyde, syringaldehyde, and sinapyl alcohol were purchased from Alfa Aesar. 5-Hydroxyvanillic acid was obtained from Chromadex, and 3,4-dihydroxybenzyl alcohol from TCI America.

pIRX5:GUS Line and GUS Staining

*Arabidopsis* line CS70758 (ecotype Columbia, Col-2) was obtained from the *Arabidopsis* Biological Resource Center (ABRC). This line has a pMLBART plasmid containing an expression cassette consisting of the genomic fragment located upstream of the CESA4 start codon fused to the GUS gene. Histochemical GUS activity was performed as previously described (Eudes et al., 2006). Various organs of soil-grown line CS70758 were incubated for 1 h or 8 h at 37° C. in the GUS assay buffer using 5-bromo-4-chloro-3-indolyl-D-glucuronic acid (Indofine Chemical Company, Inc.) as a substrate. After staining, stem samples (1 cm) were cross-sectioned (80 μm) using a vibratome before observation under the microscope (Leica).

IRX5:HCHL Construct and Plant Transformation

For HCHL expression in *Arabidopsis*, the binary vector pTKan which is derived from pPZP212 was used (Hajdukiewicz et al., 2004). A Gateway cloning cassette (Invitrogen) was inserted between XhoI and PstI restriction sites to produce a pTKan-GW vector. The nucleotide sequence of the IRX5 promoter was amplified by PCR from *Arabidopsis* (ecotype Columbia, Col-0) genomic DNA using oligonucleotides 5'-CCCGGCGGCCGCATGAAGCCATCCTC-TACCTCGGAAA-3' (SEQ ID NO:64) and 5'-CCCGGCTAGCGGCGAGGTACACTGAGCTCTCG-GAA-3' (SEQ ID NO:65) (NotI and NheI restriction sites underlined), and inserted between the ApaI and SpeI restriction sites of pTKan-GW to produce a pTKan-pIRX5-GW expression vector. A codon-optimized nucleotide sequence encoding the HCHL enzyme from *Pseudomonas fluorescens* AN103 (accession number CAA73502) for expression in *Arabidopsis* was synthesized without stop codon (Genescript) and amplified by PCR using oligonucleotides 5'-GGGGACAAGTTTGTACAAAAAAGCAGGCTT-CATGTCTACTTACGAGGGAAGATGG-3' (SEQ ID NO:66) and 5'-GGGGACCACTTGTA-CAAGAAAGCTGGGTCTCTCTTGTAAGCCTG-GAGTCC-3' (SEQ ID NO:67) (attb1 and attb2 sites underlined) for cloning into the Gateway pDONR221-fl entry vector (Lalonde et al 2010). A sequence-verified HCHL entry clone was LR recombined with the pTKan-pIRX5-GW vector to generate the final IRX5:HCHL construct. The construct was introduced into wild type *Arabidopsis* plants (ecotype Col0) via *Agrobacterium tumefaciens*-mediated transformation (Bechtold and Pelletier, 1998).

RNA Extraction and RT-PCR

Total RNA (1 μg) extracted from inflorescence stems of IRX5:HCHL T1 transformants and wild type plants using the Plant RNeasy extraction kit (Qiagen) was reverse-transcribed using the Transcriptor First Strand cDNA Synthesis Kit (Roche applied Science). The obtained cDNA preparation was quality-controlled for PCR using tub8-specific oligonucleotides (5'-GGCTAAAGGACACTA-CACTG-3' (SEQ ID NO:68)/5'-CCTCCTGCACTTC-CACTTCGTCTTC-3' (SEQ ID NO:69)). Oligonucleotides 5'-ATGTCTACTTACGAGGGAAGATGG-3' (SEQ ID NO:70) and 5'-TCTCTTGTAAGCCTGGAGTCC-3' (SEQ ID NO:71) were used for the detection of HCHL expression by PCR.

Western Blot Analysis

For protein extraction, inflorescence stems of IRX5: HCHL T2 transformants and wild type plants were ground in liquid nitrogen, and 0.25 g of the resulting powder was homogenized with the extraction buffer [100 mM Tris-HCl pH 6.5, 2% (w/v) polyvinylpyrrolidone, 2% (v/v) β-mercaptoethanol, 1% (w/v) SDS] at 1400 rpm for 30 min. The mixture was centrifuged at 20,000 g for 5 min and the supernatant collected for protein quantification using the Bradford method (Bradford, 1976) and bovine serum albumin as a standard. For electrophoresis, soluble protein (5 μg) were mixed with 0.2 M Tris-HCl, pH 6.5, 8% (w/v) SDS, 8% (v/v) β-mercaptoethanol, 40% (v/v) glycerol, and 0.04% (w/v) bromophenol blue and incubated at 40° C. for 30 min. Proteins were separated by SDS-PAGE using 8-16% (w/v) polyacrylamide gradient gels (Invitrogen) and electrotransferred (100 volts, 45 min) onto PVDF membranes (Thermo Fisher Scientific). Blotted membranes were incubated 1 h in TBS-T (20 mM Tris-HCl, 150 mM NaCl, 0.1% (v/v) Tween 20, pH 7.6) containing 2% (w/v) non-fat milk powder, and incubated overnight with the universal antibody (1:20000) in TBS-T containing 2% (w/v) non-fat milk powder. Membranes were then washed in TBS-T for 30 min and incubated for 1 h with an anti-rabbit secondary antibody conjugated to horseradish peroxidase (1:20000; Sigma-Aldrich) in TBS-T containing 2% (w/v) non-fat milk powder. Membranes were then washed in TBS-T for 30 min, and detection was performed by chemiluminescence using the SuperSignal West Dura Extended Duration Substrate (Thermo Fisher Scientific).

HCHL Activity

For protein extraction, inflorescence stems of IRX5: HCHL T2 transformants and wild type plants were ground in liquid nitrogen, and 0.25 g of the resulting powder was homogenized with 25 mg of polyvinylpolypyrrolidone and 1.25 mL of extraction buffer (EB; 100 mM Tris-HCl, pH 8.5, 20 mM DTT, and 10 mM $Na_2EDTA$). Extracts were shaken at 1400 rpm for 15 min at 4° C., and centrifuged for 30 min at 20,000 g at 4° C. Supernatants were collected, adjusted to 2.5 mL with EB, and applied to PD10 columns (GE healthcare) pre-equilibrated with 25 mL of EB. Proteins were eluted with 3.5 mL of EB and quantified using the Bradford method (Bradford, 1976) and bovine serum albumin as a standard.

For HCHL activity, 5 μL of protein extract was incubated for 15 min at 30° C. with 150 μM feruloyl-CoA in 100 mM Tris-HCl pH 8.5 in a total volume of 50 μL. Total amounts of protein per reaction varied from 4 to 6.5 μg. Reactions were stopped with 50 μL of cold acidified methanol (12% glacial acetic acid/88% methanol, v/v) and stored at −70° C. until LC-MS analysis.

Biomass

For biomass measurements, IRX5:HCHL and wild type plants were grown until senescence and dried stems collected without roots, leaves and siliques before weighing. Statistical analysis was performed using ANOVA followed by Scheffe post hoc test.

Microscopy

Five-week-old plants were use for microscopy. Stem segments cut between the first and second internodes were embedded in 4% agarose. Stem semi-thin sections (100-μm thickness) were obtained using a vibratome (Leica). For toluidine blue O (TBO) staining, sections were incubated in a 0.05% (w/v) solution of TBO (Sigma-Aldrich) in water for 30 sec and rinsed with water. For Wiesner lignin staining, sections were incubated for 3 min in phloroglucinol-HCl reagent (VWR International) and rinsed with water. For Mäule lignin staining, sections were incubated in 4% $KMnO_4$ for 5 min, rinsed with water, incubated in 37% $HCl/H_2O$ (1:1, v/v) for 2 min, and observed after addition of a drop of aqueous ammonia. Sections were immediately observed using bright field light microscopy (Leica DM4000 B).

Soluble Phenolics Extraction

For extraction of methanol soluble phenolics, approximately 200 mg of frozen stem powder was mixed with 1 mL of 80% (v/v) methanol-water and shaken for 1 h at 1400 rpm. Extracts were cleared by centrifugation (5 min, 20,000 g), mixed with 400 μL of analytical grade water and filtered using Amicon Ultra centrifugal filters (3,000 Da MW cutoff regenerated cellulose membrane; Millipore) prior to LC-MS analysis. Alternatively, an aliquot of the filtered extracts was dried under vacuum, resuspended with 1 N HCl and incubated at 95° C. for 3 h for acid hydrolysis. The mixture was subjected to three ethyl acetate partitioning steps. Ethyl acetate fractions were pooled, dried in vacuo, and resuspended in 50% (v/v) methanol-water prior to LC-MS analysis.

Cell-Wall Bound Phenolics Extraction

For extraction of cell-wall bound phenolics, mature senesced stems were collected without the leaves and siliques, and ball-milled to a fine powder using a Mixer Mill MM 400 (Retsch) and stainless steel balls for 2 min at 30 $s^{-1}$. Extract-free cell wall residues (CWR) were obtained by sequentially washing 60 mg of ball-milled stems with 1 ml of 96% ethanol at 95° C. twice for 30 min, and vortexing with 1 mL of 70% ethanol twice for 30 sec. The resulting CWR were dried in vacuo overnight at 30° C. Approximately 6 mg of CWR was mixed with 500 μL of 2 M NaOH and shaken at 1400 rpm for 24 h at 30° C. The mixture was acidified with 100 μL of concentrated HCl, and subjected to three ethyl acetate partitioning steps. Ethyl acetate fractions were pooled, dried in vacuo, and suspended in 50% (v/v) methanol-water prior to LC-MS analysis.

LC-MS

Separation of $C_6C_1$ phenolic acids and aldehydes was conducted on a Poroshell-120 column (150 mm length, 3 mm internal diameter, 2.7 μm particle size) using a 1200 Series HPLC system (Agilent Technologies Inc.). Analytes were separated using a gradient elution with mobile phase composition of 0.1% formic acid in water as solvent A, and 0.1% formic acid in acetonitrile-water (98:2, v/v) as solvent B. The elution gradient was 0-5 min 13% B, 5-7 min 50% B, 7-8 min 50% B, and 8-11 min 13% B, using a flow rate of 0.55 mL $min^{-1}$. The HPLC system was coupled to an Agilent 6210 time-of-flight (TOF) mass spectrometer (MS) via a 1:7 post-column split. Analyses were conducted using Electrospray ionization (ESI) in the positive ion mode. Detection of $[M+H]^+$ ions was carried out in full scan mode at 0.85 spectra $sec^{-1}$ and a cycle time of 1.176 sec $spectrum^{-1}$ using the following parameters: capillary voltage 3500 V, fragmentor 165 V, skimmer 50 V and OCT RF 170 V, drying gas flow rate 9 L $min^{-1}$, nebulizer pressure 15 psig, drying gas temperature 325° C. Separation of $C_6C_1$ phenolic alcohols was conducted on the same HPLC and MS system using the same HPLC column. Analytes were separated using gradient elution with a mobile phase composition of 0.1% formic acid in water as solvent A, and 0.1% formic acid in methanol-water (98:2, v/v) as solvent B. Elution conditions were the same as described above. Analyses were conducted using atmospheric pressure chemical ionization (APCI) in the positive ion mode. Detection of [M–H$_2$O+H]$^+$ ions was carried as described above except for the following parameters: capillary voltage 3200 V, corona current 4 µA, drying gas flow rate 12 L min$^{-1}$, nebulizer pressure 30 psig, vaporizer temperature 350° C. Quantification of compounds was made by comparison with standard curves of authentic compounds prepared in 50% (v/v) methanol-water.

Lignin Analysis

Extract-free samples (CWR) of ball-milled mature senesced stems were prepared using a Soxhlet apparatus by sequentially extracting the ground material with toluene:ethanol (2:1, v/v), ethanol, and water (Sluiter et al., 2008). The determination of lignin content using the standard Klason procedure (Dence, 1992) and the thioacidolysis procedure (Lapierre et al., 1995; 1999) were carried out on CWR. The lignin-derived monomers were identified by GC-MS as their trimethyl-silylated derivatives. All the lignin analyses were performed in duplicate.

Total and Hemicellulosic Sugar Analysis

For total sugar hydrolysis, CWR of ball-milled mature senesced stems (50 mg) were swelled in 500 µL H$_2$SO$_4$ (72%, w/v) at 30° C. for 60 min, and autoclaved at 120° C. for 1 h in dilute H$_2$SO$_4$ (4%, w/v) after addition of deionized water (14 mL). Samples were cooled down at room temperature and filtered using pre-weighted GF/C glass microfiber filters (Whatman). Filtrates were collected and diluted 100 times with deionized water prior to HPAEC-PAD analysis. For hemicellulose hydrolysis, CWR of ball-milled mature dried stems (5 mg) were hydrolyzed in 1 ml of 2 M trifluoroacetic acid (TFA) for 1 h at 120° C. TFA was removed by drying under vacuum and the residue suspended in deionized water (1 mL) prior to HPAEC-PAD analysis.

HPAEC-PAD Analysis

Monosaccharide composition was determined by HPAEC-PAD of hydrolyzed material. Chromatography was performed on a PA20 column (Dionex) at a flow rate of 0.5 mL min$^{-1}$. Before injection of each sample (20 µL) the column was washed with 200 mM NaOH for 10 min, then equilibrated with 10 mM NaOH for 10 min. The elution program consisted of a linear gradient from 10 mM NaOH to 5 mM NaOH from 0 to 1.5 min, followed by isocratic elution with 5 mM NaOH from 1.5 to 20 min, and a linear gradient up to 800 mM NaOH from 20 to 43 min. Monosaccharides were detected using a pulsed amperometric detector (gold electrode) set on waveform A according to manufacturer's instructions. A calibration curve of monosaccharide standards that includes L-Fuc, L-Rha, L-Ara, D-Gal, D-Glc, D-Xyl, D-GalA and D-GlcA (Sigma-Aldrich) was run for verification of response factors. Statistical analysis was performed using ANOVA followed by Tukey's test.

FT-Raman and FT-IR Spectral Analyses

FT-Raman spectroscopy was conducted on CWR of ball-milled mature senesced stems (2 mg) from three independent cultures. Raman spectra were collected using a Bruker MultiRAM FT-Raman system equipped with a 1064 nm diode laser (Bruker Optics Inc.). Five spectra were acquired for each sample with spectral resolution of 4 cm$^{-1}$ using a laser power of 50 mW and 256 scans to achieve good signal-to-noise ratio. White light correction of the acquired spectra was performed to correct the influence of the optics on the spectrometer. Spectra in the range of 200-3500 cm$^{-1}$ were smoothed and baseline corrected using OPUS software. Lignin and polysaccharides (cellulose and hemicellulose) content were determined using integrated intensities measured over the range of 1555-1690 cm$^{-1}$ and 1010-1178 cm$^{-1}$, respectively. For FT-IR spectroscopy, analyses were carried out on xylem and interfascicular fibers tissues from 50-µm thick sections of the basal region of stems of five-week-old plants. For both wild type and IRX5:HCHL (line 2), five to six sections from three different plants were analyzed. FT-IR spectra were collected from a 50 µm×50 µm window targeting xylem vessels or interfascicular fibers, and normalization of the data and statistical analysis (Student's t-test) were performed as described (Mouille et al., 2003).

Isolation of Cellulolytic Lignin (CEL) and Size Exclusion Chromatography (SEC)

CEL lignin was purified from wild type and IRX5:HCHL (line 2) plants. One gram of ball-milled mature senesced stems was mixed with 50 mM NaCl (30 ml) and incubated overnight at 4° C. After centrifugation (2,800 g, 10 min), the biomass was extracted sequentially by sonication (20 min) with 80% ethanol (three times), acetone (one time), chloroform-methanol (1:1, v/v, one time) and acetone (one time). The obtained CWR were ball-milled for 3 h per 500 mg of sample (in 10 min on/10 min off cycles) using a PM100 ball mill (Retsch) vibrating at 600 rpm with zirconium dioxide vessels (50 mL) containing ZrO$_2$ ball bearings (10×10 mm). Ball-milled walls (490 mg for wild type and 480 mg for IRX5:HCHL) were transferred to centrifuge tubes (50 mL) and digested four times over three days at 30° C. with crude cellulases (Cellulysin; Calbiochem; 60 mg g$^{-1}$ of sample) in NaOAc pH 5.0 buffer (30 mL) under gentle rotation. The obtained CEL was washed 3 times with deionized water and lyophilized overnight. CEL recovered were 131 mg for wild type (27.3%) and 101 mg for IRX5:HCHL (20.6%). For SEC analysis, 1% (w/v) CEL lignin solutions were prepared in analytical-grade 1-methyl-2-pyrrolidinone-DMSO (1:1, v/v) and sonicated for 3 hours at 40° C.

Polydispersity of dissolved lignin was determined using analytical techniques SEC UV-F and SEC UV-A as described elsewhere (George et al., 2011, submitted). An Agilent 1200 series binary LC system (G1312B) equipped with FL (G1321A) and DA (G1315D) detectors was used. Separation was achieved with a Mixed-D column (5 mm particle size, 300 mm×7.5 mm i.d., linear molecular weight range of 200 to 400,000 u, Polymer Laboratories) at 80° C. using a mobile phase of NMP at a flow rate of 0.5 mL min$^{-1}$. Absorbance of material eluting from the column was detected at 300 nm (UV-A). Excitation 250 nm and emission 450 nm were used for UV-F detection. Intensities were area normalized and molecular mass estimates were determined after calibration of the system with polystyrene standards.

Cell Wall Pretreatments and Saccharification

Ball-milled mature senesced stems (10 mg) were mixed with 340 µL of water, 340 µL of H$_2$SO$_4$ (1.2%, w/v), or 340 µL of NaOH (0.25%, w/v) for hot water, dilute acid, or dilute alkaline pretreatments, respectively, incubated at 30° C. for 30 min, and autoclaved at 120° C. for 1 h. After cooling down at room temperature, samples pretreated with dilute acid and dilute alkaline were neutralized with 5 N NaOH (25 µL) and 1.25 N HCl (25 µL), respectively. Saccharification was initiated by adding 635 µL of 100 mM sodium citrate buffer pH 6.2 containing 80 g ml$^{-1}$ tetracycline, 5% w/w cellulase complex NS50013 and 0.5% w/w glucosidase NS50010 (Novozymes). After 72 h of incubation at 50° C. with shacking (800 rpm), samples were centrifuged (20,000 g, 3 min) and 10 µL of the supernatant was collected for reducing sugar measurement using the DNS assay and glucose solutions as standards (Miller, 1959).

Transcriptome Studies

Microarray analysis was performed on complete *Arabidopsis thaliana* transcriptome microarrays containing 24,576 gene-specific tags (GSTs) corresponding to 22,089 genes from *Arabidopsis* (Crowe et al., 2003; Hilson et al., 2004). RNA samples from three independent biological replicates were isolated and separately analyzed. For each biological replicate, RNA from the main inflorescence stem (first two internodes) of three plants were pooled. For each comparison, one technical replication with fluorochrome reversal was performed for each biological replicate (i.e. nine hybridizations per comparison). Reverse transcription of RNA was conducted in the presence of Cy3-dUTP or Cy5-dUTP (PerkinElmer-NEN Life Science Products), and hybridization and scanning of the slides were performed as described in Lurin et al. (2004).

Statistical Analysis of Microarray Data

Statistical analysis was performed with normalization based on dye swapping (i.e., four arrays, each containing 24,576 GSTs and 384 controls) as previously described (Gagnot et al., 2008). For the identification of differentially expressed genes, we performed a paired t test on log ratios, assuming that the variance of the log ratios was similar for all genes. Spots with extreme variances (too small or too large) were excluded. The raw P values were adjusted by the Bonferroni method, which controls the family-wise error rate (with a type I error equal to 5%) to minimize the number of false positives in a multiple-comparison context (Ge et al., 2003). Genes with a Bonferroni P value≤0.05 were considered to be differentially expressed, as previously described (Gagnot et al., 2008).

Data Deposition

Microarray data from this article were deposited at GEO (http www address ncbi.nlm.nih.gov/geo/) and at CATdb (http urgv address evry.inra.fr/CATdb/) according to Minimum Information about a Microarray Experiment standards (MIME).

II. Results

Expression of a Bacterial HCHL Enzyme in *Arabidopsis* Stems

Figure 2:
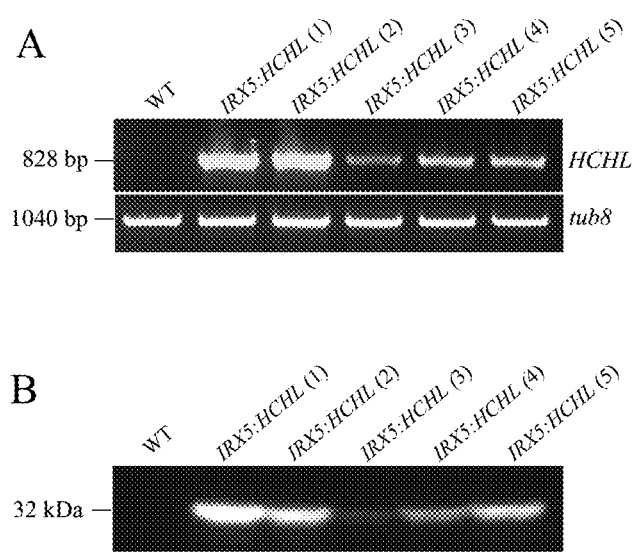
FIG. 2, Panels A and B. Analysis of HCHL expression in IRX5:HCHL lines. (Panel A) Detection by RT-PCR of HCHL transcripts using mRNA isolated from secondary stems of five independent five-week-old transformants in the T1 generation. cDNA synthesized from mRNA purified from wild type (WT) stems were used as a negative control. Tub8-specific primers were used to assess cDNA quality for each sample. (Panel B) Detection by western blot of HCHL tagged with the AttB2 peptide (approximate size 32 kDa) using the universal antibody and 5 µg of total protein extracted from the primary stem of five independent five-week-old IRX5:HCHL transformants in the T2 generation. A protein extract from wild type stems (WT) was used as a negative control.
Figure 9:
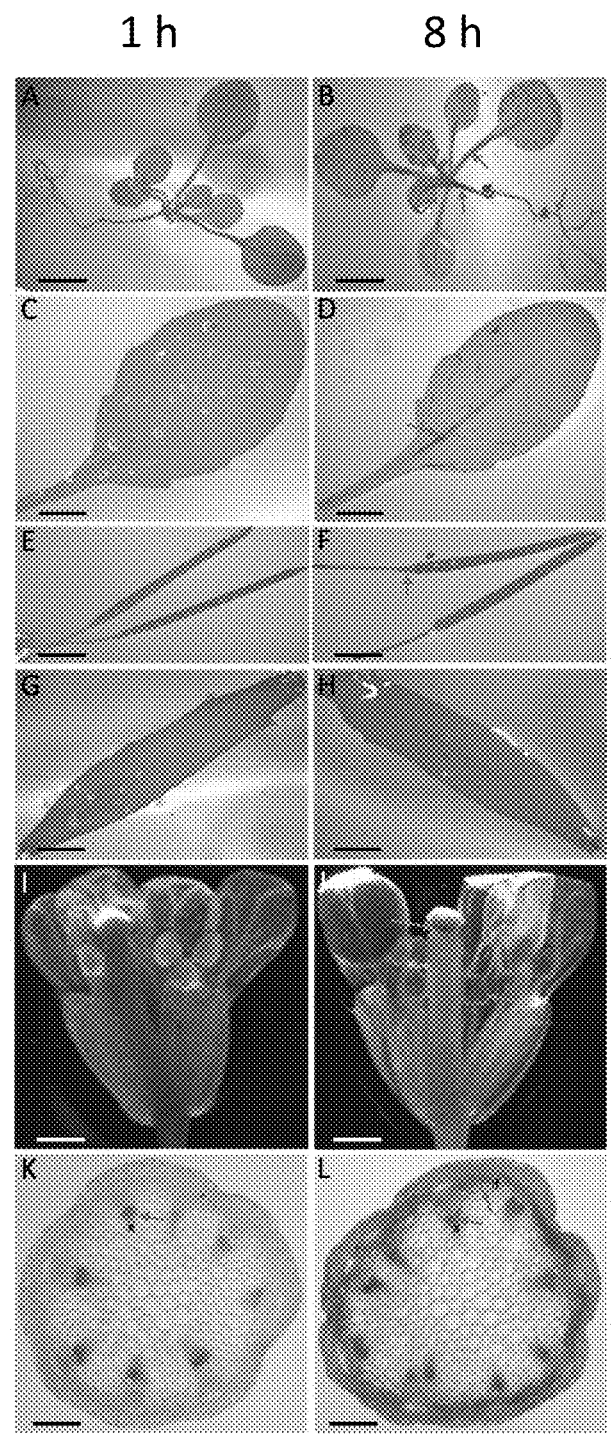
FIG. 9. Organ and tissue-specific activity of the IRX5 promoter in *Arabidopsis*. Line CS70758, which contains a pIRX5:GUS expression cassette, was used to localize the activity of the IRK5 promoter. Young seedlings (A and B), rosettes leaves (C and D), siliques (E and F), cauline leaves (G and H), flowers (I and J), and inflorescence stems (K and L) were incubated in the GUS assay buffer for 1 h and 8 h at 37° C. Gus activity was essentially detected in the stem xylem vessels after a 1-h incubation (K). For longer incubations (8 h), GUS staining was also observed in interfascicular fibers of the stem (L), the vascular system of young seedlings (A), siliques (F) rosette (D) and cauline leaves (H), as well as in the style and anthers (J). x: xylem vessels, if: interfascicular fibers. Scale bars: 2 mm (A-B, E-F), 4 mm (C-D, G-H), 500 µm (I-J), 100 µm (K-L).

The tissue specific activity of the IRX5 promoter was verified using the beta-glucuronidase (GUS) as a reporter gene. Gus activity was essentially detected in the xylem vessels of the stem. After prolonged incubations, stem interfascicular fibers also showed strong GUS activity, and more moderate staining was observed in the vascular system of young seedlings, siliques, rosette and cauline leaves. No activity was detected in other organs or tissues except for the style and anthers (FIG. 9). A codon-optimized sequence encoding HCHL from *Pseudomonas fluorescens* AN103 was designed and cloned downstream of the IRX5 promoter for preferential expression in lignified tissues of *Arabidopsis* stems. Presence of HCHL transcripts in the main stem of five independent transformants was verified by RT-PCR in the T1 generation (FIG. 2A). Plants homozygous for the IRX5: HCHL construct were identified in the T2 generation, and used to analyze HCHL protein expression and activity in stems. Western blotting analysis using the 'universal antibody' allowed detection of HCHL in stem extracts of the five selected transgenic lines (FIG. 2B; Eudes et al. 2010). Furthermore, HCHL activity could be detected in the stem of these lines, ranging from 0.025 to 0.16 pkat vanillin $\mu g^{-1}$ protein using feruloyl-CoA as substrate, whereas no detectable activity was observed in protein extracts of wild type plants (Table I). Two transgenic lines showing the highest and the lowest levels of HCHL activity, and two lines exhibiting intermediate activity level were selected for detailed analysis.

Growth Characteristics and Tissue Anatomy of IRX5:HCHL Lines

Figure 3:
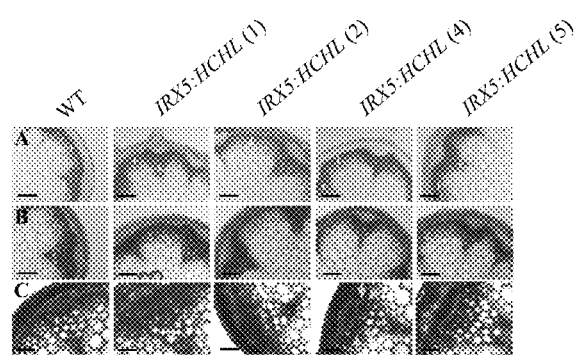
FIG. 3, Panel A (top row), Panel B (middle row), Panel C (bottom row) Histochemical staining of stem sections from five-week-old *Arabidopsis* plants. (Panel A) Mäule staining. (Panel B) Phloroglucinol-HCl staining. (Panel C) Toluidine blue O staining. i, interfascicular fibers; x, xylem. Bars represent 50 µm for (A) and (B), and 20 µm for (C). Note the collapsed xylem vessels (yellow arrows) observed for line IRX5:HCHL (4).
Figure 10:
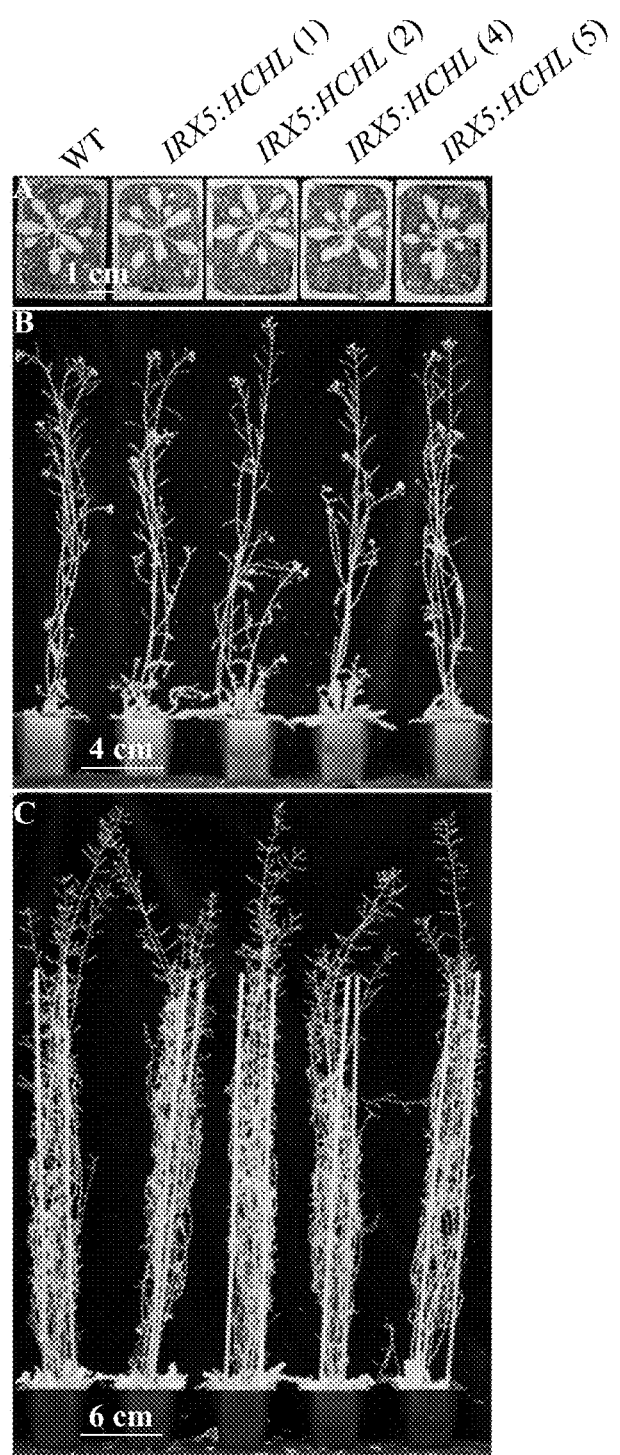
FIG. 10 Growth and development of IRX5:HCHL and wild type (WT) plants at different stages. (A, top panel) Three-week-old rosette (B, middle panel) Five-week-old flowering stage. (C, bottom panel) Eight-week-old senescing stage.

IRX5:HCHL plants had growth and development characteristics visually similar to the wild type from early rosette stage and until senescence (FIG. 10). However, mature senesced stems from lines IRX5:HCHL (4) and IRX5:HCHL (5) were little bit shorter (22% and 13% reduction) and had lower dry weight yield (30% and 16% reduction) compared to control plants, whereas those from lines IRX5:HCHL (1) and IRX5:HCHL (2) were not significantly different (Table II). Stem tissues of five-week-old IRX5:HCHL plants were inspected using light microscopy. Transverse stem cross-sections stained with Mäule and phloroglucinol-HCl reagents, which are indicative of S-units and hydroxycinnamaldehyde units in lignin, respectively, showed similar patterns between transgenic and wild type plants (FIGS. 3A and 3B). Similarly, lignin in stem sections stained with toluidine blue O did not revealed any quantitative differences between genotypes (FIG. 3C). A few collapsed xylem structures were, however, occasionally observed on some stem cross-sections of line IRX5:HCHL (4), but were absent in sections from other lines (FIG. 3C). Overall, these data suggest that lignin content is not drastically reduced in IRX5:HCHL plants.

IRX5:HCHL Lines Accumulate $C_6C_1$ Soluble Phenolics

Methanol soluble fractions from stems of five-week-old wild type and IRX5:HCHL plants were extracted and analyzed by LC-MS. Analysis was performed to focus on hydroxybenzaldehydes, direct products of HCHL activity, and possible derivatives such as hydroxybenzoyl alcohols and hydroxybenzoic acids and their glucose conjugates. Trace amounts of 4-hydroxybenzaldehyde (HBAld), 3,4-dihydroxybenzaldehyde (3,4-DHBAld), and 4-hydroxybenzoic acid (HBA) were detected in IRX5:HCHL stem soluble extracts but not in wild type (Table III). Notably, much larger quantities of 4-hydroxybenzoic acid glucoside (HBAGlc) and 4-hydroxybenzoic acid glucose ester (HBAGE) were detected in IRX5:HCHL plant soluble extracts (ranging from 0.48 to 0.57 mg $g^{-1}$ FW for HBAGlc, and from 0.96 to 1.65 mg $g^{-1}$ FW for HBAGE), whereas trace amounts of these HBA-glucose conjugates were present in wild type extracts (Table III).

Considering that other soluble $C_6C_1$ phenolics could be glycosylated, acid hydrolysis of the soluble fractions was performed to release aglycones from conjugated forms. This procedure brought down HBAGE and HBAG pools to undetectable levels, and concomitantly increased free HBA content in samples (Table IV). IBA content in the IRX5:HCHL lines ranged between 1.59 and 2.49 mg $g^{-1}$ FW, which represents a 113 to 179 fold increase compared to values observed in wild type samples, and indicates that 88-94% of HBA accumulated in transgenic lines is glycosylated. In addition to HBA, other $C_6C_1$ phenolics quantified in acid-treated extracts include vanillin (Van), 5-hydroxyvanillin (5OH-Van), syringaldehyde (Syrald), 5-hydroxyvanillic acid (5OH-VA), and syringic acid (SyrA), which are only detected in IRX5:HCHL extracts, as well as HBAld, 3,4-DHBAld, 3,4-dihydroxybenzoic acid (3,4-DHBA), and vanillic acid (VA), which are on average 14, 119, 1.6, and 40 times more abundant in IRX5:HCHL extracts compared to wild type, respectively (Table IV).

IRX5:HCHL Lines Show Enrichment in Cell Wall-Bound $C_6C_1$ Phenolics

Extract-free cell wall residues (CWR) obtained from mature senesced stems of wild type and IRX5:HCHL plants were subjected to mild alkaline hydrolysis for the release of loosely-bound phenolics. This procedure released from the cell wall samples some HBAld, 3,4-HBAld, Van, 5011-Van, SyrAld, HBA, VA, and SyrA, which were quantified using LC-MS analysis. 5OH-Van, undetectable in wild type cell wall, was present in that of IRX5:HCHL samples and HBAld, SyrAld, HBA, VA, and SyrA were increased on average by approx 2, 6, 68, 2 and 5 fold in cell walls of IRX5:HCHL plants compared to the wild type, respectively (Table V). These results indicate that larger amounts of $C_6C_1$ phenolics are loosely-bound to cell walls in IRX5:HCHL plants. On the other hand, amount of ferulate and coumarate released from cell walls using this procedure did not differ between transgenic and wild type samples.

Spectral Analysis of IRX5:HCHL Plant Stems

Figure 4:
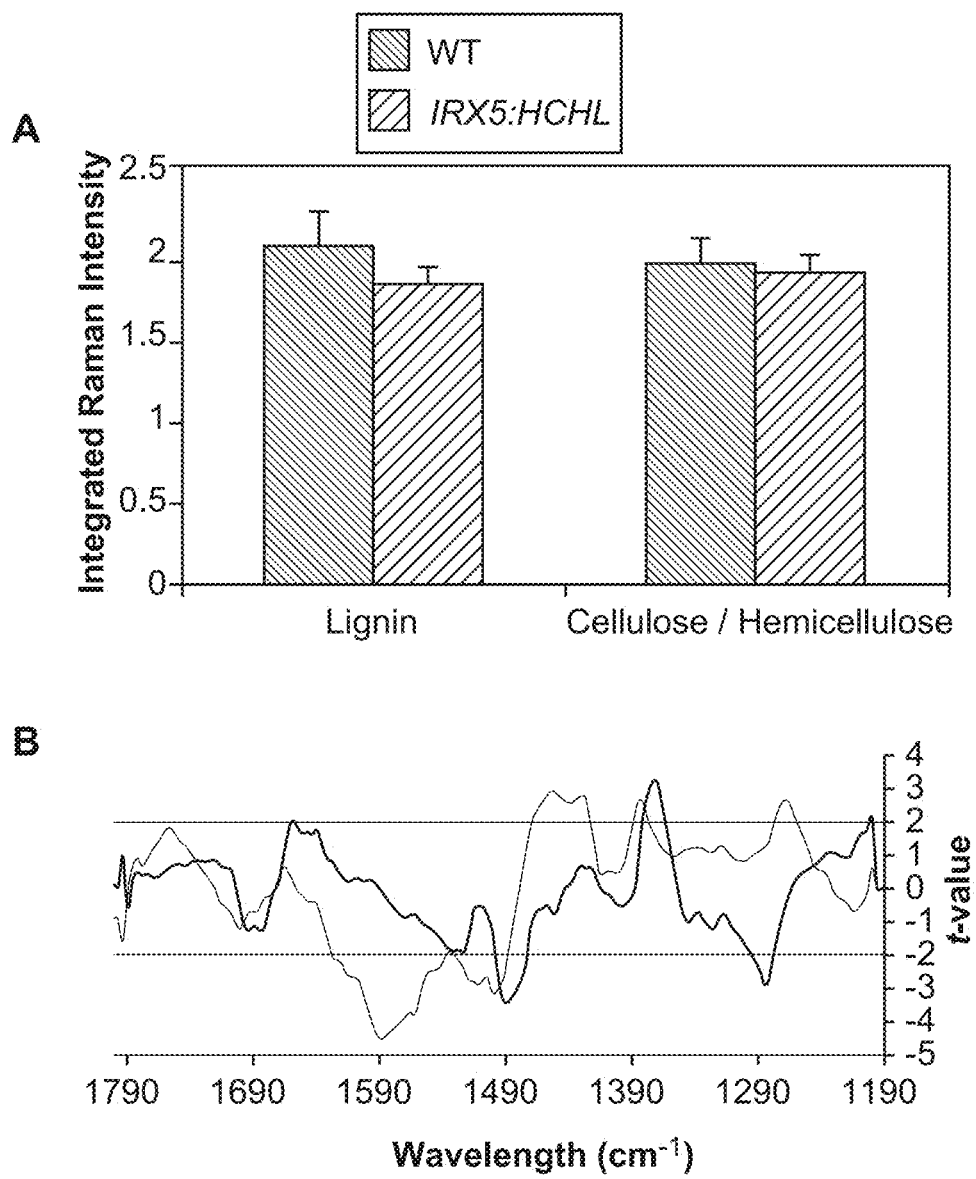
FIG. 4, Panels A and B. Spectral analysis of IRX5:HCHL and wild type plants. (Panel A) Lignin and polysaccharide content in CWR of mature senesced stems from wild type (WT) and line IRX5:HCHL (2) using FT-Raman spectroscopy. Values represent integrated intensities over the range of 1555-1690 cm$^{-1}$ and 1010-1178 cm$^{-1}$ for lignin and polysaccharides (cellulose/hemicellulose) quantification, respectively. Values are means of three biological replicates ±SE. (Panel B) Comparison of FT-IR spectra obtained from xylem (black line) and interfascicular fibers (grey line) in basal stem sections of wild type and line IRX5:HCHL (2). A Student's t-test was performed on absorbance values of wild type versus transgenic and plotted against wave numbers. At each wavelength, the zone between −2 and +2 corresponds to non-significant differences (p-value<0.05) between the two genotypes tested. Significant positive t-values indicated a higher absorbance value in wild type than in IRX5:HCHL plants.
Figure 5:
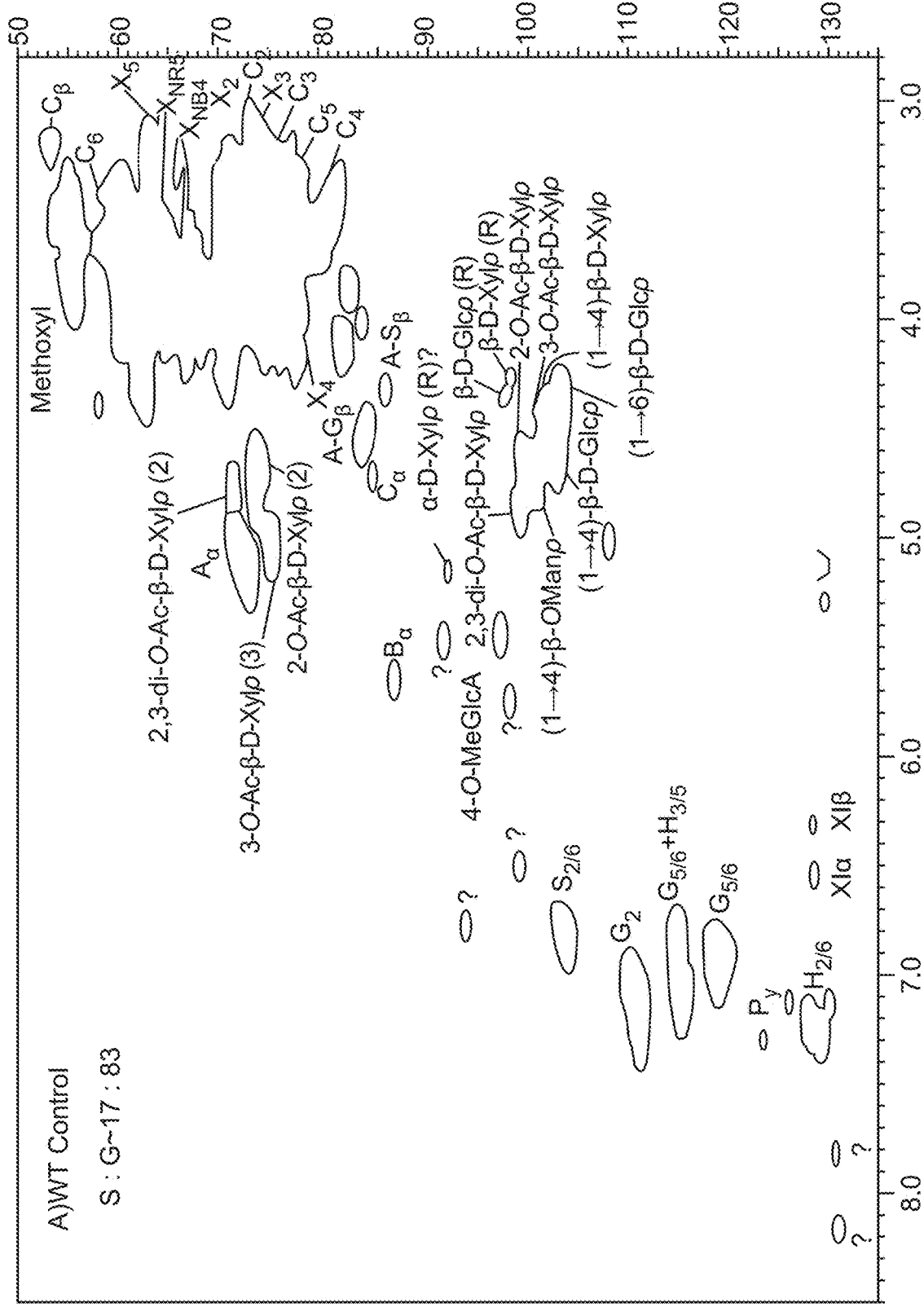
FIG. 5, Panels A and B. 2D-HSQC NMR spectra analysis of line IRX5:HCHL plants. 2D-HSQC NMR spectra of lignin from wild type (WT) stems (Panel A) and from IRX5:HCHL (FCA1) stems (Panel B); Difference spectrum (IRX5:HCHL (2)—wild type) showing the presence of new components in the aromatic region (C).
Figure 5:
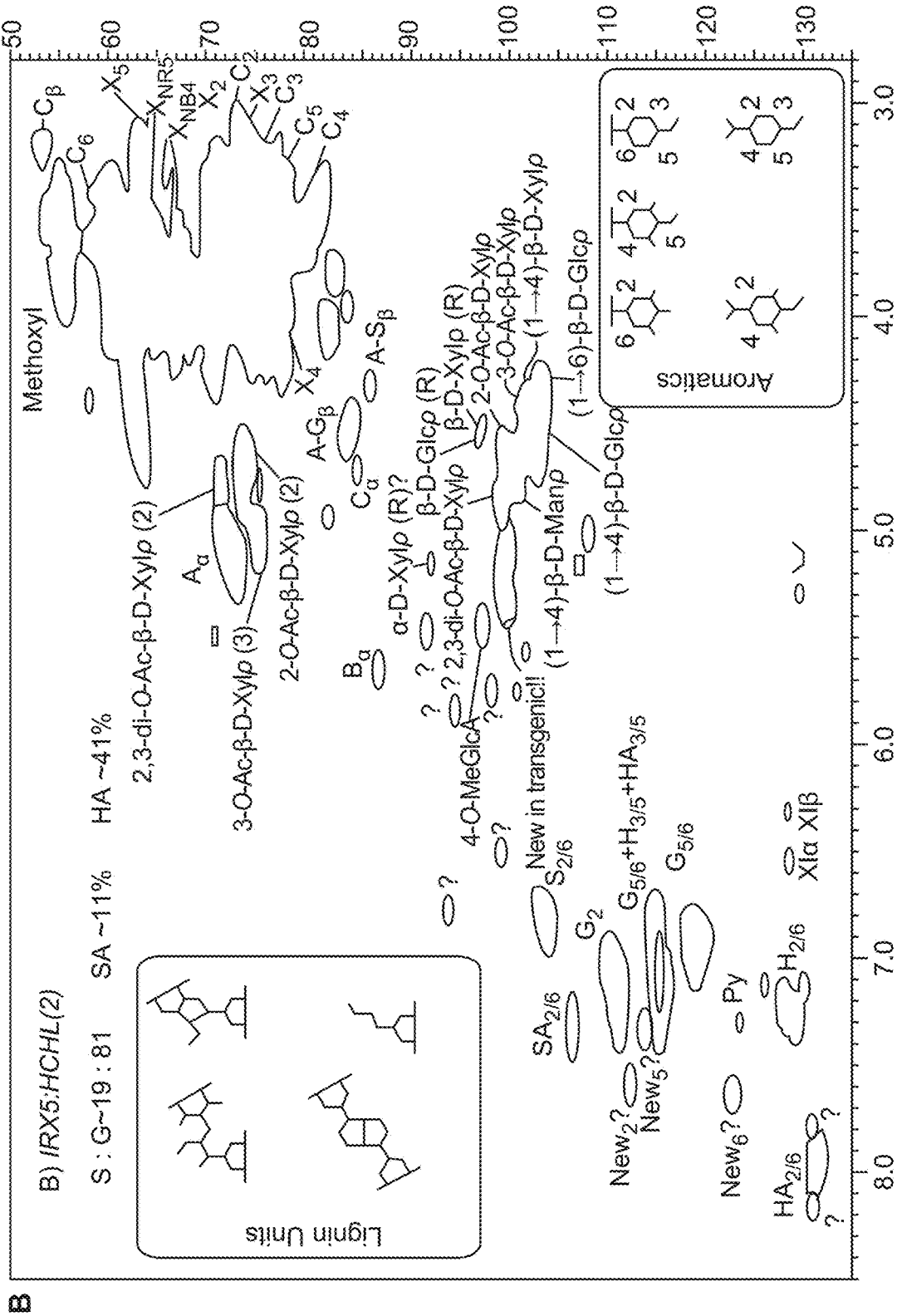

Line IRX5:HCHL (2), which showed no defective xylem structures and biomass yield similar to wild type plants, was selected for further analyses. Fourier transformed Raman (FT-Raman) spectroscopy was used to determine the chemical composition of CWR obtained from senesced stems of IRX5:HCHL plants. Compared to the wild type, data showed that lignin content and amount of polysaccharides (cellulose and hemicellulose) in IRX5:HCHL plants were not significantly different (FIG. 4A). Moreover, Fourier transformed infrared (FT-IR) spectral analysis conducted on lignified tissues (xylem and interfascicular fibers) of transverse stem sections of five-week-old IRX5:HCHL and wild type plants revealed differences between the two genotypes (FIG. 4B). In particular, significant changes in spectra were observed for bands assigned to different bending or stretching of lignin (Agarwal and Atalla, 2010, Fackler et al., 2010). For example, absorptions at wavelengths 1589 $cm^{-1}$ and 1506 $cm^{-1}$ (aryl ring stretching), 1464 $cm^{-1}$ (C—H group deformation), 1425 $cm^{-1}$ (methoxyl C—H group deformation), 1379 $cm^{-1}$ (aromatic skeletal vibrations combined with C—H group in plane deformation), and 1268 $cm^{-1}$ (aryl ring breathing with C=O group stretch) were modified in fibers, whereas the most significant difference for xylem cell walls was observed at band 1367 $cm^{-1}$ (methoxyl C—H group deformation). Overall, spectral analyses suggested compositional modifications of lignin in plants expressing HCHL.

Monosaccharide Content and Composition in IRX5:HCHL Plant Stems

Monosaccharide composition was determined after sulfuric acid hydrolysis of total cell wall polysaccharides from mature senesced stems of line IRX5:HCHL (2) and wild type plants. Although both genotypes had similar amount of total monosaccharides, IRX5:HCHL plants showed reduction in glucose (−12%) and increase in xylose (+22%) and arabinose (+16%) compared to wild type plants (Table VI). Moreover, hemicellulosic monosaccharides released from CWR using trifluoroacetic acid showed that total amount of sugar quantified in this hydrolysate was 23% higher in IRX5:HCHL stems which corresponds to higher xylose (+23%) and arabinose (+22%) contents compared to wild type (Table VI).

Incorporation of Unusual $C_6C_1$ Monomers into the Lignin of IRX5:HCHL Plants

Lignin content and monomeric composition in mature senesced stems from wild type and IRX5:HCHL (2) plants was determined on CWR. In two independent cultures, klason lignin (KL) was identical and accounted for about 20% of the CWR for both wild type and IRX5:HCHL plants (Table VII). Lignin monomer composition was evaluated by thioacidolysis, a chemical degradative method that generates thioethylated monomers from lignin units involved in labile β-O-4 bonds. Data showed that total amount of conventional H, G, and S monomers released from CWR after thioacidolysis (or total yield) was reduced by 25% and 16% in the two independent cultures of IRX5:HCHL plants compared to the wild type, indicating that fewer of these three monolignols are crosslinked as β-O-4 bond in transgenics (Table VII). Considering identical KL values for both wild type and IRX5:HCHL CWR, these data indicate higher frequency of thioacidolysis-resistant bonds between lignin monomers in transgenic plants. The relative amount of G and S units recovered from this lignin fraction was unchanged, both wild type and transgenic samples showing an S/G ratio ranging between 0.34-0.36, however, molar frequency of H units was significantly higher in IRX5:HCHL plants (Table VII). Furthermore, the content of non-conventional units such as Van, Syrald, and SyrA released by thioacidolysis showed on average a 1.44-, 20.8-, and 1.65-fold increase in IRX5:HCHL plants compared to wild type plants, respectively. Interestingly, two new lignin units were released from the lignin of transgenics plants, which were identified as $C_6C_1$ vanillyl alcohol (Vanalc) and syringyl alcohol (Syralc) (Table VIII). On the other hand, the content of coniferaldehyde end-groups (Cald) and VA was unchanged between the two genotypes (Table VIII). Overall, these data showed higher amount of $C_6C_1$ phenolic end-groups among monomers released by thioacidolysis from IRX5:HCHL stem cell walls compared to wild type.

Lignin of IRX5:HCHL Plants has Reduced Molecular Mass

Figure 6:
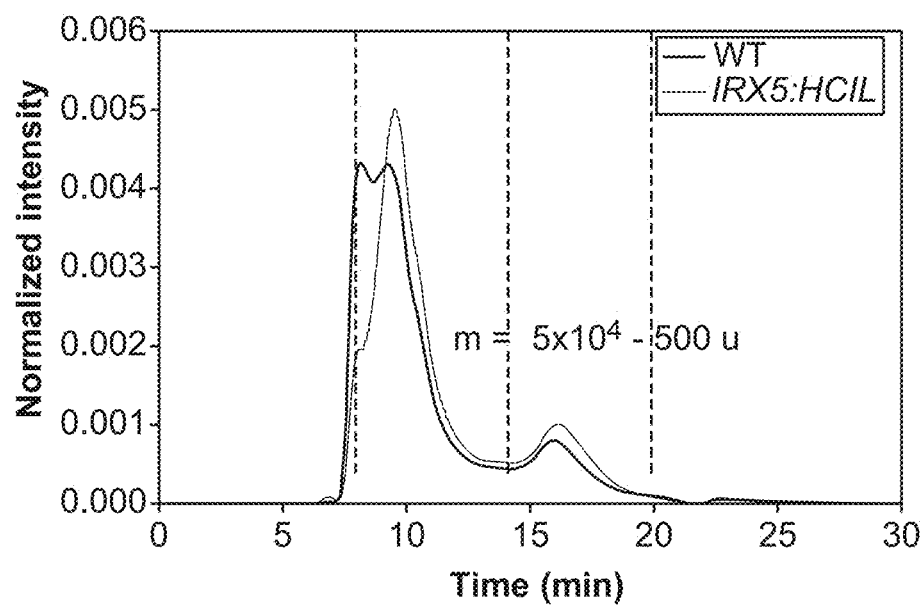
FIG. 6, panels A and B. Polydispersity profiles of CEL lignin purified from stems of wild type and line IRX:HCHL (2) plants. SEC chromatograms were obtained using (Panel A) UV-A$_{300}$ absorbance and (Panel B) UV-F$_{ex250/em450}$ fluorescence.
Figure 6:
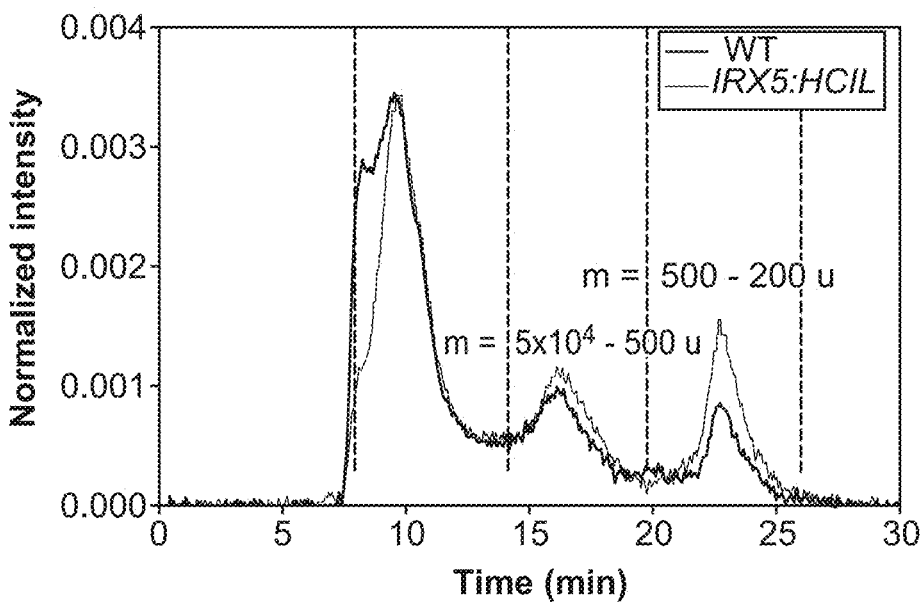

The polydispersity of cellulolytic lignin purified from wild type and IRX5:HCHL (2) stems was determined using size exclusion chromatography (SEC). Elution profiles acquired by monitoring UV-A absorbance (SEC UV-$A_{300}$) and UV-F fluorescence (SEC UV-$F_{ex}250/_{em}450$) of the dissolved lignin revealed differences between wild type and IRX5:HCHL plants (FIG. 6). First, total area corresponding to the largest mass peak detected between 7 min and 13.5 min was severely reduced in transgenics due to significant diminution of the largest lignin fragments which elute between 7 min and 9 min. Similarly, smaller molecular mass material which elutes later in a second peak between 13.5 min and 19.5 min was more abundant (increased by 27% and 16% using UV-A and UV-F detections) in IRX5:HCHL samples. Finally, the amount of the smallest lignin fragments detected between 19.5 min and 26.5 min using UV-F is increased by 55% in transgenics (FIG. 6). These results demonstrate smaller chains and reduced polymerization degree in lignin purified from IRX5:HCHL plants.

IRX5:HCHL Lines Show Increased Saccharification Efficiency

Figure 7:
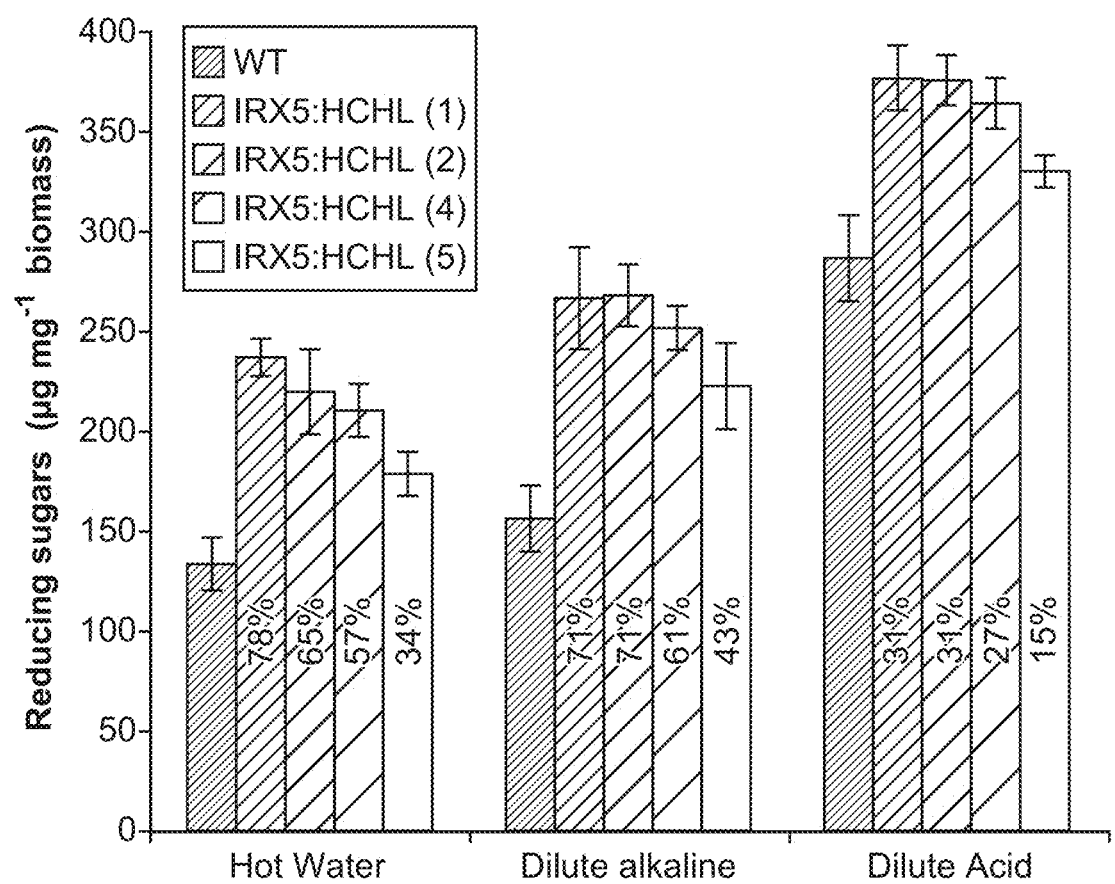
FIG. 7. Saccharification of biomass from mature senesced stems of IRX5:HCHL and wild type plants. Amount of reducing sugars released from 10 mg of biomass after hot water, dilute alkaline, or dilute acid pretreatment followed by 72-h enzymatic hydrolysis were measured using the DNS assay. Values are means of four biological replicates ±SE.
Figure 8B:
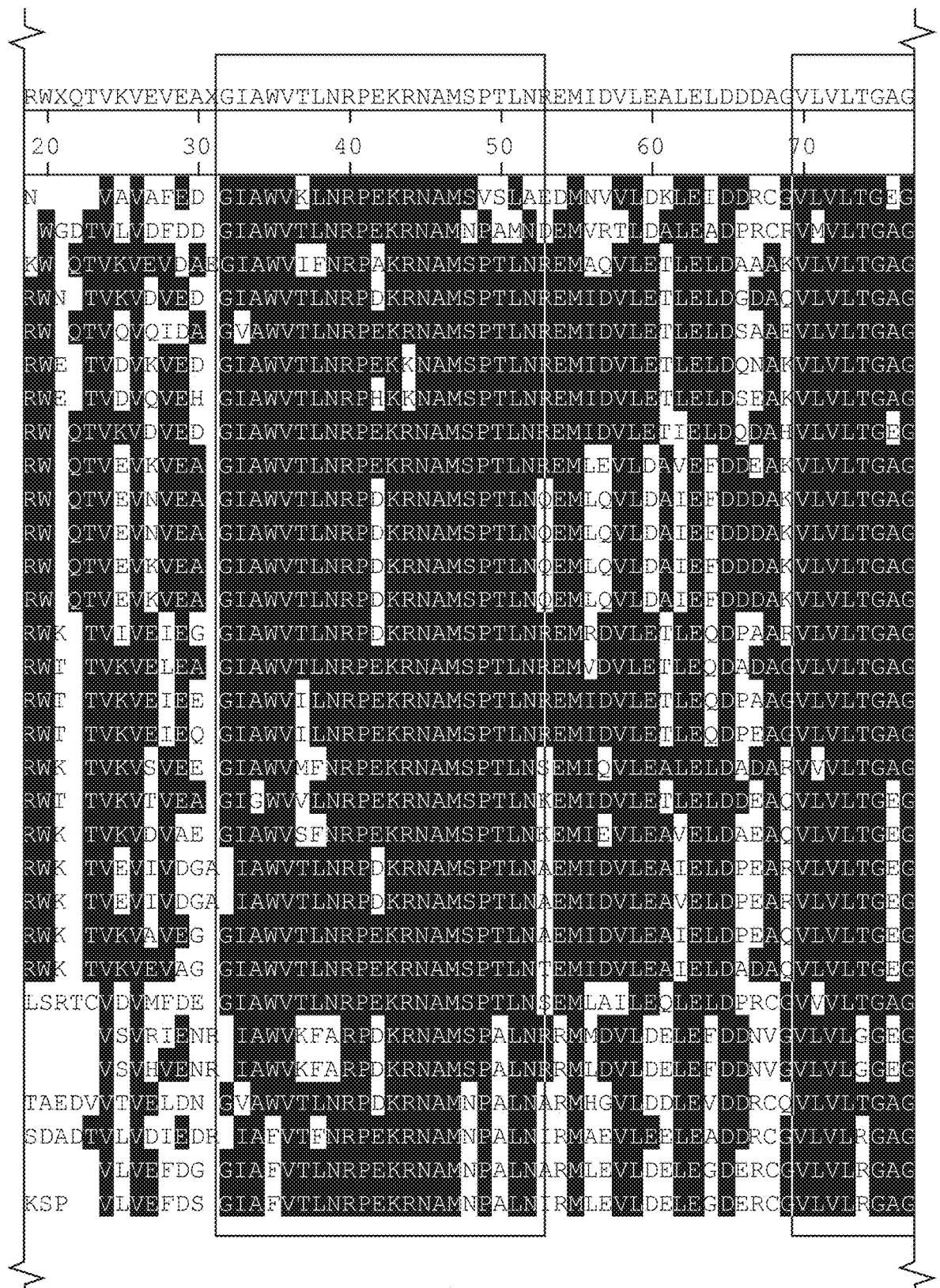
Figure 8C:
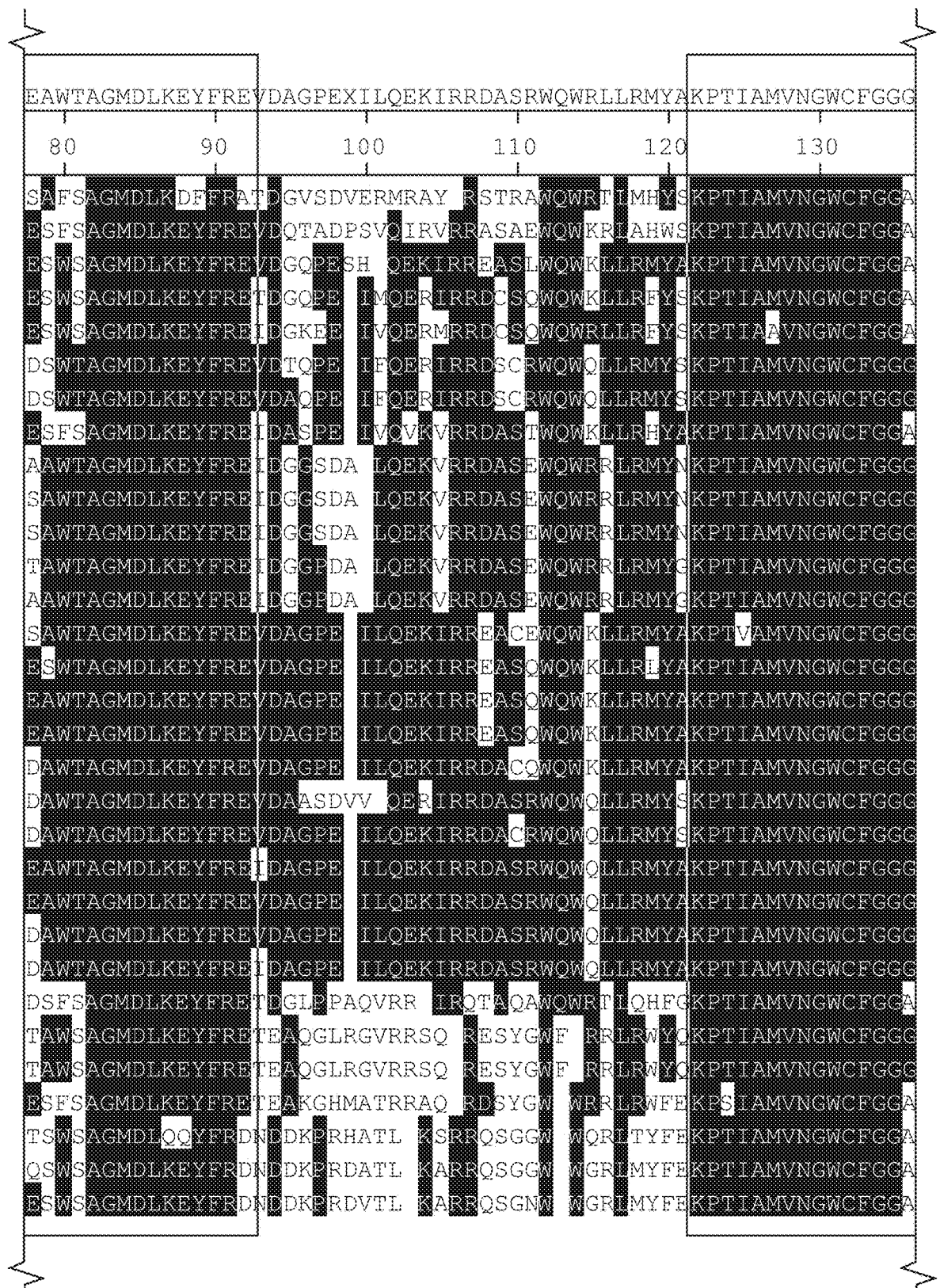
Figure 8E:
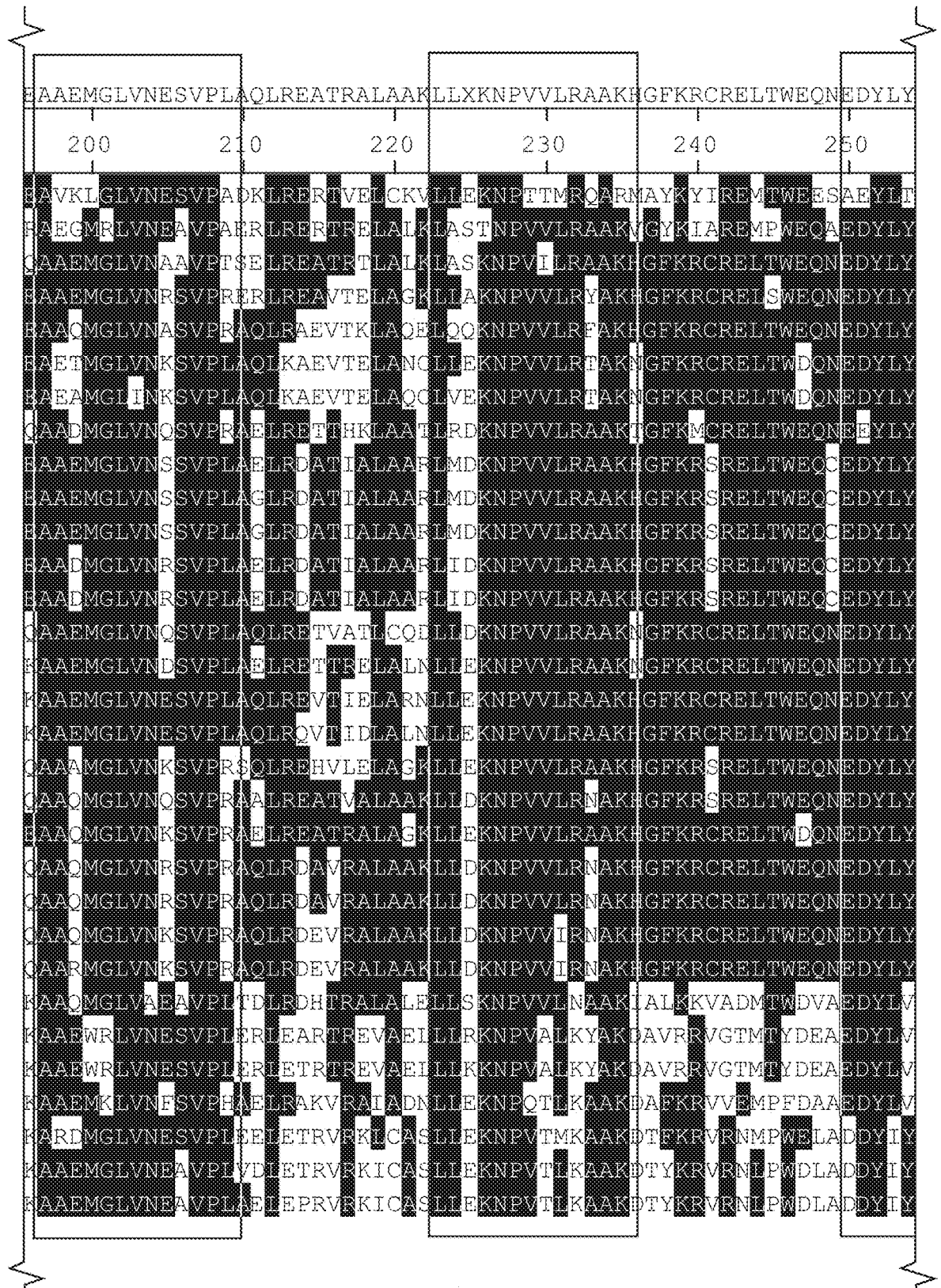

To examine impact lignin size reduction on cell wall digestibility caused by the expression of the HCHL enzyme in lignifying tissues, saccharification assays were conducted biomass derived from mature senesced stems pretreated with hot water, dilute alkaline, and dilute acid. After a 72-h incubation with cellulase and glucosidase, pretreated biomass of IRX5:HCHL plants released more reducing sugars compared to wild type (FIG. 7). In particular, improvement of saccharification efficiency observed for the different IRX5:HCHL lines ranged from 34% to 77% after hot water, from 43% to 71% after dilute alkaline, and from 15% to 31% after dilute acid pretreatments (FIG. 7).

III. Discussion

Expression of HCHL in plants has originally been considered for in-planta production of valuable and soluble compounds such as Van and HBA. Due to strong ectopic HCHL expression, however, adverse phenotypes such as chlorotic and senescing leaves, stunting, low pollen production, male sterility, collapsed xylem vessels, and reduction of biomass were observed in transgenic tobacco, and sugarcane (Mayer et al., 2001; Merali et al., 2007; McQualter et al., 2005). In this study, the inventors selected the promoter of a secondary cell wall cellulose synthase to preferentially express HCHL in the lignifying tissues of Arabidopsis stems (FIG. 9). Successfully, plants transformed with the IRX5: HCHL construct were not dwarf or sterile, and young rosette leaves did not show reduced epidermal fluorescence which is symptomatic of alteration in phenylpropanoid-derived soluble phenolic pools. Although two IRX5:HCHL lines showed reduced biomass, and in one case some occasional collapsed xylem vessels caused by stronger HCHL activity and possibly modification of call wall integrity, some other IRX5:HCHL lines were comparable to wild-type plants.

Figure 11:
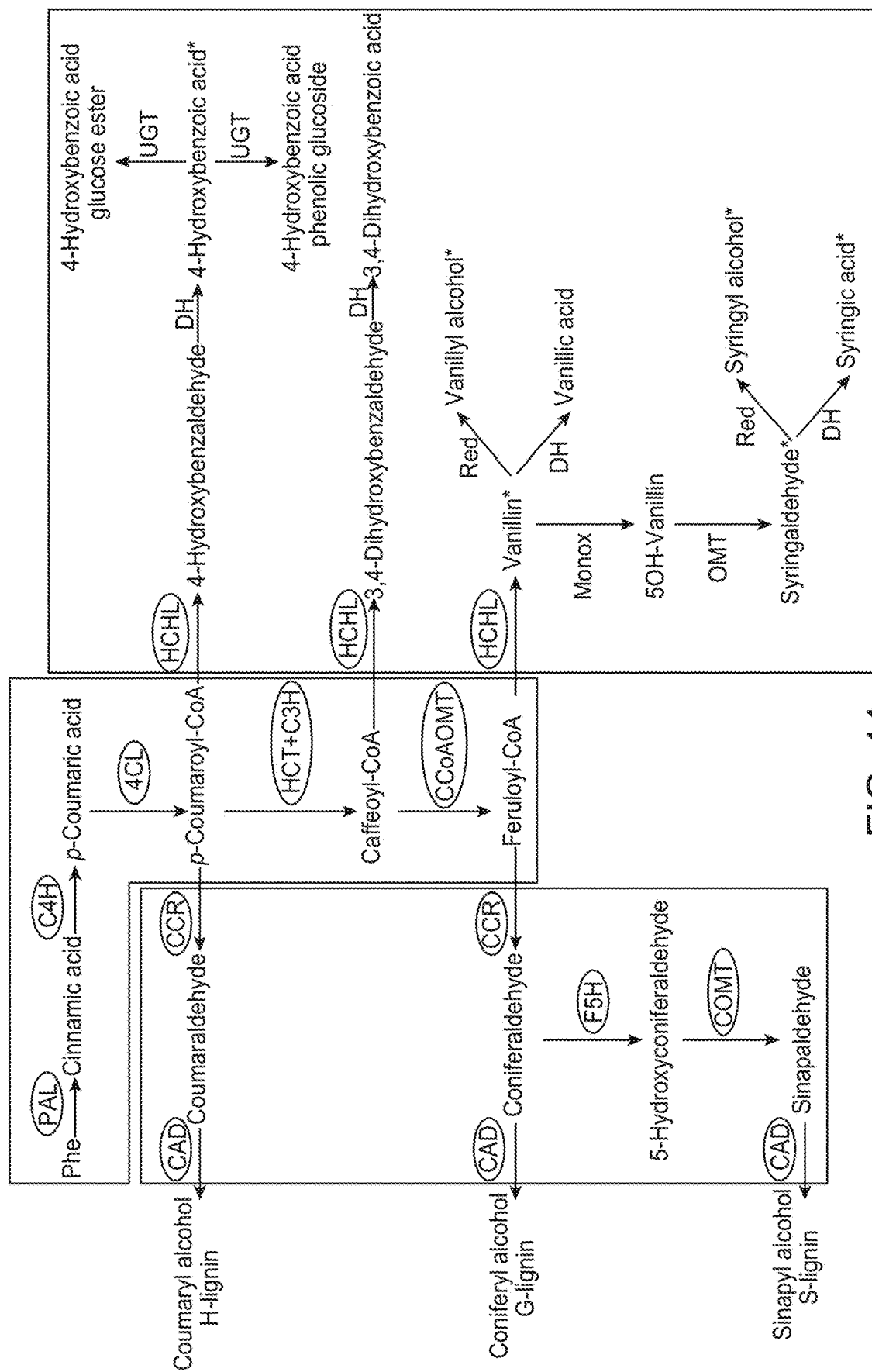
FIG. 11. Synthesis of $C_6C_1$ phenolics production upon HCHL activity and probable associated enzymes. The phenylpropanoid pathway (center box) and monolignol pathway (left box) are represented. HCHL converts hydroxycinnamoyl-CoAs into their corresponding hydroxybenzaldehydes. Metabolomic data showed occurrence of hydroxycinnamic acids and alcohols, suggesting involvement of aldehyde dehydrogenases (DH) and reductases (left box). UDP-glucosyltransferases (UGT) are responsible for the formation of C6-C1 phenolic glucose conjugates. Syringaldehyde is possibly derived from vanillin and 5OH-vanillin after successive monooxyenase (Monox) and O-methyltransferase activities (OMT). Asterisks indicate compounds found in higher amount in lignin of *Arabidopsis* expressing HCHL. Abbreviations for enzymes are: PAL, phenylalanine ammonia lyase; C4H, cinnamate 4-hydroxylase; 4CL, 4-coumarate-CoA ligase; CCR, hydroxycinnamoyl-CoA reductase; CAD, coniferyl alcohol dehydrogenase; HCT, p-hydroxycinnamoyl-CoA:quinate shikimate p-hydroxycinnamoyl-CoA transferase; C3H, p-coumarate 3-hydroxylase; CCoAOMT, caffeoyl-CoA O-methyltransferase; F5H, ferulate 5-hydroxylase (coniferaldehyde 5-hydroxylase); COMT, caffeic acid/5-hydroxyferulic acid O-methyltransferase.

As expected, the transgenic lines show increased amount of soluble $C_6C_1$ aldehydes (HBAld, 3,4-DHBAld, and Van), which are produced upon HCHL activity after cleavage of hydroxybenzoyl-CoA, 3,4-dihydroxybenzoyl-CoA, and feruloyl-CoA (FIG. 11). HCHL has no activity against sinapoyl-CoA, suggesting that Syrald is a conversion product of Van, which is supported by the identification of the new intermediate 5OH-Van (Mitra et al., 1999; FIG. 11). Similarly, the data presented herein cannot exclude that some of the 3,4-DHBald and Van accumulated in transgenics derive from HBAld after successive hydroxylation and methoxylation on the C-3 position of the phenyl ring. Interestingly, several genes encoding monooxygenases are upregulated in plants expressing HCHL, but no known or predicted O-methyltransferase showed altered expression level (Table IX). Analysis of soluble aromatics in transgenics also shows that $C_6$-$C_1$ aldehydes are oxidized into their respective acid forms. This conversion could be a response to reduce the amount of these chemically reactive compounds since several genes from the short-chain dehydrogenase/reductase (SDR), aldo-keto reductase (AKR), and aldehyde dehydrogenase (ALDH) families are upregulated in plants expressing HCHL, (FIG. 11; Kirch et al., 2004; Kavanagh et al., 2008). In particular, AKR4C9 (At3g37770) encodes an enzyme known to metabolize a range of hydroxybenzaldehydes (Simpson et al., 2009). In addition, soluble $C_6C_1$ phenolics predominantly accumulate as conjugates in transgenics since we showed that glucose conjugates (phenolic glucoside and glucose ester) represented around 90% of the HBA soluble pool, presumably for vacuolar storage as previously described for other $C_6C_1$ phenolics (Eudes et al., 2008). This $C_6C_1$ acid glucoside accumulation is in agreement with what was observed in tobacco, sugar beet, Datura and sugar cane plants expressing HCHL (Mayer et al., 2001; Mitra et al., 2002; McQualter et al., 2005; Rahman et al., 2009). Interestingly, expression analysis of HCHL plants revealed seven up-regulated genes of the UDP-glucosyltranferase (UGT) family and among them UGT75B1 and UGT73B4 were previously shown to catalyze glucose esterification and phenolic glucosylation of benzoates (Table IX; Lim et al, 2002; Eudes et al., 2008).

Furthermore, this study showed that some $C_6C_1$ phenolics are released from extract-free cell wall fractions of senesced stems upon mild alkaline hydrolysis. Higher amounts of HBAld, 5OH-Van, SyrAld, HBA, VA, and SyrA were measured in the 'loosely wall-bound' fraction of IRX5:HCHL lines compared to wild type. Although the type of linkages involved is unclear, loosely attached $C_6C_1$ phenolics were previously extracted from cell walls of Arabidopsis leaves and roots (Tan et al., 2004; Forcat et al., 2010).

The lignin from plants expressing HCHL shows increased content of $C_6C_1$ phenolics. Notably, analysis of lignin monomers released after thioacidolysis identified two novel units (Vanalc and Syralc) and showed large amounts of Syrald, Van, and SyrA. This suggests part of $C_6C_1$ aldehydes are converted into alcohols and acids and demonstrates that they are incorporated into the lignin as β-O-4-linked $C_6C_1$ monomer end-groups in lignin (FIG. 11). Due to the absence of phenyl propanoid tail, these new monolignols when incorporated in lignin end chains, should block further polymerization of the polymer and act as condensation terminator or stopper molecules. Interestingly, transgenic plants also show higher content of conventional H-units (+30%), which preferentially distribute as terminal end-groups in lignin and contribute to modifications of lignin size and structure (Lapierre, 2010; Ziebell et al., 2010). In addition, plants overproducing $C_6C_1$ monolignols and with similar lignin content as wild type plants show a lower thioacidolysis release of monolignols, indicating a reduction in the availability of free propanoid tail in lignin end-chain for polymer elongation. It also indicates higher carbon-carbon linkages and increased lignin condensation degree.

It was postulated that higher incorporation of end-group units in lignin would hinder more frequently chain elongation and ultimately reduce lignin branching and polymerization degree. This hypothesis is further supported by the analysis the polydispersity of lignin in plants overproducing theses "stopper" molecules, which shows significant reduction of high molecular masses and significant increase of low molecular masses, hence supporting smaller lignin chain length. These observations are relevant for understanding the higher susceptibility of the biomass from HCHL lines to polysaccharide enzymatic hydrolysis. Although saccharification efficiency of biomass is determined by several characteristics of cell walls, the observed saccharification efficiency improvement after different pretreatments suggests that less ramified lignin would reduce cross-linkages and embedding of cell wall polysaccharides (cellulose and hemicellulose) and would favor their accessibility to hydrolytic enzymes. This hypothesis is supported by the fact that total sugar content is unchanged in cell walls of plants overproducing theses $C_6C_1$ monomers.

it is concluded that in-planta the over-production of lignification "stopper" molecules can be used to modify the lignin structure in order to reduce lignocellulosic biomass recalcitrance. Since this approach does not require any particular genetic background, it should be easily transferable to various energy crops. Restricting the biosynthesis of these lignification "stopper" molecules in supporting lignified tissues (i.e. schlerenchyma fibers) as well as avoiding strong production in conductive tissues (i.e. vessels) should limit the risk of adverse effects on plant development and biomass yield.

Example 2: Expression of Bacterial HCHL in Rice

Figure 12:
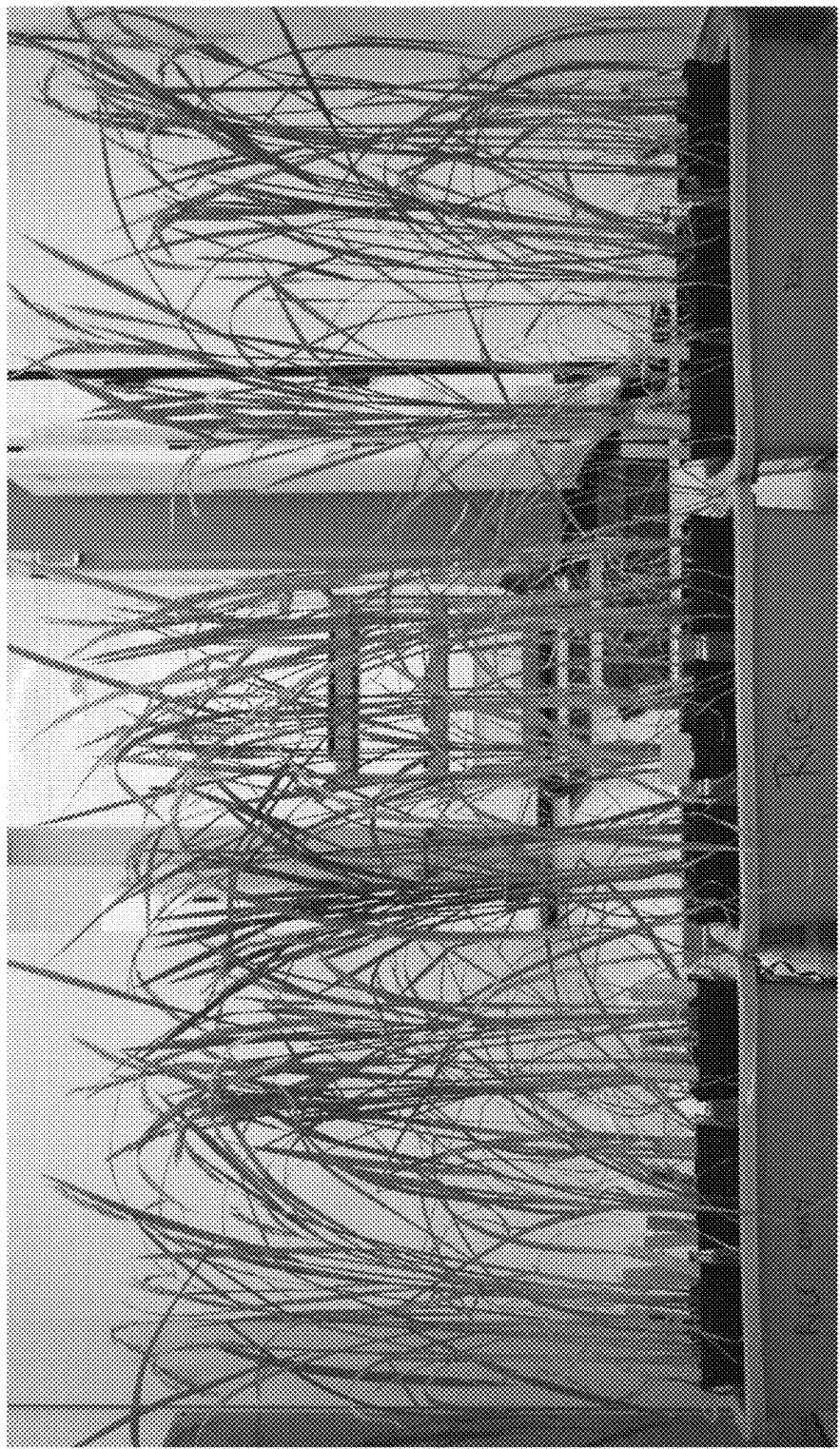
FIG. 12. Transgenic rice lines that express pAtIRX5:: HCHL.
Figure 13:
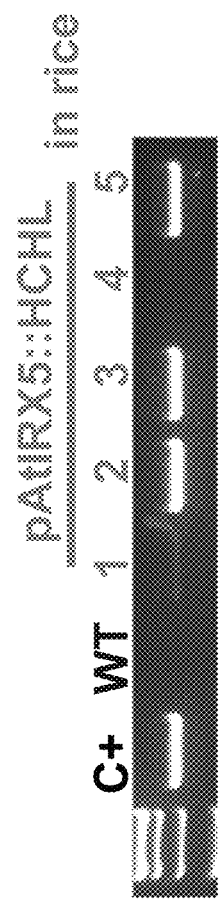
FIG. 13. Expression analysis of HCHL in the engineered rice lines. Results of an RT-PCR using RNA extracted from rice plants and HCHL-specific primers.
Figure 14:
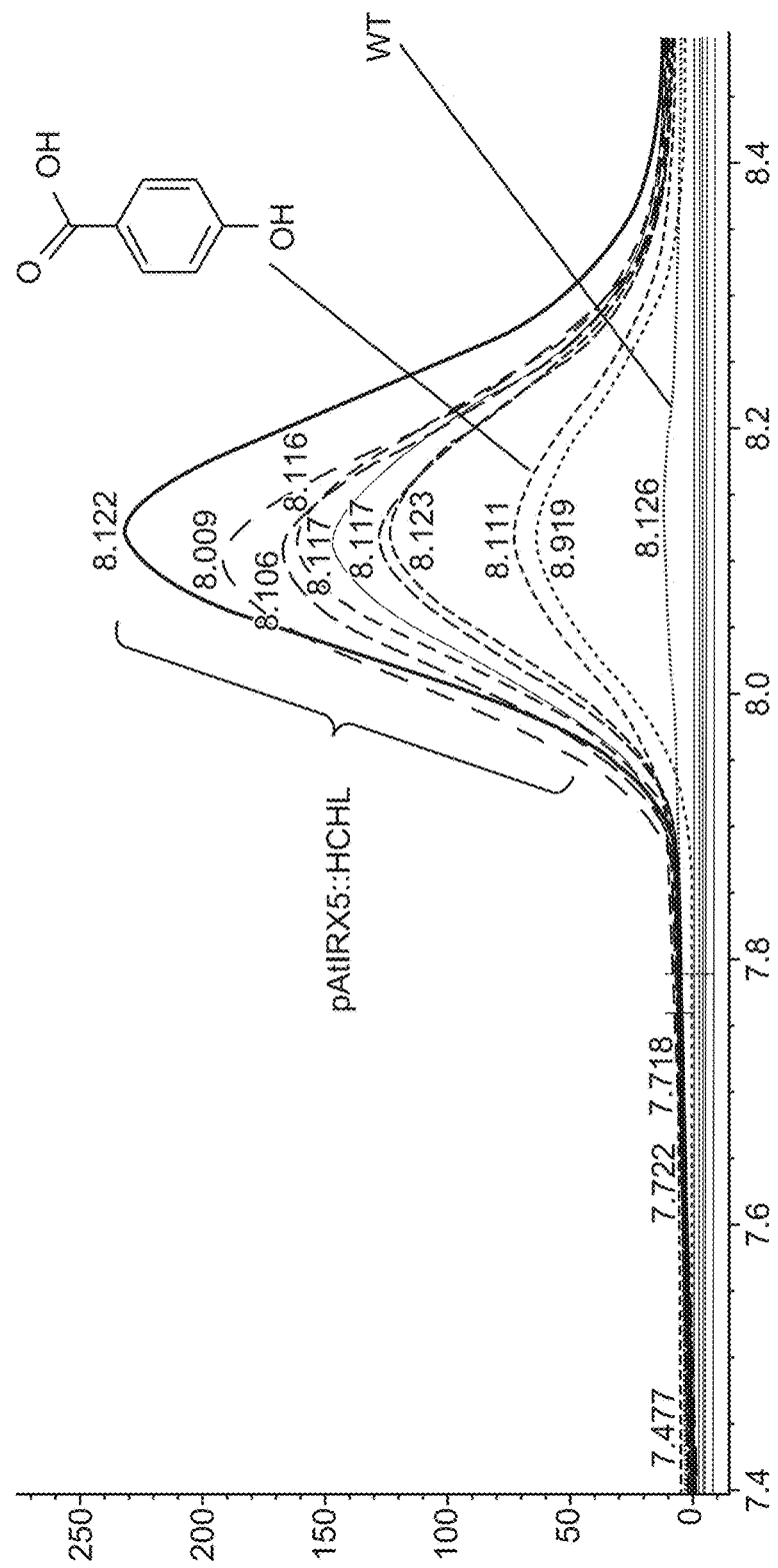
FIG. 14. Detection of pHBA in stems from the engineered rice lines.

This example illustrates expression of bacterial HCHL in a monocot, rice. Rice plants were transformed with the DNA constructs described in Example 1. Rice lines were engineered (FIG. 12) that expressed the HCHL gene, as demonstrated by RT-PCR (FIG. 13). Furthermore, evaluation of rice lines demonstrated that they accumulated pHBA (para-hydroxybenzoate) (FIG. 14), which is generated from the conversion of p-coumaroyl-CoA by HCHL.

This experiment additionally demonstrated that a secondary wall promoter, pIRX5, from a dicot (*Arabidopsis* in this example), can be used in a monocot (rice in this example).

It is understood that the examples and embodiments described herein are for illustrative purposes only and that various modifications or changes in light thereof will be suggested to persons skilled in the art and are to be included within the spirit and purview of this application and scope of the appended claims. All publications, patents, accession numbers, and patent applications cited herein are hereby incorporated by reference in their entirety for all purposes.

LIST OF REFERENCES

Agarwal U P and Aralla R H (2010) Vibrational spectroscopy. In C Heitner, D Dimmel, J Schmidt eds. Lignin and Lignans: Advances in Chemistry. CRC Press, Boca Raton, pp 103-136

Bechtold N, Pelletier G (1998) In planta *Agrobacterium*-mediated transformation of adult *Arabidopsis thaliana* plants by vacuum infiltration. Methods Mol Biol 82: 259-266

Berthet et al. Disruption of LACCASE4 and 17 results in tissue-specific alterations to lignification of *Arabidopsis thaliana* stems. The Plant cell (2011) vol. 23 (3) pp. 1124-37

Boerjan W, Ralph J, Baucher M (2003) Lignin biosynthesis. Annu Rev Plant Biol 54: 519-546

Bonawitz N D, Chapple C (2010) The genetics of lignin biosynthesis: connecting genotype to phenotype. Annu Rev Genet 44: 337-363

Boudet A M (2007) Evolution and current status of research in phenolic compounds. Phytochemistry 68: 2722-2735

Bradford M M (1976) A rapid and sensitive method for the quantitation of microgram quantities of protein utilizing the principle of protein-dye binding. Anal Biochem 72: 248-254

Brown et al. Identification of novel genes in *Arabidopsis* involved in secondary cell wall formation using expression profiling and reverse genetics. Plant Cell (2005) vol. 17 (8) pp. 2281-95

Brown et al. Characterization of IRX10 and IRX10-like reveals an essential role in glucuronoxylan biosynthesis in *Arabidopsis*. Plant J (2009) vol. 57 (4) pp. 732-46

Buer C S, Imin N, Djordjevic M A (2010) Flavonoids: new roles for old molecules. J Integr Plant Biol 52: 98-111

Carroll A, Somerville C (2009) Cellulosic biofuels. Annu Rev Plant Biol 60: 165-182

Chen et al. Disruption of the cellulose synthase gene, AtCesA8/IRX1, enhances drought and osmotic stress tolerance in *Arabidopsis*. Plant J (2005) vol. 43 (2) pp. 273-83

Chen F, Dixon R A (2007) Lignin modification improves fermentable sugar yields for biofuel production. Nat Biotechnol 25: 759-761

Crowe M L, Serizet C, Thareau V, Aubourg S, Rouze P, Hilson P, Beynon J, Weisbeek P, van Hummelen P, Reymond P, Paz-Ares J, Nietfeld W, Trick M (2003) CATMA: a complete *Arabidopsis* GST database. Nucleic Acids Res 31: 156-158

Deuce C (1992) Lignin determination. In C Dence, S Lin, eds, Methods in Lignin Chemistry. Springer-Verlag, Berlin, pp 33-61 de Vrije T, de Haas G G, Tan G B, Keijsers E R, Claassen P A (2002) Pretreatment of *Miscanthus* for hydrogen production by *Thermotoga elfii*. Int J Hydrogen Energy 27: 1381-1390

Dien B S, Jung H-J G, Vogel K P, Casler M D, Lamb J F S, Iten L, Mitchell R B, Sarath G (2006) Chemical composition and response to dilute-acid pretreatment and enzymatic saccharification of alfalfa, reed canarygrass, and switchgrass. Biomass Bioenergy 30: 880-891

Dien B S, Sarath G, Pedersen J F, Satler S E, Chen H, Funnell-Harris D L, Nichols N N, Cotta M A (2009) Improved sugar conversion and ethanol yield for forage sorghum (*Sorghum bicolor* (L.) Moench) lines with reduced lignin contents. Bioenerg Res 2: 153-164

Dien B S, Miller D J, Hector R E, Dixon R A, Chen F, McCaslin M, Reisen P, Sarath G, Cotta M A (2011) Enhancing alfalfa conversion efficiencies for sugar recovery and ethanol production by altering lignin composition. Bioresour Technol 102: 6479-6486

Elissetche J P, Valenzuela S, García R, Norambuena M, Iturra C, Rodríguez J, Teixeira Mendonça R, Balocchi C (2011) Transcript abundance of enzymes involved in lignin biosynthesis of *Eucalyptus globulus* genotypes with contrasting levels of pulp yield and wood density. Tree Genet Gen DOI: 10.1007/s 11295-011-0367-5

Eudes A, Pollet B, Sibout R, Do C T, Séguin A, Laplerre C, Jouanin L (2006) Evidence for a role of AtCAD 1 in lignification of elongating stems of *Arabidopsis thaliana*. Planta 225: 23-39

Eudes A, Baidoo E E, Yang F, Burd H, Hadi M Z, Collins F W, Keasling J D, Loqué D (2011) Production of tranilast [N-(3',4'-dimethoxycinnamoyl)-anthranilic acid] and its analogs in yeast *Saccharomyces cerevisiae*. Appl Microbiol Biotechnol 89: 989-1000

Eudes A, Bozzo G G, Waller J C, Naponelli V, Lim E K, Bowles D J, Gregory J F 3rd, Hanson A D (2008) Metabolism of the folate precursor p-aminobenzoate in plants: glucose ester formation and vacuolar storage. J Biol Chem 283: 15451-15459

Fackler K, Stevanic J S, Ters T, Hinterstoisser B, Schwanninger M, Salmén L (2010) Localisation and characterisation of incipient brown-rot decay within spruce wood cell walls using FT-IR imaging microscopy. Enzyme Microb Technol 47: 257-267

Forcat S, Bennett M, Grant M, Mansfield J W (2010) Rapid linkage of indole carboxylic acid to the plant cell wall identified as a component of basal defence in *Arabidopsis* against hrp mutant bacteria. Phytochemistry 71: 870-876

Franke et al. The *Arabidopsis* REF8 gene encodes the 3-hydroxylase of phenylpropanoid metabolism. Plant J (2002) vol. 30 (1) pp. 33-45

Fu C, Mielenz J R, Xiao X, Ge Y, Hamilton C Y, Rodriguez M Jr, Chen F, Foston M, Ragauskas A, Bouton J, Dixon R A, Wang Z Y (2011) Genetic manipulation of lignin reduces recalcitrance and improves ethanol production from switchgrass. Proc Natl Acad Sci USA 108: 3803-3808

Gagnot S, Tamby J P, Martin-Magniette M L, Bitton F, Taconnat L, Balzergue S, Aubourg S, Renou J-P, Lecharny A, Brunaud V (2008) CATdb: a public access to *Arabidopsis* transcriptome data from the URGV-CATMA platform. Nucleic Acids Res 36 (database issue): D986-990

Gallego-Giraldo L, Jikumaru Y, Kamiya Y, Tang Y, Dixon R A (2011) Selective lignin downregulation leads to constitutive defense response expression in alfalfa (*Medicago sativa* L.). New Phytol 190: 627-639

Gasson M J, Kitamura Y, McLauchlan W R, Narbad A, Parr A J, Parsons E L, Payne J, Rhodes M J, Walton N J (1998) Metabolism of ferulic acid to vanillin. A bacterial gene of the enoyl-SCoA hydratase/isomerase superfamily encodes an enzyme for the hydration and cleavage of a hydroxycinnamic acid SCoA thioester. J Biol Chem 273: 4163-4170

Ge Y C, Dudoit S, Speed T P (2003) Resampling-based multiple testing for microarray data analysis. Test 12: 1-77

George A, Tran K, Morgan T J, Benke P I, Berrueco C, Lorente E, Wu B C, Simmons B A and Holmes B M (2011) The effect of ionic liquid cation and anion combinations on the macromolecular structure of lignins. Green Chemistry. (Submitted)

Gou J Y, Yu X H, Liu C J (2009) A hydroxycinnamoyltransferase responsible for synthesizing suberin aromatics in *Arabidopsis*. Proc Natl Acad Sci USA 106: 18855-18860

Grabber J H, Hatfield R D, Lu F, Ralph J (2008) Coniferyl ferulate incorporation into lignin enhances the alkaline delignification and enzymatic degradation of cell walls. Biomacromolecules 9: 2510-2516

Ha et al. Structure of cellulose-deficient secondary cell walls from the irx3 mutant of *Arabidopsis thaliana*. Phytochemistry (2002) vol. 61 (1) pp. 7-14

Hajdukiewicz P, Svab Z, Maliga P (1994) The small, versatile pPZP family of *Agrobacterium* binary vectors for plant transformation. Plant Mol Biol 25: 989-994

Hilson P, Allemeersch J, Altmann T, Aubourg S, Avon A, Beynon J, Bhalerao R P, Bitton F, Caboche M, Cannoot B, Chardakov V, Cognet-Holliger C, Colot V, Crowe M, Darimont C, Durinck S, Eickhoff H, de Longevialle A F, Farmer E E, Grant M, Kuiper M T, Lehrach H, Leon C, Leyva A, Lundeberg J, Lurin C, Moreau Y, Nietfeld W, Paz-Ares J, Reymond P, Rouze P, Sandberg G, Segura M D, Serizet C, Tabrett A, Taconnat L, Thareau V, Van Hummelen P, Vercruysse S, Vuylsteke M, Weingartner M, Weisbeek P J, Wirta V, Wittink F R, Zabeau M, Small I (2004) Versatile gene-specific sequence tags for *Arabidopsis* functional genomics: transcript profiling and reverse genetics applications. Genome Res 14: 2176-2189

Jones et al. Cloning and characterization of irregular xylem4 (irx4): a severely lignin-deficient mutant of *Arabidopsis*. Plant J (2001) vol. 26 (2) pp. 205-16

Kavanagh K L, Jörnvall H, Persson B, Oppermann U (2008) Medium- and short-chain dehydrogenase/reductase gene and protein families: the SDR superfamily: functional and structural diversity within a family of metabolic and regulatory enzymes. Cell Mol Life Sci 65: 3895-3906

Keasling J D (2010) Manufacturing molecules through metabolic engineering. Science 330: 1355-1358

Kim H, Ralph J, Yahiaoui N, Pean M, Boudet A M (2000) Cross-coupling of hydroxycinnamyl aldehydes into lignins. Org Lett 2: 2197-2200

Kim H, Ralph J, Lu F, Ralph S A, Boudet A M, MacKay J J, Sederoff R R, Ito T, Kawai S, Ohashi H, Higuchi T (2003) NMR analysis of lignins in CAD-deficient plants. Part 1. Incorporation of hydroxycinnamaldehydes and hydroxybenzaldehydes into lignins. Org Biomol Chem 1: 268-281

Kim H, Ralph J (2010) Solution-state 2D NMR of ball-milled plant cell wall gels in DMSO-d(6)/pyridine-d(5). Org Biomol Chem 8: 576-591

Kirch H H, Bartels D, Wei Y, Schnable P S, Wood A J (2004) The ALDH gene superfamily of *Arabidopsis*. Trends Plant Sci 9: 371-377

Ko et al. Ectopic expression of MYB46 identifies transcriptional regulatory genes involved in secondary wall biosynthesis in *Arabidopsis*. The Plant journal: for cell and molecular biology (2009) vol. 60 (4) pp. 649-65

Lalonde S, Sero A, Pratelli R, Pilot G, Chen J, Sardi M I, Parsa S A, Kim D Y, Acharya B R, Stein E V, Hu H C, Villiers F, Takeda K, Yang, Y, Han Y S, Schwacke R, Chiang W, Kato N, Loqué D, Assmann S M, Kwak J M, Schroeder J, Rhee S Y and Frommer W B (2010) A membrane protein/signaling protein interaction network for *Arabidopsis* version AMPv2, Frontiers in Plant Physiology doi: 10.3389/fphys.2010.00024

Lapierre C, Pollet B, Rolando R (1995) New insights into the molecular architecture of hardwood lignins by chemical degradation methods. Res Chem Intermed 21: 397-412

Lapierre C, Pollet B, Petit-Conil M, Toval G, Romero J, Pilate G, Leple J C, Boerjan W, Ferret V V, De Nadai V, Jouanin L (1999) Structural alterations of lignins in transgenic poplars with depressed cinnamyl alcohol dehydrogenase or caffeic acid O-methyltransferase activity have an opposite impact on the efficiency of industrial kraft pulping. Plant Physiol 119: 153-164

Lapierre C (2010) Determining [sic] lignin structure by chemical degradations. In C Heitner, D Dimmel, J Schmidt eds. Lignin and Lignans: Advances in Chemistry. CRC Press, Boca Raton, pp 11-48

Lim E K, Doucet C J, Li Y, Elias L, Worrall D, Spencer S P, Ross J, Bowles D J (2002) The activity of *Arabidopsis* glycosyltransferases toward salicylic acid, 4-hydroxybenzoic acid, and other benzoates. J Biol Chem 277: 586-592

Li X, Weng J K, Chapple C (2008) Improvement of biomass through lignin modification. Plant J 54: 569-581

Luo J, Fuell C, Parr A, Hill L, Bailey P, Elliott K, Fairhurst S A, Martin C, Michael A J (2009) A novel polyamine acyltransferase responsible for the accumulation of spermidine conjugates in *Arabidopsis* seed. Plant Cell 21: 318-333.

Lurin C, Andres C, Aubourg S, Bellaoui M, Bitton F, Bruyere C, Caboche M, Debast C, Gualberto J, Hoffmann B, Lecharny A, Le Ret M, Martin-Magniette M L, Mireau H, Peeters N, Renou J P, Szurek B, Taconnat L, Small I (2004) Genome-wide analysis of *Arabidopsis* pentatricopeptide repeat proteins reveals their essential role in organelle biogenesis. Plant Cell 16: 2089-2103

Mayer M J, Narbad A, Parr A J, Parker M L, Walton N J, Mellon F A, Michael A J (2001) Rerouting the plant phenylpropanoid pathway by expression of a novel bacterial enoyl-CoA hydratase/lyase enzyme function. Plant Cell 13: 1669-1682

McCarthy et al. MYB83 is a direct target of SND1 and acts redundantly with MYB46 in the regulation of secondary cell wall biosynthesis in *Arabidopsis*. Plant Cell Physiol (2009) vol. 50 (11) pp. 1950-64

McQualter R B, Chong B F, Meyer K, Van Dyk D E, O'Shea M G, Walton N J, Viitanen P V, Brumbley S M (2005) Initial evaluation of sugarcane as a production platform for p-hydroxybenzoic acid. Plant Biotechnol J 3: 29-41

Merali Z, Mayer M J, Parker M L, Michael A J, Smith A C, Waldron K W (2007) Metabolic diversion of the phenylpropanoid pathway causes cell wall and morphological changes in transgenic tobacco stems. Planta 225: 1165-1178

Meyer et al. Lignin monomer composition is determined by the expression of a cytochrome P450-dependent monooxygenase in *Arabidopsis*. Proc Nati Acad Sci USA (1998) vol. 95 (12) pp. 6619-23

Milkowski C, Strack D (2010) Sinapate esters in brassicaceous plants: biochemistry, molecular biology, evolution and metabolic engineering. Planta 232: 19-35

Miller G L (1959) Use of dinitrosalicylic acid reagent for determination of reducing sugar. Anal Chem 31: 426-428

Mitra A, Kitamura Y, Gasson M J, Narbad A, Parr A J, Payne J, Rhodes M J, Sewter C, Walton N J (1999) 4-hydroxycinnamoyl-CoA hydratase/lyase (HCHL)—An enzyme of phenylpropanoid chain cleavage from *Pseudomonas*. Arch Biochem Biophys 365: 10-16

Mitra A, Mayer M J, Mellon F A, Michael A J, Narbad A, Parr A J, Waldron K W, Walton N J (2002) 4-Hydroxycinnamoyl-CoA hydratase/lyase, an enzyme of phenylpropanoid cleavage from *Pseudomonas*, causes formation of C(6)-C(1) acid and alcohol glucose conjugates when expressed in hairy roots of *Datura stramonium* L. Planta 215: 79-89

Mitsuda et al. The NAC transcription factors NST1 and NST2 of *Arabidopsis* regulate secondary wall thickenings and are required for anther dehiscence. Plant Cell (2005) vol. 17 (11) pp. 2993-3006

Mitsuda et al. NAC transcription factors, NST1 and NST3, are key regulators of the formation of secondary walls in woody tissues of *Arabidopsis*. Plant Cell (2007) vol. 19 (1) pp. 270-80

Mouille G, Robin S, Lecomte M, Pagant S, Hofte H (2003) Classification and identification of *Arabidopsis* cell wall mutants using Fourier-Transform InfraRed (FT-IR) microspectroscopy. Plant J 35: 393-404

Moura J C, Bonine C A, de Oliveira Fernandes Viana J, Dornelas M C, Mazzafera P (2010) Abiotic and biotic stresses and changes in the lignin content and composition in plants. J Integr Plant Biol 52: 360-376

Morreel K, Ralph J, Lu F, Goeminne G, Busson R, Herdewijn P, Goeman J L, Van der Eycken J, Boerjan W, Messens E (2004) Phenolic profiling of caffeic acid O-methyltransferase-deficient poplar reveals novel benzodioxane oligolignols. Plant Physiol 136: 4023-4036

Naoumkina M A, Zhao Q, Gallego-Giraldo L, Dai X, Zhao P X, Dixon R A (2010) Genome-wide analysis of phenylpropanoid defence pathways. Mol Plant Pathol 11: 829-846

Rahman L, Kouno H, Hashiguchi Y, Yamamoto H, Narbad A, Parr A, Walton N, Ikenaga T, Kitamura Y (2009) HCHL expression in hairy roots of *Beta vulgaris* yields a high accumulation of p-hydroxybenzoic acid (pHBA) glucose ester, and linkage of pHBA into cell walls. Bioresour Technol 100: 4836-4842

Ralph J, Lapierre C, Marita J M, Kim H, Lu F, Hatfield R D, Ralph S, Chapple C, Franke R, Hemm M R, Van Doorsselaere J, Sederoff R R, O'Malley D M, Scott J T, MacKay J J, Yahiaoui N, Boudet A, Penn M, Pilate G, Jonanin L, Boerjan W (2001) Elucidation of new structures in lignins of CAD- and COMT-deficient plants by NMR. Phytochemistry 57: 993-1003

Ralph J, Kim H, Lu F, Grabber J H, Leplé J C, Berrio-Sierra J, Derikvand M M, Jouanin L, Boerjan W, Lapierre C (2008) Identification of the structure and origin of a thioacidolysis marker compound for ferulic acid incorporation into angiosperm lignins (and an indicator for cinnamoyl CoA reductase deficiency). Plant J 53: 368-379

Reddy M S, Chen F, Shadle G, Jackson L, Aljoe H, Dixon R A (2005) Targeted downregulation of cytochrome P450 enzymes for forage quality improvement in alfalfa (*Medicago sativa* L.). Proc Natl Acad Sci USA 102: 16573-16578

Rohde et al. Molecular phenotyping of the pal1 and pal2 mutants of *Arabidopsis thaliana* reveals far-reaching consequences on phenylpropanoid, amino acid, and carbohydrate metabolism. Plant Cell (2004) vol. 16 (10) pp. 2749-71

Sibout et al. CINNAMYL ALCOHOL DEHYDROGENASE-C and -D are the primary genes involved in lignin biosynthesis in the floral stem of *Arabidopsis*. Plant Cell (2005) vol. 17 (7) pp. 2059-76

Simmons B A, Loqué D, Ralph J (2010) Advances in modifying lignin for enhanced biofuel production. Curr Opin Plant Biol 13: 313-320

Simpson P J, Tantitadipatak C, Reed A M, Mather O C, Bunce C M, White S A, Ride J P (2009) Characterization of two novel aldo-keto reductases from *Arabidopsis*: Expression patterns, broad substrate specificity, and an open active-site structure suggest a role in toxicant metabolism following stress. J Mol Biol 392: 465-480

Sluiter A, Crocker D, Hames B, Ruiz R, Scarlata C, Sluiter J, Templeton, D (2008) Determination of Structural Carbohydrates and Lignin in Biomass NREL/TP-510-42618. Laboratory Analytical Procedure, National Renewable Energy Laboratory, Golden, Colo., USA Studer M H, Demartini J D, Davis M F, Sykes R W, Davison B, Keller M, Tuskan G A, Wyman C E (2011) Lignin content in natural *Populus* variants affects sugar release. Proc Natl Acad Sci USA 108: 6300-6305

Taboada A, Novo-Uzal E, Flores G, Loureda M, Ros Barceló A, Masa A, Pomar F (2010) Digestibility of silages in relation to their hydroxycinnamic acid content and lignin composition. J Sci Food Agric 90:1155-1162.

Tan J, Bednarek P, Liu J, Schneider B, Svatos A, Hahlbrock K (2004) Universally occurring phenylpropanoid and species-specific indolic metabolites in infected and uninfected *Arabidopsis thaliana* roots and leaves. Phytochemistry 65: 691-699

Turner and Somerville. Collapsed xylem phenotype of *Arabidopsis* identifies mutants deficient in cellulose deposition in the secondary cell wall. Plant Cell (1997) vol. 9 (5) pp. 689-701

Umezawa T (2010) The cinnamate/monolignol pathway. Phytochem rev 9: 1-17

Weng J K, Chapple C (2010) The origin and evolution of lignin biosynthesis. New Phytologist 187:273-285

Weng J K, Mo H, Chapple C (2010) Over-expression of F5H in COMT-deficient *Arabidopsis* leads to enrichment of an unusual lignin and disruption of pollen wall formation. Plant J 64: 898-911

Wu et al. Analysis of the *Arabidopsis* IRX9/IRX9-L and IRX14/IRX14-L pairs of glycosyltransferase genes reveals critical contributions to biosynthesis of the hemicellulose glucuronoxylan. Plant Physiol (2010) vol. 153 (2) pp. 542-54

Zhong et al. SND1, a NAC domain transcription factor, is a key regulator of secondary wall synthesis in fibers of *Arabidopsis*. Plant Cell (2006) vol. 18 (11) pp. 3158-70

Zhong et al. The MYB46 transcription factor is a direct target of SND1 and regulates secondary wall biosynthesis in *Arabidopsis*. Plant Cell (2007) vol. 19 (9) pp. 2776-92

Zhong and Ye. Regulation of cell wall biosynthesis. Curr Opin Plant Biol (2007) vol. 10 (6) pp. 564-72

Zhou et al. MYB58 and MYB63 are transcriptional activators of the lignin biosynthetic pathway during secondary cell wall formation in *Arabidopsis*. Plant Cell (2009) vol. 21 (1) pp. 248-66

Ziebell A, Gracom K, Katahira R, Chen F, Pu Y, Ragauskas A, Dixon R A, Davis M (2010) Increase in 4-coumaryl alcohol units during lignification in alfalfa (*Medicago sativa*) alters the extractability and molecular weight of lignin. J Biol Chem 285:38961-38968

| ILLUSTRATIVE SEQUENCES |
|---|

SEQ ID NO: 1
Amino acid sequence for *Pseudomonas fluorscens* HCHL (GenBank Accession No. CAA73502)
MSTYEGRWKTVKVEIEDGIAPVILNRPEKRNAMSPTLNREMIDVLETLEQDPAAGVLVLTGAGEAWTAGMDLKEYFREVDAGPE
ILQEKIRREASWQWKLLRMYAKPTIAMVNGWCFGGGFSPLVACDLAICADEATFGLSEINWGIPPGNLVSKAMADTVGHRQSL
YYIMTGKTFGGQKAAEMGLVNESVPLAQLREVTIELARNLLEKNPVVLRAAKHGFKRCRELTWEQNEDYLYAKLDQSRLLDTEG
GREQGMKQFLDDKSIKPGLQAYKR SEQ ID NO: 2
Polynucleotide sequence encoding SEQ ID NO: 1 (codon-optimized by GenScript)
ATGTCTACTTACGAGGGAAGATGGAAGACTGTTAAGGTTGAGATCGAGGATGGAATCGCTTTCGTTATCCTCAACAGACCTGAG
AAGAGAAACGCTATGTCTCCTACTCTCAACAGAGAGATGATCGATGTTCTCGAGACTCTCGAGCAGGATCCTGCTGCTGGAGTT
CTCGTTCTCACTGGAGCTGGAGAGGCTTGGACTGCTGGTATGGATCTCAAGGAGTACTTCAGAGAGGTTGATGCTGGACCTGAG
ATCCTCCAGGAGAAGATCAGAAGAGAGGCTTCTCAGTGGCAGTGGAAGCTCCTCAGAATGTACGCTAAGCCTACTATCGCTATG
GTTAACGGATGGTGCTTCGGAGGAGGATTCTCTCCTCTCGTTGCTTGCGATCTCGCTATCTGCGCTGATGAGGCTACTTTCGGA
CTCTCTGAGATCAACTGGGGAATCCCTCCTGGAAACCTCGTTTCTAAGGCTATGGCTGATACTGTTGGACATAGACAGTCTCTC
TACTACATCATGACTGGAAAGACTTTCGGAGGACAGAAGGCTGCTGAGATGGGACTCGTTAACGAGTCTGTTCCTCTCGCTCAG
CTCAGAGAGGTTACTATCGAGCTCGCTAGAAACCTCCTCGAGAAGAACCCTGTTGTTCTCAGAGCTGCTAAGCATGGATTCAAG
AGATGCAGAGAGCTCACTTGGGAGCAGAACGAGGATTACCTCTACGCTAAGCTCGATCAGTCTAGACTCCTCGATACTGAGGGA
GGAAGAGAGCAGGGTATGAAGCAGTTCCTCGATGATAAGTCTATCAAGCCTGGACTCCAGGCTTACAAGAGA SEQ ID NO: 3
Polynucleotide sequence containing IRX5 promoter (pIRX5)
ATGAAGCCATCCTCTACCTCGGAAAAACTTGTTGCGAGAAGAAGACATGCGATGGCATGGATGCTTGGATCTTTGACATTGATG
ACACTCTTCTCTCAACCATTCCTTACCACAAGAGCAACGGTTGTTTCGGGTAAATAAACTAAACTTAACCATATACATTAGCCT
TGATTCGGTTTTTGGTTTGATTTATGGATATTAAAGATCCGAATTATATTTGAACAAAAAAAAATGATTATGTCACATAAAAAA
AAATTGGCTTGAATTTTGGTTTAGATGGGTTTAAATGTCTACCTCTAATCATTTCATTTGTTTTCTGGTTAGCTTTAATTCGGT
TTAGAATGAAACCGGGATTGACATGTTACATTGATTTGAAACAGTGGTGAGCAACTGAACACGACCAAGTTCGAGGAATGGCAA
AATTCGGGCAAGGCACCAGCGGTTCCACACATGGTGAAGTTGTACCATGAGATCAGAGAGAGAGGTTTCAAGATCTTTTTGATC
TCTTCTCGTAAAGAGTATCTCAGATCTGCCACCGTCGAAAATCTTATTGAAGCCGGTTACCACAGCTGGTCTAACCTCCTTCTG
AGGTTCGAATCATATTTAATAACCGCATTAAACCGAAATTTAAATTCTAATTTCACCAAATCAAAAAGTAAAACTAGAACACTT
CAGATAAATTTTGTCGTTCTGTTGACTTCATTTATTCTCTAAACACAAAGAACTATAGACCATAATCGAAATAAAAACCCTAAA
AACCAAATTTATCTATTTAAAACAAACATTAGCTATTTGAGTTTCTTTTAGGTAAGTTATTTAAGGTTTTGGAGACTTTAAGAT
GTTTTCAGCATTTATGGTTGTGTCATTAATTTGTTTAGTTTAGTAAAGAAAGAAAAGATAGTAATTAAAGAGTTGGTTGTGAAA
TCATATTTAAAACATTAATAGGTATTTATGTCTAATTTGGGGACAAAATAGTGGAATTCTTTATCATATCTAGCTAGTTCTTAT
CGAGTTTGAACTCGGGTTATGATTATGTTACATGCATTGGTCCATATAAATCTATGAGCAATCAATATAATTCGAGCATTTTGG
TATAACATAATGAGCCAAGTATAACAAAAGTATCAAACCTATGCAGGGGAGAAGATGATGAAAAGAAGAGTGTGAGCCAATACA
AAGCAGATTTGAGGACATGGCTTACAAGTCTTGGGTACAAGAGTTTGGGGAGTGATGGGTGCAATGGAACAGCTTCTCTGGTT
GTCCAGTTCCCAAGAGAACCTTCAAGCTCCCTAACTCCATCTACTATGTCGCCTGATTAAATCTTATTTACTAACAAACAATA
AGATCAGAGTTTCATTCTGATTCTTGAGTCTTTTTTTCTCTCTCCCTCTTTTCATTTCTGGTTTATATAACCAATTCAAATGC
TTATGATCCATGCATGAACCATGATCATCTTTGTGTTTTTTTTCCTTCTGTATTACCATTTTGGGCCTTTGTGAAATTGATTT
TGGGCTTTTGTTATATAATCTCCTCTTTCTCTTTCTCTACCTGATTGGATTCAAGAACATAGCCAGATTTGGTAAAGTTTATAA
GATACAAAATATTAAGTAAGACTAAAGTAGAAATACATAATAACTTGAAAGCTACTCTAAGTTATACAAATTCTAAAGAACTCA
AAAGAATAACAAACAGTAGAAGTTGGAAGCTCAAGCAATTAAATTATATAAAAACACTAACTACACTGAGCTGTCTCCTTCTTC
CACCCAAATCTTGTTGCTGTCTCTTGAAGCTTTCTTATGACACAAACCTTAGACCCAATTTCACTCACAGTTTGGTACAACCTCA
GTTTTCTTCACAACAAATTCAAACATCTTACCCTTATATTACCTCTTTATCTCTTCAATCATCAAAACACATAGTCACATACAT
TTCTCTACCCCACCTTCTGCTGCTTCCGAGAGCTCAGTGTACCTCGCC SEQ ID NO: 4
*Sagittula_stellata*_E-37_ZP_01746375 (amino acid sequence)
MTATEATLPANDPDLSGDNVAVAFEDGIAWVKLNRPEKRNAMSVSLAEDMNVVLDKLEIDDRCGVLVLTGEGSAFSAGMDLKDF
FRATDGVSDVERMRAYRSTRAWQWRTLMHYSKPTIAMVNGWCFGGAFTPLICCDLAISSDDAVYGLSEINWGIIPGGVVSKAIS
TLMSDRQALYYVMTGEQFGGQEAVKLGLVNESVPADKLRERTVELCKVLLEKNPTTMRQARMAYKYIREMTWEESAEYLTAKGD
QTVFDKEKGREQGLKQFLDDKTYRPGLGAYKR SEQ ID NO: 5
*Saccharopolyspora_erythraea*_NRRL_2338_YP_001105000 (amino acid sequence)
MSTPTTDPGTTTPWGDTVLVDFDDGIAWVTLNRPEKRNAMNPAMNDEMVRTLDALEADPRCRVMVLTGAGESFSAGMDLKEYF
REVDQTADPSVQIRVRRASAEWQWKRLAHWSKPTIAMVNGWCFGGAFTPLVACDLAISDEEARYGLSEINWGIPPGGVVSRALA
AAVSQRDALYFIMTGETFDGRRAEGMRLVNEAVPAERLRERTRELALKLASTNPVVLRAAKVGYKIAREMPWEQAEDYLYAKLE
QSQFLDAERGREKGMAQFLDDKSYRPGLSAYSTD SEQ ID NO: 6
*Solibacter_usitatus*_Ellin6076_YP_821552 (amino acid sequence)
MDQYEEKWQTVKVEVDAEGIAWVIFNRPAKRNAMSPTLNREMAQVLETLELDAAAKVLVLTGAGESWSAGMDLKEYFREVDGQP
ESHQEKIRREASLWQWKLLRMYAKPTIAMVNGWCFGGAFSPLVACDLAIADEKAVFGLSEINWGIPPGNLVSKAVADTMGHRKA
LHYIMTGETFTGAQAAEMGLVNAAVPTSELREATRTLALKLASKNPVILRAAKHGFKRCRELTWEQNEDYLYAKLDQALHRDPE
DARAEGMKQFLDEKSIKPGLQSYKRS SEQ ID NO: 7
*Ralstonia_solanacearum*_GMI1000_NP_521786 (amino acid sequence)
MATYEGRWNTVKVDVEDGAIWVTLNRPDKRNAMSPTLNREMIDVLETLELDGDAQVLVLTGAGESWSAGMDLKEYFRETDGQPE
IMQERIRRDCSQWQWKLLRFYSKPTIAMVNGWCFGGAFSPLVACDLAIAADDAVFGLSEINWGIPPGNLVSKAVADTMGHRAAL
HYIMTGETFTGREAAEMGLVNRSVPRERLREAVTELAGKLLAKNPVVLRYAKHGFKRCRELSWEQNEDYLYAKVDQSNHRDPEK
GRQHGLKQFLDDKTIKPGLQTYKRA SEQ ID NO: 8
*Xanthomonas_albilineans*_YP_003377516 (amino acid sequence)
MSNYQDRWQTVQVQIDAGVAWVTLNRPEKRNAMSPTLNREMIDVLETLELDSAAEVLVLTGAGESWSAGMDLKEYFREIDGKEE
IVQERMRRDCSQWQWRLLRFYSKPTIAAVNGWCFGGAFSPLVACDLAIAADEAVFGLSEINWGIPPGNLVSKAVADTMGHRNAM

| ILLUSTRATIVE SEQUENCES |
| --- |
| LYIMTGRTFTGTEAAQMGLVNASVPRAQLRAEVTKLAQELQQKNPVVLRFAKHGFKRCRELTWEQNEDYLYAKVDQSNHRDPEK<br>GRQQGLKQFLDDKTIKPGLQTYKR<br><br>SEQ ID NO: 9<br>*Acinetobacter_baumannii*_ATCC_17978_YP_001084143 (amino acid sequence)<br>MKMSYENRWETVDVKVEDGIAWVTLNRPEKKNAMSPTLNREMIDVLETLELDQNAKVLVLTGAGDSWTAGMDLKEYFREVDTQP<br>EIFQERIRRDSCRWQWQLLRMYSKPTIAMVNGWCFGGGFSPLVACDLAIAADEATFGLSEINWGIPPGNLVSKAMADTVGHRAS<br>LYYIMTGKTFSGKEAETMGLVNKSVPLAQLKAEVTELANCLLEKNPVVLRTAKNGFKRCRELTWDQNEDYLYAKLDQCIHRDTE<br>NGRQEGLKQFLDEKSIKPGLQSYKRTG<br><br>SEQ ID NO: 10<br>*Acinetobacter_sp.*_ADP1_YP_046390 (amino acid sequence)<br>MTYDKRWETVDVQVEHGIAWVTLNRPHKKNAMSPTLNREMIDVLETLELDSEAKVLVLTGAGDSWTAGMDLKEYFREVDAQPEI<br>FQERIRRDSCRWQWQLLRMYSKPTIAMVNGWCFGGGFSPLVACDLAIAADEATFGLSEINWGIPPGNLVSKAMADTVGHRASLY<br>YIMTGKTFTGKEAEAMGLINKSVPLAQLKAEVTELAQCLVEKNPVVLRTAKNGFKRCRELTWDQNEDYLYAKLDQCNHRDTEGG<br>RQEGLKQFLDEKSIKPGLQSYKRTG<br><br>SEQ ID NO: 11<br>*Chromohalobacter_salexigens*_DSM_3043_YP_572340 (amino acid sequence)<br>MSDYTNRWQTVKVDVEDGIAWVTLNRPEKRNAMSPTLNREMIDVLETIELDQDAHVLVLTGEGESFSAGMDLKEYFRIEDASPE<br>IVQVKVRRDASTWQWKLLRHYAKPTIAMVNGWCFGGAFSPLVACDLAIAADESVFGLSEINWGIPPGNLVSKAMADTVGHRQAL<br>YYIMTTGETFTGPQAADMGLVNQSVPRAELRETTHKLAATLRDKNPVVLRAAKTGFKMCRELTWEQNEEYLYAKLDQAQQLDPE<br>HGREQGLKQFLDDKSIKPGLESYRR<br><br>SEQ ID NO: 12<br>*Burkholderia_cenocepacia*_AU_1054_ZP_04942909 (amino acid sequence)<br>MSKYDNRWQTVEVKVEAGIAWVTLNRPEKRNAMSPTLNREMLEVLDAVEFDDDEAKVLVLTGAGAAWTAGMDLKEYFREIDGGSD<br>ALQEKVRRDASEWQWRRLRMYNKPTIAMVNGWCFGGGFSPLVACDLAIAADDAVFGLSEINWGIPPGNLVSKAMADTVGHRRAL<br>HYIMTGDTFTGAEAAEMGLVNSSVPLAELRDATIALAARLMDKNPVVLRAAKHGFKRSRELTWEQCEDYLYAKLDQAQLRDPER<br>GREQGLKQFLDDKTIKPGLQAYKR<br><br>SEQ ID NO: 13<br>*Burkholderia_ambifaria*_MC40-6_YP_776799 (amino acid sequence)<br>MSKYDNRWQTVEVNVEAGIAWVTLNRPDKRNAMSPTLNEQEMLQVLDAIEFDDDAKVLVLTGAGSAWTAGMDLKEYFREIDGGS<br>DALQEKVRRDASEWQWRRLRMYNKPTIAMVNGWCFGGGFSPLVACDLAIAADEAVFGLSEINWGIPPGNLVSKAMADTVGHRRA<br>LHYI8MTGDTFTGVEAAEMGLVNSSVPLAGLRDATIALAARLMDKNPVVLRAAKHGFKRSRELTWEQCEDYLYAKLDQAQLRDP<br>ERGREQGLKQFLDDKAIKPGLQAYKR<br><br>SEQ ID NO: 14<br>*Burkholderia_cepaica*_AMMD_YP_776799 (amino acid sequence)<br>MSKYDNRWQTVEVNVEAGIAWVTLNRPDKRNAMSPTLNQEMLQVLDAIEFDDDAKVLVLTGAGSAWTAGMDLKEYFREIDGGSD<br>ALQEKVRRDASEWQWRRLRMYNKPTIAMVNGWCFGGGFSPLVACDLAIAADEAVFGLSEINWGIPPGNLVSKAMADTVGHRRAL<br>HYIMTGDTFTGVEAAEMGLVNSSVPLAGLRDATIALAARLMDKNPVVLRAAKHGFKRSRELTWEQCEDYLYAKLDQAQLRDPER<br>GREQGLKQFLDDKAIKPGLQAYKR<br><br>SEQ ID NO: 15<br>*Burkholderia_thailandensis*_MSMB43_ZP_02468311 (amino acid sequence)<br>MSKYDNRWQTVEVKVEAGIAWVTLNRPDKRNAMSPTLNQEMLQVLDAIEFDDDAKVLVLTGAGTAWTAGMDLKEYFREIDGGPD<br>ALQEKVRRDASEWQWRRLRMYGKPTIAMVNGWVFGGGFSPLVACDLAIAADEAVFGLSEINWGIPPGNLVSKAMADTVGHRCAL<br>HYIMTGDTFTGVEAADMGLVNRSVPLAELRDATIALAARLIDKNPVVLRAAKHGFKRSRELTWEQCEDYLYAKLDQAQLRDPER<br>GREQGLKQFLDDKAIKPGLQAYKR<br><br>SEQ ID NO: 16<br>*Burkholderia_ubonensis*_Bu_ZP_02382374 (amino acid sequence)<br>MSKYENRWQTVEVKVEAGIAWVTLNRPDKRNAMSPTLNQEMLQVLDAIEFDDDAKVLVLTGAGAAWTAGMDLKEYFREIDGGPD<br>ALQEKVRRDASEWQWRRLRMYGKPTIAMVNGWCFGGGFSPLVACDLAIAADEAVFGLSEINWGIPPGNLVSKAMADTVGHRRAL<br>HYIMTGDTFTGVEAADMGLVNRSVPLAELRDATIALAARLIDKNPVVLRAAKHGFKRSRELTWEQCEDYLYAKLDQAQLRDPER<br>GREQGLKQFLDDKAIKPGLQAYKR<br><br>SEQ ID NO: 17<br>*Azotobacter_vinelandii*_AvOP_YP_002798614 (amino acid sequence)<br>MNKYEGRWKTVIVEIEGGIAWVTLNRPDKRNAMSPTLNREMRDVLETLEQDPAARVLVLTGAGSAWTAGMDLKEYFREVDAGPE<br>ILQEKIRREACEWQWKLLRMYAKPTVAMVNGWCFGGGFSPLVACDLAICADEATFGLSEINWGIPPGNLVSKAMADTVGHRQAL<br>YYIMTGKTFDGRQAAEMGLVNQSVPLAQLRETVATLCQDLLDKNPVVLRAAKNGFKRCRELTWEQNEDYLYAKLDQSRLLDEEG<br>GREEGMRQFLDEIKSIKPGLQAYKR<br><br>SEQ ID NO: 18<br>*Pseudomonas_putida*_KT2440_NP_745498 (amino acid sequence)<br>MSKYEGRWTTVKVELEAGIAWVTLNRPEKRNAMSPTLNREMVDVLETLEQDADAGVLVLTGAGESWTAGMDLKEYFREVDAGPE<br>ILQEKIRREASQWQWKLLRLYAKPTIAMVNGWCFGGGFSPLVACDLAICANEATFGLSEINWGIPPGNLVSKAMADTVGHRQSL<br>YYIMTGKTFDGRKAAEMGLVNDSVPLAELRETTRELALNLLEKNPVVLRAAKNGFKRCRELTWEQNEDYLYAKLDQSRLLDTTG<br>GREQGMKQFLDDKSIKPGLQAYKR<br><br>SEQ ID NO: 19<br>*Pseudomonas_fluorescens*_SBW25_YP_002872871 (amino acid sequence)<br>MSNYEGRWTTVKVEIEEGGIAWVILNRPEKRNAMSPTLNREMIDVLETLEQDPAAGVLVLTGAGEAWTAGMDLKEYFREVDAGPE<br>ILQEKIRRREASQWQWKKLLRMYAKPTIAMVNGWCFGGGFSPLVACDLAICADEATFGLSEINWGIPPGNLVSKAMADTVGHRQSL |

| ILLUSTRATIVE SEQUENCES |
| --- |
| YYIMTGKTFGGQKAAEMGLVNESVPLAQLREVTIELARNLLEKNPVVLRAAKRGFKRCRELTWEQNEDYLYAKLDQSRLLDTEG<br>GREQGMKQFLDDKSIKPGLQAYKR<br><br>SEQ ID NO: 20<br>Pseudomonas_syringae_NP_792742 (amino acid sequence)<br>MSKYEGRWTTVKVEIEQGIAWVILNRPEKRNAMSPTLNREMIDVLETLEQDPEAGVLVLTGAGEAWTAGMDLKEYFREVDAGPE<br>ILQEKIRREASQWQWKLLRMYAKPTIAMVNGWCFGGGFSPLVACDLAICADEATFGLSEINWGIPPGNLVSKAMADTVGHRQSL<br>YYIMTGKTFDGKKAAEMGLVNESVPLAQLRQVTIDLALNLLEKNPVVLRAAKHGFKRCRELTWEQNEDYLYAKLDQSRLLDKEG<br>GREQGMKQFLDDKSIKPGLEAYKR<br><br>SEQ ID NO: 21<br>Ralstonia_eutropha_JMP134_YP_299062 (amino acid sequence)<br>MANYEGRWKTVKVSVEEGIAWVMFNRPEKRNAMSPTLNSEMIQVLEALELDADARVVVLTGAGDAWTAGMDLKEYFREVDAGPE<br>ILQEKIRRDACWQWKLLRMYAKPTIAMVNGWCFGGGFSPLVACDLAIAADEAVFGLSEINGWIPPGNLVSKAMADTVGHRQAL<br>HYIMTGDTFTGQQAAAMGLVNKSVPRSQLREHVLELAGKLLEKNPVVLRAAKHGFKRSRELTWEQNEDYLYAKLDQAQLRDPEH<br>GREQGLKQFLDDKSIKPGLQAYKRA<br><br>SEQ ID NO: 22<br>Burkholderia_glumae_BGR1_YP_002908688 (amino acid sequence)<br>MSYEGRWTTVKVTVEAGIGWVVLNRPEKRNAMSPTLNKEMIDVLETLEDDEAQVLVLTGEGDAWTAGMDLKEYFREVDAASDV<br>VQERIRRDASRWQWQLLRMYSKPTIAMVNGWCFGGGFSPLVACDLAIAADEATFGLSEINWGIPPGNLVSKAMADTVGHRQALY<br>YIMTGDTFTGKQAAQMGLVNQSVPRAALREATVALAAKLLDKNPVVLRNAKHGFKRSRELTWEQNEDYLYAKLDQANYRDKEGG<br>REKGLKQFLDDKSIKPGLQAYKR<br><br>SEQ ID NO: 23<br>Burkholderia_phytofirmans_PsJN_YP_001887778 (amino acid sequence)<br>MSYEGRWKTVKVDVAEGIAWVSFNRPEKRNAMSPTLNKEMIEVLEAVELDAEAQVLVLTGEGDAWTAGMDLKEYFREVDAGPEI<br>LQEKIRRDACRWQWQLLRMYSKPTIAMVNGWCFGGGFSPLVACDLAIAADEATFGLSEINWGIPPGNLVSKAMADTVGHRQALY<br>YIMTGETFTGQEAAQMGLVNKSVPRAELREATRALAGKLLEKNPVVLRAAKHGFKRCRELTWDQNEDYLYAKLDQAQLRDPEGG<br>REQGLKQFLDDKAIKPGLQTYKR<br><br>SEQ ID NO: 24<br>Burkholderia_mallei_ATCC_23344_YP_105383 (amino acid sequence)<br>MSYEGRWKTVEVIVDGAIAWVTLNRPDKRNAMSPTLNAEMIDVLEAIELDPEARVLVLTGEGEAWTAGMDLKEYFRIEDAGPEI<br>LQEKIRRDASRWQWQLLRMYAKPTIAMVNGWCFGGGFSPLVACDLAIAADEAVFGLSEINWGIPPGNLVSKAMADTVGHRQALY<br>YIMTGETFTGAQAAQMGLVNRSVPRAQLRDAVRALAAKLLDKNPVVLRNAKHGFKRCRELTWEQNEDYLYAKLDQAQLRDPEHG<br>REQGLKQFLDDKTIKPGLQAYRR<br><br>SEQ ID NO: 25<br>Burkholderia_pseudomallei_Pasteur_ZP_01765668 (amino acid sequence)<br>MSYEGRWKTVEVIVDGAIAWVTLNRPDKRNAMSPTLNAEMIDVLEAVELDPEARVLVLTGEGEAWTAGMDLKEYFREVDAGPEI<br>LQEKIRRDASRWQWQLLRMYAKPTIAMVNGWCFGGGFSPLVACDLAIAADEAVFGLSEINWGIPPGNLVSKAMADTVGHRQALY<br>YIMTGETFTGAQAAQMGLVNRSVPRAQLRDAVRALAAKLLDKNPVVLRNAKHGFKRCRELTEWQNEDYLYAKLDQAQLRDPEHG<br>REQGLKQFLDDKTIKPGLQAYRR<br><br>SEQ ID NO: 26<br>Burkholderia_multivorans_ATCC_17616_YP_001583186 (amino acid sequence)<br>MSYEGRWKTVKVAVEGGIAWVTLNRPEKRNAMSPTLNAEMIDVLEAIELDPEAQVLVLTGEGDAWTAGMDLKEYFREVDAGPEI<br>LQEKIRRDASRWQWQLLRMYAKPTIAMVNGWCFGGGFSPLVACDLAIAADEAVFGLSEINWGIPPGNLVSKAMADTVGHRQALY<br>YIMTGDTFTGQQAAQMGLVNKSVPRAQLRDEVRALAAKLLDKNPVVIRNAKHGFKRCRELTEWQNEDYLYAKLDQANYRDPEGG<br>REQGLKQFLDEKSIKPGLQQYKR<br><br>SEQ ID NO: 27<br>Burkholderia_vietnamiensis_G4_YP_001116289 (amino acid sequence)<br>MGYEGRWKTVKVEVAGGIAWVTLNRPEKRNAMSPTLNTEMIDVLEAIELDADAQVLVLTGEGDAWTAGMDLKEYFREIDAGPEI<br>LQEKIRRDASRWQWQLLRMYAKPTIAMVNGWCFGGGFSPLVACDLAIAADEAVFGLSEINWGIPPGNLVSKAMADTVGHREALY<br>YIMTGDTFTGQQAARMGLVNKSVPRAQLRDEVRALAAKLLDKNPVVIRNAKHGFKRCRELTEWQNEDYLYAKLDQANYRDPEGG<br>REQGLKQFLDDKSIKPGLQAYKR<br><br>SEQ ID NO: 28<br>Sphingobium_japonicum_UT26S_YP_003543683 (amino acid sequence)<br>MSEYLTEGPDLSRTCVDVMFDEGIAWVTLNRPEKRNAMSPTLNSEMLAIEQLELDPRCGVVVLTGAGDSFSAGMDLKEYFRET<br>DGLPPAQVRRIRQTAQAWQWRTLQHFGKPTIAMVNGWCFGGAFTPLVACDLAIAANEAVFGLSEINWGIIPGGNVTKAIQERLR<br>PQDAALYIMTGRNFTGEKAAQMGLVAEAVPLTDLRDHTRALALELLSKNPVVLNAAKIALKKVADMTWDVAEDYLVAKGAQTRV<br>ADKTDGRNKGITQFLDEKSYKPGLEGYRRDK<br><br>SEQ ID NO: 29<br>Xanthomonas_axonopodis_NP_641235 (amino acid sequence)<br>MNEHDVVSVRIENRIAWVKFARPDKRNAMSPALNRRMMDVLDELEFDDNVGLVLGGEGTAWSAGMDLKEYFRETEAQGLRGVRR<br>SQRESYGWFRRLRWYQKPTIAMVNGWCFGGGFGPLFACDLAIAADEAQFGLSEINWGILPGGGVTKVAVELLSMRDAMWMTLTG<br>EMVDGKKAAEWRLVNESVPLERLEARTREVAELLLRKNPVALKYAKDAVRRVGTMTYDEAEDYLVRMQEAANSFDNNARKEGIR<br>QFIDEKSYKPGLGEYDLSKHSA<br><br>SEQ ID NO: 30<br>Xanthomonas_campestris_ATCC_33913_NP_636201 (amino acid sequence)<br>MNEHDVVSVHVENRIAWVKFARPDKRNAMSPALNRRMLDVLDELEFDDNVGLVLGGEGTAWSAGMDLKEYFRETEAQGLRGVR<br>RSQRESYGWFRRLRWYQKPTIAMVNGWCFGGGFGPLFACDLAIAADEAQFGLSEINWGILPGGGVTKVAVELLSMRDAMWMTLT |

| ILLUSTRATIVE SEQUENCES |
|---|
| GELVDGRKAAEWRLVNESVPLERLETRTREVAELLLKKNPVALKYAKDAVRRVGTMTYDEAEDYLVRMQEAANSFDNNARKEGI<br>RQFIDEKRYKPGLGAYEPDAGTN<br><br>SEQ ID NO: 31<br>*Azospirillum_sp._B510_YP_003451575* (amino acid sequence)<br>MTQQQAAARTGTAEDVVTVELDNGVAWVTLNRPDKRNAMNPALNARMHGVLDDLEVDDRCQVLVLTGAGESFSAGMDLKEYFRE<br>TEAKGHMATRRAQRDSYGWWRRLRWFEKPSIAMVNGWCFGGAFSPLFACDLAVAADEAQFGLSEINWGIIPGGNVTKVVADLMS<br>QREAMYYILTGETFDGRKAAEMKLVNFSVPHAELRAKVRAIADNLLEKNPQTLKAAKDAFKRVVEMPFDAAEDYLVVRQESLNY<br>LDKSEGRKQGIKQFIDDKTYRPGLGAYKR<br><br>SEQ ID NO: 32<br>*Agrobacterium_vitis_S4_YP_002549228* (amino acid sequence)<br>MTVAEKSDADTVLVDIEDRIAFVTFNRPEKRNAMNPALNIRMAEVLEELEADDRCGVLVLRGAGTSWSAGMDLQQYFRDNDDKP<br>RHATLKSRRQSGGWWQRLTYFEKPTIAMVNGWCFGGAFNPLVACDLAIAANEATFGLSEINWGILPGGNVTRAVAEVMNHRDSL<br>YYIMTGEPFGGEKARDMGLVNESVPLEELETRVRKLCASLLEKNPVTMKAAKDTFKRVRNMPWELADDYIYAKLEQMLLLDKTR<br>GRDEGLKQFLDDKTYRPGLGAYKRK<br><br>SEQ ID NO: 33<br>*Rhizobium_etli_Brasil_5_YP-001985541* (amino acid sequence)<br>MTENTSPVLVEFDGGIAFVTLNRPEKRNAMNPALNARMLEVLDELEGDERCGVLVLRGAGQSWSAGMDLKEYFRDNDDKPRDAT<br>LKARRQSGGWWGRLMYFEKPTIAMVNGWCFGGAFTPLVSCDLAIAAEEANFGLSEINWGILPGGNVTRAVAEVMRHRDALYYIM<br>TGELFGGRKAAEMGLVNEAVPLVDLETRVRKICASLLEKNPVTLKAAKDTYKRVRNLPWDLADDYIYAKLEQMLFLDKTKGRDE<br>GLKQFLDDKTYQPGLGAYKRGR<br><br>SEQ ID NO: 34<br>*Rhizobium_leguminosarium_bv_trifolii_WSM1325_YP_002973001* (amino acid sequence)<br>MTEDKSPVLVEFDSGIAFVTLNRPEKRNAMNPALNIRMLEVLDELEGDERCGVLVLRGAGESWSAGMDLKEYFRDNDDKPRDVT<br>LKARRQSGNWWGRLMYFEKPTIAMVNGWCFGGAFTPLVSCDLAIAAEEANFGLSEINWGILPGGNVTRAVAEVMRHRDALYYIM<br>TGELFGGRKAAEMGLVNEAVPLAELEPRVRKICASLLEKNPVTLKAAKDTYKRVRNLPWDLADDYIYAKLEQMLFLDKTKGRDE<br>GLKQFLDDKTYQPGLGAYKRGR<br><br>SEQ ID NO: 35<br>Amino acid sequence for IRX5 (GenBank Accession No. AF458083_1)<br>MEPNTMASFDDEHRHSSFSAKICKVCGDEVKDDDNGQTFVACHVCVYPVCKPCYEYERSNGNKCCPQCNTLYKRHKGSPKIAGD<br>EENNGPDDSDDELNIKYRQDGSSIHQNFAYGSENGDYNSKQQCRPNGRAFSSTGSVLGKDFEAERDGYTDAEWKERVDKWKARQ<br>EKRGLVTKGEQTNEDKEDDEEEELLDAEARQPLWRKVPISSSKISPYRIVIVLRLVILVFFFRFILTPKADAYPLWLISVICEI<br>WFALSWILDQFPKWFPINRETYLDRLSMRFERDGEKNKLAPVD VFVSTVDPLKEPPIITANTILSILAVDYPVNKVSCYVSDD<br>GASMLLFDTLSETSERARRWVPFCKKYNVEPRAPEFYFSEKIDYLKDKVQTTFVKDRRAMKREYEEFKVRINALVAKAQKKPEE<br>GWVMQDGTPWPGNNTRDHPGMIQVYLGKEGAFDIDGNELPRLVYVSREKRPGYAHHKKAGAMNAMVRVSAVLTNAPFMLNLDCD<br>HYINNSKAIRESMCFLMDPQLGKKLCYVQFPQRFDGIDHNDRYANRNIVFFDINMRGLDGIQGPVYVGTGCVFNRPALYGYEPP<br>VSEKRKKMTCDCWPSWICCCCGGGNRNHHKSKSSDSSSKKKSGIKSLLSKLKKKNKKKSDDKTMSSYSRKRSATEAIFDLELIE<br>EGLEGYDELEKSSLMSQKNFEKRFGMSPVFIASTLMENGGLPEATNTSSLIKEAIHVISCGYEEKTEWGKEIGWIYGSVTEDIL<br>TGFRMHCRGWKSVYCMPKRPAFKGSAPINLSDRLHQVLRWALGSVEIFFSRHCPLWYAWGGKLKILERLAYINTIVYPFTSIPL<br>LAYCTIPAVCLLTGKFIIPTINNFASIWFLALFLSHATAILELRWSGVSINDLWRNEQFQVIGGVSAHLFAVFQGLLKVLFGVD<br>TNFTVTSKGASDEADEFGDLYLFKWTTLLIPPTTLIILNMVGVVAGVSDAINNGYGSWGPLFGKLFFAFWVIVHLYPFLKGLMG<br>RQNRTPTIVVLWSILLASIFSLVWVRIDPFLPKQTGPLLKQCGVDC<br><br>SEQ ID NO: 36<br>Polynucleotide sequence PATCESA7_PATIRX3<br>TGGGAACTTTCGGTACATTTTCCAATAAAATCTATATACTATAAGATATTAAATATACACAAATATATCTAAGTGAATCATACA<br>AATTATGTAGGCACACAGGAAGAGGCTGCTGAGGCTTATGACATTGCAGCCATTAAATTCAGAGGATTAAGCGCAGTGACTAAC<br>TTCGACATGAACAGATACAATGTTAAAGCAATCCTCGAGAGCCCGAGTCTACCTATTGGTAGTTCTGCGAAACGTCTCAAGGAC<br>GTTAATAATCCGGTTCCAGCTATGATGATTAGTAATAACGTTTCAGAGAGTGCAAATAATGTTAGCGGTTGGCAAAACACTGCG<br>TTTCAGCATCATCAGGGAATGGATTTGAGCTTATTGCAGCAACAGCAGGAGAGGTACGTTGGTTATTACAATGGAGGAAACTTG<br>TCTACCGAGAGTACTAGGGTTTGTTTCAAACAAGAGGAGGAACAACAACACTTCTTGAGAAACTCGCCGAGTCACATGACTAAT<br>GTTGATCATCATAGCTCGACCTCTGATGATTCTGTTACCGTTTGTGAAGATTGTTAGTTATGGTGGTTATCAAGGATTCGCA<br>ATCCCTGTTGGAACATCGGTTAATTACGATCCCTTTACTGCTGCTGAGATTGCTTACAACGCAAGAAATCATTATTACTATGCT<br>CAGCATCAGCAACAACAGCAGATTCAGCAGTCGCCGGGAGGAGATTTTCCGGTGGCGATTTCGAATAACCATAGCTCTAACATG<br>TACTTTCACGGGGAAGGTGGTGGAGAAGGGGCCTCCAACGTTTTCAGTTTGGAACGACACTTAGAAAAATAAGTAAAAGATCTTT<br>TAGTTGTTTGCTTTGTATGTTGCGAACAGTTTGATTCTGTTTTTCTTTTTCCTTTTTTGGGTAATTTTCTTATAACTTTTTTC<br>ATAGTTTCGATTATTTGGATAAAATTTTCAGATTGAGGATCATTTTATTTATTTATTTATTAGTGTAGTCTAATTTAGTTGTATAACT<br>ATAAAATTGTTGTTTGTTTCCGAATCATAAGTTTTTTTTTTTTTGGTTTTGTATTGATAGGTGCAAGAGACTCAAAATTCTGG<br>TTTCGATGTTAACAGAATTCAAGTAGCTGCCCACTTGATTCGATTTGTTTTGTATTTGGAACAACCATGGCTGGTCAAGGCCC<br>AGCCCGTTGTGCTTCTGAACCTGCCTAGTCCCATGGACTAGATCTTTATCCGCAGACTCCAAAGAAAAAGGATTGGCGCAGAG<br>GAATTGTCATGGAAACAGAATGAACAAGAAAGGGTGAAGAAGATCAAAGGCATATATGATCTTTACATTCTCTTTAGCTTATGT<br>ATGCAGAAAATTCACCTAATTAAGGACAGGGAACGTAACTTGGCTTGCACTCCTCTCACCAAACCTTACCCCCTAACTAATTTT<br>AATTCAAAATTACTAGTATTTTGGCCGATCACTTTATATAATAAAGATACCAGATTTATTATATTTACGAATTATCAGCATGCAT<br>ATACTGTATATAGTTTTTTTTTGTTAAAGGGTAAAATAATAGGATCCTTTTGAATAAAATGAACATATATAATTAGTATAATG<br>AAAACAGAAGGAAATGAGATTAGGACAGTAAGTAAAATGAGAGAGACCTGCAAAGGATAAAAAGAGAAGCTTAAGGAAACCGC<br>ACGATGAAAGAAAGACATGTCATCAGCTGATGGATGTGAGTGATGAGTTTGTTGCAGTTGTGTAGAAATTTTTACTAAAACAGT<br>TGTTTTTACAAAAAAGAAATAATATAAACGAAAGCTTAGCTTGAAGGCAATGGAGACTCTACAACAAACTATGTACCCATACAG<br>AGAGAGAAACTAAAAGCTTTTCACACATAAAAACCAAACTTATTCGTCTCTCATTGATCACCGTTTTGTTCTCTCAAGATCGCT<br>GCTAATCTCCGGCCGTCCCT |

| ILLUSTRATIVE SEQUENCES |
| --- |

SEQ ID NO: 37
Polynucleotide sequence PATCESA8_PATIRX1
TTTAGTGCAGTCTAGGAAGACGGATCCAAAGGAGATAAACAGAGTTCAAGAAGCTCTTAACTACTATACAATCGAATCGTCAGC
CGCGCTTTTGTTTCGTTCATGATCAATTTGTTTGTAACTGCGGTTTTCGCGAAAGGGTTTTATGGAACCAAACAAGCTGATAG
TATAGGACTGGTTAACGCGGGATATTACCTACAAGAGAAATATGGCGGTGGTGTTTTCCCGATACTATACATTTGGGGGATTGG
TTTATTAGCTGCTGGACAAAGCAGTACTATAACCGGGACTTATGCTGGACAGTTTATAATGGAAGGGTTCTTAGATCTTCAAAT
GGAACAATGGCTATCAGCTTTTATAACGAGAAGCTTTGCTATTGTACCTACTATGTTTGTTGCTATTATGTTTAACACATCCGA
GGGCTCGCTCGATGTTTTAAACGAATGGCTTAACATTCTTCAGTCGATGCAGATTCCTTTCGCGGTTATTCCTCTTTTGACTAT
GGTTTCTAATGAACATATCATGGGTGTCTTCAAGATCGGACCTTCGCTTGAGGTAAAGCAATTTTTTGTCATCTCTCTTTATTG
TTATGTGCTTTTGATTGTAACGAGTTAGTTGGGATCTTTGCAGAAGCTAGCTTGGACTGTGGCGGTGTTTGTGATGATGATAAA
TGGGTATCTTCTTCTAGATTTCTTCATGGCTGAAGTGGAAGGGTTTCTTGTTGGGTTTCTGGTTTTTGGTGGAGTAGTTGGATA
CATCAGTTTCATCATCTATCTTGTTTCTTATAGAAGCTCACAATCTTCTTCCTGGTCGAGTTTAGAAATGTCAGAGAGAGTTGT
TTCCACAGAGACGTAGAAACCCATAACTTTAGTATTCTTCAACCCTTACAACTTATCTGAGCAAAATCAGAAGGTCGAATTTGA
TGGATGGTTTTGCTGTATTTGGTCAACGGTTTTATTTGAGACAGTAGACCAGAGGAAACTCAGATGTGATGATGCAAAGACTGA
ATTGGTTAAGAGTGTAGATTGATTTGTTCTAACATTGCAAATGTAGAGTAGAATTATGCAAAAAACGTTAATGAACAGAGAAGT
GATTAAGCAGAAACAAAATTAGAGAAGTGATATTATATCTCAAAATTTATTTTTGGTACAGCTAAAGCTCAAATTGTTATAGAG
ATTAGAGATATTAAACCAAATGACGAGTGTTTTCTTTAGTAGTAAACGGTGAAAATTCTCTTCTGACAAAGACAATTAAAATTT
TAGGTTTAAGACTTTAATATTTGTCACAAATTGTCATTTACCTAAATAAAAAAAAAACTAAATATTTTTTTTAGATACATATGT
GTCTTATAATTTTAACTATAAATTTAATTTTATGTCTTAAATAATTGTTTACACTATAAATTTAAATATTTTAATGCTAAAAT
TAATTTGATTCAAAAAGTGATTTTAATTCTTATTTTTCTTATAGAAAGTTGGTGATTGAAAAGATTTACTTAAAAATTATAACA
ACTTCAATGGTGAATAACCCGACCCGAATAAACCGGATATAACAACTTCAATGTTAGCTTGATATAGAAAGTACGGTGACGCTT
AGGAGGCAAGCAAGCTAGTATCTGCCGCTGGTTAGAGACAAAGAACATGTGTCACTCCTCTCAACTAAAACTTTCCTTCACTTT
CCCGCAAAATCATTTCAAAAAAGCTCCAAATTTAGCTTACCCATCAGCTTTCTCAGAAAACCAGTGAAAGAAACTTCTCAACTT
CCGATTTTTCACAATCCACCAAACTTTTTTTAATAACTTTTTTTCCTCTTATTACAAAACCTCCACTCTCATGGCTTCTCAAAC
TTGTTATCCATCCAAATCTCAATCCCTAATTAGGGTTCATTTCTCTGTTTCTCCAAACAGGGGAATTCGAAG SEQ ID NO: 38
Polynucleotide sequence PATNST1
GTTTGTAGAGTTGGATCAGCATCCAGATTTAAACCCTTATTTTTGTTTTTGCCAAGCATCCAGACTTAATCCTATATTAGATAC
TGTATATGCATCTTGATGGAATATAGACTATATAGAAAGACCAAAAATGGAAGAGTACGAATAAAAATGCATAATATACCTTGG
AAATTATTCTTGGTTATTGTGAAACTTAAAACATTTCAACGAAGTCATATACTATTATTTAATCATTGATTTAAAATTGCTAAT
CAAATCACGTGTTGTTGTTATATATGGATAAAGAGTTAAACTATAACACAACTGAGAAAAAAATAAAGTTATCAATTTTGTTAA
GAATCAATGAAGGTTTCACAAGACTGGGAAGAAAAAAAATAGATATATGGAGTACATAAAACATTAAAATTTGCTAAATTTTA
CTTTTGAACTCTATTGATTCGGGTTGACATGATGATAATGTTACATTCGTACAATTTCACAATGAAAAAAACGAGTACTAAATA
TTGTCAATCAAACATATGAATGTACAAAAATCCATAAACTCTACCAAAATAGAATGAGATTCTGAAATCAAACCTACTTTTTC
TTTTTAATTATAAATTCAACTATATTATAAATTTATTTATCACAAATAATAGAGGAGTGAGAATATTTTAGACAACGCAAATTT
CTTTTATTTAGTTCTTATACTTTATTTTTTACCAAACGTTAATTAAAAAAATCACACATACATAATTTCTAAAAAAAATGTATT
CTTCAAGTAATATATCTTTCTGAGTACTAGTTTATCTATTTATCTCCGTATTTAATAATCAAAAGTTACGTTTAAAATAGAAAC
AACTTTTATCAAACAAAATATATTAGAAAACGCATGGTACTGGCTACTGGAAAGAATCATGACCTGTAAATTTCTACAGTTTTC
CCGTTTTATATAGTACTTAGAAACTTTGGATTTTCATAGCGCAACCAATAAACACATGGACTTAAGACACAAAAAAAGTTGGGT
GCAATGTCATTAATCAAACTAAAAAAATAATGATTAAAAGCATGGAATTCCGAAAACGCAACAAAATGATTCTGTGTTTAGACA
AATGCAGAAAGGCCTCTTAACTAATCTTAAATAAAGTCTTAGTTCCAACCACATAAACACTCCTTAGCTCCATTAATTTTGGTT
TTCTTAATTACGTTTCTACACAAGTACACGTACTTACACATACAATTCCACAGTCTAAATGATAAAACTATGTGGTTTTTGACG
TCATCGTTACCTTTCTGTCGTCTCACCTTTATATAGTGTCTCTAACAGAACGTAACAACCAAATGTTTAAAAAAATAAAAACAG
CACCCCTTAATTAGGCTCATTCGTTTTGCACTAACCATACTACAAATCATCTCGAACGATCGAGCAAAGATTTGAAAATAAAT
AAACGTATAACTCTAGAGATTTTCATTAGCTAAGAAAAGTGAAATCGATTGTTAATCCTATTTCAGACGGGACAGGAACACTCA
TTACCCAACTCTATCATCTCTCGAACACCAAACTATATCTACCGTTTGGGGCATTATTTCCCACTTTCTTTCGAAGACAATTTC
CCATATATAACATATACACATTATTACTAATATATTTTTATAAATTTTCGTCACATCCCAAAAAAAAACACTCTTTGTCACATC
AACTAGTTTTTTTGTAACGATCAAACCTTTTCGTTTAAAAAAAAAAACTTTTGTAGTGTAAACGTTTATTTATCGATGAAAA
AGCCACATCTTCCGGAGGGAAACTTTTTAAGACACCCTATTTCGACTTTATTTTGTAAATACAGTGTGCATGTGCATATAAGA
GAGATATCATTTGTATAAATATCAAGAATTAGAAGAGAAAAAGAGAGAAGAAGACAATCTATTACTATTACGATGTGTGGGTTG
TTAATTTGTTAAAGGGAGCTTTTCTATAGAGATTTTTAAGGTCAAGGGTCATCGTTCGATGTGGGCTTGCTTCCTACAATCTA
GTTGCCTTACGGGGCCTACTCTTTTTCTTTTGATAACTACATCACCTTTTTTTTCTCCGACAACTATATCACTTTTTTTATGTT
TTCCTTTTTTCTTCACAATAATTCTTTACTCGTTGCAAATGTAAAGATCACAAAGTTACTTATTTTGTTTACGATGGTTCTT
AGTAGTTTAAAGAATTAATGAATAAGATAAACCTAAACTTTGAAAAGACTAAAAAAAATGTATAACAACATACATTATACGTAT
TTGAAATAGTCCAAGTGATATTATGTCATTGATATTAGCACAAATTATTTCGTCATGCCTGATATTGTCACATTTGATGATTTAA
GTTCTTGTAAAAGATAAGTGTAACTAAATCACTATAGTGAGGCCCACGTTTAATTTCTAAACTAATTACAATGACAATAAAAT
AGCAAAACTATTTAAAACTAGACGCCAAAAAAATTGAAACTAATAATTGTGAAAAAAGAACAAGAGAATAATAATCATTAATA
ATTGACAAGTGAAATTAATATATTGCTCTTGGAGGGTATATTTTAATTTTCAAACTAAATAATGAATACAAATGGAAAAGCTA
ATGATAAGAGTTGAATTTTAATAATTAAGAAAAACAAAAAAAGGTGTACAAGGAGACACATGCGTTTTCCTCATGCATCTTGTT
TTTATACAACAATATATATATATTGAGTCATTCTCTGCTAGCTCTCTCATCTCCAACTTTCAGTATGATATATAGTTACAAT
TAAATAAACCTCACATGCTCTATTCTTGCTTGATTTTTGAGTTAATCTTGAATCTCTTTG SEQ ID NO: 39
Polynucleotide sequence PATCESA4_PATIRX5
ATGAAGCCATCCTCTACCTCGGAAAAACTTGTTGCGAGAAGAAGACATGCGATGGCATGGATGCTTGGATCTTTGACATTGATG
ACACTCTTCTCTCAACCATTCCTTACCACAAGAGCAACGGTTGTTTCGGGTAAATAAACTAAACTTAACCATATACATTAGCCT
TGATTCGGTTTTTGGTTTGATTTATGGATATTAAAGATCCGAATTATATTTGAACAAAAAAAATGATTATGTCACATAAAAAA
AAATTGGCTTGAATTTTGGTTTAGATGGGTTTAAATGTCTACCTCTAATCATTTCATTTGTTTTCTGGTTAGCTTTAATTCGGT
TTAGAATGAAACCGGGATTGACATGTTACATTGATTTGAAACAGTGGTGGCAACTGAACACGACCAAGTTCGAGGAATGGCAA
AATTCGGGCAAGGCACCAGCGGTTCCACACATGGTGAAGTTGTACCATGAGATCAGAGAGAGGTTTCAAGATCTTTTTGATCTC
TTCTCGTAAAGAGTATCTCAGATCTGCCACCGTCGAAAATCTTATTGAAGCCGGTTACCACAGCTGGTCTAACCTCCTTCTGAG
GTTCGAATCATATTTAATAACCGCATTAAACCGAAATTTAAATTCTAATTTCACCAAATCAAAAGTAAAACTAGAACACTTCA
GATAAATTTTGTCGTTCTGTTGACTTCATTTATTCTCTAAACACAAAGAACTATAGACCATAATCGAAATAAAAACCCTAAAAA
CCAAATTTATCTATTTAAAACAAACATTAGCTATTTGAGTTTCTTTTAGGTAAGTTATTTAAGGTTTTGGAGACTTTAAGATGT
TTTCAGCATTTATGGTTGTGTCATTAATTTGTTTAGTTTAGTAAAGAAAGAAAAGATAGTAATTAAAGAGTTGGTTGTGAAATC

| ILLUSTRATIVE SEQUENCES |
|---|
| ATATTTAAAACATTAATAGGTATTTATGTCTAATTTGGGGACAAAATAGTGGAATTCTTTATCATATCTAGCTAGTTCTTATCG |
| AGTTTGAACTCGGGTTATGATTATGTTACATGCATTGGTCCATATAAATCTATGAGCAATCAATATAATTCGAGCATTTTGGTA |
| TAACATAATGAGCCAAGTATAACAAAAGTATCAAACCTATGCAGGGGAGAAGATGATGAAAAGAAGAGTGTGAGCCAATACAAA |
| GCAGATTTGAGGACATGGCTTACAAGTCTTGGGTACAGAGTTTGGGGAGTGATGGGTGCACAATGGAACAGCTTCTCTGGTTGT |
| CCAGTTCCCAAGAGAACCTTCAAGCTCCCTAACTCCATCTACTATGTCGCCTGATTAAATCTTATTTACTAACAAACAATAAG |
| ATCAGAGTTTCATTCTGATTCTTGAGTCTTTTTTTTCTCTCTCCCTCTTTTCATTTCTGGTTTATATAACCAATTCAAATGCTT |
| ATGATCCATGCATGAACCATGATCATCTTTGTGTTTTTTTTCCTTCTGTATTACCATTTTGGGCCTTTGTGAAATTGATTTTG |
| GGCTTTTGTTATATAATCTCCTCTTTCTCTTTCTCTACCTGATTGGATTCAAGAACATAGCCAGATTTGGTAAAGTTTATAAGA |
| TACAAAATATTAAGTAAGACTAAAGTAGAAATACATAATAACTTGAAAGCTACTCTAAGTTATACAAATTCTAAAGAACTCAAA |
| AGAATAACAAACAGTAGAAGTTGGAAGCTCAAGCAATTAAATTATATAAAAACACTAACTACACTGAGCTGTCTCCTTCTTCCA |
| CCAATCTTGTTGCTGTCTCTTGAAGCTTTCTTATGACACAAACCTTAGACCCAATTTCACTCACAGTTTGGTACAACCTCAGTT |
| TTCTTCACAACAAATTCAAACATCTTACCCTTATATTACCTCTTTATCTCTTCAATCATCAAAACACATAGTCACATACATTTC |
| TCTACCCCACCTTCTGCTCTGCTTCCGAGAGCTCAGTGTACCTCGCCT |
| |
| SEQ ID NO: 40 |
| Polynucleotide sequence PATGAUT8_PATIRX8 |
| ACGAGCTGACTTGTACCGATGAGCTGGCTCTTCTGGGCGAGCTGGCTGATCTTGACGAGCAGACTTCTCCCGACGAGCTGACTT |
| GTGTCGATGAGCTGGCTCTTCTGGGCGAGTTGGCTGATCTTGACGAGCAGACTTCTCCCGACGAGCTGACTTGTGTCGATGAGC |
| TGGCTCTTCTGGGCGAACTGGCTGATCTTGACGAGCAGACTTCTCCCGACGAGCTGACTTGTGCTATCCTTTCTCCAGGTCTCG |
| AAAAAGTCCCCTTTCCCGAGACTTTCTATTCCTTATTTATACCCGTCCGTATAGTAGGGTACGCAAGGTGAATTCTCGAGAGTG |
| CCCCTTTTCTACGCAGCCGAACTCACATCCTGACCAGGCCGGGCTTCGGCCTGCTGGGGCCGGCTCGAGTTCTAAAGTGATGGTC |
| GGGGCTGGGTCGTTATTCCTTGAAATGGGCCGGTTGATCACTGAGGCCCAATTGATGTATCAACATGTGGTTTTTATAAAAGA |
| GTCGTGAGAAGAGTTTTCTCTAAAAATCCCTTGTGTTTGGTAATCAAACTTCATTCAACCAACGAATTCCAAAAAAACAACTAA |
| ATTGTTCGGGTATATAAAATGATTGGTAATGATATATCCCATAGAGGCCGTAGACATAGGCCCAAAAGTTTCCATAACTAGCA |
| GAAATTGAAACTTGCAAGTTGCAAATATTATTACACTGGAAAGGCAACAAGTCTTGAAGTACAAACTACAAAGACTTCTTGTTT |
| GGATGGGGACGACTGACGAGTTTGAATAACTTAAGAGAAAAGGGTCGCAATGAAATTAGACAAGAAATTAGTCCTCAAAAAGT |
| AAATTCTGAAGTTGAAGCTCCAATGTCTTTGTTCAAAGACTTTATTTAGATGTAAAGTTATGTCTTGTAACCACCAAACAGCTC |
| CTTTTCATCTACACTCCCAATTTTTTTAACATCTATGTTTTGCATTGCCTTTGACTTGTCTTTCTCTCTCCAACTTCCTTCTCCTT |
| CAACATAAAGCCAAATCCTAAATCCAAATCCCTTAAACCGAACCGAATTAAACCGAAGCTGTTGAACTATCGCAAAATTTCAGA |
| TCTTACTAATCATAAACATGTGACGTTTAATTCATTTTAAGAGTTTCATGATTTGCACTGAATGGTATTCCGAGTCCACCGGAA |
| AAAAACTTTTCCTACAAGTAGAAAAAGGATAACCCCATAAATCCAAATAACCTAACCGATCAAACATATACCAATATAAACCAA |
| AACAAGATTCAGATTCATCGGTTTAGTAATCGAAGTAATGTACTAAATGTACTGATTTCCGTAATTGATTCCACCACCAGCTTAGAGATTCGA |
| ACCAAAAACCGAATAGCGCATAACCGAGAAAACCCAAAGCTTCCTAACAAATACATAAAACCGTGGTGTTTCTAATTCTAACCA |
| ACACACGTTTCCTTTTTATTCACAAGAAACATCAGAGTTATGATCTGCCATTAATAACCTAAACACAAAGCAAGGTTAGGTAAA |
| TGATATGGACCCCTAATGAATAATCATACAATACATAACAACGTAAGATCCAGTTTCCCTCTTCG |
| |
| SEQ ID NO: 41 |
| Polynucleotide sequence PATNST2 |
| AACGGTGGCGTGATGGAGCTTCATCCTCCCATCTTCGCCGAATTCATCACCAACGAATTTCCCGGCCATGTCATCCACGACTCT |
| TTAAGCCTCCGCCACTCATCTCCACCGCTTCTCCACGGCGAAGAACTCTTTCCCGGTAACATCTACTACCTCCTTCTCTTTCT |
| TCTTCCGCAGCCGCGACCGCTCAACTGGATTCCTCCGACCAACTATCAACGCCGTACAGAATGTCTTTCGGGAAGACGCCGATA |
| ATGGCGGCTTTGAGTGCCGGTGGTTGTGGAGTGTGGAAGGTGAGGCTTGTGATAAGTCCGGAGCAGTTGGCGGAAATTCTTGCG |
| GAGGATGTGGAAACGGAAGCGTTGGTGGAAAGTGTGAGGACGGTGGCGAAGTGTGGCGGTTACGGCTGCGGCGGAGGAGTTCAT |
| TCGAGAGCGAATTCAGACCAGCTAAGCGTTACGAGTAGCTTTAAAGGGAAATTGTGGTAAAATTTCGAATTATGAATAAACTAC |
| GTTTATGTTTAATCTGTTTCACGATTTAAGCATTTAAATTAGTATTGTTGATTTCCGTATTCATTGAAGACTTGGAACGATTAT |
| ATAAGTTTATCAACGTAGATATATTTGAAATATCATTGTTATCTCTCATGAAACAATTAATTTATGAAGTCGTAGACTCGTAGT |
| TAGAGATTATTTAATCTTCCCTATTCAATGCCAAAAGTCTAGAAGAGCAAACAAAAGGGAGAAACTCTTTTATTTCAGGCCCA |
| ATGACACAAAGCTGGCCAGAAACAGTTTAAGATTAGGCTAAAGTTATAAGTCCGACAAGCACGAGTGCTAATATATATAGTTAT |
| ATGACGTCTCACCATTAAGGGTTTAATAAATTTTGAAACACCTCAAATTAAGATTGCTTCCCATGCAAACTTCCTTCATCTTCT |
| AGAAAAATTACGATTTGTAATACTTCAATTATATCATTTTAGTTTTTTGTCACTAATTATCATCAATTTATCATAGCTCCGTGC |
| CGCAACAACGTTCGTTTTAATCAGATTATATATTACTCTGCTATAAACTCAGAACCATGTTAGAAAAATGAAAAGACATTTCA |
| GAATATTCATTAACTCAAAATTTTAATCTCATGATTTAATTTTTTATTAACAATGTTATCCTATAGCACATGGCAAATTTGAAC |
| GGCCCTTGCGTATTAATCTATTATAATCTCAAAACCATGTGTAACAAAAAGGAAATTCAGAAAATAACCTTTTGTAAATAGGCC |
| CCCACAAAATCTACAACATACGTAGATACCTCCTCGCTTACAGTTGTAAACAACTGTTCATCTAGATTCATGCCGTCATTCAAG |
| TTTAAATTAATACAATAATTTAAAATTTTAATTGGATGAATGAATCCACCGTCGTTTCCTGAATACCAGATAGGTTAACTTTA |
| TGATTAGTTCGAGTGAACCACATGCACAATATTCGAATCTTAGACATTCGTTGCAATGTTAACTTCACATATATTTGATAAACG |
| CTTCTTGAATCAGATCTTAATCTCTTTCTTTCTCTCCATCTTCTAAGGAGGTTGTGATTAGTAGTCATGATGTATATCATTATCTTC |
| GCATCACCTTCAACAAGAACAAGCTACGAGCTTTAAAGTCGTATTTAACACAATAATGTATAAAGTCTTTCTTCATCACATCAC |
| ATACATTTTTGTTGCCATCACCCTTCATTCACTTTTTTGTTAACACTATTCGTTTCTATATAAAATAAAAATAAAATGAGGA |
| ATGTCTTGTCCATAGAGATTTTTAAGGTCGAGGGTCATCGGAGCGATGTGGGCTTGCTTCCTACATTATAGTTGATATGTGGAT |
| CCCGCGTGGACCATATTTTTACCCAATAGCTACGTGCATGGTCCCACCGCTCTCTCACGCACTATTCCGAAATTGCCATAAACA |
| ATTTCACCGGACAAAAAGAGCAAATAATTTCGATGTTTAATAAAGAGACCATTAGTATATTTGACCCAAAAAAAATAAAAAAA |
| AAAGAGAGACATTACTATAACTTTTATTAGATGAAATATTGCAACATTGTATTTATAACGGATCTAATTTACTGAATCATATTT |
| TTTTTCTTTGTTAAAGAGATACTGAATCATGCAGAAAATAGATAGATTTTTAAATACTAGGTGAACTCATGACGAATCAACCA |
| TTACGAGAGATTTCTGGATAAAAGCAAAAACAAAACAAAACTAACATGCTAATCTAGGCAATTAGTAGAGCGAAAAGTCGGCAA |
| AACCAAAGGCCGAAGAAGCTTGATCGATATACTTTTTTTTTTTGTTTTGGCTGGATATCTTGGTATGAACTAAGAATTAAGT |
| AAAAACTCATAGGGAGTAATTTTTCGAGAAGTGCATTCACTATGAGTATAAAACAGACATTTTCAAATTATTAAAACAAGCTCT |
| TAGAGGCTCATATGTTTAATTGTAAGTGGCGGCTCATGCGAACTTATAATGAAAACATCAAATATTCGGAAAATAATACTCCA |
| CTGTTAAAAAGAAAACTTAACAAAGGAATTAAAAATATGAGAGCAAAAGAACACATGCATTTTCTCATGCATGTACTATTATTT |
| ATTTTTTGCAGAGTTGATGTAAAAAATATACACATATATAGACATACTTTGGTTAGTTATAAACTCGTTCTATTTTCTTCT |
| CCTTTTTCTATCTTTAGCA |
| |
| SEQ ID NO: 42 |
| Polynucleotide sequence PATNST3 |
| ATTCTACACATTCACAAAGTTTACTACACTATATATAATTTACCCAACAAACACTTATTTTACTGCATTATTCAGTATATTATC |
| TTACCTATAAATGTGTATCATCATCATCAATAACGCGATTATTTGTGCTGAAGGATTATATATTCAAAATGATCTAGTTATATA |
| TGTCACATGATTGCCGTTAACAAGACACATTTGAAGAAGCTAAGCAAGAAAAACGGACACTTTTGCGACTTGTTACATAATTTA |

ILLUSTRATIVE SEQUENCES

```
ACTTATAGGTCAAAAGAATTTGATTAGTCATTGCAACTACGTGTGGATGTCACTTTCTATTCAACCAAAACTCACAATATTATA
TGATCTAGTTTTGTCGTATTACTGATTTGTATTATAAAATGTTATTTAATTTGAATTCTACGTAGATATTGCTCATGCATGATA
GTATGTATCTAAACTATTCAAATAACTAACTACGTGGATATTTTATAATCCAAGTAAAAAGCAGAAAGTGGGTAACTACGTCAG
TATGACTATACTTTTATCGGAATTGCTTGACATCCAAACTTTTGCTATGCTTCACCAACCAATGCAGTTTCACTTAATTATTAA
CTATTGACTATGTCTTATTAAGTTAGCACTAATTCGTTAATCATTCAAAACGTTATTTGATTGAATTACATATTACACTCTCTT
TCTGCATCACCACTCACACCATATGCAACTATAACCAACTCATCACATTCAAATGTATTAATTGGATTTTGGTGCGAGATTAAA
AATTGAAAGGAAACAAAATATGATAATGGGATAAAATCTTGAACGGAAACTCAAACTAATCCTCATAAGGTATAACAAAATAAC
AATTTAAGCTAAGCACAACAACATACAAGTTCGACCTTTTCCTTTGATGATCCAGCCCAACAGTTCTCTTATATCTCAAACCAT
TCGACCATTTGAGCCAAACTAGCTAAACCTGCAGGAATCAAAACCAACAAAGATTCAGATTAGCTAAACCGTTTCATCCCTTTG
TCACATGACTCACATCCGTCTTCTACATAACGATTTCTAATGATGTGAGCTCTTAACTTGCTCCAGCAAGATCATCAACTTTGG
AGCACCTTCAATGATTTAGTTAACATGTTAGATAAATTAAATATTCTTGTTTCAATATATATCAACTTTAGTGTAAAAGCCTTA
ACATTCTCTTGAATATTTAATTTATTTCTCCTTATTTCGATTTAATGACAAATGTGAATTAATTTTTGTGATATTTTTGTTCGA
AATTAGTTTTCAGTTAATAACATACATGTGAGCATGGGACACACATGATTTAACAAAAGGGAATGACGAATGATATATCAAAA
TATTAGTATGGGAACAAATTACGAGGTGAAACTTCACACTCAACTCAATTAAAACTAGAATAAAGAAATGGAAAAAGTGAAAGA
ATGAGAGGTCAAATGTGGTTAATCATTATGTGGTATTAGTTAATCCATCAATTGTGTACCCAAAAGCATGATTAAGCATGATTA
AGCATAGAATTTAGAGAAACAAAACATCATTATTAATGTTGAAACACAAAGATCCCATCAACAGACAAATGATAAGTACAGTGC
ATGTAGGGTAACAACTTTTATGTACATGTTATATACTTATATTATATAATAAGAAAACGATTAAAGTGTCATTGCTCCAGCCTC
TATTTGTAAATCATATTTATATCAGTATGCTTAATTCCAATAATTAAGTCCATAACTAAAATATATACACATATATGTATGTTAA
ATGGTTGAATATATACATATATTTTCATAAACAAATATTGCTAATTAATTCAGTTATTTGTGTACATAATCCAACTATCACCTT
TTTAGCTGGAAGTGGATATTCCAACATGTCAGTCTGTCACTCCCACATTCATACTCTCTATTCTTTTTAGCTATTTCAATATCT
ACGGTTAAATATTAATGGCTATATAGCCTTACCCTTCATTTTAGTTTTTTTTGGTATTCGCATAACCATCGAATACTCAAACT
TACTATGTAAGATGGTCTGAATAACTATTTCCGATTTAAGATGAATAGCTAGATTGAAATATACATGCACTAATTGGACATGCA
CTAAAGGCAGAGGTGAATTAAATGATGAAATGAAGATGAAGTGTCACACTTGTGCAAAAGCATGTCCCCTGCTCTTCTCCGCT
TGTTTCAATTTCTTTGACTTTCATCACGTTTTGTCACTTAAATACACCAAAAAATATAGTACAATTAAACATCGAAAATCGTC
CAAAAAGAAGAAAAAAAAATCATGGAAAGTTCTTTCGTTAATGTTACACACATTATCTTGATTAGGTGACACCAGATATTAGAAT
AAAAATGATAGATTATGAAAAGAAAAAAAAAAATTGATGTATTTTAGGATACATCGAAAGGAATGAACATACCAAAACATGGG
AAAAAATAGATAACTAATTAACATGGTAGAATGTAGATGACGTAGATCATGAAACGAGTGTGTGATATATTAATGAAAATTATT
TTAATATACGTAGCTATATTAGAAAATAATTTACATTTATTTTCTTCTAAACAAATCTATACTTTATATTTACATACATTAGTA
AAGACCAAAACACATGGAATTCAAATTCTGCAATAAGTAATTGCAAGAAAACACAAAGATTAATCCCCCACTAAACCCGTTTAT
TTACGTTAGTATTTTTCCGTTTTATACATTACACATGACATGACATTACACGTCAAAAGAAATATGTCTTACGTCAGAACTTAC
GTATGATCAAACTCGATTTAAACATAGAAACATCTGTTTACTAAATTATACTAATTTCATAAAGACACTTTAATGCATGAACTT
CTTTGTTAAATAACAATTTCCCCCTTTTGGGGGCTATGTCTCGTCGAGTCCTACCACCATTATAAATTATCTCATCGTTTGCT
TTCTTTTTTTAAGTTGTAACCATTTCCACTCGTAATCATACAACTTCTCTACTCTTCTAGAGCAAAAACCCAAAAATATATTG
CTATCTTCGTTA

SEQ ID NO: 43
Polynucleotide sequence PATFRA8_PATIRX7
CTTCAAATCTCTTGTATCATTAAATAGTAACGTTTTAAATATTTTCTGGATAAGCATAAGTTTCTTTGAAAACTATTTTGTATA
TATTCCTACTTCTCCATTTTTCTAAATTATTTTATATTATACATAGTTTTCCAAATTATCAAACATTTTTACATGTTTTGACTA
ATAAATAAACATATTACTGCGAATTAATTAAAAATAAATATTCCACACAATAATTACCTTACAAGCGAATAAACTTTTACTATG
TTTTCGATGTAAATTTTTCTTACATATTTGTAACTGAAATTTCTAACTTGTTGTTTCATAAGTTTTAAAATTTATTATCTAATT
ATCTACTTTTATGTGTTCTAGAGCAAAGTGCTAAATGTATATATACTTAGATGTTGTGTTGTAATCCAATGTCAATATAATCAA
TGATTTAGCTATTTGTAAACATACTAAATAGTATTCCACCAAAAAAAAAACATACTAAACAGTAAACAAACAGCAAAAACAAAA
TCCACATGTCCTAAAAGATAGTCTGATTTTCGTTCATAATGCTCTGGTTTTTGAAAGATAATAATTGTGTTGTATGAGTGTATG
ACAAATATTCATTGGTTTGAGAAGTTAACAAAATTTGGTGGCTACAAATGGTTTCCTATTCGAGTTGGGTCCATTATCCCTTGG
CGTGTACGGAAATAATACCTACCCATCATAATCTGATCAAAGATGAGGTAGTCTTTAAATAAATTTTCGGCTTATATCAATCT
TTATGTACTATAAACTGTGAACTTTTTGTTCTTCAGGACTTCCACATCATTGCCCAATCCGGTTATACCTTCGCTAGTTAATAT
GTTAATTAACATTAAATTAAAGAGCTAACATTTCTTAGGTAGTAAAATAGAAGTTTTGAACTACTATACTACTAACATGTGAAA
ATACTTTAGTCACAAATATGACAATATACAAATTTATTGGAATGCAAATTCTTGAATTTCAATTGTTTGAAAATTATATATTTC
TACATAACAATTCTTTATAAACTAAAAATATTAATTTTCCATGGCTATGCGTTATACGTATATGTCAAATATTTTTATTATTTA
TATAATTTTACGATAAATTAGTACTCCACTTTACTATATTACTCAACACTAAAAGACCTCTTTAACTCCGCCTAACATAGATAT
GTTTTCTTTTGAATGTTTCGGTTAAACATGACAGAGATTTGTTTTCTTGCTTTCGCTCAATACATATTTGTGCTCCTTTAGAAA
AGTAGTATTTCCTAACAATCCAACATTTTCATATTTATTATATCTTTTAAATATTATCATGGTTCTTTTTCTTTCGTCATGTTT
GGCCTCTTTAAAATAATTCTTGAATTGTATGAGCATTAATCCAATAACGTCCTGATCCCAAAAACCTCATATTAGGTTTGAGAG
TCCGAAAATATACTTTTCACATAAAGCACCTAAGGTGTCATACTTTAACAACTTCACAAAATATGCAAAATTTGTCATTGTCAC
TTTGAGATGTAAGTTTTTTTTACATGCAAATAGATTGAGTCTCTTTACGTGTAAATTCATTTAATAAAATTGTATGGAATATC
TATTTATATCATATATTTCTAACATATATATAAATATCTATACAAAAATACGATCTTTTGGCACATGTAATTAGAAAAATCCAC
AAGAAACAGAAAAAGAAACACCCAAATACAACGAAATGAAGAAATTATTATAAATTTGAATGGCTTAACATCTCTTAAGAGTCA
ACAAGGTAAAGGATTAATTAGTAGTCTTCATCAATCTTTCTCCACCTTCTTCTATTCCTTAATCTCCACTTTATCTCCCAAACC
CGAAAACTCCTCTTCACCAACTTAAACCCTATTAACTAATCCCAACAATCAGATGTTTCGAATTCAACAACCAGCTCAGGCCAT
AAGATTCATCCCGGAGAAACAAGAACG SEQ ID NO: 44
Polynucleotide sequence PATIRX9
CGGGTTTTCGGTTCGACCCGGACTCGAAACGGGTCTAGATGAAGAAAACCTCATCTCTTTTTGTGTCTAAGGATTTTTTGGTAC
TGAAACTCTCACTCTTTTTTTGGTTCCTCTGGTCCCTCTCTATATGATTCAGATCGAACACTGTGGTTTTATATTTTTTAATG
TTTTGTTATGTTCACACGTTGGGTTCAGAAAAATTGACGGCCGAGATCTTTTCTATAAGAGGAAATCGGTGGTTCTACTTAGCT
AATCCTTTTTACTAGAAAAGTTTAACATTTTGTACTTTTTGTCTGTATGCTCTAGTTGTTTGTTGAGATCTCTTGCTGCTAGAT
TCACTTTTTGGGACACATTGCTTTGTATTTGAAGCTAGAAAGTTTATATCAACATGATCTAAAAAAGTATTTTAAGAGAACTAC
ATTGAGGTAGTTATTTCTTTTCCTAAATTAGTCATTGGTAAATTACATCGTGACATTTATAGAACATTGCAGAGCATAAAGAT
TGAAAAAAAAATGAGCTGAGATTTGTATGTATATAAAGAAAACGTATTAGCATAGCTTTCTTTCAGATTTAACGGTGGAAATCA
TACAAAACTTTCTTGCAGAACAATGAGTATATATATGAAGGACTCGTTAACGAAAATATTAGTTTAAATCTAGATATCTTCCAG
TAAAAATATGAGTTTCGCCTTCGTATATGATACGGCAATAACTTTGGGACCAACTAATTTGCATATCACATGTTGATATCTCTTT
CAGTTCTACTCATTCTTTTTTTTTGAAACAACAAATTATTGGCTGCAAATGTTTTTGGTTTAACTAGTGCTTCTCTAATTGT
CAAGTATCTTAGTCTAGAGTTAATTACTTAAATACTAAAAGGCTGTCGACAAAATCAAGCTTGAATCTCCTTGTGGTATCTTCA
ACTCTTCGTTGTCTGCTTACGAGTGGTTTACTCAGTAATTATCTATAATATGTTATTTTTTTCCCTCATCTTTTAGTTGTTGT
TTCATTACATTGAAAAGCTTGTAATGTCTTTATATGGTATATATGGATCTTATGAGTGAGGCAAGATCCATGATGTTTTTGATC
```

| ILLUSTRATIVE SEQUENCES |
|---|
| TTAGAATGTATATGATGATCTTAGAATGTATTTGACCGCCCACAAATTATTGTTCATTGGGATTATATCTCTAGTCCAACTCCA<br>AGCAATCGAAATGGGTCCTGCTTTTAAGAACAACAGTATATGTTTAAGAATAATAACTTTATATATTCTCGATTTTAAGATCTT<br>TTGACAAAACCTCCTTTTCGTTAGGAGCGTACTAATTTCCAAGTGTTTGATTAGTGGGGTCTCCGTAAATTTATTTAGAGTTTC<br>TATCTATTTATTAATAGCTCAATTAATTAATCTATACTGTATCTAAACATCAATTTATATATTTACTCTTGAGACCAAAACTGT<br>CAATTTATAACATTGGATAGTTTCTTAATTCTTATTATATTTTTCAAACACTTTTCAAGACTAATCTCCACATTAGGTACTCTC<br>TCTAGAGATAAAATATTTATCAAAAACATTTTTATTTATTTATTAAGTAGTAGATAAACTACTGTGGCAAAATCGTAAATGTC<br>TAAATGCTGATGAATTTTTTTGCTGCTCCAATCTGGTTTAGTGCTCCATATACATCCACGGCCAAAATGAATCTATGGCGGCA<br>TTAAGATTCATTAGTAAGCAACGATTATATTAATATAATTGTTTTTAGCAATGATTTTCCGTAATTTCCCAAATATGTTTCAGT<br>TAATGTGTTCCAATCCCAACAACTGGTTGTTGCAAAAGACCACCAACGCAAGCAATCATCAAACATCAAAATAATCTTACCTTA<br>GCGAACAAACAATAACTACACAATTCTCATAAAGCTCTTATATCACTAACTTCACACTTTTGTTTTCCACAAAAATAAAAACGG<br>AACTCACTCAAGAAACCTTCTTCCTTGAAGAGAGGGTT |

SEQ ID NO: 45
Polynucleotide sequence PATGUT1_PATIRX10
AATAACAACCACTTAAGTTACTGCAAGTTACCACAAAGAAAAATGATCTAGCAAATGAGTAGCATCATATTGATCAAAGACACT
GCAAGATAAAAGTCACCTTGCTAATGTTCGAGATAATGATAAAGTGTAGACTTGGAGCAAGAAGCCATTTAAACTAACAACTTC
CTAATTGAGACCTTTCATGTAACTTAATGTCAAAATCACAAGCAACTAGAGGAAGAAATAAAAATGTACCAGGTAGCTTCTTGG
GCTTCCTCATGGGAACAAATTTGGCACCAATAGCCAACGCAATAGGAGGGCCAAAAATGAAACCTCTAGCTTCAACACCTGCAT
TTACCACAACATCAATTTAGGCAGAACCAAAAATCATCCACCAATTCATTTCAACTTTTCAGTTTAAGCTAAAGCACTCAGTAT
CTAAAAAGGCCAAAAGAAACTAAATCCACAAGCTGTTAATCGATTGGAGTACCAAACAGAACCATACGAGTTGTTACCTGCAAC
AACAGATATGCCTTTATCTTTGTATCTATCAACAAACAAAGCAATAGTATCCTTAAAGGCCTCAGTGTCGAGAAGAAGCGTCGT
TATGTCCTGAAACATGATTCCTGCCAAGTATCCAAATTAAAACCTTAAGATCCCAACGCAGATCAAGACTAGAGACGATATTAA
TCGGTATAAATGGAAAAATGGAGACCTGGTTTAGGGAAGTCGGGGATGACTCTAATGGAAGAGGCAATCTTAGCGATTCTGGG
ATCTTGCACATCTTCAGTCGCCATTTCACTGTCCCGACTGGCTGCTTTAGCAAAATACTCGGCGTCAGATTTGCAAACACA
GAGAGACCCTAAAGACTCAATAGAGAGACACAGTGATGAAAAATGACCAATTTATCCCGAATGGTAACGCTTTGACGGAATTG
CCCCACGCAAGCAAAATATCTTTTTCAAAAGGAAACAAAAAGTTTAAAAGGGAAATAGAAGGTGGTGGGGTCTACCGGCGGAGG
AGAAGAGGCGGAGTGAGGTGGTTGAACGGTGGTTTGAGAGGCGGATCGAAGGAGGAGCACGGTGGTGGTTGTTGAGAAGACGGT
TGCAAGGAACAGCACGAGCAAGACAGAGACGATGAGAACAAGTGGAGAAATTATTATTGTTTGCATTGTCTTTGGACTGAGAG
ATCTTAAAGAGAATGTAAATTACTTTAAACACGGAATAATGGACAAAAGCCGTGATCAATGACTTTTCAAGTCTTAACCAAAC
CTATAACTCATCCATTGTTTGTTTTTTCTACATATTTCTTCACATAAAATTGGATGATTTAGAATCTTTCAGAGTGTTCACACT
CCAACAGATTATTATCCACAATGTTATGGTTACATTTAGAGATATATAACAATGTTCATTTCATCGTTGCTAATGACATAAAAC
GATCAAAAACTGAATCATAGTACTTCTTTTACAGTGATCTCAAATATATTAATCGCTAATCAATGAATTATGTCACCTATAATT
GTCGTATTACCAACAACTATAAAACATATATAAAAAATTGTTGTCGTTAACTAGTTGTTGATAGTGGCCACTCTAAAACGATCA
TGACCTACTACGGAAGTTATAACTAGTCAACGTTGGACGTTAGCAAGGCCCAATGGACATTAACTCAGCCCATAATAGCACGCG
CCTTGTGATGTGCACCAGTTTCCGTCTTTGGTCGTTGAATTCAAGGAAAAAAAAGTACATCACAAGCAATTTCTTACTTATCT
GTGACTTGAAGCTATTTCTCCAATTTCGTTTTCCATCGACACTCTATTTCATTTTCACCATTCACGTCTTCCTTCTGAATAAAA
TAAACCCTAAAACCTAATACCGAAGTAAACTCGTCAACCACTGCGCCCATGACCTCCCAACGATACTCTTCCCTTATATTCTTC
CTCTTCCTTCTTCCTTTCTGCGATCCAAACCTTCAAACACATCTCCGGTAGAT SEQ ID NO: 46
Polynucleotide sequence PATIRX14
ACCTGCATCGAATTTATATAAATTTAAAACACATTATCATCATCTCTAACTTGAACTTTTAAACAAGTTTATCTTTTTGTTTCA
CAAAAAAAAAACAAGTTTATCTTTATGTCCCTCCTGAGACATATAAACAAGATTATCTTTCTTCTTAGTAGGGATATAGCAAGTC
CGGACGAGATCAAAGTAGATTGACTCTTAAGATCTTACTAAGTTTGAGCTTGCTTTGGTTCCCACCTCTAAAAACCAGTTTTG
CATAGTCTGAGACTCGTGTTAAATTCGATCAAATCTCTCTTTCAACGACGGTTAACTATGGACGTATTCGCAAAACATCACATA
AAAACATCTCTAAAGTATTTGGCTATTTGCATAAATATTTCACTCTTACAGTCGTCAAAAGTATGAATGAACTCTACATATCGG
CCCAATATGAACCAATTTGTAAGACCATAATGGAAAGCCCATGTTTCTCTTGTGCTTGTTTTAGTTGCAGAATCATTAGTTCAC
ATATTGACCGGATTATATTAGTTTTTAAAAACGCATGTATGATGTAGTCACTGTATCATACCCAAGTTACTGTATTCATTACCC
AAGTTCAAACTCGATAAAATGCATAAACTAAACATACGTTCTTTAGCCTTTTGTTTTCACTTCAATTAACTCATTTTGTGCGTT
GTATATTTTTTTCTTTCCAACAGCTACTTTTCTCACGTCTATATTTTTACCGTTTGTGATTTTGAGTCTCAAATATATGGA
ATTGTTTTTTTAAATGGCTACTTTCCAAAGTCTTATATTTTTTACCGTTGTAAATGTTCAGTTTCAGATATATATGGATTTCT
TTTTCTAATGGCTACTTCTCTAACGTCTATATCTTTTACCGTTGTAAATTTTAAATTCTGAAATATATTACCGTTTGTGATTGA
GTTCACTTGACACACCTTCGTTAAAAATTACACAACAAAAAGCGTTCACAATAAGCCCAATGGGCCTAAAAGACCCTAACAATC
GAACATACCCTTCTGACCAACACATTTTCTTAAGGAGACACTGTTGGTCCATTTACTCATTTAAGTAGGATTCATAACACTTGT
CATGGTCGTCATTTCTTGTTCAAATGCCTTTTTAAGTAATAACGCAATGGAAGCATATATATACTTTAAACCCACAAATTAATA
ATGCATATGTATCTATTTTTCTTGCATATACTAAACATGTCTAAGTATGATATAAACTTTGACACTTTGGTGGTGCTGAGTAAT
CATCATATTTATGCTTTGTGTGCAAGTGAAAACGAACCGATAACAATCTTTAAGCTTTCCCTACCAAACCGGTTTAACCTTCAC
AACAAACAAACCTAGATCAATTATCTCTAAACCAAAACCCTTCAAACCATGTCTTTTGTCGGACCAAACTGTACTCTTATATAT
GACATGCAGATACGTCGTTTTCATGGGCCTTACTAATGGCCCATTAAAAACATTCGTAATCAATTATTTTGGTTAGTCTTTCCC
AAATTCGTCTACATTCCTCCTCGATAATCACTTTTAATTAAAACCATATGAATTTACGAAAAAAACAAAAACACAATTATCATT
ATGCAAACATTTAATTCAATAAATTGAGGGATGTTTAATGTTAACATGCAACCAAAAATTATTACCAAAAATTGACTTCAATTAGAGA
CATATTAAAACGACCCTGATTTTACTCAAAACTTAATTGAAAGATTTAATTATCCAATAATAAAACGACACGTGTACCTCCTTG
TCGCTTTCCTCTGCTTTCTTCGATGGCGTTGCATCGAAGCATCAGAGAGATTGGTATGGTGGTGGTGGTGAGAGAGCAGCAACA
ACAGCAAGAAGAGAAAGCGATAATCGAACTGATTAAGATCGTGAAATCCAAGTAATCTCTGTTGCTTAATCTCAGATCTTTTTG
ATAAGGAGAAGGAAGCAGAAGAAAGAGGTCAACGAAGAAG SEQ ID NO: 47
Polynucleotide sequence PATMYB46
GTTACACTAACGGTTTCTTGTTAGATTTAGCTGACGTGTCTTTATGAATATATATAGAGTTAAATTTTAATATTTTAAGAGTAG
TATTACTTCATTAAAAGCTTAGTTGTAAAATTACTAAAGATTTTCATATATTTATAAACTATTTTTTCCTGGCAAACTTATATTA
TAAAATTTGTTGAGCGATTGTGTGATTCTTTCATCCACAATTAGATTAAAAAAATCGCAAAAGTAATACAAGAAAAATAAT
AATTTTACAAATTAATAATGATTGTTTCTTTGGCTAAGAGTTCAGATTTGCAGAGTGTTTTTTGGTCCTTGGGCGATATTACGA
AAAGTGAATTGTAAAGATATGTATAGATTGTGAGGAAATGCGAGAATAACTGAGAGCTAGGGCTATGCATGAGATGATTGAAA
TATCATGAACCAAATGGTTAGATGAGAGCTTGGAGTGAGAGGTGACACTTGTTTGAGATGGGGAATAGCGGATTAATGTGCTTG
CATGACCTTGGTTCTGAATTTTCGATTGATGAAATCTTGCATTTCGTTATTTTCAAACTTTGTCCACGAGTTTTACATAACTAG
GTTCATTCAAGTTACAACTTAAATTGGTTAGCTGACGTCTTTTTCATGCATATACAAGAGGTTGCATTTGCAAGCTTCAAAAG
AGATTACACCAAAAACAATTTCCCCTAAAGGTTAAGATATATCTTTGGCCTTCAATTCGACATTAGGAATTATGTTCAAGATTC

| ILLUSTRATIVE SEQUENCES |
|---|
| AAGATTCAGTACTATTCTAACTTCTTTTGTACTTTATCTATGGATGTCTTGTTTATGATTGTATAAAAGTTTTGTTTTTTCGG
ATGGGTGGGCTATTAATATTATAAATCATATAATATGAGTGTTCTGTAAAAAATAAAAATGATATGAGTGTAAATCGAGAACT
TAAAAAATCATGACACACGTTTATATATTAAAGAAAAAACGAATATAAAATATATGGATAAAAGGAGTATAACATTTTCTTCAT
TACAATAATTAGATTTCTTCAAGTATACGTGTTGGTGCGCGAGAGGTGGTTGTGTGAAGCCGAAGCAAAACTTCTTGCTCGCTA
AGCCTCATATAACACAAAAAAGGGTTCTGTGACACACGTCGATTTATTTTATACAATTGAAATATGCTTACATACGTATACAA
TTAATTAAATAACACAACATTTGCTTACCTTGAAAATGAAGACATCTTTGAATAGAAATAGACATGCTCATGAATATATATTAA
TGTTATATACTATCATATATCAATGTTTATATCATATATATACACACGTAAGGTTAACGAATTAGATATGTCTGTAATGTATACC
TTGTGAATGAAGAAACTAATAGAAATGAGTTATATATTCAAAAAGAACAAGAAAAGAAGAAAATAAAATTAAGAACAAGTGAAG
AGCACTTCTCCTTTTTTCTTTGATGTTTTGCATATCGGGTCTTTTTCAAAACCGTTTTCGTCCATGACCGATCAACTAACGTT
TCTTCATTTCGTCAAATTAGTTATATACAAAACATACATTTGTTGTTGGTGTATTTTATTTTATTTACCTTACACAATATATGC
CGACAAAAAAAATGTGTTTAATTTGAAAAAGAGCCAGGGTTCGGATGTTTTTCTTTTATGTTTTAAAACAAAGCAACACTATAT
TATAAATATAATATATACAATAAAAATATAATTAAGGAATAGAGATTAAAAAGGAAGAAGTGCAAATGGTTTTTCTTCCCAGAA
TTGTAAGCAAACCATACAACCATCCCTTTCTCATCATCATCATTCTCCCTTCATCAAGTCTTCTCTCTTTTCTCTCTCTATTAT
AAAACAAACTTCACTCGTTCACATCAATGGATCCTTGAGAAAGACAAACAAATTGAAGAGAAATAATAACAATTAACTCAACCA
AAAAT

SEQ ID NO: 48
Polynucleotide sequence PATMYB58
CAAAGACTAGAGACAGAGGCGTGCCAATAGCAACACGTTTGCTTTCGTCATGCAAATTGGGATATTTCAACTTTCTTCCATTTT
TTCAACCTAGTTTACTAAACTTTTCTTTTTCCAGTGCGAACCTAATTGGTTCTAGTTAAAATAACATTTTCGTAAGTTGTTCAC
CAAACAAAGGAACATATGATTATAACTTTACTAGAGATGCATGCACAATAATGCTATTGTCGAATAAATACTTATATCTTCTCC
AAAAAAGTTTCTTTATTATGTTAGAAGATCCATCAATATACTAATTGATTTTTGGTTATATGTTTTGATTTAAAGACAAAACTA
TACAGGACATGCATGTGAGAACAAAAATTGTTGTTGTTGTAGTTGCTAGTTGAGTTTTATTTATGTTGCCAAAATAACACCATG
TCAACTTTAATTTTCGTCATATAATTTAACGTAAGCATGATGTGTTTCGTCATATCTTGTTTGGCATATGGAATATAAATCATA
CTATTGATTTGGAATCTTTAACTTAACTTCCTATTAAGTAAGCGATTGATGCTGATATGTATGTTTCTTTAGATTGATGAACGT
AATATTAATCAGTAGTGGATATACATTGTATCTTTAGAATTTAGGTTAGTATATTATGGCCAAAATGACTAAATTGAGTACCAT
AAACTAAAGTTAAAGTAGTGGTAAAAGCTTACGATATTGTTTTATAACAATTTTCAAAAAGTAAAAGATATATAAATGTTAGAG
GTTTTGGATAACCATATTGTTCTATAACATTTTAAACATATGTCATATATGTTTCGTTTATAATATTTATGACTTGACCAAATA
ATTTGTGTATGTTATTTAAATCCAAATATATATGAGAAATATATAGACGACATGATTAAAATTATTTAAAAGAGTCATGATGAG
AGGGATGGAGACTAAAAAAAAGAGGAGAAAAAGATAGAACGTCGAGAAATGTTGTGTGTATAAAGTAAAGGAAAGCTAATTT
GATCATTGTATTCGAAGAAAACAAAAAAGTATACACATGTTACAGGGTTATAGGACCCATTTTCTTTAAAATAAATCCACTATG
GACTGATGTACATATTTTTTCTTACTGTTCTTAAGCATGATTTTATATGTAATAATATGGTTATAGATTAGAATTTTATTCAGCC
TTCCACGATTCTTAACCCTAACCAGTCAATTTTTTCTTCCTTATAAATATGAGTGCCAATCGGAAGGTGATAGCATCCTTACGT
CTTGTTTGGTAGATTACTAAGTCAAGTTTTATTCATGAAATTTCCACTTATCAAACTTTCTCATTTTGTTAAAATTTAAAACCG
TTTTTCAAAAGTTGGTATAGCCATAGACAGAAAAAAATTATTACAATCCTATCTGATTTGACTCAGACACCCTAATTAGTCAAA
TCTCAAAATTAGCTAATATTAACTAACGAGTTGCGCATTTTGCAGCAGTACAAAAATATGAAAAATAATTTAGGATAACAG
CACTAATCACAGGAACAGGTATTTTTTTTTTCCTTCTTTTGACATCATAAAGATGGATTCAACTTATAGATTGGTCAGAGGC
AATCTTTATAGGTTTCATGATTGAATAAAAAATATGAGACTCAGTATCTAAGTTTCAAACATGTTTCATCTGTGTTTAGTTGAT
TACATTTTCATAATAGTTTATTAATGACATATAGAAATGCGAACTATACAATTATAAAAAAGATGTGAATTTTGCCAGATACTC
ATCCACAATATAGACAAGTTTTTAACCTCAACAAATCTGATGTGACATTTGTCAATGTCTGTGGTTTATAACATGTTTCTCAAT
GTCAGGATCACACACACCCACTTCTCATGTATAAATACACATAAAAGCAATTGGATTTGGTAAGAGGGAATCTCAAAAGTGTGTG
TCTGTGAGAGAGGAGAGAGAGAAT SEQ ID NO: 49
Polynucleotide sequence PATMYB63
GTTGATATATATTAATATGTGTCCCTATTATGATCACACAAAACATACACATGCAGAGCTTTATTCCAATAGCTAAAATCTGAA
CTGAACTTTAAAGTCAGTACACTCGAAATTGATATTGACGTATGTATTACTAATAGCAACATGTGTTCTTTCATCATAAGTTTA
CATAATTTTTTAATTTTATTCTACTTAATTAATGTCACAGTTTCCATCGTTTTGATAAGGTCCATACTCCATAGGGACGTTGAA
AATTTAATTTAATTTTTCCACTCATAGTTGTCCTTTTTTTCTTAGTAAAGTTTGGGAAAGTTTTCCCACTCATACTTGTTTGT
TCACCAACCTTCTGATTACCAAGAGTCGTATAAAAATGCAAAACTAATAGATCGTCATTTATATATGTTGCTCCTATAGACTTT
TATCGACAAAATTTCCGAATTAATCATTTGTAACTTCAATACATATACGTCCAGATATTTACCCTAGTGAAAAATATTTCTTC
TTTTTCAAACCTCTTTTCCTCTCTATTCCTCCTAAGAGCTTGTTAACGTAACAAAATTGTTGGGTTTATTAACTTCAATTATTG
TCGATACTTAGTACTTTAAAATATTTGGAGTAATAGATGTAGTGATGGCTGTCGTAATTGCTTGAATAATTTTGGATGGGTA
CAGAGGAATTAATTAAGTAATGAAGGTTTGGTGGAATTAAGTAATTAACGTAGCCAAGAGCCAACAACAACACCAAACCCACCA
AACATTAAAAAAGTCAAAAAGACGTAAGTCTTTGACCTCTTCCACTCTCTTTGGTCTTTAGTTTGGTGAGTTCGTGCACTATGC
TCACACACTCCTTACGCCTTTTGGTGTTTTCGGATGTGATTAGAAATGACTTTTTAACAGTTTTTTTTTTTTCTGTCTCTCAT
TTTAATGTTATATTTAAGGATTATATATATTTCTGCTTTTTTGTATACAAAATACATAAAATCTTATCATTACCGCTGTAAATTC
TGACTGCGTACTTAGTAAAACAGCATTATTAGTGAGAGTTCATTTTTCTCGTGTTACACTGTATCTACATGATGATCACGGGAC
TATCTATTATTCAAAGTTGGTAATTATACACTGAGCCTGATTACAGAAGACTCGCAGACAAAACTAATATAATCAATTCCTC
CTATGTATACCTTAAGCTAATTCTTAATTAACAAGTTGCAGATTTACAATCTTATTTTAGTCAAAACACTACCTAATATTTTGC
CACTTTATAACTATATATTCTTACTCCTCCAAAGTATTTTTAATTAGAAATACATAAAATCTTATCATTACCGCTGTAAATTC
CTAAGACCATTTCAATTAACACTCGTCGACATGTAGTAGTTTCTTACATTAGCGAAATTTATTTCAGACAATTTTATAAGATAT
GTCAAATCTGATAATATTTTTAACACGAGATGCTAGTTTCCATTATTACTTGATGTCAAAAAAGAAGAAAATATTTAAGGA
TTTTGGTTTCTAAAAACGAATGTGAAATATTCATGCATCGGTGTTAGAAGGAAAGATAAGTTGCATGCATCATAAGGATGCCAA
ATGAAGTAAAAATGAGAAAATGGAATCATACCAAATAATCAACCATACCACAGACAGACAACCTTTTCCCACTCAACAAATCTG
ATTTGACATTTATCAATTCCTCTGTTTACATATTCATCTTTTCTCATGTCAAGATCACACACTCTTACCTCTCATATATATAAA
ACAGAACCAAATTATCTTTGGTAAAAGTGAATCTCATCAGGAACTGAGTGATATAAAGTTATATATAGAGGAGAGAGGGAGT
GAGAGGGAGTGAGAGAGAGAGA SEQ ID NO: 50
Polynucleotide sequence PATMYB83
TTTGATACAGCAACAGAAAAAAATAAAAATACAGAAGAACATTAAGAATGATCTTCTACCATCTGAGAATGGCAAATCCAGAA
AGGATGAGAGAAGAGATGATCATGATAATAGACATTCCTGGGAAACAAGAGGCTCCTGTCTGTGACTCTGAATCGTACTGTGCG
GAGGCGGTAAAGACAGAGGAGAGCGTCATTGGCGAAAACAGCCATCGCTGTGTATTGATTGTAGCCAGAAGCCATGTTTACT
AAATTTGACCCTCTCAAAACCAATTATGTCACCTTTGGCTTTGGCTTTACCAATGTTGTTGTTTTATAGGGAAAGAAGAAGTTC
GTGGGGACGTGAAGAGCATAAGGTTAATGCTCATTTCATAAAACCCCACTTTCTGTTTGTTGGTCAACGATTGTTATTGTAATG
ACTAATGACCTATAGAACAAAACCCATCTAACATGAATCTTCTTTTAAATGGATTTGGTGAAAAGACCAAGTTTTAAAATCATC |

ILLUSTRATIVE SEQUENCES

ATACGTGCGATGAAAGAATACCCAATTTGAAGCATGAGCCCAATGATAGTTTATAGGCCCAAATAATTTTGATTTATAGTCACA
GACAGGACAGGAGCCTCTTGTTTTATGAGTTGAATTGGGCCGAAGATGATACAATATAAAGCATGAGACCAATAGAGGACTGAC
CAGTTTCTTACCTTCGTTCGTCGAAGAATCGAACAGTCCCTTAATTTTTCCAGATTCAGATTAATAGCCTATGTATCATCTGTT
TGGATGTGTTAGGCTCTTTTGAATTTCTTAAAATTAGTCTAGATTTTGATTTGTGATATCCTTGTTATACAAAATTTGAATTTT
TCAGAAAATTCATACTTAATTTCATGGTAGACTTGTCGAACACTGTGATTGTTTGGGAAAAAAAAGGTTTAGTTTATATTCAT
TACGTACGTGATGCATGATGCTTAGTATGCATTAAGATAGAGTATATGATCCGTGCTCCATCATTACTTGCTATTATCGATCGA
TACTTACTATTATTGATCCTTAAAAGCTGATTTTTGCATGCGCATTATTTTCAATATGCTATTTTGAAAATATTTTTTGATGAT
GATGATTGTTTTATTTCGGTTATAAGTTATAAACGGACTCGTTTTTGTGATTGAATTATGGGCTTTTGATATCACATCAAATGT
TATTTATGTGGAAATGAATTGAGAAAAAATGATGATTTTATCTTGCACCTATTCTTAAGTTTGGCTTTGATGTGTTTGGCTTTT
GATGCTATATTTCTGTCAAAGAATCCTGAATTTATTTATTTATTTAGATTCGGTTGATTGTGTCGTAAAATGGAAGTTACTTCA
AAATAAGCCTCCTTGCAAGAGTATATATACTATATTACTTTTAGATAGTGAAAATTGGTTATTAGTTGTCGTTTAGAAAGAAGG
AAATTTTAAGAAAAAATACTGATCGTAAACTATAACCAATGTATGTATTAGTATACTTTGATACTTCAAACACACGTGTGTGGT
GCGGGGATGAGACAGAGAAAGAGGTTGGTCTTGTTCTTGTCTTTGACTCTAAACCAGTCTTTTTCGATACATTTTTCTTCACTC
ACAAGTCTATCATCATGTTTCTAACGAAGACATTTATTTTATTTATATTTTGTAACAAAAAAATGAAGACCCACCTCTTGCTTC
TTCTTCACATCCCCATTTCATCTTCTCTCTGTCTCTCTATTAGAGACTCTCTCTACTCTACCCATCAATCTCAACAAACACT
ACTTTCTATCTCTTTCTCTCTTTGTCATATCCATTACGCATATTCGTATCATTCCAAAGCAATCCCCACAAATCATATCATCCT
CTCCATCTTTCCTTGCTTCTTACAATCTCTCCAATTTCAAATCTGTATACTCTTCTTCAAAAAGGCTCCACCAGTCCAAA

SEQ ID NO: 51
Polynucleotide sequence PATMYB85
CTTAGCATACAATCTTTAATTTTTCATGGAAGATTTTTAAAACATTTCCGATCCGATTAAACAAAGAAGCGAGCGAGCCACATT
CTGACAATAATTAAGTAGACACTATGATACGACGAAGAATATTAATTTAATATTGAAAGATAGATCAATTTGTAGCAAAACCAT
GAAGCCAAAATTGCAAGTCACCCACAAGTCGCAAAGATTAGAAACATATATTGATACAGTGATCTATACGTGTACACCATGTGT
CAAATGGATATTCGTCTATACTTATTTTTCGTATCGGCGACAAAGTATTTTGTGCGGCAATTCATTATTGAAGCTTTTAAGTTT
CTTCTATGTTATGTAAAAACAAATCTTACCAAAATTAGAGACTCGTATATAATATACTTAATAGGTTTGTTAGGGTTGCCAAA
AAAAATGGTTTATCGCAATGGACTAAAGATCTCAATTCTCAAAACTTATCGGATTTTGCCATAGTTGAACCGGACCAAGCCAAT
TATTTGAGATTCTGAAAAGAGTATTATTATGGGCAAATTCTGAATATTTATGTAAAATCGGTTTTGTAAAGACTGGATCATATT
TTTATTCGTGTTTATTTCACAGCTGATAGCGACAACAATGAAAAATTCATTTTTTTGTGTGTGTCATCAACTATTAGAGTCGG
TGATTTATATACAGTTTTGGTGACAGAATAAGTGCCTACAACTTAAAACTACACTAGTTTTAGTTATCAAGATCCTTAGTACTT
AATGTTGAAATTAATACATTTTTTAATAAATAAATACAAAGTATATTTATTTGAAACTTGAGCAAGTATTTGAGTAAAAAAGGT
ATGAATCGCACGTGTGATTGCGTACATTCGCACGCATCCTATCCTTTCACATTAGTTCCAAAGTCATTTTCACCAACCAAATGC
GACATCTCCAATACTCCTTTCTATGATCCTACTAGCAACAGATTTGACAAAGTAAGCAAAATTATATTTCTTAACCTTAATCAT
TTCTGACCAAAAAAAACCTGAATCATTATTTATTAGAATAATCTTATTTTATCAGAATTCGTAATTCTTTAGCTGACTAACTCC
TAATTAAAATGAACCATTCAATATAAAAATATAAACGAACGTATTATGTATAAAGTCAGATACGAAGATCTTCTTTGAAACTG
TTGTAATTTCCCCATCATGACACCTGTATATACATACGTACCTTAAAAAAAATTCTGATCTATATGTACTTTTGTATGAACGAGT
AATGCATAATTCTTATTTAGATTAGACATTCTTTAATGATAAAATAGTGAAGACGGGTATTATACATATATTAAGTCACTATTA
GGGTGATTAATTGTATTTATATACCAAGAAATCTCTAAGTGACAACATTATGAGGGTGATTAGTAGTCCGTACTGTTTTTCATT
CTAACCAATCACATAAAAGAATACTAAAAGCGACAAAAAAAACTATTATCAGCTTTTTATCCATTTTATATGTTCGTTATTTA
TACCGTTTTTAATTATTTATATGTTATCAATTACTTTTTTCATATCGACAAAAGATTTTATAATTTTTTGTGTTACCAATCGAA
CCATGTATATATATAACCGTTACTAGTTAAAATGCTTTGCCATAATGCCACTAGAATTTTTAATAAAAGTTACTAAAACAATTT
CGAAAATATTAAGATGTAAAGTTATTTTTTCCTGAAACCATTGTGGGGGAAAGGTGTGAGAAGGTTATATATAGGTGGGTGAGC
TTTGGTAAGCTTTTGACATAACTTGCAAGCTGTTGAGATTTTCCATCCTCGATAACTTTATTCTTCCATATCTCTTCCATTTCG
CTCTCTATTTCACATCCCCATATAACATAATATACAATACACACATATCATTTCTATATAGTATTTA SEQ ID NO: 52
Polynucleotide sequence PATMYB103
TGGTGCCCTGGTCTACAGTTCCCTAGTTAAGATTCTATTTTGACAACAAAATTGATGATTCCAATCATCCATATTTGTTATAGG
GAGAAATTGAGCATGCTATATACGGTGATATATGATATTTATTTAATATATTGAATAACAAACACAGAACTAGTGTTATAGGTG
CAGGTAGTGTAAATATAATGTGTAAAACATTTTTTATATAGATTGGAAAGAATACGAGATTGTTGTTGCTCTGTTAGAACGAACA
AACAGAACTAGTGTTATAGGTGCAGGTAAGGTAAATATAATGTGATAAACATTTTTTATATAGATTGGAACAAATAAACATTTT
TCTGTTAGAACGAACAAAGGCCTGTCAAAAGAACAAACCTGATGTGACATATTACATATATGATTATAATTGATTATTGTATAT
ATAGTATTGCATGACTATCTTTACAAGATTTCAATACGAAAATAAATTAAAAGGAGAAAATTTATAAACGAAGCGATTTCATTC
TCGGTAAGGTTTTCCGATATGTCTCCTAACTAAATCAAAGCCTTGTAATTGAAACTTGTAATGATTGTTATTCTATATATCTTT
GAAGAAAGCTTCGGTATTGGACGTACTTAATATAATTGGATTTTATTTAAATTACAAAAATCACTGTATAATTCGGCTACATGA
CTTAATCAATTATTTCACGTTGAAAACAATACTATATCAACTTCAAATACACTCCTTGTGTATGGATTCCACAAGTTCTTTTCT
ATCTATAGAAATATAGAATCCACAAGTTCTATCTACTTTTATTAGAATTTTTATTGTTCGTTGTTGTTAACATAATTATAAGC
AATAAATTCAAAAAAAAAAAATCTAAAAGACACAAAATTTCCATCTTTGATAGGGCTTCGGAATCATTAATTACTTTTTACAA
ACAAAAAAGAAGAAGATAGGGCTTCGGAATTATTAGAAAGATGGAAGGATATTGTATTAAATTTGGCTTCATATTTTCCTTTG
GTTTGCGGCCATCAAGTACTAGTACTACTCAGTACCCACAGGCCACAGGAAAAAAGTAGTACTGCTTTATTAAGTGTGTTACG
ATAAATGGAAAGCGTTTTAGTATGTGATTACAAATTGTTGTATGTGATCATTAATTAGTTATTGGTCCGACTTCTAAGTTTAAA
TATTTTCAGAATTCAGTTAGTTTAATTATACATGTTAGACGAAATGACTCTTTTTGAGCCAATATATGTATCTGAATTTTT
CATTTTGAAAAATCTTTTTATAAAATAATAGGTCAACCTCGAATTATTATAATAAATAAATAATTTGCGTTACTATGAAAATT
AATTTACTGAATACAGTATATGAGAGAGATAGAAATAGAGGAAAACAGTGGATAATACATGATTAGTTGATACTCATGTGCAGC
GAGTCTATATATTATATACTCATGATTAGTTGATACATATGTGACGATTAGTTCTACGAATCAATCTCTAGTTTTCGTCTTAAA
ATCATTTGGTTTTATAGAATATAAGAAACAAAGAAACAGGAACTTTCGCGGGAGACAGAAGGGTACGTGAAGAGAAAAACACA
TAAAAGTGATAAGGGCTTAACGTAATAATACTACAACAAAACCTCTCTACGTACAACGAGTAATAACATAGAAAATAGAAAGT
CGATGAGACATCGTTTTAAGGTTAGATCGATGAAGAAATATCTCAGGCCCCACCCCTGGGACCCGACCCGACCCGACCCGACCCT
GACCTTTGTCTCCTCTCCTTTTAAAAACTCTCCATTGCTTCTTTGTCTTCTCTCTTCTATAACATAACTCAAGAAATTAAAGAA
GATAGATAGAGAGAGAGAGAGAGAGTAAAAACCTAAAGGGTGATATACTTATATAAAAATTAATTTAAGATTGTGATTAAGTGG
TTCACTATATTTAAGTTACTTTGAGGAGCTACTAATC SEQ ID NO: 53
Polynucleotide sequence PATCADC
AAAGCAAATCGATCTGCCAAACATATCACAGCTCTTGGAGAAAATGCAGGTCTCTTCAGACTCTGATATTTCGGATCTCGATAG
CCTTAAATTCGATGCTCCATTGCCTAGTCATATGCAACTAAGCTTTAATTTGTTGAAATCTAGAGTCGAAACTTGTGACAAAAA
TTAGATTTTTTTTCTTACCGAGCTTTCTTCTTTGTGTTCATTGAGGCCCAAGTATTTGTGTATTTGGACCTGAATATTCTCATA
CAAAGATAAATAATTATAATTAAATGATTTTTCGCATATAATCATTATTGTGGTATGATTAACACAGTTGGTGTGATGACTGAT

| ILLUSTRATIVE SEQUENCES |
|---|
| TGACACAATAATCCACCGTTTGGATTCGATTCCTTTAATACTTGTCACTAGAGTTGTTTGACTAAACAGCTAACTTGTCACTAG<br>AGTTATTGTGTTTGTATTTTGATCTGTTATTAATCTGATTGGGTATAATTACAGATAGAGAGACATCTATATTGTAATTAAGAC<br>AATCTTAAAGTGTAAACTAAAAAGATCTCTCTGACCTCTGGAAAACGAAAGGTGGGTGACACATCACTCTAGCTATGAATATGA<br>TGAATATTCAGTACCTAACCGAACAAAGACTGGTTTGGTATTTTTATTGGAAAAAAGAGATAAATAATTGTGAATGTGAATTAT<br>CCTGTCTGAAAGGTAAGCTGATGACATGGCGTTATATGATTGGACGAGCTTCAGAACAAAAGAGTAGCGTCGAATCGAATCTTT<br>ACCTACTACACTTTGAACTTTGAAGTACATTACCTACTTCCTCCTTGATCGAACGTCTTTTCTCAAAACTATTTTATTTCCCCA<br>ATTAAAGTAGTGGTGATAAATTCACAAAAATACAAACACTTTTATTTTTGACGTCAAAAACAAATACTTCTTTGAACAGGCTAT<br>TACAATATTTTTAAGAAAAAAGTAAGCAAAATAGTCCACAAACCAAAATCTGTAACATATTAAACGATTTATGTTTTTTTTTT<br>TTTTCTTAACTAGAGAACAATTCGGGCTTTTACTAAGGATGATGAGTGTAGTTACCGAATAGTGTATTCATATAATCTTTTAAT<br>GAGCTTAAGATATGATATTATTTCGACTAATCAGATAAGAGTAGTTAGATAATTTCGTAATAGAGCAACTCTTTCGCAAATAAA<br>ACCATTGTAAACATTACCAATTAGTTTTTCTTTTTTTTGGTCACAACCAATTAGTTTGTTTGTTCTATTTTATGAAGTGCGTA<br>TTAAAGCTAACGTGTTTACAGTAACGCCACACAAATAAAAATAAAAATAATTATGTACTTTATGGATTTATAGAAAAAACAAGA<br>ATAGTCACCAAAAATTGATTGTGTCATATATCTTTTGTCAACTATTTTATCTTATTTTTCTATGGATATGTATGTCCAAAATGT<br>TAGACAAAAAACCAAAAAATCATGTCCAAAATTTCGTTAGGCTGCCGATATCTCTGTTTCCCTTTCAACGACTATCTATTTAAT<br>TACCGTCGTCCACATTGTTTTTAATATCTTTATTCGAGGTTGGTTTAGTTTTTTTTACCAAACTCACTTTGCTACGTTTTTGCC<br>TTTTTGGTATGGTTGTATTTGTACCACCGGGAAAAAAAAGATAAGAGGTTTGGTTGGTCGAGCTTACTGATTAAAAAATATACA<br>CGTCCACCAAATATTAAACAATATATCCCATTTTTCCTCCTCTCTTTTGGTATTACATTAATATTTTATTATTTCCCCATTTG<br>CTCTGTATAATAAACATATGTCAATAGAGTGCCTCTACAGTCATGTTTCCATAGACATAATCTCTCACCATTGTTTTTCTCTGC<br>AAAACTAAAGAAACAAAAAAGAAAAATCGGAGAAACCAAGAAAAAAGAA<br><br>SEQ ID NO: 54<br>Polynucleotide sequence PATCADD<br>GCTTCGGTGATGCATTTCTCCTTCTCATCAATCATCCTAGCAATGTTTTGAAGCTGAGAAATTCTCCACTCGTAGCTCTTCGTT<br>CTGCCAGAGTTGAAGTTGCTTCTGAGCTCATCTACAAGCAAAGCTGCTTCTTTTCCACTAAAGTCTGATGCTTGCTCCTTTACC<br>ACAGCAGATAGTGTTGCATAACAAGTACTGATTCAAGACACCAAAACCGCAATGTGAGAGACTTTAAGACTAAAAATCATGGAT<br>AAGACTAAAAAAACATGGATAAGTATCAACTGTTCTCACGATTATTTATTCATACCACTGTACTTAAACTTAAAACCCACTATA<br>CTAAATAGAAAGGTAATCATCAAAAAATCAGTATGTAAAAACCACTTTTGTGAATAAAATATGTAAAATGGGTGAATAAAGAAA<br>TGTGCTTACAATTTCAACCGATAAGGGATACAAGCATTGCTGCAATATCTCCACCACCACCACGACGAGATATCCGAAAAGGTGAA<br>GTTGCAACATTTAATCTGCAACAAAAGAGGCCATTCATTAAAATGGTACTAATTAGATCTAATCATATCATATTGAATGACCAA<br>ATCATTCACAGAAGCATCCATTGCTCCAATTAACATTCTAGACCAAATTCAACTTAAAGGTAACTCTTTTATACAGGAAACCGA<br>GAAACCGAAAACGCAATTCACATAAAAAGGAAGGCTTGTTTGGAGAAGCAGAATCGAACAAGTCAATCTCAAACCCTGATGAGC<br>AGGTTTTTCAAGTTACCTGGCAGGAGAAAAACCCTTGGCAAAACAAAGGGTTTGAATATGATTAATCTCTAGAAGCTTCGTCAT<br>GACTTGGGTTCAGTTAAAAATCTCAAATTGGAGACATTATTGGTGTTTATATATTTGAGAGAGAGAGCCAGAGAGGAGACGTTG<br>AATTGAATGAAGGGTGTGGTCGGAAGAGAAGACGTGTAGAAGAGACGAGACAAGTAAATTTAAGCATTGGCCCCATTTACAGCC<br>ACAAGTCCGCTACAACAAATTATTTCCAAGAAACTCTGAGATAACGTCGTGATGAAACGGCTCATGCTGCTGTTGTGATTCGTG<br>AATTAGAGGTTTATCTTTTGAAGTGTTACTTAATTGGACGGTCGATTTTTCAAACTGGGTGTGAAATGTGAATGGGT<br>CATTCATAATGGGCTTTTGTTTTAATGTGAAGCCATTCACACACTCTTTGTCCTTCTTTTCTATTATTCATAACTGTCACTCTT<br>TGTTCTTCGAAATAGTAAAGAGCAAATCGATTCTTTGTTGATCTGGGCCGTAAAATTTCCATGGTTGTGGGAAGTATTCTCGCA<br>GCTGATCTGGGCCGTCAATGCTACAGTTTCATGTCAGAGAGAGGTCAAGAATCAACACGTGGCCAACCATGATTTTAAACCAAA<br>GCAAACACACGATTAGACCCCACATTGTTTGTTCACCAACCCCCGTGGACCCTCCTTTAGCCGACGTGTCCACGTCAATAGTGG<br>TTTTTCTTCCTTTCAAAGTACACAAATTCCATTCTTTCTCATTTTACTTTTTGGATTACGTTGTTGTTATAAACTGGTAAAATG<br>AATTATGAATGCAAATAAATTTCATTTAAGTTTTGTTGGCTTCTAATATTTTTTCACCTAAAATTCTAATAAACTACACAGCC<br>ATGAGCCATCGTATGAAAGAAGAAGAAAAAAATGTCTTTTCTAGAAGGATCTTTCAACGACTAAAAAGATTTTAAGCTTT<br>TGACTAATTTTGTCAATAATATACACAAATTTACACTCAATTATAGCCATCAAATGTGTGCTATGCAGAAACACCAATTATTTC<br>ATCACACATACGCATACGTTACGTTTCCAACTTTCTATATATATATAGTAATACACACACATAAACAGCAAAAGCGTGAAAGCA<br>GCAGATCAAGATAAGAAAGAAGAAAGAATCATCAAAAA<br><br>SEQ ID NO: 55<br>Polynucleotide sequence PATPAL1<br>TTTTCCCAATGATACAACTATAAATCAAAAAGAAAAAATGTACTGATAAACGAAACTAAACGTATAAATTAATATATTTCTTGA<br>CATAAATAGGAGGCTTTTGCCTGCTAGTCTGCTACGATGGAAGGAAAAATGCATGCACACATGACACATGCAAATGTTTCAAT<br>GAAGACGCATTGCCCAATTAACCAACACACCACTTCTTCCATTCCACCCATATTATTTATTTCTACCATTTTCTTTAATTTATT<br>GTTTTTTCTTTGATTCATACACTGTTTATGACTATTACATTTTCCCTTTCGACTAATAATTAACGCGTTTAAACCAAAGAATGGA<br>TTTGATAATGAAATTTTATTTTATTAGCATATAGATAATGGATGGCTTCATGCTTGGTTTCCATGCAAGGAATGACACAAGAT<br>AATTATTTTGAATAAAATCATAAATATGATAATACTAGTTGTAAAAAAACTTGAGTGTTTCGTGTGTTATTTTTCGGTTTCTTG<br>ACTTTTTATATTTCTCGTTTTTTGTAATTTTAGGATGGATTATTTAGCTTGCTTTTCTCTTTTATTACTTTCTAAAATTTTATT<br>TATAAACTCATTTTTAATATATTGACAATCAATAAATGAGTTATCTTTTAATTAATAAAAATTTGTAAACTCTTGTAAACAGA<br>TCATAGTCACTAAAAGCTATTATAAGTTATTTGTAGCTATATTTTTTATTTCATGAACTTAGGATAAGATACGAAAATGGAGG<br>TTATATTTACATAAATGTCACCACATTGCCTTTGTCATGCAAACGGCGTGTTGCGTCACTCGCCTCCTATTGGGAATCTTATAA<br>TCGCGTGAATATTATTAGAGTTTGCGATATTTCCACGTAATAGTTATCTTTCACAAATTTTATACTCAATTACAAAATCAACGA<br>AAATGTCATTTGTATCTTTAACTATTTACGTTTTTTTTACGTATCAACTTTCAGTTATATGTTTTGGATAATATATTTTTTA<br>CTTTTGACTTTTCAGTTTTCACCTAATGATTGGGATATACATATGCATGCATAGTTTCCCATTATTTAAATGTAAGCTAAGTGA<br>TATGAACTGTTAGTCAAAATTACGAAGTTTATTTGTACATATATAGTTATAACAAAATGGTACAGTAAATTAAACAGAACAT<br>CAAGAAAGTACAAAAGACTGAACACAATAATTTACATGAAAACAAAACACTTAAAAAATCATCCGATAAAATCGAAATGATATC<br>CCAAATGACAAAAATAACAATATAGAAAATACAAAAACAAAAACAAAATATGAAAGAGTGTTATGGTGGGGACGTTAATTGACT<br>CAATTACGTTCATACATTATACACACCTACTCCCATCACAATGAAACGCTTTACTCCAAAAAAAAAAAAAACCACTCTTCAA<br>AAAATCTCGTAGTCTCACCAACCGCGAAATGCAACTATCGTCAGCCACCAGCCACGACCACTTTTACCACCGTGACGTTGACGA<br>AAACCAAAGAAATTCACCACCGTGTTAAAATCAAATTAAAAATAACTCTCTTTTTGCGACTTAAACCAAATCCACGAATTATAA<br>TCTCCACCACTAAAATCCATCACTCACTCTCCATCTAACGGTCATCATTAATTCTCAACCAACTCCTTCTTTCTCACTAATTTT<br>CATTTTTTCTATAATCTTTATATGGAAGAAAAAAGAAACTAGCTATCTCTATACGCTTACCTACCAACAAACACTACCACCTT<br>ATTTAAACCACCCTTCATTCATCTAATTTTCCTCAGGAACAAATACAATTCCTTAACCAACAATATTACAAATAAGCTCCTATC<br>TTCTTTCTTTCTTTTAGAGATCTTGTAATCTCCTCTTAGTTAATCTTCTATTGTAAAACTAAGATCAAAAGTCTAA<br><br>SEQ ID NO: 56<br>Polynucleotide sequence PATPAL2<br>TTTCCCTGTTTTTTTCCCCTCTTTCTGTTTCCCATTTGAAAGTAAAAGATCATTTAAGCACCTAACTCAATTTTATTTTATTT<br>TAAACACCTAATGTCATGCTCCTTGGCTCCTTGTAATTAGTTGATCGTTTCAATTTAGACCAGCAAAACATTTAGTATGTTCGT |

| ILLUSTRATIVE SEQUENCES |
|---|
| AAATATTGCGTACATGCCATTTCGTTTGTCATGCAAACGGTGTGTGTTTCTTTACTTAGCTTCTAGTTGGTGTATATTGCGTCG
CATTAATATCGGTTTACCTTCCTCCTGTCTACGTAATGATATATTCTCCACCACAAATTTAAATTCTTATTGAAATTTCCTAAT
TTTTTAGGTAGCTCAAGGTCTCAAGTATACTACGTACCCTATTTTTTTGAATATCTATCTATATTATAACAAGAGTTTTTCTGA
GCTAGTTAATGAGATGACAATATTCTACATAAATAAATGACCCTCGAAAGTTTCAAGTACTTTAGGGATCTGACCAAATCGGGGT
AAAACATTTTGAAACTAATTACGTTCACATCTACCATCGATGATTGACAAGCTTATTGTCACCTTTTATGTTAAAGTGACATGG
TCTTGACGTTAATTTGCATGTTATTCTACATCTATAGTCCAAAGATAGCAAACCAAAGAAAAAAAATTGTCACAGAGGGTTCAAT
GTTACTTAGATAGAAATGGTTCTTTACAATAATAAATTTATGTTCCATTCTTCATGGACCGATGGTATATATGACTATATATAT
GTTACAAGAAAAACAAAAACTTATATTTTCTAAATATGTCTTCATCCATGTCACTAGCTCATTGTGTATACATTTACTTGCTTC
TTTTTGTTCTATTTCATTTCCTCTAACAAATTATTCCTTATATTTTGTGATGTACTGAATTATTATGAAAAAAAACCTTTACAC
TTGATAGAGAAGCATATTTGGAAACGTATATAATTTGTTTAATTGGAGTCACCAAAATTATACAAATCTTGTAATATCATTAAC
ATAATAGCAAACTAATTAAATATATGTTTTGAGGTCAAATGTTCGGTTTAGTGTTGAAACTGAAAAAAATTATTGGTTAATAAA
ATTTCAAATAAAAGGACAGGTCTTTCTCACCAAAACAAATTTCAAGTATAGATAAGAAAAATATAATAAGATAAACAATTCATG
CTGGTTTGGTTCGACTTCAACTAGTTAGTTGTATAAGAATATATTTTTTAATACATTTTTTTAGCAACTTTTGTTTTTGATAC
ATATAAACAAATATTCACAATAAAACCAAACTACAAATAGCAACTAAAATAATTTTTTGAAAACGAAATTAGTGGGGACGACCT
TGAATTGACTGAACTACATTCCTACGTTCCACAACTACTCCCATTTCATTCCCAAACATAATCAATCACTCGTATAAACATTTT
TGTCTCCAAAAAGTCTCACCAACCGCAAAACGCTTATTAGTTATTACCTTCTCAATTCCTCAGCCACCAGCCACGACTACCTTT
TCGATGCTTGAGGTTGATATTTGACGGAACACACAAATTTAACCAAACCAAACCAAAACCAAACGCGTTTTAAATCTAAAAACT
AATTGACAAACTCTTTTTGCGACTCAAACCAAATTCACGTTTTCCATTATCCACCATTAGATCACCAATCTTCATCCAACGGTC
ATCATTAAACTCTCACCCACCCCTCATACTTCACTTTTTTTCTCCAAAAAATCAAAACTTGTGTTCTCTCTTCTCTCTTCTCTT
GTCCTTACCTAACAACAACACTAACATTGTCCTTCTTATTTAAACGTCTCTTCTCTCTTCTTCCTCCTCAGAAAACCAAAACC
ACCAACAATTCAAACTCTCTCTTTCTCCTTTCACCAAACAATACAAGAGATCTGATCTCATTCACCTAAACACAACTTCTTGAA
AACCA |

SEQ ID NO: 57
Polynucleotide sequence PATC3H
ATCGTAAGTTTTTTTGTGTGTGTGTTAACAATGTACTCACTACTCACTGTTCCATATTTTTGATGTACGTATATCGAAAACATT
CTGCCAACAAATGCAAACATAACAAAAGTCAAAAACAATAACATAACCGGGAATTAAACCAAAATGTAATTGCTTTTTATTAGT
GTCAGGCCTTCTGCTTAAAAATATTCTCGGCCCAGAGCCCATTAACACCTATCTCAATTCATATTGAAGAAAATGACTATATTA
CTTGACAAAAACTTTAGTCAGAAAAATATGGAATCTCTTTCGGTACTGCTAAGTGCTAACCTTAAATAGTATAGAATTCTTAGT
TCATTCTCAAAAACATAGCTATATGTAGATTATAAAAGTTCGATATTATTTCCTGCAAAAGATGTTATAATGTTACAACTTACA
AGAAAATGATGTATATGTAGATTTTATAAACTGGTACCGTAATTCATAAAAGATGGTGGTGGGTATGTATCAGTAACGGAACTT
ACATATGCGTGTGTATTACTATGTCTATATGGTGTATTCCTTTGTGTGGAACAATGCACGTCAGAGTTGTTTATTTTCTTATAG
AATTTAAGGAATCAATTATTGGATTTCTCAAGGTGAAAGTGGACTTCTTTGCACGCAAGGTCTAGTTGCCGACTTGCCGTTGCA
TGTAACATGATTGTTGAAATAAAGTGAATTGAGAGAAGTTTGGCCAGACATTTTAAATTTAACCCAAAAAAAAGTAGGGCCTAAC
ACAAAATATAACCTCTCTTTGTTCAAAGGAAATAACACCTACGTCTTATAATTGAACAAACATTGAATCATTGAACTCCACCTA
TAATAATTATAATAACACGATTCACAAGACACCTAAAAGAAAAAGTTCACAAAAACAAATAAAAATTTACCTCTCACCAAACAC
ACTCACCTACCCGTCTGGTCCCACTGACCCCAACATACAACACCGACTCTCTCCCACACCAATTTTTTTTTTTGGCGTTTTAAA
ACAAATAAACTATCTATTTTTTTTTCTTACCAACTGATTAATTCGTGAATAATCTATTATCTTCTTCTTTTTTTGTGACGGAT
GATTAGTGCGTGGGGAAATCAAAATTTACAAAATTTGGGATGATTCCGATTTTTGCCATTCGATTAATTTTGGTTAAAAGATAT
ACTATTCATTCACCAAGTTTTCAGATGAGTCTAAAAGATAATATCATTTCACTAGTCACTTAAAAAAAGGGTTAAAAGAACATC
AATAATATCACTGGTTTCCTTAGGTGACCCAAAAAAAGAAGAAAAAGTCACTAGTTTCTTTTTGGAAATTTTACTGGGCATATA
GACGAAGTTGTAATGAGTGAGTTTAAATTTATCTATGGCACGCAGCTACGTCTGGTCGGACTATACCAAGTTACCAACTCTCTC
TACTTCATGTGATTGCCAATAAAAGGTGACGTCTCTCTCTCTCACCAACCCCAAACCACTTTCCCCACTCGCTCTCAAAACG
CTTGCCACCCAAATCTATGGCTTACGGGGACATGTATTAACATATATCACTGAGTGAAAAGAAGGGTTTATTACCGTTGGACCA
GTGATCAAACGTGTTTTATAAAAATTTGGAATTGAAAACATGATTTGACATTTTTAAGTGGCAGCAGACGAAACCAACAACA
CTAAGTTTAACGTTCGTGGAGTATACTTTTCTATTTTCGAAGAAGACATATAACTAAGCTGATTGTTATTCTTCATAGATTTCT
TTTCACTGCGAATAAAAGTTTGTGAACATGTCACCGTTTGAACACTCAACAATCATAAGCGTTTTACCTTTGTGGGGTGGAGAA
GATGACAATGAGAAAGTCGTCGTACATATAATTTAAGAAAATACTATTCTGACTCTGGAACGTGTAAATAATTATCTAAACAGA
TTGCGAATGTTCTCTACTTTTTTTTTGTTTACATTAAAAATGCAAATTTTATAACATTTTACATCGCGTAAATATTCCTGTTTT
ATCTATAATTAATGAAAGCTACTGAAAAAAAACATCCAGGTCAGGTACATGTATTTCACCTCAACTTAGTAAATAACCAGTAAA
ATCCAAAGTAATTACCTTTTCTCTGGAAATTTTCCTCAGTAGTTTATACCAGTCAAATTAAAACCTCAAATCGAATGTTGAAA
ATTTGATATCCAAGAAATTTTCTCATTGGAATAAAAGTTCAATCTGAAAATAGATATTTCTCTACCTCTGTTTTTTTTTTCTC
CACCAACTTTCCCCTACTTATCACTATCAATAATCGACATTATCCATCTTTTTTATTGTCTTGAACTTTGCAATTTAATTGCAT
ACTAGTTTCTTGTTTTACATAAAAGAAGTTTGGTGGTAGCAAATATATATGTCTGAAATTGATTATTTAAAAACAAAAAAGAT
AAATCGGTTCACCAACCCCCTCCCTAATATAAATCAAAGTCTCCACCACATATATCTAGAAGAATTCTACAAGTGAATTCGATT
TACACTTTTTTTGTCCTTTTTTATTAATAAATCACTGACCCGAAAATAAAAATAGAAGCAAAACTTC SEQ ID NO: 58
Polynucleotide sequence PATCCR1_PATIRX4
AAAATTGTGTCTAAGAATGTGGAACCGAGTAGTTCTCCAGAAGTCAGGTATGAAAGTATATAAGAATTCTAGTTTTAGTTGTTT
GAAAGTTTGATCCGTGAGTGAATTAGTTCACAATTATGGATGTAGATCCTCTATGCAAACAATGAAGAAGAAAGACTCTGTAAC
AGACTCCATTAAGCAAACAAAAAAGAACCAAAGGTGCACTGAAGGCTGTAAGCAATGAACCAGAAAGCACTACAGGGGAAAAATCT
TAAATCCTTGAAAAAGCTGAATGGTGAACCTGATAAAACAAGAGGCAGAACTGGCAAAAAGCAGAAGGTGACTCAAGCTATGCA
CCGGAAAATCGAAAAGATTGTGATGAGCAGGAAGACCTCGAAACCAAAGATGAAGAAGCAGTCTGAAATTGGGGAAAGAATC
AGATGCAGAGCCTGATCGTATGGAAGATCACCAAGAATTGCCTGAAAATCACAATGTAGAAACCACTGATCGTATGGAAGATCA
CCAAGAATTGCCTGAAAATCACAATGTAGAAACCAATGATGGAAGAGCAGGAGGCGACGAAAAGAGCCAACGGCAGAGTC
TAAAACTAATGGAGAGGAGCCAAATGCAGAACCCGAAACTGATGGAAAAGAGCATAAATCATTGAAGGAGCCAAATGCAGAGCC
CAAATCTGATGGAGAAGAGCAGGAGGCAGCAAAAGAGCCAAATGCTGAGCTCAAAACTGATGGAGAAATCAGGAGGCAGCAAA
AGAGCTAACTGCAGAACGCAAAACTGATGAGGAAGAGCACAAGGTAGCTGATGAGGTAGAGCAAAAGTCACAGAAAGAGACAAA
TGTAGAACCGGAAGCTGAGGGAGAAGAGCAAAAGTCAGTGGAAGAGCCAAATGCAGAACCCAAGACCAAGGTAGAAGAGAAAGA
GTCAGCAAAAGAGCAAACTGCAGACACAAAATTGATTGAGAAGGAGGATATGTCTAAGACAAAGGGAGAAGAGATTGATAAAGA
AACATATTCAAGCATCCCTGAGACTGGTAAAGTAGGGAAACGAAGCTGAAGAAGATGATCAGAGAGTGATTAAGGAACTGGAAGA
AGAGTCTGACAAGGCAGAAGTCAGTACTACGGTGCTTGAGGTTGATCCATGAATGAAGGATTGTTAGGTAAATGTTAATCCAGG
AAAAAAAGATTGGTTCTTGTGGTTTAGGTAACTTATGTATTAAGTGAAGCTGCTTGTTTAGAGACTAATGGTGTGTTTTATGAG
TAGATTCTTCTGACCTATGTCTCGTTATGGAACTAGTTTGATCTTATGTCACCTTGCTAGCAGCAGATATTGATATTTATATAT
TTAAGAGACATGCGCATGAGAATGAGGGTATGGAAAAGTCCATATCAGATGACACAAACAATGATCGTATGTGTAGTCACTTGT
GCATTTCCAGTTTTGGACATAAAATTCTGATATTGCATAGAAATGTTTTTAAATAACACTAATCCAAACCTAAATAAAATATCT

| ILLUSTRATIVE SEQUENCES |
|---|
| CTATACATCATCTAGAAATGTATGGCTTGATCAAGAATTGTAGATAATAATACCCTGAGTTAAATGATTGTAGGTATTATTTCA<br>GTTTTCAAAATTGTCCAAATTTATGAGCTATATTAAAGATAATATTTTCAATAAGGTGTGTAGTTCTAAATGTTTCTTCTTCTT<br>CCACCAACCCCTCTTTCTATATGTAGTTCTTTTTTCTAAAATAATTGTTTGTTCTTTTTTAGATATATCAAATTAAATATAAAA<br>AATATTGACAAAACTTATTTACCATTGTTAGGTGAACTTGGCAAGTGTGTAAATATAAAGATAACATTCCTTTTCGTTCTTTAT<br>ATATACGAAACGTACCACAAATTTCTAACTAAAGCATTCATAGTCTCTCGAAAGCCTCTTTTCAGAACCGAAGCTCTTTACTTT<br>CGTCCACCGGGAAAT<br><br>SEQ ID NO: 59<br>Polynucleotide sequence PATF5H<br>AAATTTTTGTATGAAATATTTCTTTAACGAAAATAAATTAAATAAAATTTAAAATTTATATTTGGAGTTCTATTTTTAATTTAG<br>AGTTTTTATTGTTACCACATTTTTTGAATTATTCTAATATTAATTTGTGATATTATTACAAAAAGTAAAAATATGATATTTTAG<br>AATACTATTATCGATATTTGATATTATTGACCTTAGCTTTGTTTGGGTGGAGACATGTGATTATCTTATTACCTTTTTATTCCA<br>TGAAACTACAGAGTTCGCCAGGTACCATACATGCACACCCTCGTGAAACGAGCGTGACTTAATATGATCTAGAACTTAAATAGT<br>ACTACTAATTGTGTCATTTGAACTTTCTCCTATGTCGGTTTCACTTCATGTATCGCAGAACAGGTGGAATACAGTGTCCTTGAG<br>TTTCACCCAAATCGGTCCAATTTTGTGATATATATTGCGATACAGACATACAGCCTACAGAGTTTTGTCTTAGCCCACTGGTTG<br>GCAAACGAAATTGTCTTTATTTTTTATGTTTTGTTGTCAATGTGTCTTTGTTTTTAACTAGATTGAGGTTTAATTTTAATACA<br>TTTGTTAGTTTACAGATTATGCAGTGTAATCTGATAATGTAAGTTGAACTGCGTTGGTCAAAGTCTTGTGTAACGCACTGTATC<br>TAAATTGTGAGTAACGACAAAATAATTAAAATTAAAGGGACCTTCAAGTATTATTAGTATCTCTGTCTAAGATGCACAGGTATT<br>CAGTAATAGTAATAAATAATTACTTGTATAATTAATATCTAATTAGTAAACCTTGTGTCTAAACCTAAATGAGCATAAATCCAA<br>AAGCAAAAATCTAAACCTAACTGAAAAAGTCATTACGAAAAAAGAAAAAAAAAGAGAAAAAACTACCTGAAAAGTCATGCAC<br>AACGTTCATCTTGGCTAAATTTATTTAGTTTATTAAATACAAAAATGGCGAGTTTCTGGAGTTTGTTGAAAATATATTTGTTTA<br>GCCACTTTAGAATTTCTTGTTTTAATTTGTTATTAAGATATATCGAGATAATGCGTTTATATCACCAATATTTTTGCCAAACTA<br>GTCCTATACAGTCATTTTTCAACAGCTATGTTCACTAATTTAAAACCCACTGAAAGTCAATCATGATTCGTCATATTTATATGC<br>TCGAATTCAGTAAAATCCGTTTGGTATCTATTTATTTCGTATAAGTATGTAATTCCACTAGATTTCCTTAAACTAAATTATAT<br>ATTTACATAATTGTTTCTTTAAAAGTCTACAACAGTTATTAAGTTATAGGAAATTATTTCTTTTATTTTTTTTTTTTAGG<br>AAATTATTTCTTTTGCAACACATTTGTCGTTTGCAAACTTTTAAAAGAAAATAAATGATTGTTATAATTGATTACATTTCAGTT<br>TATGACAGATTTTTTTTATCTAACCTTTAATGTTTGTTTCCTGTTTTTAGGAAAATCATACCAAAATATATTTGTGATCACAGT<br>AAATCACGGAATAGTTATGACCAAGATTTTCAAAGTAATACTTAGAATCCTATTAAATAAACGAAATTTTAGGAAGAAATAATC<br>AAGATTTTAGGAAACGATTTGAGCAAGGATTTAGAAGATTTGAATCTTTAATTAAATATTTTCATTCCTAAATAATTAATGCTA<br>GTGGCATAATATTGTAAATAAGTTCAAGTACATGATTAATTTGTTAAAATGGTTGAAAAATATATATATGTAGATTTTTTCAAA<br>SEQ ID NO: 60AGGTATACTAATTATTTTCATATTTTCAAGAAAATATAAGAAATGGTGTGTACATATATGGATGAAGAAAT<br>TTAAGTAGATAATACAAAAATGTCAAAAAAAGGGACCACACAATTTGATTATAAAACCTACCTCTCTAATCACATCCCAAAATG<br>GAGAACTTTGCCTCCTGACAACATTTCAGAAAATAATCGAATCCAAAAAAAACACTCAAT<br><br>SEQ ID NO: 60<br>Polynucleotide sequence PATLAC4<br>CAATTATATTTGGTTTCGATTGAAATTCAATCTAATGTGGTTAGATGAGTCCTATATTACCATGTCATTGTTAATACCCATTGC<br>CAAAAATAAAAGTGAAGCAGAAGGAGAAATTGTTTTTGTATACCCGAAGGAATTAAGATGTACGATCTTAAAATAGACATTTCG<br>GCCATCTATCAAATAAATGTCTAAAAGTTTTGTGGTCGTCTTAAATACTACTTCGAGTTCAGACGTATACGTCTCACCAAAGT<br>AATGCACATACTTGATGTTAAGTTTATCTCTTTTTACTATTTCAAATTTCGCGTTTGACAACACTTTAAGTCTACATTATCCAT<br>AGAGAATATAACATAAAGATCATGAACTTCTCATGAATGTATAAGACAAATCAAGCTTATATATGAGATCTATTTAGTAATTTG<br>ATATGTATGTAATATATGATAAATCTTTGATGCAATATTTTATTATGATTATTAGATATACACTAGTCAACTTTAACTTTAGAA<br>GATTAATCATTCCGTCGCAAACCATACCATAAATTAGCAAGGGATCGACTTAATATCTCCGATCCGCTATATATTTAAGAAGCA<br>TTTAGATTGTTTATAATACATGTCATGATTTTATAATTATGTATATATAAATACTAATTGATGTATGAAGTACGTAGATAATGT<br>TACGATCTATTAATCTATTTACATTAACTTTTAATTAGTGTTGAGTAGGGAAAATTAACATATAAACCTTTAGCAGTTGGTTGT<br>ATTATTAAAAATAATTTGAACTTAAAATCCACCTTCGAAAAGATAAATCAAACAAGTATAAAAAATGCTATAAATCCAGAATAT<br>TTACCTAAGGTTTTTATTCTTCTACTTAATAATGTAAGATAAAACCGGCACAATACTTGTTACGTATGCATGGTAGGTACCGCA<br>ATTGTGTAAGCAAATCGGCACAATACTAAGGTTACATATACTAACTAAATAAAACAATCTGATTTCAGTGACACCGTATATCTA<br>ACCTTTATTCAAATCCAAGGGAACATGACTTGACTTCTTCTGTTGGAACTAATTAAGATTGGAACTAGAAAATAGTTGAATATCCTTTAC<br>AGTTAGTAAAATCAAACTTGAAGTGAGGAAGTAAGCAGTTTAACGACTCCATATGACTACAGTTATATACAAAGTTGGGCACAA<br>AGTACAAGTACTAAATACTCAAAGTCAGATAATAATTTTAATAAGTACAAACTATATATATGCAGTACAATTATTGAGTATATA<br>TAAACGAGACTGGTGATTTGGGGCATTGTCCACCAGGGTGTTATATCCCAATTGAAATTTGAAAATTTAAGTGTGTGAGTGTTA<br>CGACAAAAAAAGTGTGTGAATTGTAGGCGCGGTGAAAAGGTAAATTAAGATTGGAACTAGAAAAATAGTTGAATATCCTTTAC<br>TAAAAGTTGTCAATTCCGGTTTTAGTAAAAAAAAATTTTAAAATAGAAATTTTATCCAAAAGACTTCAAACACACATATTCGCA<br>TATATAACATAAGATATCATTTTTTGTAAACAGTTAAAAAGAAAAACACATGTTTTTTTTTTAATTTAGAAAAAAACATGTTA<br>TTATACAAAACAGAGTTTTGCCCACTTTTAATATGTTATGAAAAGAAAAATGATTTTCTTGGGTTTGGTCAGAGAGATTGGTTG<br>TGGTAAGAATGGGAATCTTAATTACAAAGAATTGGATTTTGGGTCGACCTACCACCTAAAACGACGTCGCCTCCATCTCTGGTT<br>TCCAAATCTCTTTCTCCTCTCCCTTTATAAGCTTGCGTTGGCCAGTCGCTCATCTCGAAAACAGAGAGAAAAAGACTAAAAACA<br>CAGTTTAAGAAGGAGGAGATAGAGAGAGAAGAGAAAGATAGAGAGGGAG<br><br>SEQ ID NO: 61<br>Polynucleotide sequence PATLAC17<br>TAAGTTTAAGTCCAATAATTTCATTTTACTAGTAAAGATCACAATGTCATTTACCGCATTCACTTAATAATTGCTGAATTCACA<br>TAGTGCCTGTAAATTAAGACTAATTTTAGGTTTCAAATAATTTTTCTTTTTTACATAACTTACGATCGATATTTAAATGGTAT<br>TGGTAAGTTTAAGGTATATAGATAGTGTGTCTAAACTAGAGTTCGTTGAAATTGGTCTGAGGTATAAATACCTAAAAGGTTATA<br>TATGTTTTTAGTTTAATGTAATTTCAGTAAATTTTAGTCGAAACCGTTAAGAGATATCAGAATTTCGTTTTCAAATAATATGGA<br>TATAATTACCCGGGATTAACCGTACCTGATAAAATATAGCTCTCGTACGTGTCACATGCCTAATGCCTAGTTAAACTTAAAACG<br>AATATCTATATTTACTGTTATTGATTGTGAGTTACCAACTAAAATATTGTTAAAAGACATTGTAAAACTACAAATGGTTCGAAC<br>TGTATACTAATGATGTAAACTCGTGTTTCATCGTTATGTCCGATATTTTTTCATTCAACCATTATTCAATTTCAAGATTTCTT<br>TATTGTCTTTTTTCTTTCTAGAAAGCCTATATATTTAATTACCCACTTTGCATATTCAGAGGATAAGTTGATACGTACTTGTT<br>AGCAACCTGTCTAGATCATCTTTTGATTGTAGATTTGACTTTAAATTTCTCACAATTATAAATATGAAAAATAACAAGCAAAGA<br>ATTTACAAATGTATATAATTATATACACGCATTGATGAATAAACATATTTAGAAAATAATGTGTTCTAAGGAAATTTTGTGGCA<br>TTTTTTAAAAAATAATTAAACAAATAAGAATAGTGTAAAGTTGTTTAAATATGTATGTATAAGTGGCATGCCTTTGAGGATACG<br>AACTTAAAAGGGAGTTAGGTAACTTGCTTGGGAATAAAATAGCCAACCTTAATTTGAGGTTTCCTCAATGTTCTTATCAAAAA<br>GAATAAAAATTTCGGAAATTCCCTTCATGGATTTTGATATCTAACCCTAATCGTGACCTTCTTTGATAGCTACAATCTCCCTCT<br>CCCTCTCTTTGCTTATTCCCCAAGCAATTTTAGCTTACGAATGTTTTGACTAACTCCACATCGGTTTATCTCTTAAGTTCCCCA<br>CCTACAAATATACAAAAAAAGAAGTAAAATAAAAATAATTATTAACAAACCGATGAAGTACTTATCATTTATAAACATGCTTAT |

| ILLUSTRATIVE SEQUENCES |
|---|
| GAAATGTATTTTCTAAAACATAACCGCTAACCAGAGAAGTTTCCTAGAGTTCTGCTTCAGACTCTTTTGGTCGATCAAGAAGTC |
| TCCAAGAGTTGTTTTTGTTGGGTCTAAACAAAACTTGGCCAGGGAACAAATCAAACTATATTATTAATCTTCTACATCTGGTCC |
| TAAGTTCCTTACTATCTCATGTTAAAATTTGAAGTCTAATATACTCAAAGCTGTCAAAGAAGCAGAACATGGAAGAGGAACTGT |
| CATATCTGAGAAACCAAAATTGGCAATCTTGCATTTCATATTTAGAATCTACGCCATAGTATTGAGATGGAAACAAAGAGTTTT |
| CGAAGAGGGTCAAAGAGTTTGACTTATCTTTGACACCACTCATACATTAGCTGTTCATATAATCTAACAACTAGTCAATATCAA |
| GTGTCTCCAAATTACGGAGAGTACTTCTCTACCAATTATCTTTTTGTTTTTCATAAACATTTTACTAATTGTTTTTTCTATATC |
| TCCTGCTCAAGCAAACACCTAACTCTCCTTTCCTATATATACACTAAAGGTTGAAAACAATGAATCCACAATCTACAGCAAAAC |
| ATAAGCGAGGCAGAGTCTTCAGAAAACTTACCTGCTCTAAACAACGCCTCCGTGTCCAAGCTCACTTCA |

TABLE I

In-vitro HCHL enzyme activities in stems of five-week-old wild type (WT) and IRX5:HCHL plants. Values are means of three biological replicates.

| Plant line | Enzyme activity ± SE (pkat vanillin μg$^{-1}$ protein) |
|---|---|
| WT | nd[a] |
| IRX5:HCHL (1) | 0.112 ± 0.026 |
| IRX5:HCHL (2) | 0.075 ± 0.022 |
| IRX5:HCHL (3) | 0.042 ± 0.006 |
| IRX5:HCHL (4) | 0.160 ± 0.038 |
| IRX5:HCHL (5) | 0.025 ± 0.002 |

[a]nd, not detected.

TABLE II

Height of the main inflorescence stem and total stem dry weight of senesced wild type (WT) and IRX5:HCHL plants n, number of plants analyzed.

| Plant line | Height (cm) Mean ± SE | Dry weight (mg) Mean ± SE | n |
|---|---|---|---|
| WT | 62.4 ± 4.6 | 477.7 ± 51.3 | 16 |
| IRX5:HCHL (1) | 60.3 ± 5.0 | 501.6 ± 62.8 | 14 |
| IRX5:HCHL (2) | 56.0 ± 4.6 | 435.3 ± 62.5 | 12 |
| IRX5:HCHL (4) | 48.3 ± 4.4*** | 335.7 ± 63.4*** | 15 |
| IRX5:HCHL (5) | 54.1 ± 7.6** | 399.1 ± 61.1* | 16 |

Asterisks indicate significant differences from the wild-type
(*$P < 0.05$,
**$P < 0.01$,
***$P < 0.0001$)

TABLE III

Quantitative analysis of soluble phenolics in stems from five-week-old wild type (WT) and IRX5:HCHL plants. Values are means of four biological replicates.

| | Mean ± SE (μg g$^{-1}$ fresh weight) | | | | |
|---|---|---|---|---|---|
| Plant line | HBAld | 3,4-DHBAld | HBA | HBAGlc | HBAGE |
| WT | nd[a] | nd[a] | nd[a] | 2.32 ± 0.20 | 1.34 ± 0.41 |
| IRX5:HCHL (1) | 1.02 ± 0.07 | 0.33 ± 0.02 | 5.53 ± 0.36 | 544.87 ± 157.79 | 1653.74 ± 504.38 |
| IRX5:HCHL (2) | 0.62 ± 0.08 | 0.23 ± 0.02 | 4.77 ± 0.41 | 569.23 ± 138.73 | 1046.97 ± 439.35 |
| IRX5:HCHL (4) | 0.83 ± 0.18 | 0.29 ± 0.03 | 4.64 ± 0.57 | 484.06 ± 74.23 | 959.79 ± 189.25 |
| IRX5:HCHL (5) | 1.04 ± 0.09 | 0.34 ± 0.02 | 5.59 ± 0.27 | 531.29 ± 51.13 | 1360.03 ± 178.03 |

[a]nd, not detected

TABLE IV

Quantitative analysis of acid-hydrolyzed soluble phenolics in stems from five-week-old wild type (WT) and IRX5:HCHL plants. Values are means of four biological replicates.

| | Mean ± SE (μg g$^{-1}$ fresh weight) | | | | | | | | | |
|---|---|---|---|---|---|---|---|---|---|---|
| Plant line | HBAld | 3,4-DHBAld | Van | 5OH-Van | SyrAld | HBA | 3,4-DHBA | VA | 5OH-VA | SyrA |
| WT | 0.6 ± 0.1 | 0.1 ± 0.0 | nd[a] | nd[a] | nd[a] | 14.0 ± 2.8 | 10.2 ± 2.7 | 5.0 ± 0.9 | nd[a] | nd[a] |
| IRX5:HCHL (1) | 11.8 ± 2.1 | 14.3 ± 2.0 | 11.9 ± 3.8 | 24.3 ± 2.0 | 1.7 ± 0.0 | 2492.4 ± 534.9 | 17.3 ± 2.4 | 226.9 ± 32.6 | 8.1 ± 0.7 | 44.7 ± 7.6 |
| IRX5:HCHL (2) | 5.7 ± 1.5 | 10.4 ± 2.6 | 3.9 ± 1.28 | 12.4 ± 6.1 | 1.6 ± 0.1 | 1726.1 ± 706.7 | 13.7 ± 3.4 | 175.9 ± 37.1 | 6.2 ± 1.5 | 45.9 ± 10.9 |
| IRX5:HCHL (4) | 7.2 ± 0.8 | 9.9 ± 0.6 | 6.4 ± 1.26 | 10.7 ± 1.7 | 1.7 ± 0.1 | 1588.3 ± 181.1 | 15.4 ± 1.7 | 183.6 ± 19.0 | 5.8 ± 0.3 | 31.3 ± 2.4 |
| IRX5:HCHL (5) | 9.9 ± 1.2 | 12.8 ± 0.7 | 8.0 ± 1.73 | 16.9 ± 2.5 | 1.9 ± 0.1 | 2061.3 ± 336.2 | 16.4 ± 1.2 | 202.3 ± 9.2 | 7.0 ± 0.5 | 39.5 ± 3.2 |

[a]nd, not detected

TABLE V

Quantitative analysis of cell wall-bound phenolics in stems from extract-free senesced mature dried wild type (WT) and IRX5:HCHL plants. Values are means of four biological replicates.

| | Mean ± SE ($\mu g \, g^{-1}$ dry weight) | | | | | | | | | |
|---|---|---|---|---|---|---|---|---|---|---|
| Plant line | HBAld | 3,4-DHBAld | Van | 5OH-Van | SyrAld | HBA | 3,4-DHBA | VA | 5OH-VA | SyrA |
| WT | 5.8 ± 0.6 | 1.1 ± 0.0 | 59.4 ± 6.5 | nd[a] | 17.8 ± 1.0 | 6.2 ± 0.9 | nd[a] | 24.2 ± 2.0 | nd[a] | 10.6 ± 0.3 |
| IRX5:HCHL (1) | 11.1 ± 0.4 | 0.6 ± 0.0 | 36.9 ± 2.7 | 0.8 ± 0.1 | 107.8 ± 6.4 | 486.4 ± 28.2 | nd[a] | 42.2 ± 3.2 | nd[a] | 47.5 ± 2.3 |
| IRX5:HCHL (2) | 8.9 ± 0.4 | 0.6 ± 0.0 | 25.7 ± 5.9 | 0.6 ± 0.1 | 99.9 ± 4.6 | 427.9 ± 49.3 | nd[a] | 39.6 ± 1.9 | nd[a] | 43.3 ± 0.9 |
| IRX5:HCHL (4) | 9.1 ± 0.9 | 0.7 ± 0.0 | 29.9 ± 2.7 | 0.8 ± 0.1 | 122.2 ± 14.8 | 421.8 ± 28.2 | nd[a] | 36.8 ± 1.4 | nd[a] | 54.1 ± 6.1 |
| IRX5:HCHL (5) | 9.1 ± 0.7 | 0.7 ± 0.0 | 45.6 ± 6.2 | 0.7 ± 0.0 | 122.4 ± 5.9 | 349.6 ± 27.6 | nd[a] | 47.7 ± 3.0 | nd[a] | 59.3 ± 3.1 |

[a] nd, not detected.

TABLE VI

Chemical composition of total and hemicellulosic cell wall sugars in senesced mature dried stems from wild type (WT) and line IRX5:HCHL (2). Values are means ± SE of three biological replicates.

| | Mean ± SE (mg $g^{-1}$ CWR) | | | |
|---|---|---|---|---|
| | Total Sugars | | Hemicellulosic Sugars | |
| Sugar | WT | IRX5:HCHL | WT | IRX5:HCHL |
| Fucose | 2.23 ± 0.08 | 2.21 ± 0.05 | 1.44 ± 0.03 | 1.49 ± 0.05 |
| Rhamnose | 10.83 ± 0.35 | 11.71 ± 0.19 | 9.12 ± 0.23 | 9.76 ± 0.26 |
| Arabnose | 16.01 ± 0.56 | 18.58 ± 0.54* | 10.15 ± 0.30 | 12.40 ± 0.38* |
| Galactose | 23.06 ± 0.66 | 22.69 ± 0.82 | 15.34 ± 0.33 | 16.49 ± 0.50 |
| Glucose | 442.76 ± 7.09 | 388.66 ± 7.58* | 10.09 ± 0.34 | 11.25 ± 0.33 |
| Xylose | 201.63 ± 1.71 | 245.20 ± 3.31* | 114.39 ± 0.97 | 141.16 ± 4.20* |
| Galacturonic acid | 93.74 ± 2.56 | 99.96 ± 1.52 | 37.13 ± 1.86 | 40.58 ± 1.12 |
| Glucuronic acid | 4.10 ± 0.16 | 4.60 ± 0.39 | 2.66 ± 0.17 | 3.12 ± 0.09 |
| Total | 794.36 ± 13.17 | 793.61 ± 14.85 | 191.32 ± 4.23 | 236.25 ± 6.93* |

Asterisks indicate significant differences from the wild type ($P < 0.001$).

TABLE VII

Lignin content and main H, G and S lignin-derived monomers obtained by thioacidolysis of extract-free senesced mature dried stems from wild-type (WT) and line IRX5:HCHL (2). Values are means ± SE from duplicate analyses.

| Plant line | | Klason lignin KL % of CWR | Total yield (H + G + S) $\mu$mol $g^{-1}$ KL | % H | % G | % S | S/G |
|---|---|---|---|---|---|---|---|
| Culture 1 | WT | 20.42 ± 0.14 | 1356 ± 40 | 0.98 ± 0.00 | 73.2 ± 0.3 | 25.9 ± 0.3 | 0.35 ± 0.01 |
| | IRX5:HCHL | 20.12 ± 0.15 | 1014 ± 5 | 1.48 ± 0.04 | 73.7 ± 0.5 | 25.2 ± 0.3 | 0.34 ± 0.01 |
| Culture 2 | WT | 20.32 ± 0.25 | 1238 ± 13 | 1.09 ± 0.00 | 73.8 ± 0.3 | 25.2 ± 0.3 | 0.34 ± 0.01 |
| | IRX5:HCHL | 21.29 ± 0.14 | 1041 ± 7 | 1.47 ± 0.00 | 72.7 ± 0.1 | 25.9 ± 0.1 | 0.36 ± 0.00 |

TABLE VIII

Minor monomers obtained by thioacidolysis of extract-free mature senesced dried stems from wild-type (WT) and line IRX5:HCHL (2). Values are means ± SE of duplicate analyses. Values are expressed in µmol g$^{-1}$ KL and as a relative percentage of the total main H, G and S monomers released by thioacidolysis.

| Plant line | | Vanalc µmol g$^{-1}$ KL (% H + G + S) | Syralc µmol g$^{-1}$ KL (% H + G + S) | Van µmol g$^{-1}$ KL (% H + G + S) | Syrald µmol g$^{-1}$ KL (% H + G + S) | Cald µmol g$^{-1}$ KL (% H + G + S) | VA µmol g$^{-1}$ KL (% H + G + S) | SyrA µmol g$^{-1}$ KL (% H + G + S) |
|---|---|---|---|---|---|---|---|---|
| Culture 1 | WT | nd* | nd* | 4.3 ± 1 (0.31) | 0.9 ± 0.3 (0.06) | 7.2 ± 0.6 (0.53) | 6.7 ± 0.2 (0.49) | 1.4 ± 0.0 (0.10) |
|  | IRX5:HCHL | 5.0 ± 0.1 (0.49) | 2.6 ± 0.2 (0.25) | 6.5 ± 1.4 (0.64) | 18.7 ± 3.5 (1.84) | 7.9 ± 0.3 (0.77) | 6.8 ± 0.2 (0.67) | 2.2 ± 0.0 (0.21) |
| Culture 2 | WT | nd* | nd* | 4.6 ± 0.7 (0.37) | 0.8 ± 0.3 (0.06) | 6.9 ± 0.1 (0.55) | 6.2 ± 0.2 (0.50) | 1.2 ± 0.0 (0.09) |
|  | IRX5:HCHL | 5.3 ± 0.1 (0.50) | 2.9 ± 0.1 (0.28) | 6.3 ± 0.7 (0.60) | 16.7 ± 1.9 (1.60) | 6.8 ± 0.1 (0.66) | 7.0 ± 0.0 (0.65) | 2.1 ± 0.0 (0.20) |

*nd, not detected

TABLE IX

Comparative transcriptomics of IRX5:HCHL stems and WT. Positive and negative ratios are indicative of upregulation and downregulation of the gene in plants expressing HCHL.

| AGI Gene ID | Annotated Function | log2 ratio | P value |
|---|---|---|---|
| MONOOXYGENASES | | | |
| AT1G62570 | flavin-containing monooxygenase family protein | 1.13 | 0.00E+0 |
| AT3G28740 | cytochrome P450 family protein | 1.10 | 0.00E+0 |
| AT4G15760 | monooxygenase, putative (MO1) | 0.86 | 7.69E−12 |
| AT4G37370 | CYP81D8 | 0.72 | 1.20E−7 |
| AT3G28740 | cytochrome P450 family protein | 0.70 | 5.58E−7 |
| AT2G12190 | cytochrome P450, putative | 0.65 | 8.60E−6 |
| AT1G69500 | CYP704B1 | 0.58 | 7.38E−4 |
| AT3G14610 | CYP72A7 | 0.51 | 2.96E−2 |
| DEHYDROGENASES/REDUCTASES | | | |
| AT4G13180 | short-chain dehydrogenase/reductase (SDR) family protein | 1.67 | 0.00E+0 |
| AT2G37770 | aldo/keto reductase family protein. Transcript variant 1 | 1.04 | 0.00E+0 |
| AT2G37770 | aldo/keto reductase family protein. Transcript variant 2 | 0.96 | 0.00E+0 |
| AT2G29350 | SAG13 (Senescence-associated gene 13); short-chain dehydrogenase/reductase (SDR) family protein | 0.83 | 4.62E−11 |
| AT1G14130 | 2-oxoglutarate and Fe(II)-dependent oxygenase superfamily protein | 0.72 | 9.59E−8 |
| AT1G72680 | cinnamyl-alcohol dehydrogenase. putative | 0.90 | 0.00E+0 |
| AT1G60730 | aldo/keto reductase family protein | 0.65 | 8.30E−8 |
| AT1G18020 | FMN-linked oxidoreductases superfamily protein, Transcript variant 1 | 0.62 | 7.14E−5 |
| AT1G18020 | FMN-linked oxidoreductases superfamily protein, Transcript variant 2 | 0.59 | 4.38E−4 |
| AT2G47130 | short-chain dehydrogenase/reductase (SDR) family protein, Transcript variant 1 | 0.58 | 7.60E−4 |
| AT2G47130 | short-chain dehydrogenase/reductase (SDR) family protein, Transcript variant 2 | 0.58 | 8.36E−4 |
| AT1G18020 | FMN-linked oxidoreductases superfamily protein, Transcript variant 3 | 0.54 | 6.80E−3 |
| AT5G14780 | FDH (FORMATE DEHYDROGENASE); NAD binding/oxidoreductase, acting on the CH—OH group of donors | 0.53 | 1.24E−2 |
| AT1G54100 | ALDH7B4 (ALDEHYDE DEHYDROGENASE 7B4); 3-chloroallyl aldehyde dehydrogenase | 0.51 | 3.00E−2 |
| UDP-GLUCOSYLTRANSFERASES | | | |
| AT1G05560 | UGT75B1 | 1.67 | 0.00E+0 |
| AT2G15490 | UGT73B4 | 1.26 | 0.00E+0 |
| AT4G34138 | UGT73B1 | 1.25 | 0.00E+0 |
| AT2G30140 | UGT87A2 | 0.79 | 5.31E−10 |
| AT4G34131 | UGT73B3 | 0.58 | 8.09E−4 |
| AT3G11340 | UGT76B1 | 0.58 | 8.97E−4 |
| AT4G01070 | UGT72B1 | 0.52 | 2.00E−2 |
| TRANSPORTERS | | | |
| AT3G23560 | ALF5 (ABERRANT LATERAL ROOT FORMATION 5); antiporter/transporter | 1.18 | 0.00E+0 |
| AT2G36380 | PDR6 (PLEIOTROPIC DRUG RESISTANCE 6); ATPase, coupled to transmembrane movement of substances | 1.13 | 0.00E+0 |
| AT3G51860 | CAX3 (cation exchanger 3); cation:cation antiporter | 1.07 | 0.00E+0 |
| AT5G65380 | Multidrug and toxic compound extrusion (MATE) efflux family protein | 0.92 | 0.00E+0 |
| AT1G79410 | ATOCT5 (organic cation/carnitine transporter 5) | 0.89 | 0.00E+0 |
| AT5G13750 | ZIFL1 (ZINC INDUCED FACILITATOR-LIKE 1); tetracycline:hydrogen antiporter/transporter | 0.78 | 1.18E−9 |
| AT1G76520 | auxin efflux carrier family protein | 0.70 | 4.27E−7 |
| AT1G76530 | auxin efflux carrier family protein | 0.69 | 8.91E−7 |
| AT4G18197 | AT4G18200/PUP7 (purine permease 7); purine transporter | 0.64 | 1.62E−5 |
| AT4G28390 | AAC3 (ADP/ATR CARRIER 3); ATP:ADP antiporter/binding | 0.62 | 6.57E−5 |
| AT5G45380 | DUR3 (DEGRADATION OF UREA 3); sodium:solute symporter family protein | 0.61 | 1.05E−4 |
| AT3G18830 | PLT5 (POLYOL TRANSPORTER 5) | 0.57 | 1.56E−3 |
| AT2G17500 | auxin efflux carrier family protein | 0.55 | 3.26E−3 |

TABLE IX-continued

Comparative transcriptomics of IRX5:HCHL stems and WT. Positive and negative ratios are
indicative of upregulation and downregulation of the gene in plants expressing HCHL.

| AGI Gene ID | Annotated Function | log2 ratio | P value |
|---|---|---|---|
| | DETOXIFICATION | | |
| AT1G17170 | ATGSTU24 (Glutathione S-transferase (class tau) 24) | 1.32 | 0.00E+0 |
| AT2G29420 | ATGSTU7 (GLUTATHIONE S-TRANSFERASE 25) | 1.22 | 0.00E+0 |
| AT2G47730 | ATGSTF8 (GLUTATHIONE S-TRANSFERASE 8) | 1.16 | 0.00E+0 |
| AT4G02520 | ATGSTF2 (Glutathione S-transferase (class phi) 2) | 0.78 | 2.04E−9 |
| AT3G09270 | ATGSTU8 (Glutathione S-transferase (class tau) 8) | 0.65 | 1.43E−5 |
| AT2G29490 | ATGSTU1 (GLUTATHIONE S-TRANSFERASE 19) | 0.54 | 7.21E−3 |
| AT4G19880 | unknown protein, Glutathione S-transferase family protein | 0.76 | 6.73E−9 |
| AT5G39050 | ATPMaT1 (phenolic glucoside malonyltransferase 1); transferase family protein | 0.77 | 3.95E−9 |
| AT5G39090 | ATPMaT1-like; transferase family protein | 0.52 | 2.13E−2 |
| | JASMONIC ACID METABOLISM | | |
| AT1G76680 | OPR1 (12-oxophytodienoate reductase 1) | 1.27 | 0.00E+0 |
| AT5G54206 | 12-oxophytodienoate reductase-related | 0.99 | 0.00E+0 |
| | STRESS INDUCIBLE/DEFENSE/SENESCENCE | | |
| AT5G49480 | ATCP1 (CA2+-BINDING PROTEIN 1); calcium ion binding. NaCl stress inducible | 1.24 | 0.00E+0 |
| AT1G35260 | Bet v I allergen family protein, defense response | 0.88 | 0.00E+0 |
| AT3G62550 | universal stress protein (USP) family protein, Adenine nucleotide alpha-like protein | 0.87 | 0.00E+0 |
| AT1G73500 | ATMKK9 (Arabidopsis thaliana MAP kinase kinase 9) | 0.80 | 3.62E−10 |
| AT4G02380 | SAG21 (SENESCENCE-ASSOCIATED GENE 21) | 0.77 | 3.99E−9 |
| AT3G04720 | PR4 (PATHOGENESIS-RELATED 4), similar to the antifungal chitin-binding protein hevein | 0.64 | 2.04E−5 |
| AT1G75270 | DHAR2; glutathione dehydrogenase (ascorbate) | 0.61 | 1.17E−4 |
| AT1G70530 | CRK3 (CYSTEINE-RICH RLK (RECEPTOR-LIKE PROTEIN KINASE) 3), protein kinase family protein | 0.60 | 2.36E−4 |
| AT3G50970 | LTI30/XERO2 (LOW TEMPERATURE-INDUCED 30); dehydrin stress-related | 0.58 | 8.28E−4 |
| AT5G27760 | hypoxia-responsive family protein | 0.54 | 6.87E−3 |
| AT3G56710 | SIB1 (SIGMA FACTOR BINDING PROTEIN 1); binding | 0.51 | 2.30E−2 |
| | MISCELLANEOUS | | |
| | Transcription factor | | |
| AT5G63790 | ANAC102 (Arabidopsis NAC domain containing protein 102); transcription factor. Transcript variant 1 | 1.87 | 0.00E+0 |
| AT1G77450 | ANAC032 (Arabidopsis NAC domain containing protein 32); transcription factor | 1.14 | 0.00E+0 |
| AT5G63790 | ANAC102 (Arabidopsis NAC domain containing protein 102); transcription factor. Transcript variant 2 | 0.65 | 1.26E−5 |
| AT1G01720 | ATAF1 (Arabidopsis NAC domain containing protein 2); transcription factor | 0.54 | 7.23E−3 |
| | Glycine-rich protein | | |
| AT2G05380 | GRP3S (GLYCINE-RICH PROTEIN 3 SHORT ISOFORM) Transcript variant 1 | 2.03 | 0.00E+0 |
| AT2G05380 | GRP3S (GLYCINE-RICH PROTEIN 3 SHORT ISOFORM) Transcript variant 2 | 1.03 | 0.00E+0 |
| AT2G05530 | glycine-rich protein | 0.96 | 0.00E+0 |
| AT2G05540 | glycine-rich protein | 0.90 | 0.00E+0 |
| | Auxin metabolism | | |
| AT3G44300 | NIT2 (NITRILASE 2) | 1.22 | 0.00E+0 |
| AT3G44310 | NIT1 (NITRILASE 1) | 0.51 | 3.32E−2 |
| | Other | | |
| AT5G30870 | transposable element gene; pseudogene, hypothetical protein | 1.24 | 0.00E+0 |
| AT3G14990 | 4-methyl-5(b-hydroxyethyl)-thiazole monophosphate biosynthesis protein, putative | 1.20 | 0.00E+0 |
| AT1G65280 | heat shock protein binding/unfolded protein binding | 1.07 | 0.00E+0 |
| AT4G16190 | cysteine proteinase, putative | 0.89 | 0.00E+0 |
| AT1G02850 | glycosyl hydrolase family 1 protein BGLU11 | 0.86 | 7.69E−12 |
| AT1G17860 | trypsin and protease inhibitor family protein/Kunitz family protein | 0.86 | 7.69E−12 |
| AT3G49780 | ATPSK4 (PHYTOSULFOKINE 4 PRECURSOR); growth factor | 0.82 | 5.38E−11 |
| AT2G41380 | embryo-abundant protein-related, methyltransferase activity | 0.82 | 6.15E−11 |
| AT3G24420 | hydrolase, alpha/beta fold family protein | 0.79 | 1.07E−9 |
| AT5G52810 | ornithine cyclodeaminase/mu-crystallin family protein | 0.67 | 2.65E−6 |
| AT5G17380 | pyruvate decarboxylase family protein | 0.64 | 1.84E−5 |
| AT1G23890 | NHL repeat-containing protein | 0.59 | 3.35E−4 |
| AT4G28380 | leucine-rich repeal family protein, zinc ion binding | 0.59 | 3.52E−4 |
| AT4G01870 | tolB protein-related | 0.59 | 4.41E−4 |
| AT1G37130 | NIA2 (NITRATE REDUCTASE 2) | 0.62 | 6.75E−5 |
| AT1G24610 | SET domain-containing protein, unknown protein | 0.58 | 9.14E−4 |
| AT4G11600 | ATGPX6 (GLUTATHIONE PEROXIDASE 6); glutathione peroxidase | 0.52 | 1.83E−2 |
| | UNKNOWN | | |
| AT5G61820 | unknown protein | 1.68 | 0.00E+0 |
| AT1G76600 | unknown protein | 1.18 | 0.00E+0 |
| AT1G76960 | unknown protein | 0.71 | 2.01E−7 |
| AT4G17840 | unknown protein | 0.67 | 2.77E−6 |
| AT1G21680 | unknown protein | 0.61 | 1.38E−4 |
| AT5G40960 | unknown protein, DUF3339 | 0.59 | 5.08E−4 |

TABLE IX-continued

Comparative transcriptomics of IRX5:HCHL stems and WT. Positive and negative ratios are indicative of upregulation and downregulation of the gene in plants expressing HCHL.

| AGI Gene ID | Annotated Function | log2 ratio | P value |
|---|---|---|---|
| AT4G08555 | unknown protein | 0.58 | 8.16E−4 |
| AT2G30690 | unknown protein, DUF593 | 0.53 | 8.86E−3 |
| AT5G86052 | unknown protein | 0.50 | 4.05E−2 |
| CARBOHYDRATE METABOLISM | | | |
| AT2G06850 | EXGT-A1 (ENDO-XYLOGLUCAN TRANSFERASE); hydrolase, acting on glycosyl bonds | −0.51 | 2.51E−2 |
| AT3G52840 | BGAL2 (beta-galactosidase 2), Glycoside hydrolase family 35. putative lactase | −0.52 | 1.83E−2 |
| AT3G01345 | Glycoside hydrolase family 35, beta-galactosidase putative | −0.53 | 1.13E−2 |
| AT3G53190 | pectate lyase family protein | −0.56 | 1.69E−3 |
| AT5G03350 | legume lectin family protein, carbohydrate binding | −0.57 | 1.28E−3 |
| AT1G25810 | GALT1 (galactosyltransferase 1), Glycoside transferase family 31 | −0.61 | 1.02E−4 |
| AT1G19600 | pfk8-type carbohydrate kinase family protein | −0.63 | 3.41E−5 |
| AT4G28250 | ATEXPB3 (*ARABIDOPSIS THALIANA* EXPANSIN B3) | −0.79 | 7.46E−10 |
| AT3G30720 | unknown protein, QUA-QUINE STARCH (QQS) | −1.08 | 0.00E+0 |
| MISCELLANEOUS | | | |
| AT4G27440 | PORB (PROTOCHLOROPHYLLIDE OXIDOREDUCTASE B), protochlorophyllide reductase | −0.50 | 4.45E−2 |
| AT5G02890 | HXXXD-type acyl-transferase family protein | −0.50 | 3.86E−2 |
| AT1G18950 | aminoacyl-tRNA synthetase family | −0.51 | 3.29E−2 |
| AT5G47330 | palmitoyl protein thioesterase family protein | −0.53 | 1.07E−2 |
| AT1G03870 | FLA9 (FLA9) | −0.54 | 4.82E−3 |
| AT1G20530 | unknown protein, DUF630 and DUF632 | −0.55 | 4.67E−3 |
| ATCG00470 | ATP SYNTHASE EPSILON CHAIN, rotational mechanism | −0.55 | 3.12E−3 |
| AT5G51720 | unknown protein, 2 iron, 2 sulfur cluster binding | −0.56 | 2.02E−3 |
| ATCG00330 | RPS14 CHLOROPLAST RIBOSOMAL PROTEIN S14 | −0.58 | 8.70E−4 |
| ATCG00340 | D1 subunit of photosystem I and II reaction centers, Transcript variant 1 | −0.62 | 5.42E−5 |
| AT2G38870 | serine-type endopeptidase inhibitor activity, pathogenesis-related peptide of the PR-6 proteinase inhibitor family | −0.64 | 1.54E−5 |
| ATCG00340 | D1 subunit of photosystem I and II reaction centers, Transcript variant 2 | −0.71 | 2.75E−7 |

What is claimed is:

1. A method of obtaining a plant having improved digestability as forage, the method comprising:
   introducing a polynucleotide encoding a hydroxycinnamoyl-CoA hydratase-lyase (HCHL) polypeptide having at least 95% identity to SEQ ID NO:1 into a population of plants, wherein the polynucleotide is operably linked to a secondary wall-specific promoter;
   culturing the population of plants under conditions in which the HCHL is expressed;
   chemically analyzing the lignin monomer structure of plant cell walls; and
   selecting a plant that has cell wall lignin that comprises β-O-4-linked $C_6C_1$ monomer end-groups lacking phenyl propanoid tails, thereby obtaining a plant that has improved digestibility as forage compared to a counterpart wildtype plant.

2. The method of claim 1, wherein the polypeptide comprises the amino acid sequence of SEQ ID NO:1.

3. The method of claim 1, wherein the plant is a monocot.

4. The method of claim 1, wherein the plant is a grass.

5. The method of claim 1, wherein the plant is selected from the group consisting of sorghum, millet, corn, soy, barley, wheat, rice, sugarcane, bamboo, rape, sunflower, hemp, switchgrass, miscanthus, alfalfa, turfgrass, and *Brachypodium*.

6. A plant having improved digestibility as forage obtained by the method of claim 1.

7. Forage material comprising the plant of claim 6.

8. A method of improving digestion of forage material in an animal, the method comprising providing forage material of claim 7 to the animal.

* * * * *

SEQUENCE LISTING

```
<160> NUMBER OF SEQ ID NOS: 71

<210> SEQ ID NO 1
<211> LENGTH: 276
<212> TYPE: PRT
<213> ORGANISM: Pseudomonas fluorescens
<220> FEATURE:
<223> OTHER INFORMATION: Pseudomonas fluorescens biovar V strain AN103
      p-hydroxycinnamoyl-CoA hydratase-lyase (HCHL),
      trans-feruloyl-CoA hydratase

<400> SEQUENCE: 1

Met Ser Thr Tyr Glu Gly Arg Trp Lys Thr Val Lys Val Glu Ile Glu
1               5                   10                  15

Asp Gly Ile Ala Phe Val Ile Leu Asn Arg Pro Glu Lys Arg Asn Ala
                20                  25                  30

Met Ser Pro Thr Leu Asn Arg Glu Met Ile Asp Val Leu Glu Thr Leu
            35                  40                  45

Glu Gln Asp Pro Ala Ala Gly Val Leu Val Leu Thr Gly Ala Gly Glu
        50                  55                  60

Ala Trp Thr Ala Gly Met Asp Leu Lys Glu Tyr Phe Arg Glu Val Asp
65                  70                  75                  80

Ala Gly Pro Glu Ile Leu Gln Glu Lys Ile Arg Arg Glu Ala Ser Gln
                85                  90                  95

Trp Gln Trp Lys Leu Leu Arg Met Tyr Ala Lys Pro Thr Ile Ala Met
            100                 105                 110

Val Asn Gly Trp Cys Phe Gly Gly Gly Phe Ser Pro Leu Val Ala Cys
        115                 120                 125

Asp Leu Ala Ile Cys Ala Asp Glu Ala Thr Phe Gly Leu Ser Glu Ile
```

```
                  130                 135                 140
Asn Trp Gly Ile Pro Pro Gly Asn Leu Val Ser Lys Ala Met Ala Asp
145                 150                 155                 160

Thr Val Gly His Arg Gln Ser Leu Tyr Tyr Ile Met Thr Gly Lys Thr
                165                 170                 175

Phe Gly Gly Gln Lys Ala Ala Glu Met Gly Leu Val Asn Glu Ser Val
            180                 185                 190

Pro Leu Ala Gln Leu Arg Glu Val Thr Ile Glu Leu Ala Arg Asn Leu
        195                 200                 205

Leu Glu Lys Asn Pro Val Val Leu Arg Ala Ala Lys His Gly Phe Lys
    210                 215                 220

Arg Cys Arg Glu Leu Thr Trp Glu Gln Asn Glu Asp Tyr Leu Tyr Ala
225                 230                 235                 240

Lys Leu Asp Gln Ser Arg Leu Leu Asp Thr Gly Gly Arg Glu Gln
                245                 250                 255

Gly Met Lys Gln Phe Leu Asp Asp Lys Ser Ile Lys Pro Gly Leu Gln
                260                 265                 270

Ala Tyr Lys Arg
        275

<210> SEQ ID NO 2
<211> LENGTH: 828
<212> TYPE: DNA
<213> ORGANISM: Artificial Sequence
<220> FEATURE:
<223> OTHER INFORMATION: synthetic p-hydroxycinnamoyl-CoA hydratase-
      lyase (HCHL) codon-optimized for expression in Arabidopsis by
      GenScript

<400> SEQUENCE: 2
atgtctactt acgagggaag atggaagact gttaaggttg agatcgagga tggaatcgct     60
ttcgttatcc tcaacagacc tgagaagaga aacgctatgt ctcctactct caacagagag    120
atgatcgatg ttctcgagac tctcgagcag atcctgctgc tggagttctc gttctcact    180 ggagctggag aggcttggac tgctggtatg gatctcaagg agtacttcag agaggttgat    240
gctggacctg agatcctcca ggagaagatc agaagagagg cttctcagtg gcagtggaag    300
ctcctcagaa tgtacgctaa gcctactatc gctatggtta acggatggtg cttcggagga    360
ggattctctc tctcgttgc ttgcgatctc gctatctgcg ctgatgaggc tactttcgga    420
ctctctgaga tcaactgggg aatccctcct ggaaacctcg tttctaaggc tatggctgat    480
actgttggac atagacagtc tctctactac atcatgactg gaaagacttt cggaggacag    540
aaggctgctg agatgggact cgttaacgag tctgttcctc tcgctcagct cagagaggtt    600
actatcgagc tcgctagaaa cctcctcgag aagaaccctg ttgttctcag agctgctaag    660
catggattca agagatgcag agagctcact tgggagcaga acgaggatta cctctacgct    720
aagctcgatc agtctagact cctcgatact gagggaggaa gagagcaggg tatgaagcag    780
ttcctcgatg ataagtctat caagcctgga ctccaggctt acaagaga                 828

<210> SEQ ID NO 3
<211> LENGTH: 1982
<212> TYPE: DNA
<213> ORGANISM: Artificial Sequence
<220> FEATURE:
<223> OTHER INFORMATION: synthetic polynucleotide sequence containing
      Arabidopsis thaliana ecotype Columbia, Col-0 IRX5
      promoter (pIRX5), promoter and transcriptional
      regulatory elements for IRX5
```

<400> SEQUENCE: 3

```
atgaagccat cctctacctc ggaaaaactt gttgcgagaa aagacatgc gatggcatgg      60
atgcttggat ctttgacatt gatgacactc ttctctcaac cattccttac cacaagagca    120
acggttgttt cgggtaaata aactaaactt aaccatatac attagccttg attcggtttt    180
tggtttgatt tatggatatt aaagatccga attatatttg aacaaaaaaa aatgattatg    240
tcacataaaa aaaattggc ttgaattttg gtttagatgg gttaaatgt ctacctctaa      300
tcatttcatt tgttttctgg ttagctttaa ttcggtttag aatgaaaccg ggattgacat    360
gttacattga tttgaaacag tggtgagcaa ctgaacacga ccaagttcga ggaatggcaa    420
aattcgggca aggcaccagc ggttccacac atggtgaagt tgtaccatga gatcagagag    480
agaggtttca agatcttttt gatctcttct cgtaaagagt atctcagatc tgccaccgtc    540
gaaaatctta ttgaagccgg ttaccacagc tggtctaacc tccttctgag gttcgaatca    600
tatttaataa ccgcattaaa ccgaaattta aattctaatt tcaccaaatc aaaaagtaaa    660
actagaacac ttcagataaa ttttgtcgtt ctgttgactt catttattct ctaaacacaa    720
agaactatag accataatcg aaataaaaac cctaaaaacc aaatttatct atttaaaaca    780
aacattagct atttgagttt cttttaggta agttatttaa ggttttggag actttaagat    840
gttttcagca tttatggttg tgtcattaat ttgtttagtt tagtaaagaa agaaaagata    900
gtaattaaag agttggttgt gaaatcatat ttaaaacatt aataggtatt tatgtctaat    960
ttggggacaa aatagtggaa ttctttatca tatctagcta gttcttatcg agtttgaact   1020
cgggttatga ttatgttaca tgcattggtc catataaatc tatgagcaat caatataatt   1080
cgagcatttt ggtataacat aatgagccaa gtataacaaa agtatcaaac ctatgcaggg   1140
gagaagatga tgaaaagaag agtgtgagcc aatacaaagc agatttgagg acatggctta   1200
caagtcttgg gtacagagtt tgggagtga tgggtgcaca atggaacagc ttctctggtt    1260
gtccagttcc aagagaacc ttcaagctcc ctaactccat ctactatgtc gcctgattaa    1320
atcttattta ctaacaaaac aataagatca gagtttcatt ctgattcttg agtctttttt   1380
ttctctctcc ctctttcat ttctggttta tataaccaat tcaaatgctt atgatccatg    1440
catgaaccat gatcatcttt gtgttttttt ttccttctgt attaccattt tgggcctttg   1500
tgaaattgat tttgggcttt tgttatataa tctcctcttt ctctttctct acctgattgg   1560
attcaagaac atagccagat ttggtaaagt ttataagata caaatatta agtaagacta     1620
aagtagaaat acataataac ttgaaagcta ctctaagtta tacaaattct aaagaactca   1680
aaagaataac aaacagtaga agttggaagc tcaagcaatt aaattatata aaaacactaa    1740
ctacactgag ctgtctcctt cttccaccaa atccttgttgc tgtctcttga agctttctta   1800
tgacacaaac cttagaccca atttcactca cagtttggta caacctcagt tttcttcaca   1860
acaaattcaa acatcttacc cttatattac ctctttatct cttcaatcat caaaacacat   1920
agtcacatac atttctctac cccaccttct gctctgcttc cgagagctca gtgtacctcg   1980
cc                                                                  1982
```

<210> SEQ ID NO 4
<211> LENGTH: 285
<212> TYPE: PRT
<213> ORGANISM: Sagittula stellata
<220> FEATURE:
<223> OTHER INFORMATION: Sagittula stellata strain E-37 p-
      hydroxycinnamoyl-CoA hydratase-lyase (HCHL) homolog, COG1024 enoyl-CoA hydratase/carnithine racemase, locus SSE37_01000

<400> SEQUENCE: 4

Met Thr Ala Thr Glu Ala Thr Leu Pro Ala Asn Asp Pro Asp Leu Ser
1               5                   10                  15

Gly Asp Asn Val Ala Val Ala Phe Glu Asp Gly Ile Ala Trp Val Lys
            20                  25                  30

Leu Asn Arg Pro Glu Lys Arg Asn Ala Met Ser Val Ser Leu Ala Glu
        35                  40                  45

Asp Met Asn Val Val Leu Asp Lys Leu Glu Ile Asp Asp Arg Cys Gly
    50                  55                  60

Val Leu Val Leu Thr Gly Glu Gly Ser Ala Phe Ser Ala Gly Met Asp
65                  70                  75                  80

Leu Lys Asp Phe Phe Arg Ala Thr Asp Gly Val Ser Asp Val Glu Arg
                85                  90                  95

Met Arg Ala Tyr Arg Ser Thr Arg Ala Trp Gln Trp Arg Thr Leu Met
            100                 105                 110

His Tyr Ser Lys Pro Thr Ile Ala Met Val Asn Gly Trp Cys Phe Gly
        115                 120                 125

Gly Ala Phe Thr Pro Leu Ile Cys Cys Asp Leu Ala Ile Ser Ser Asp
130                 135                 140

Asp Ala Val Tyr Gly Leu Ser Glu Ile Asn Trp Gly Ile Ile Pro Gly
145                 150                 155                 160

Gly Val Val Ser Lys Ala Ile Ser Thr Leu Met Ser Asp Arg Gln Ala
                165                 170                 175

Leu Tyr Tyr Val Met Thr Gly Glu Gln Phe Gly Gly Gln Glu Ala Val
            180                 185                 190

Lys Leu Gly Leu Val Asn Glu Ser Val Pro Ala Asp Lys Leu Arg Glu
        195                 200                 205

Arg Thr Val Glu Leu Cys Lys Val Leu Leu Glu Lys Asn Pro Thr Thr
    210                 215                 220

Met Arg Gln Ala Arg Met Ala Tyr Lys Tyr Ile Arg Glu Met Thr Trp
225                 230                 235                 240

Glu Glu Ser Ala Glu Tyr Leu Thr Ala Lys Gly Asp Gln Thr Val Phe
                245                 250                 255

Val Asp Lys Glu Lys Gly Arg Gln Gly Leu Lys Gln Phe Leu Asp
            260                 265                 270

Asp Lys Thr Tyr Arg Pro Gly Leu Gly Ala Tyr Lys Arg
        275                 280                 285

<210> SEQ ID NO 5
<211> LENGTH: 286
<212> TYPE: PRT
<213> ORGANISM: Saccharopolyspora erythraea
<220> FEATURE:
<223> OTHER INFORMATION: Saccharopolyspora erythraea strain NRRL_2338
      p-hydroxycinnamoyl-CoA hydratase-lyase (HCHL) homolog,
      enoyl-CoA hydratase/carnithine racemase

<400> SEQUENCE: 5

Met Ser Thr Pro Thr Thr Asp Pro Gly Thr Thr Thr Pro Trp Gly
1               5                   10                  15

Asp Thr Val Leu Val Asp Phe Asp Asp Gly Ile Ala Trp Val Thr Leu
            20                  25                  30

Asn Arg Pro Glu Lys Arg Asn Ala Met Asn Pro Ala Met Asn Asp Glu
        35                  40                  45

```
Met Val Arg Thr Leu Asp Ala Leu Glu Ala Asp Pro Arg Cys Arg Val
 50                  55                  60

Met Val Leu Thr Gly Ala Gly Glu Ser Phe Ser Ala Gly Met Asp Leu
 65                  70                  75                  80

Lys Glu Tyr Phe Arg Glu Val Asp Gln Thr Ala Asp Pro Ser Val Gln
                 85                  90                  95

Ile Arg Val Arg Arg Ala Ser Ala Glu Trp Gln Trp Lys Arg Leu Ala
            100                 105                 110

His Trp Ser Lys Pro Thr Ile Ala Met Val Asn Gly Trp Cys Phe Gly
        115                 120                 125

Gly Ala Phe Thr Pro Leu Val Ala Cys Asp Leu Ala Ile Ser Asp Glu
    130                 135                 140

Glu Ala Arg Tyr Gly Leu Ser Glu Ile Asn Trp Gly Ile Pro Pro Gly
145                 150                 155                 160

Gly Val Val Ser Arg Ala Leu Ala Ala Val Ser Gln Arg Asp Ala
                165                 170                 175

Leu Tyr Phe Ile Met Thr Gly Glu Thr Phe Asp Gly Arg Arg Ala Glu
                180                 185                 190

Gly Met Arg Leu Val Asn Glu Ala Val Pro Ala Glu Arg Leu Arg Glu
        195                 200                 205

Arg Thr Arg Glu Leu Ala Leu Lys Leu Ala Ser Thr Asn Pro Val Val
    210                 215                 220

Leu Arg Ala Ala Lys Val Gly Tyr Lys Ile Ala Arg Glu Met Pro Trp
225                 230                 235                 240

Glu Gln Ala Glu Asp Tyr Leu Tyr Ala Lys Leu Glu Gln Ser Gln Phe
                245                 250                 255

Leu Asp Ala Glu Arg Gly Arg Glu Lys Gly Met Ala Gln Phe Leu Asp
            260                 265                 270

Asp Lys Ser Tyr Arg Pro Gly Leu Ser Ala Tyr Ser Thr Asp
        275                 280                 285

<210> SEQ ID NO 6
<211> LENGTH: 278
<212> TYPE: PRT
<213> ORGANISM: Candidatus Solibacter usitatus
<220> FEATURE:
<223> OTHER INFORMATION: Candidatus Solibacter usitatus strain Ellin6076
      p-hydroxycinnamoyl-CoA hydratase-lyase (HCHL) homolog,
      locus Acid_0255

<400> SEQUENCE: 6

Met Asp Gln Tyr Glu Glu Lys Trp Gln Thr Val Lys Val Glu Val Asp
 1               5                  10                  15

Ala Glu Gly Ile Ala Trp Val Ile Phe Asn Arg Pro Ala Lys Arg Asn
             20                  25                  30

Ala Met Ser Pro Thr Leu Asn Arg Glu Met Ala Gln Val Leu Glu Thr
         35                  40                  45

Leu Glu Leu Asp Ala Ala Ala Lys Val Leu Val Leu Thr Gly Ala Gly
     50                  55                  60

Glu Ser Trp Ser Ala Gly Met Asp Leu Lys Glu Tyr Phe Arg Glu Val
 65                  70                  75                  80

Asp Gly Gln Pro Glu Ser His Gln Glu Lys Ile Arg Arg Glu Ala Ser
                 85                  90                  95

Leu Trp Gln Trp Lys Leu Leu Arg Met Tyr Ala Lys Pro Thr Ile Ala
            100                 105                 110

Met Val Asn Gly Trp Cys Phe Gly Gly Ala Phe Ser Pro Leu Val Ala
```

```
            115                 120                 125
Cys Asp Leu Ala Ile Ala Asp Glu Lys Ala Val Phe Gly Leu Ser Glu
    130                 135                 140

Ile Asn Trp Gly Ile Pro Pro Gly Asn Leu Val Ser Lys Ala Val Ala
145                 150                 155                 160

Asp Thr Met Gly His Arg Lys Ala Leu His Tyr Ile Met Thr Gly Glu
                165                 170                 175

Thr Phe Thr Gly Ala Gln Ala Ala Glu Met Gly Leu Val Asn Ala Ala
                180                 185                 190

Val Pro Thr Ser Glu Leu Arg Glu Ala Thr Arg Thr Leu Ala Leu Lys
                195                 200                 205

Leu Ala Ser Lys Asn Pro Val Ile Leu Arg Ala Ala Lys His Gly Phe
    210                 215                 220

Lys Arg Cys Arg Glu Leu Thr Trp Glu Gln Asn Glu Asp Tyr Leu Tyr
225                 230                 235                 240

Ala Lys Leu Asp Gln Ala Leu His Arg Asp Pro Glu Asp Ala Arg Ala
                245                 250                 255

Glu Gly Met Lys Gln Phe Leu Asp Glu Lys Ser Ile Lys Pro Gly Leu
                260                 265                 270

Gln Ser Tyr Lys Arg Ser
                275

<210> SEQ ID NO 7
<211> LENGTH: 277
<212> TYPE: PRT
<213> ORGANISM: Ralstonia solanacearum
<220> FEATURE:
<223> OTHER INFORMATION: Ralstonia solanacearum strain GMI1000
      p-hydroxycinnamoyl-CoA hydratase-lyase (HCHL) homolog,
      RS05198 gene, fca gene, locus RSp0225

<400> SEQUENCE: 7

Met Ala Thr Tyr Glu Gly Arg Trp Asn Thr Val Lys Val Asp Val Glu
1               5                   10                  15

Asp Gly Ile Ala Trp Val Thr Leu Asn Arg Pro Asp Lys Arg Asn Ala
                20                  25                  30

Met Ser Pro Thr Leu Asn Arg Glu Met Ile Asp Val Leu Glu Thr Leu
            35                  40                  45

Glu Leu Asp Gly Asp Ala Gln Val Leu Val Leu Thr Gly Ala Gly Glu
    50                  55                  60

Ser Trp Ser Ala Gly Met Asp Leu Lys Glu Tyr Phe Arg Glu Thr Asp
65                  70                  75                  80

Gly Gln Pro Glu Ile Met Gln Glu Arg Ile Arg Arg Asp Cys Ser Gln
                85                  90                  95

Trp Gln Trp Lys Leu Leu Arg Phe Tyr Ser Lys Pro Thr Ile Ala Met
            100                 105                 110

Val Asn Gly Trp Cys Phe Gly Gly Ala Phe Ser Pro Leu Val Ala Cys
        115                 120                 125

Asp Leu Ala Ile Ala Ala Asp Asp Ala Val Phe Gly Leu Ser Glu Ile
    130                 135                 140

Asn Trp Gly Ile Pro Pro Gly Asn Leu Val Ser Lys Ala Val Ala Asp
145                 150                 155                 160

Thr Met Gly His Arg Ala Ala Leu His Tyr Ile Met Thr Gly Glu Thr
                165                 170                 175

Phe Thr Gly Arg Glu Ala Ala Glu Met Gly Leu Val Asn Arg Ser Val
                180                 185                 190
```

Pro Arg Glu Arg Leu Arg Glu Ala Val Thr Glu Leu Ala Gly Lys Leu
            195                 200                 205

Leu Ala Lys Asn Pro Val Val Leu Arg Tyr Ala Lys His Gly Phe Lys
        210                 215                 220

Arg Cys Arg Glu Leu Ser Trp Glu Gln Asn Glu Asp Tyr Leu Tyr Ala
225                 230                 235                 240

Lys Val Asp Gln Ser Asn His Arg Asp Pro Glu Lys Gly Arg Gln His
                245                 250                 255

Gly Leu Lys Gln Phe Leu Asp Asp Lys Thr Ile Lys Pro Gly Leu Gln
            260                 265                 270

Thr Tyr Lys Arg Ala
        275

<210> SEQ ID NO 8
<211> LENGTH: 276
<212> TYPE: PRT
<213> ORGANISM: Xanthomonas albilineans
<220> FEATURE:
<223> OTHER INFORMATION: Xanthomonas albilineans strain GPE PC73 p-
     hydroxycinnamoyl-CoA hydratase-lyase (HCHL) homolog, enoyl-CoA
     hydratase, locus XALc_3045

<400> SEQUENCE: 8

Met Ser Asn Tyr Gln Asp Arg Trp Gln Thr Val Gln Val Gln Ile Asp
1               5                   10                  15

Ala Gly Val Ala Trp Val Thr Leu Asn Arg Pro Glu Lys Arg Asn Ala
            20                  25                  30

Met Ser Pro Thr Leu Asn Arg Glu Met Ile Asp Val Leu Glu Thr Leu
        35                  40                  45

Glu Leu Asp Ser Ala Ala Glu Val Leu Val Leu Thr Gly Ala Gly Glu
    50                  55                  60

Ser Trp Ser Ala Gly Met Asp Leu Lys Glu Tyr Phe Arg Glu Ile Asp
65                  70                  75                  80

Gly Lys Glu Glu Ile Val Gln Glu Arg Met Arg Arg Asp Cys Ser Gln
                85                  90                  95

Trp Gln Trp Arg Leu Leu Arg Phe Tyr Ser Lys Pro Thr Ile Ala Ala
            100                 105                 110

Val Asn Gly Trp Cys Phe Gly Gly Ala Phe Ser Pro Leu Val Ala Cys
        115                 120                 125

Asp Leu Ala Ile Ala Ala Asp Glu Ala Val Phe Gly Leu Ser Glu Ile
    130                 135                 140

Asn Trp Gly Ile Pro Pro Gly Asn Leu Val Ser Lys Ala Val Ala Asp
145                 150                 155                 160

Thr Met Gly His Arg Asn Ala Met Leu Tyr Ile Met Thr Gly Arg Thr
                165                 170                 175

Phe Thr Gly Thr Glu Ala Ala Gln Met Gly Leu Val Asn Ala Ser Val
            180                 185                 190

Pro Arg Ala Gln Leu Arg Ala Glu Val Thr Lys Leu Ala Gln Glu Leu
        195                 200                 205

Gln Gln Lys Asn Pro Val Val Leu Arg Phe Ala Lys His Gly Phe Lys
    210                 215                 220

Arg Cys Arg Glu Leu Thr Trp Glu Gln Asn Glu Asp Tyr Leu Tyr Ala
225                 230                 235                 240

Lys Val Asp Gln Ser Asn His Arg Asp Pro Glu Lys Gly Arg Gln Gln
                245                 250                 255

Gly Leu Lys Gln Phe Leu Asp Asp Lys Thr Ile Lys Pro Gly Leu Gln
            260                 265                 270

Thr Tyr Lys Arg
    275

<210> SEQ ID NO 9
<211> LENGTH: 279
<212> TYPE: PRT
<213> ORGANISM: Acentobacter baumannii
<220> FEATURE:
<223> OTHER INFORMATION: Acentobacter baumannii strain ATCC 17978
      p-hydroxycinnamoyl-CoA hydratase-lyase (HCHL) homolog,
      locus A1S_1111

<400> SEQUENCE: 9

Met Lys Met Ser Tyr Glu Asn Arg Trp Glu Thr Val Asp Val Lys Val
1               5                   10                  15

Glu Asp Gly Ile Ala Trp Val Thr Leu Asn Arg Pro Glu Lys Lys Asn
            20                  25                  30

Ala Met Ser Pro Thr Leu Asn Arg Glu Met Ile Asp Val Leu Glu Thr
        35                  40                  45

Leu Glu Leu Asp Gln Asn Ala Lys Val Leu Val Leu Thr Gly Ala Gly
    50                  55                  60

Asp Ser Trp Thr Ala Gly Met Asp Leu Lys Glu Tyr Phe Arg Glu Val
65                  70                  75                  80

Asp Thr Gln Pro Glu Ile Phe Gln Glu Arg Ile Arg Arg Asp Ser Cys
                85                  90                  95

Arg Trp Gln Trp Gln Leu Leu Arg Met Tyr Ser Lys Pro Thr Ile Ala
            100                 105                 110

Met Val Asn Gly Trp Cys Phe Gly Gly Gly Phe Ser Pro Leu Val Ala
        115                 120                 125

Cys Asp Leu Ala Ile Ala Ala Asp Glu Ala Thr Phe Gly Leu Ser Glu
    130                 135                 140

Ile Asn Trp Gly Ile Pro Pro Gly Asn Leu Val Ser Lys Ala Met Ala
145                 150                 155                 160

Asp Thr Val Gly His Arg Ala Ser Leu Tyr Tyr Ile Met Thr Gly Lys
                165                 170                 175

Thr Phe Ser Gly Lys Glu Ala Glu Thr Met Gly Leu Val Asn Lys Ser
            180                 185                 190

Val Pro Leu Ala Gln Leu Lys Ala Glu Val Thr Glu Leu Ala Asn Cys
        195                 200                 205

Leu Leu Glu Lys Asn Pro Val Val Leu Arg Thr Ala Lys Asn Gly Phe
    210                 215                 220

Lys Arg Cys Arg Glu Leu Thr Trp Asp Gln Asn Glu Asp Tyr Leu Tyr
225                 230                 235                 240

Ala Lys Leu Asp Gln Cys Ile His Arg Asp Thr Glu Asn Gly Arg Gln
                245                 250                 255

Glu Gly Leu Lys Gln Phe Leu Asp Glu Lys Ser Ile Lys Pro Gly Leu
            260                 265                 270

Gln Ser Tyr Lys Arg Thr Gly
        275

<210> SEQ ID NO 10
<211> LENGTH: 277
<212> TYPE: PRT
<213> ORGANISM: Acinetobacter sp.
<220> FEATURE:
<223> OTHER INFORMATION: Acinetobacter sp. strain ADP1 p- hydroxycinnamoyl-CoA hydratase-lyase (HCHL) homolog, hcaA gene,
locus ACIAD1726

<400> SEQUENCE: 10

Met Thr Tyr Asp Lys Arg Trp Glu Thr Val Asp Val Gln Val Glu His
1               5                   10                  15

Gly Ile Ala Trp Val Thr Leu Asn Arg Pro His Lys Lys Asn Ala Met
            20                  25                  30

Ser Pro Thr Leu Asn Arg Glu Met Ile Asp Val Leu Glu Thr Leu Glu
        35                  40                  45

Leu Asp Ser Glu Ala Lys Val Leu Val Leu Thr Gly Ala Gly Asp Ser
    50                  55                  60

Trp Thr Ala Gly Met Asp Leu Lys Glu Tyr Phe Arg Glu Val Asp Ala
65                  70                  75                  80

Gln Pro Glu Ile Phe Gln Glu Arg Ile Arg Arg Asp Ser Cys Arg Trp
                85                  90                  95

Gln Trp Gln Leu Leu Arg Met Tyr Ser Lys Pro Thr Ile Ala Met Val
            100                 105                 110

Asn Gly Trp Cys Phe Gly Gly Phe Ser Pro Leu Val Ala Cys Asp
        115                 120                 125

Leu Ala Ile Ala Ala Asp Glu Ala Thr Phe Gly Leu Ser Glu Ile Asn
    130                 135                 140

Trp Gly Ile Pro Pro Gly Asn Leu Val Ser Lys Ala Met Ala Asp Thr
145                 150                 155                 160

Val Gly His Arg Ala Ser Leu Tyr Tyr Ile Met Thr Gly Lys Thr Phe
                165                 170                 175

Thr Gly Lys Glu Ala Glu Ala Met Gly Leu Ile Asn Lys Ser Val Pro
            180                 185                 190

Leu Ala Gln Leu Lys Ala Glu Val Thr Glu Leu Ala Gln Cys Leu Val
        195                 200                 205

Glu Lys Asn Pro Val Val Leu Arg Thr Ala Lys Asn Gly Phe Lys Arg
    210                 215                 220

Cys Arg Glu Leu Thr Trp Asp Gln Asn Glu Asp Tyr Leu Tyr Ala Lys
225                 230                 235                 240

Leu Asp Gln Cys Asn His Arg Asp Thr Glu Gly Gly Arg Gln Glu Gly
                245                 250                 255

Leu Lys Gln Phe Leu Asp Glu Leu Ser Ile Lys Pro Gly Leu Gln Ser
            260                 265                 270

Tyr Lys Arg Thr Gly
        275

<210> SEQ ID NO 11
<211> LENGTH: 276
<212> TYPE: PRT
<213> ORGANISM: Chromohalobacter salexigens
<220> FEATURE:
<223> OTHER INFORMATION: Chromohalobacter salexigens strain DSM 3043
      p-hydroxycinnamoyl-CoA hydratase-lyase (HCHL) homolog,
      locus Csal_0278

<400> SEQUENCE: 11

Met Ser Asp Tyr Thr Asn Arg Trp Gln Thr Val Lys Val Asp Val Glu
1               5                   10                  15

Asp Gly Ile Ala Trp Val Thr Leu Asn Arg Pro Glu Lys Arg Asn Ala
            20                  25                  30

Met Ser Pro Thr Leu Asn Arg Glu Met Ile Asp Val Leu Glu Thr Ile
        35                  40                  45

Glu Leu Asp Gln Asp Ala His Val Leu Val Leu Thr Gly Glu Gly Glu
        50                  55                  60

Ser Phe Ser Ala Gly Met Asp Leu Lys Glu Tyr Phe Arg Glu Ile Asp
 65                  70                  75                  80

Ala Ser Pro Glu Ile Val Gln Val Lys Val Arg Arg Asp Ala Ser Thr
                    85                  90                  95

Trp Gln Trp Lys Leu Leu Arg His Tyr Ala Lys Pro Thr Ile Ala Met
                100                 105                 110

Val Asn Gly Trp Cys Phe Gly Gly Ala Phe Ser Pro Leu Val Ala Cys
            115                 120                 125

Asp Leu Ala Ile Ala Ala Asp Glu Ser Val Phe Gly Leu Ser Glu Ile
130                 135                 140

Asn Trp Gly Ile Pro Pro Gly Asn Leu Val Ser Lys Ala Met Ala Asp
145                 150                 155                 160

Thr Val Gly His Arg Gln Ala Leu Tyr Tyr Ile Met Thr Gly Glu Thr
                165                 170                 175

Phe Thr Gly Pro Gln Ala Ala Asp Met Gly Leu Val Asn Gln Ser Val
                180                 185                 190

Pro Arg Ala Glu Leu Arg Glu Thr Thr His Lys Leu Ala Ala Thr Leu
            195                 200                 205

Arg Asp Lys Asn Pro Val Val Leu Arg Ala Ala Lys Thr Gly Phe Lys
210                 215                 220

Met Cys Arg Glu Leu Thr Trp Glu Gln Asn Glu Glu Tyr Leu Tyr Ala
225                 230                 235                 240

Lys Leu Asp Gln Ala Gln Gln Leu Asp Pro Glu His Gly Arg Glu Gln
                245                 250                 255

Gly Leu Lys Gln Phe Leu Asp Asp Lys Ser Ile Lys Pro Gly Leu Glu
            260                 265                 270

Ser Tyr Arg Arg
        275

<210> SEQ ID NO 12
<211> LENGTH: 276
<212> TYPE: PRT
<213> ORGANISM: Burkholeria cenocepacia
<220> FEATURE:
<223> OTHER INFORMATION: Burkholeria cenocepacia strain PC184
      p-hydroxycinnamoyl-CoA hydratase-lyase (HCHL) homolog,
      enoyl-CoA hydratase/carnithine racemase, locus BCPG_04453

<400> SEQUENCE: 12

Met Ser Lys Tyr Asp Asn Arg Trp Gln Thr Val Glu Val Lys Val Glu
 1               5                  10                  15

Ala Gly Ile Ala Trp Val Thr Leu Asn Arg Pro Glu Lys Arg Asn Ala
                20                  25                  30

Met Ser Pro Thr Leu Asn Arg Glu Met Leu Glu Val Leu Asp Ala Val
            35                  40                  45

Glu Phe Asp Asp Glu Ala Lys Val Leu Val Leu Thr Gly Ala Gly Ala
        50                  55                  60

Ala Trp Thr Ala Gly Met Asp Leu Lys Glu Tyr Phe Arg Glu Ile Asp
 65                  70                  75                  80

Gly Gly Ser Asp Ala Leu Gln Glu Lys Val Arg Arg Asp Ala Ser Glu
                    85                  90                  95

Trp Gln Trp Arg Arg Leu Arg Met Tyr Asn Lys Pro Thr Ile Ala Met
                100                 105                 110

```
Val Asn Gly Trp Cys Phe Gly Gly Phe Ser Pro Leu Val Ala Cys
            115                 120                 125

Asp Leu Ala Ile Ala Ala Asp Ala Val Phe Gly Leu Ser Glu Ile
        130                 135                 140

Asn Trp Gly Ile Pro Pro Gly Asn Leu Val Ser Lys Ala Met Ala Asp
145                 150                 155                 160

Thr Val Gly His Arg Arg Ala Leu His Tyr Ile Met Thr Gly Asp Thr
                165                 170                 175

Phe Thr Gly Ala Glu Ala Ala Glu Met Gly Leu Val Asn Ser Ser Val
            180                 185                 190

Pro Leu Ala Glu Leu Arg Asp Ala Thr Ile Ala Leu Ala Arg Leu
        195                 200                 205

Met Asp Lys Asn Pro Val Val Leu Arg Ala Ala Lys His Gly Phe Lys
    210                 215                 220

Arg Ser Arg Glu Leu Thr Trp Glu Gln Cys Glu Asp Tyr Leu Tyr Ala
225                 230                 235                 240

Lys Leu Asp Gln Ala Gln Leu Arg Asp Pro Glu Arg Gly Arg Glu Gln
                245                 250                 255

Gly Leu Lys Gln Phe Leu Asp Asp Lys Thr Ile Lys Pro Gly Leu Gln
            260                 265                 270

Ala Tyr Lys Arg
        275

<210> SEQ ID NO 13
<211> LENGTH: 276
<212> TYPE: PRT
<213> ORGANISM: Burkholderia ambifaria
<220> FEATURE:
<223> OTHER INFORMATION: Burkholderia ambifaria strain AMMD p-
      hydroxycinnamoyl-CoA hydratase-lyase (HCHL) homolog, locus
      Bamb_4916

<400> SEQUENCE: 13

Met Ser Lys Tyr Asp Asn Arg Trp Gln Thr Val Glu Val Asn Val Glu
1               5                   10                  15

Ala Gly Ile Ala Trp Val Thr Leu Asn Arg Pro Asp Lys Arg Asn Ala
            20                  25                  30

Met Ser Pro Thr Leu Asn Gln Glu Met Leu Gln Val Leu Asp Ala Ile
        35                  40                  45

Glu Phe Asp Asp Asp Ala Lys Val Leu Val Leu Thr Gly Ala Gly Ser
    50                  55                  60

Ala Trp Thr Ala Gly Met Asp Leu Lys Glu Tyr Phe Arg Glu Ile Asp
65                  70                  75                  80

Gly Gly Ser Asp Ala Leu Gln Glu Lys Val Arg Arg Asp Ala Ser Glu
                85                  90                  95

Trp Gln Trp Arg Arg Leu Arg Met Tyr Asn Lys Pro Thr Ile Ala Met
            100                 105                 110

Val Asn Gly Trp Cys Phe Gly Gly Phe Ser Pro Leu Val Ala Cys
        115                 120                 125

Asp Leu Ala Ile Ala Ala Asp Glu Ala Val Phe Gly Leu Ser Glu Ile
    130                 135                 140

Asn Trp Gly Ile Pro Pro Gly Asn Leu Val Ser Lys Ala Met Ala Asp
145                 150                 155                 160

Thr Val Gly His Arg Arg Ala Leu His Tyr Ile Met Thr Gly Asp Thr
                165                 170                 175

Phe Thr Gly Val Glu Ala Ala Glu Met Gly Leu Val Asn Ser Ser Val
```

```
                    180                 185                 190
Pro Leu Ala Gly Leu Arg Asp Ala Thr Ile Ala Leu Ala Ala Arg Leu
            195                 200                 205

Met Asp Lys Asn Pro Val Val Leu Arg Ala Ala Lys His Gly Phe Lys
        210                 215                 220

Arg Ser Arg Glu Leu Thr Trp Glu Gln Cys Glu Asp Tyr Leu Tyr Ala
225                 230                 235                 240

Lys Leu Asp Gln Ala Gln Leu Arg Asp Pro Glu Arg Gly Arg Glu Gln
                245                 250                 255

Gly Leu Lys Gln Phe Leu Asp Asp Lys Ala Ile Lys Pro Gly Leu Gln
            260                 265                 270

Ala Tyr Lys Arg
        275

<210> SEQ ID NO 14
<211> LENGTH: 276
<212> TYPE: PRT
<213> ORGANISM: Burkholderia ambifaria
<220> FEATURE:
<223> OTHER INFORMATION: Burkholderia ambifaria strain AMMD p-
      hydroxycinnamoyl-CoA hydratase-lyase (HCHL) homolog, locus
      Bamb_4916

<400> SEQUENCE: 14

Met Ser Lys Tyr Asp Asn Arg Trp Gln Thr Val Glu Val Asn Val Glu
1               5                   10                  15

Ala Gly Ile Ala Trp Val Thr Leu Asn Arg Pro Asp Lys Arg Asn Ala
            20                  25                  30

Met Ser Pro Thr Leu Asn Gln Glu Met Leu Gln Val Leu Asp Ala Ile
        35                  40                  45

Glu Phe Asp Asp Asp Ala Lys Val Leu Val Leu Thr Gly Ala Gly Ser
    50                  55                  60

Ala Trp Thr Ala Gly Met Asp Leu Lys Glu Tyr Phe Arg Glu Ile Asp
65                  70                  75                  80

Gly Gly Ser Asp Ala Leu Gln Glu Lys Val Arg Arg Asp Ala Ser Glu
                85                  90                  95

Trp Gln Trp Arg Arg Leu Arg Met Tyr Asn Lys Pro Thr Ile Ala Met
            100                 105                 110

Val Asn Gly Trp Cys Phe Gly Gly Gly Phe Ser Pro Leu Val Ala Cys
        115                 120                 125

Asp Leu Ala Ile Ala Ala Asp Glu Ala Val Phe Gly Leu Ser Glu Ile
    130                 135                 140

Asn Trp Gly Ile Pro Pro Gly Asn Leu Val Ser Lys Ala Met Ala Asp
145                 150                 155                 160

Thr Val Gly His Arg Arg Ala Leu His Tyr Ile Met Thr Gly Asp Thr
                165                 170                 175

Phe Thr Gly Val Glu Ala Ala Glu Met Gly Leu Val Asn Ser Ser Val
            180                 185                 190

Pro Leu Ala Gly Leu Arg Asp Ala Thr Ile Ala Leu Ala Ala Arg Leu
        195                 200                 205

Met Asp Lys Asn Pro Val Val Leu Arg Ala Ala Lys His Gly Phe Lys
    210                 215                 220

Arg Ser Arg Glu Leu Thr Trp Glu Gln Cys Glu Asp Tyr Leu Tyr Ala
225                 230                 235                 240

Lys Leu Asp Gln Ala Gln Leu Arg Asp Pro Glu Arg Gly Arg Glu Gln
                245                 250                 255
```

```
Gly Leu Lys Gln Phe Leu Asp Asp Lys Ala Ile Lys Pro Gly Leu Gln
            260                 265                 270

Ala Tyr Lys Arg
        275

<210> SEQ ID NO 15
<211> LENGTH: 276
<212> TYPE: PRT
<213> ORGANISM: Burkholderia thailandensis
<220> FEATURE:
<223> OTHER INFORMATION: Burkholderia thailandensis strain MSMB43
      p-hydroxycinnamoyl-CoA hydratase-lyase (HCHL) homolog,
      COG1024 en <220> FEATURE:
<223> OTHER INFORMATION: Burkholderia ubonensis strain Bu p-
hydroxycinnamoyl-CoA hydratase-lyase (HCHL) homolog, COG1024
enoyl-CoA hydratase/carnithine racemase, locus BuboB_010100031920

<400> SEQUENCE: 16

Met Ser Lys Tyr Glu Asn Arg Trp Gln Thr Val Glu Val Lys Val Glu
1               5                   10                  15

Ala Gly Ile Ala Trp Val Thr Leu Asn Arg Pro Asp Lys Arg Asn Ala
            20                  25                  30

Met Ser Pro Thr Leu Asn Gln Glu Met Leu Gln Val Leu Asp Ala Ile
        35                  40                  45

Glu Phe Asp Asp Asp Ala Lys Val Leu Val Leu Thr Gly Ala Gly Ala
    50                  55                  60

Ala Trp Thr Ala Gly Met Asp Leu Lys Glu Tyr Phe Arg Glu Ile Asp
65                  70                  75                  80

Gly Gly Pro Asp Ala Leu Gln Glu Lys Val Arg Arg Asp Ala Ser Glu
                85                  90                  95

Trp Gln Trp Arg Arg Leu Arg Met Tyr Gly Lys Pro Thr Ile Ala Met
            100                 105                 110

Val Asn Gly Trp Cys Phe Gly Gly Phe Ser Pro Leu Val Ala Cys
        115                 120                 125

Asp Leu Ala Ile Ala Ala Asp Glu Ala Val Phe Gly Leu Ser Glu Ile
    130                 135                 140

Asn Trp Gly Ile Pro Pro Gly Asn Leu Val Ser Lys Ala Met Ala Asp
145                 150                 155                 160

Thr Val Gly His Arg Arg Ala Leu His Tyr Ile Met Thr Gly Asp Thr
                165                 170                 175

Phe Thr Gly Val Glu Ala Ala Asp Met Gly Leu Val Asn Arg Ser Val
            180                 185                 190

Pro Leu Ala Glu Leu Arg Asp Ala Thr Ile Ala Leu Ala Ala Arg Leu
        195                 200                 205

Ile Asp Lys Asn Pro Val Val Leu Arg Ala Ala Lys His Gly Phe Lys
    210                 215                 220

Arg Ser Arg Glu Leu Thr Trp Glu Gln Cys Glu Asp Tyr Leu Tyr Ala
225                 230                 235                 240

Lys Leu Asp Gln Ala Gln Leu Arg Asp Pro Glu Arg Gly Arg Glu Gln
                245                 250                 255

Gly Leu Lys Gln Phe Leu Asp Asp Lys Ala Ile Lys Pro Gly Leu Gln
            260                 265                 270

Ala Tyr Lys Arg
        275

<210> SEQ ID NO 17
<211> LENGTH: 276
<212> TYPE: PRT
<213> ORGANISM: Azotobacter vinelandii
<220> FEATURE:
<223> OTHER INFORMATION: Azotobacter vinelandii strain DJ = ATCC BAA-
1303 p-hydroxycinnamoyl-CoA hydratase-lyase (HCHL) homolog,
ech gene, locus Avin_14230

<400> SEQUENCE: 17

Met Asn Lys Tyr Glu Gly Arg Trp Lys Thr Val Ile Val Glu Ile Glu
1               5                   10                  15

Gly Gly Ile Ala Trp Val Thr Leu Asn Arg Pro Asp Lys Arg Asn Ala
            20                  25                  30

Met Ser Pro Thr Leu Asn Arg Glu Met Arg Asp Val Leu Glu Thr Leu
        35                  40                  45

Glu Gln Asp Pro Ala Ala Arg Val Leu Val Leu Thr Gly Ala Gly Ser
 50                  55                  60

Ala Trp Thr Ala Gly Met Asp Leu Lys Glu Tyr Phe Arg Glu Val Asp
 65                  70                  75                  80

Ala Gly Pro Glu Ile Leu Gln Glu Lys Ile Arg Arg Glu Ala Cys Glu
                 85                  90                  95

Trp Gln Trp Lys Leu Leu Arg Met Tyr Ala Lys Pro Thr Val Ala Met
                100                 105                 110

Val Asn Gly Trp Cys Phe Gly Gly Phe Ser Pro Leu Val Ala Cys
                115                 120                 125

Asp Leu Ala Ile Cys Ala Asp Glu Ala Thr Phe Gly Leu Ser Glu Ile
        130                 135                 140

Asn Trp Gly Ile Pro Pro Gly Asn Leu Val Ser Lys Ala Met Ala Asp
145                 150                 155                 160

Thr Val Gly His Arg Gln Ala Leu Tyr Tyr Ile Met Thr Gly Lys Thr
                165                 170                 175

Phe Asp Gly Arg Gln Ala Ala Glu Met Gly Leu Val Asn Gln Ser Val
                180                 185                 190

Pro Leu Ala Gln Leu Arg Glu Thr Val Ala Thr Leu Cys Gln Asp Leu
        195                 200                 205

Leu Asp Lys Asn Pro Val Val Leu Arg Ala Ala Lys Asn Gly Phe Lys
210                 215                 220

Arg Cys Arg Glu Leu Thr Trp Glu Gln Asn Glu Asp Tyr Leu Tyr Ala
225                 230                 235                 240

Lys Leu Asp Gln Ser Arg Leu Leu Asp Glu Glu Gly Arg Glu Glu
                245                 250                 255

Gly Met Arg Gln Phe Leu Asp Glu Lys Ser Ile Lys Pro Gly Leu Gln
                260                 265                 270

Ala Tyr Lys Arg
        275

<210> SEQ ID NO 18
<211> LENGTH: 276
<212> TYPE: PRT
<213> ORGANISM: Pseudomonas putida
<220> FEATURE:
<223> OTHER INFORMATION: Pseudomonas putida strain KT2440 p-
      hydroxycinnamoyl-CoA hydratase-lyase (HCHL) homolog, ech gene,
      locus PP_3358

<400> SEQUENCE: 18

Met Ser Lys Tyr Glu Gly Arg Trp Thr Thr Val Lys Val Glu Leu Glu
 1               5                  10                  15

Ala Gly Ile Ala Trp Val Thr Leu Asn Arg Pro Glu Lys Arg Asn Ala
                20                  25                  30

Met Ser Pro Thr Leu Asn Arg Glu Met Val Asp Val Leu Glu Thr Leu
        35                  40                  45

Glu Gln Asp Ala Asp Ala Gly Val Leu Val Leu Thr Gly Ala Gly Glu
 50                  55                  60

Ser Trp Thr Ala Gly Met Asp Leu Lys Glu Tyr Phe Arg Glu Val Asp
 65                  70                  75                  80

Ala Gly Pro Glu Ile Leu Gln Glu Lys Ile Arg Arg Glu Ala Ser Gln
                 85                  90                  95

Trp Gln Trp Lys Leu Leu Arg Leu Tyr Ala Lys Pro Thr Ile Ala Met

Val Asn Gly Trp Cys Phe Gly Gly Gly Phe Ser Pro Leu Val Ala Cys
            100                 105                 110
Asp Leu Ala Ile Cys Ala Asn Glu Ala Thr Phe Gly Leu Ser Glu Ile
        115                 120                 125
Asn Trp Gly Ile Pro Pro Gly Asn Leu Val Ser Lys Ala Met Ala Asp
130                 135                 140
Thr Val Gly His Arg Gln Ser Leu Tyr Tyr Ile Met Thr Gly Lys Thr
145                 150                 155                 160
Phe Asp Gly Arg Lys Ala Ala Glu Met Gly Leu Val Asn Asp Ser Val
                165                 170                 175
Pro Leu Ala Glu Leu Arg Glu Thr Thr Arg Glu Leu Ala Leu Asn Leu
            180                 185                 190
Leu Glu Lys Asn Pro Val Val Leu Arg Ala Ala Lys Asn Gly Phe Lys
        195                 200                 205
Arg Cys Arg Glu Leu Thr Trp Glu Gln Asn Glu Asp Tyr Leu Tyr Ala
210                 215                 220
Lys Leu Asp Gln Ser Arg Leu Leu Asp Thr Thr Gly Gly Arg Glu Gln
225                 230                 235                 240
Gly Met Lys Gln Phe Leu Asp Asp Lys Ser Ile Lys Pro Gly Leu Gln
                245                 250                 255
Ala Tyr Lys Arg
            260                 265                 270

275

<210> SEQ ID NO 19
<211> LENGTH: 276
<212> TYPE: PRT
<213> ORGANISM: Pseudomonas fluorescens
<220> FEATURE:
<223> OTHER INFORMATION: Pseudomonas fluorescens strain SBW25 p-
    hydroxycinnamoyl-CoA hydratase-lyase (HCHL) homolog, locus
    PFLU3300

<400> SEQUENCE: 19

Met Ser Asn Tyr Glu Gly Arg Trp Thr Thr Val Lys Val Glu Ile Glu
1               5                   10                  15
Glu Gly Ile Ala Trp Val Ile Leu Asn Arg Pro Glu Lys Arg Asn Ala
            20                  25                  30
Met Ser Pro Thr Leu Asn Arg Glu Met Ile Asp Val Leu Glu Thr Leu
        35                  40                  45
Glu Gln Asp Pro Ala Ala Gly Val Leu Val Leu Thr Gly Ala Gly Glu
    50                  55                  60
Ala Trp Thr Ala Gly Met Asp Leu Lys Glu Tyr Phe Arg Glu Val Asp
65                  70                  75                  80
Ala Gly Pro Glu Ile Leu Gln Glu Lys Ile Arg Arg Glu Ala Ser Gln
                85                  90                  95
Trp Gln Trp Lys Leu Leu Arg Met Tyr Ala Lys Pro Thr Ile Ala Met
            100                 105                 110
Val Asn Gly Trp Cys Phe Gly Gly Gly Phe Ser Pro Leu Val Ala Cys
        115                 120                 125
Asp Leu Ala Ile Cys Ala Asp Glu Ala Thr Phe Gly Leu Ser Glu Ile
    130                 135                 140
Asn Trp Gly Ile Pro Pro Gly Asn Leu Val Ser Lys Ala Met Ala Asp
145                 150                 155                 160
Thr Val Gly His Arg Gln Ser Leu Tyr Tyr Ile Met Thr Gly Lys Thr
                165                 170                 175

```
Phe Gly Gly Gln Lys Ala Ala Glu Met Gly Leu Val Asn Glu Ser Val
            180                 185                 190

Pro Leu Ala Gln Leu Arg Glu Val Thr Ile Glu Leu Ala Arg Asn Leu
        195                 200                 205

Leu Glu Lys Asn Pro Val Val Leu Arg Ala Ala Lys His Gly Phe Lys
    210                 215                 220

Arg Cys Arg Glu Leu Thr Trp Glu Gln Asn Glu Asp Tyr Leu Tyr Ala
225                 230                 235                 240

Lys Leu Asp Gln Ser Arg Leu Leu Asp Thr Glu Gly Arg Glu Gln
                245                 250                 255

Gly Met Lys Gln Phe Leu Asp Asp Lys Ser Ile Lys Pro Gly Leu Gln
            260                 265                 270

Ala Tyr Lys Arg
        275

<210> SEQ ID NO 20
<211> LENGTH: 276
<212> TYPE: PRT
<213> ORGANISM: Pseudomonas syringae
<220> FEATURE:
<223> OTHER INFORMATION: Pseudomonas syringae pathovar tomato strain
      DC3000 p-hydroxycinnamoyl-CoA hydratase-lyase (HCHL) homolog,
      locus PSPTO_2944

<400> SEQUENCE: 20

Met Ser Lys Tyr Glu Gly Arg Trp Thr Thr Val Lys Val Glu Ile Glu
1               5                   10                  15

Gln Gly Ile Ala Trp Val Ile Leu Asn Arg Pro Glu Lys Arg Asn Ala
            20                  25                  30

Met Ser Pro Thr Leu Asn Arg Glu Met Ile Asp Val Leu Glu Thr Leu
        35                  40                  45

Glu Gln Asp Pro Glu Ala Gly Val Leu Val Leu Thr Gly Ala Gly Glu
    50                  55                  60

Ala Trp Thr Ala Gly Met Asp Leu Lys Glu Tyr Phe Arg Glu Val Asp
65                  70                  75                  80

Ala Gly Pro Glu Ile Leu Gln Glu Lys Ile Arg Arg Glu Ala Ser Gln
                85                  90                  95

Trp Gln Trp Lys Leu Leu Arg Met Tyr Ala Lys Pro Thr Ile Ala Met
            100                 105                 110

Val Asn Gly Trp Cys Phe Gly Gly Phe Ser Pro Leu Val Ala Cys
        115                 120                 125

Asp Leu Ala Ile Cys Ala Asp Glu Ala Thr Phe Gly Leu Ser Glu Ile
    130                 135                 140

Asn Trp Gly Ile Pro Pro Gly Asn Leu Val Ser Lys Ala Met Ala Asp
145                 150                 155                 160

Thr Val Gly His Arg Gln Ser Leu Tyr Tyr Ile Met Thr Gly Lys Thr
                165                 170                 175

Phe Asp Gly Lys Lys Ala Ala Glu Met Gly Leu Val Asn Glu Ser Val
            180                 185                 190

Pro Leu Ala Gln Leu Arg Gln Val Thr Ile Asp Leu Ala Leu Asn Leu
        195                 200                 205

Leu Glu Lys Asn Pro Val Val Leu Arg Ala Ala Lys His Gly Phe Lys
    210                 215                 220

Arg Cys Arg Glu Leu Thr Trp Glu Gln Asn Glu Asp Tyr Leu Tyr Ala
225                 230                 235                 240
```

Lys Leu Asp Gln Ser Arg Leu Leu Asp Lys Glu Gly Gly Arg Glu Gln
            245                 250                 255

Gly Met Lys Gln Phe Leu Asp Asp Lys Ser Ile Lys Pro Gly Leu Glu
        260                 265                 270

Ala Tyr Lys Arg
        275

<210> SEQ ID NO 21
<211> LENGTH: 277
<212> TYPE: PRT
<213> ORGANISM: Ralstonia eutropha
<220> FEATURE:
<223> OTHER INFORMATION: Ralstonia eutropha strain JMP134 p-
      hydroxycinnamoyl-CoA hydratase-lyase (HCHL) homolog, locus
      Reut_B4870

<400> SEQUENCE: 21

Met Ala Asn Tyr Glu Gly Arg Trp Lys Thr Val Lys Val Ser Val Glu
1               5                   10                  15

Glu Gly Ile Ala Trp Val Met Phe Asn Arg Pro Glu Lys Arg Asn Ala
            20                  25                  30

Met Ser Pro Thr Leu Asn Ser Glu Met Ile Gln Val Leu Glu Ala Leu
        35                  40                  45

Glu Leu Asp Ala Asp Ala Arg Val Val Leu Thr Gly Ala Gly Asp
    50                  55                  60

Ala Trp Thr Ala Gly Met Asp Leu Lys Glu Tyr Phe Arg Glu Val Asp
65                  70                  75                  80

Ala Gly Pro Glu Ile Leu Gln Glu Lys Ile Arg Arg Asp Ala Cys Gln
                85                  90                  95

Trp Gln Trp Lys Leu Leu Arg Met Tyr Ala Lys Pro Thr Ile Ala Met
            100                 105                 110

Val Asn Gly Trp Cys Phe Gly Gly Phe Ser Pro Leu Val Ala Cys
            115                 120                 125

Asp Leu Ala Ile Ala Ala Asp Glu Ala Val Phe Gly Leu Ser Glu Ile
        130                 135                 140

Asn Trp Gly Ile Pro Pro Gly Asn Leu Val Ser Lys Ala Met Ala Asp
145                 150                 155                 160

Thr Val Gly His Arg Gln Ala Leu His Tyr Ile Met Thr Gly Asp Thr
                165                 170                 175

Phe Thr Gly Gln Gln Ala Ala Ala Met Gly Leu Val Asn Lys Ser Val
            180                 185                 190

Pro Arg Ser Gln Leu Arg Glu His Val Leu Glu Leu Ala Gly Lys Leu
        195                 200                 205

Leu Glu Lys Asn Pro Val Val Leu Arg Ala Ala Lys His Gly Phe Lys
    210                 215                 220

Arg Ser Arg Glu Leu Thr Trp Glu Gln Asn Glu Asp Tyr Leu Tyr Ala
225                 230                 235                 240

Lys Leu Asp Gln Ala Gln Leu Arg Asp Pro Glu His Gly Arg Glu Gln
                245                 250                 255

Gly Leu Lys Gln Phe Leu Asp Asp Lys Ser Ile Lys Pro Gly Leu Gln
            260                 265                 270

Ala Tyr Lys Arg Ala
        275

<210> SEQ ID NO 22
<211> LENGTH: 275
<212> TYPE: PRT

<213> ORGANISM: Burkholderia glumae
<220> FEATURE:
<223> OTHER INFORMATION: Burkholderia glumae strain BGR1 p-
hydroxycinnamoyl-CoA hydratase-lyase (HCHL) homolog, locus
bglu_2g10520

<400> SEQUENCE:

```
Ser Pro Thr Leu Asn Lys Glu Met Ile Glu Val Leu Glu Ala Val Glu
        35                  40                  45

Leu Asp Ala Glu Ala Gln Val Leu Val Leu Thr Gly Glu Gly Asp Ala
    50                  55                  60

Trp Thr Ala Gly Met Asp Leu Lys Glu Tyr Phe Arg Glu Val Asp Ala
65                  70                  75                  80

Gly Pro Glu Ile Leu Gln Glu Lys Ile Arg Arg Asp Ala Cys Arg Trp
                85                  90                  95

Gln Trp Gln Leu Leu Arg Met Tyr Ser Lys Pro Thr Ile Ala Met Val
            100                 105                 110

Asn Gly Trp Cys Phe Gly Gly Phe Ser Pro Leu Val Ala Cys Asp
            115                 120                 125

Leu Ala Ile Ala Ala Asp Glu Ala Thr Phe Gly Leu Ser Glu Ile Asn
    130                 135                 140

Trp Gly Ile Pro Pro Gly Asn Leu Val Ser Lys Ala Met Ala Asp Thr
145                 150                 155                 160

Val Gly His Arg Gln Ala Leu Tyr Tyr Ile Met Thr Gly Glu Thr Phe
                165                 170                 175

Thr Gly Gln Glu Ala Ala Gln Met Gly Leu Val Asn Lys Ser Val Pro
            180                 185                 190

Arg Ala Glu Leu Arg Glu Ala Thr Arg Ala Leu Ala Gly Lys Leu Leu
        195                 200                 205

Glu Lys Asn Pro Val Val Leu Arg Ala Ala Lys His Gly Phe Lys Arg
    210                 215                 220

Cys Arg Glu Leu Thr Trp Asp Gln Asn Glu Asp Tyr Leu Tyr Ala Lys
225                 230                 235                 240

Leu Asp Gln Ala Gln Leu Arg Asp Pro Glu Gly Gly Arg Glu Gln Gly
                245                 250                 255

Leu Lys Gln Phe Leu Asp Asp Lys Ala Ile Lys Pro Gly Leu Gln Thr
            260                 265                 270

Tyr Lys Arg
        275

<210> SEQ ID NO 24
<211> LENGTH: 275
<212> TYPE: PRT
<213> ORGANISM: Burkholderia mallei
<220> FEATURE:
<223> OTHER INFORMATION: Burkholderia mallei ATCC 23344 p-
      hydroxycinnamoyl-CoA hydratase-lyase (HCHL) homolog, locus
      BMAA0629

<400> SEQUENCE: 24

Met Ser Tyr Glu Gly Arg Trp Lys Thr Val Glu Val Ile Val Asp Gly
1               5                   10                  15

Ala Ile Ala Trp Val Thr Leu Asn Arg Pro Asp Lys Arg Asn Ala Met
            20                  25                  30

Ser Pro Thr Leu Asn Ala Glu Met Ile Asp Val Leu Glu Ala Ile Glu
        35                  40                  45

Leu Asp Pro Glu Ala Arg Val Leu Val Leu Thr Gly Glu Gly Glu Ala
    50                  55                  60

Trp Thr Ala Gly Met Asp Leu Lys Glu Tyr Phe Arg Glu Ile Asp Ala
65                  70                  75                  80

Gly Pro Glu Ile Leu Gln Glu Lys Ile Arg Arg Asp Ala Ser Arg Trp
                85                  90                  95
```

```
Gln Trp Gln Leu Leu Arg Met Tyr Ala Lys Pro Thr Ile Ala Met Val
                100                 105                 110

Asn Gly Trp Cys Phe Gly Gly Phe Ser Pro Leu Val Ala Cys Asp
            115                 120                 125

Leu Ala Ile Ala Ala Asp Glu Ala Val Phe Gly Leu Ser Glu Ile Asn
        130                 135                 140

Trp Gly Ile Pro Pro Gly Asn Leu Val Ser Lys Ala Met Ala Asp Thr
145                 150                 155                 160

Val Gly His Arg Gln Ala Leu Tyr Tyr Ile Met Thr Gly Glu Thr Phe
                165                 170                 175

Thr Gly Ala Gln Ala Ala Gln Met Gly Leu Val Asn Arg Ser Val Pro
            180                 185                 190

Arg Ala Gln Leu Arg Asp Ala Val Arg Ala Leu Ala Ala Lys Leu Leu
        195                 200                 205

Asp Lys Asn Pro Val Val Leu Arg Asn Ala Lys His Gly Phe Lys Arg
        210                 215                 220

Cys Arg Glu Leu Thr Trp Glu Gln Asn Glu Asp Tyr Leu Tyr Ala Lys
225                 230                 235                 240

Leu Asp Gln Ala Gln Leu Arg Asp Pro Glu His Gly Arg Glu Gln Gly
                245                 250                 255

Leu Lys Gln Phe Leu Asp Asp Lys Thr Ile Lys Pro Gly Leu Gln Ala
            260                 265                 270

Tyr Arg Arg
        275

<210> SEQ ID NO 25
<211> LENGTH: 275
<212> TYPE: PRT
<213> ORGANISM: Burkholderia pseudomallei
<220> FEATURE:
<223> OTHER INFORMATION: Burkholderia pseudomallei strain 305 p-
      hydroxycinnamoyl-CoA hydratase-lyase (HCHL) homolog, locus
      BURPS305_5356, protein family HMM PF00378

<400> SEQUENCE: 25

Met Ser Tyr Glu Gly Arg Trp Lys Thr Val Glu Val Ile Val Asp Gly
1               5                   10                  15

Ala Ile Ala Trp Val Thr Leu Asn Arg Pro Asp Lys Arg Asn Ala Met
            20                  25                  30

Ser Pro Thr Leu Asn Ala Glu Met Ile Asp Val Leu Glu Ala Val Glu
        35                  40                  45

Leu Asp Pro Glu Ala Arg Val Leu Val Leu Thr Gly Glu Gly Glu Ala
    50                  55                  60

Trp Thr Ala Gly Met Asp Leu Lys Glu Tyr Phe Arg Glu Val Asp Ala
65                  70                  75                  80

Gly Pro Glu Ile Leu Gln Glu Lys Ile Arg Arg Asp Ala Ser Arg Trp
                85                  90                  95

Gln Trp Gln Leu Leu Arg Met Tyr Ala Lys Pro Thr Ile Ala Met Val
                100                 105                 110

Asn Gly Trp Cys Phe Gly Gly Phe Ser Pro Leu Val Ala Cys Asp
            115                 120                 125

Leu Ala Ile Ala Ala Asp Glu Ala Val Phe Gly Leu Ser Glu Ile Asn
        130                 135                 140

Trp Gly Ile Pro Pro Gly Asn Leu Val Ser Lys Ala Met Ala Asp Thr
145                 150                 155                 160

Val Gly His Arg Gln Ala Leu Tyr Tyr Ile Met Thr Gly Glu Thr Phe
```

```
                165                 170                 175
Thr Gly Ala Gln Ala Ala Gln Met Gly Leu Val Asn Arg Ser Val Pro
            180                 185                 190

Arg Ala Gln Leu Arg Asp Ala Val Arg Ala Leu Ala Ala Lys Leu Leu
        195                 200                 205

Asp Lys Asn Pro Val Val Leu Arg Asn Ala Lys His Gly Phe Lys Arg
    210                 215                 220

Cys Arg Glu Leu Thr Trp Glu Gln Asn Glu Asp Tyr Leu Tyr Ala Lys
225                 230                 235                 240

Leu Asp Gln Ala Gln Leu Arg Asp Pro Glu His Gly Arg Glu Gln Gly
                245                 250                 255

Leu Lys Gln Phe Leu Asp Asp Lys Thr Ile Lys Pro Gly Leu Gln Ala
            260                 265                 270

Tyr Arg Arg
        275

<210> SEQ ID NO 26
<211> LENGTH: 275
<212> TYPE: PRT
<213> ORGANISM: Burkholderia multivorans
<220> FEATURE:
<223> OTHER INFORMATION: Burkholderia multivorans strain ATCC 17616
      p-hydroxycinnamoyl-CoA hydratase-lyase (HCHL) homolog,
      locus Bmul_3210

<400> SEQUENCE: 26

Met Ser Tyr Glu Gly Arg Trp Lys Thr Val Lys Val Ala Val Glu Gly
1               5                   10                  15

Gly Ile Ala Trp Val Thr Leu Asn Arg Pro Glu Lys Arg Asn Ala Met
            20                  25                  30

Ser Pro Thr Leu Asn Ala Glu Met Ile Asp Val Leu Ala Ala Ile Glu
        35                  40                  45

Leu Asp Pro Glu Ala Gln Val Leu Val Leu Thr Gly Glu Gly Asp Ala
    50                  55                  60

Trp Thr Ala Gly Met Asp Leu Lys Glu Tyr Phe Arg Glu Val Asp Ala
65                  70                  75                  80

Gly Pro Glu Ile Leu Gln Glu Lys Ile Arg Arg Asp Ala Ser Arg Trp
                85                  90                  95

Gln Trp Gln Leu Leu Arg Met Tyr Ala Lys Pro Thr Ile Ala Met Val
            100                 105                 110

Asn Gly Trp Cys Phe Gly Gly Gly Phe Ser Pro Leu Val Ala Cys Asp
        115                 120                 125

Leu Ala Ile Ala Ala Asp Glu Ala Val Phe Gly Leu Ser Glu Ile Asn
    130                 135                 140

Trp Gly Ile Pro Pro Gly Asn Leu Val Ser Lys Ala Met Ala Asp Thr
145                 150                 155                 160

Val Gly His Arg Gln Ala Leu Tyr Tyr Ile Met Thr Gly Asp Thr Phe
                165                 170                 175

Thr Gly Gln Gln Ala Ala Gln Met Gly Leu Val Asn Lys Ser Val Pro
            180                 185                 190

Arg Ala Gln Leu Arg Asp Glu Val Arg Ala Leu Ala Ala Lys Leu Leu
        195                 200                 205

Asp Lys Asn Pro Val Val Ile Arg Asn Ala Lys His Gly Phe Lys Arg
    210                 215                 220

Cys Arg Glu Leu Thr Trp Glu Gln Asn Glu Asp Tyr Leu Tyr Ala Lys
225                 230                 235                 240
```

Leu Asp Gln Ala Asn Tyr Arg Asp Pro Glu Gly Gly Arg Glu Gln Gly
                245                 250                 255

Leu Lys Gln Phe Leu Asp Glu Lys Ser Ile Lys Pro Gly Leu Gln Ala
            260                 265                 270

Tyr Lys Arg
        275

<210> SEQ ID NO 27
<211> LENGTH: 275
<212> TYPE: PRT
<213> ORGANISM: Burkholderia vietnamiensis
<220> FEATURE:
<223> OTHER INFORMATION: Burkholderia vietnamiensis strain G4 p-
      hydroxycinnamoyl-CoA hydratase-lyase (HCHL) homolog, locus
      Bcep1808_3841

<400> SEQUENCE: 27

Met Gly Tyr Glu Gly Arg Trp Lys Thr Val Lys Val Glu Val Ala Gly
1               5                   10                  15

Gly Ile Ala Trp Val Thr Leu Asn Arg Pro Glu Lys Arg Asn Ala Met
            20                  25                  30

Ser Pro Thr Leu Asn Thr Glu Met Ile Asp Val Leu Glu Ala Ile Glu
        35                  40                  45

Leu Asp Ala Asp Ala Gln Val Leu Val Leu Thr Gly Glu Gly Asp Ala
    50                  55                  60

Trp Thr Ala Gly Met Asp Leu Lys Glu Tyr Phe Arg Glu Ile Asp Ala
65                  70                  75                  80

Gly Pro Glu Ile Leu Gln Glu Lys Ile Arg Arg Asp Ala Ser Arg Trp
                85                  90                  95

Gln Trp Gln Leu Leu Arg Met Tyr Ala Lys Pro Thr Ile Ala Met Val
            100                 105                 110

Asn Gly Trp Cys Phe Gly Gly Gly Phe Ser Pro Leu Val Ala Cys Asp
        115                 120                 125

Leu Ala Ile Ala Ala Asp Glu Ala Val Phe Gly Leu Ser Glu Ile Asn
    130                 135                 140

Trp Gly Ile Pro Pro Gly Asn Leu Val Ser Lys Ala Met Ala Asp Thr
145                 150                 155                 160

Val Gly His Arg Glu Ala Leu Tyr Tyr Ile Met Thr Gly Asp Thr Phe
                165                 170                 175

Thr Gly Gln Gln Ala Ala Arg Met Gly Leu Val Asn Lys Ser Val Pro
            180                 185                 190

Arg Ala Gln Leu Arg Asp Glu Val Arg Ala Leu Ala Lys Leu Leu
            195                 200                 205

Asp Lys Asn Pro Val Val Ile Arg Asn Ala Lys His Gly Phe Lys Arg
    210                 215                 220

Cys Arg Glu Leu Thr Trp Glu Gln Asn Glu Asp Tyr Leu Tyr Ala Lys
225                 230                 235                 240

Leu Asp Gln Ala Asn Tyr Arg Asp Pro Glu Gly Gly Arg Glu Gln Gly
                245                 250                 255

Leu Lys Gln Phe Leu Asp Asp Lys Ser Ile Lys Pro Gly Leu Gln Ala
            260                 265                 270

Tyr Lys Arg
        275

<210> SEQ ID NO 28
<211> LENGTH: 283

```
<212> TYPE: PRT
<213> ORGANISM: Sphingobium japonicum
<220> FEATURE:
<223> OTHER INFORMATION: Sphingobium japonicum strain UT26S p-
      hydroxycinnamoyl-CoA hydratase-lyase (HCHL) homolog, naphthoate
      synthase, enoyl-CoA hydratase/carnithine racemase, menB gene,
      locus SJA_C1-02370

<400> SEQUENCE: 28
```

Met Ser Glu Tyr Leu Thr Glu Gly Pro Asp Leu Ser Arg Thr Cys Val
1               5                   10                  15

Asp Val Met Phe Asp Glu Gly Ile Ala Trp Val Thr Leu Asn Arg Pro
            20                  25                  30

Glu Lys Arg Asn Ala Met Ser Pro Thr Leu Asn Ser Glu Met Leu Ala
        35                  40                  45

Ile Leu Glu Gln Leu Glu Leu Asp Pro Arg Cys Gly Val Val Val Leu
    50                  55                  60

Thr Gly Ala Gly Asp Ser Phe Ser Ala Gly Met Asp Leu Lys Glu Tyr
65                  70                  75                  80

Phe Arg Glu Thr Asp Gly Leu Pro Pro Ala Gln Val Arg Arg Ile Arg
                85                  90                  95

Gln Thr Ala Gln Ala Trp Gln Trp Arg Thr Leu Gln His Phe Gly Lys
            100                 105                 110

Pro Thr Ile Ala Met Val Asn Gly Trp Cys Phe Gly Gly Ala Phe Thr
        115                 120                 125

Pro Leu Val Ala Cys Asp Leu Ala Ile Ala Ala Asn Glu Ala Val Phe
    130                 135                 140

Gly Leu Ser Glu Ile Asn Trp Gly Ile Ile Pro Gly Gly Asn Val Thr
145                 150                 155                 160

Lys Ala Ile Gln Glu Arg Leu Arg Pro Gln Asp Ala Ala Leu Tyr Ile
                165                 170                 175

Met Thr Gly Arg Asn Phe Thr Gly Glu Lys Ala Ala Gln Met Gly Leu
            180                 185                 190

Val Ala Glu Ala Val Pro Leu Thr Asp Leu Arg Asp His Thr Arg Ala
        195                 200                 205

Leu Ala Leu Glu Leu Leu Ser Lys Asn Pro Val Leu Asn Ala Ala
    210                 215                 220

Lys Ile Ala Leu Lys Lys Val Ala Asp Met Thr Trp Asp Val Ala Glu
225                 230                 235                 240

Asp Tyr Leu Val Ala Lys Gly Ala Gln Thr Arg Val Ala Asp Lys Thr
                245                 250                 255

Asp Gly Arg Asn Lys Gly Ile Thr Gln Phe Leu Asp Glu Lys Ser Tyr
            260                 265                 270

Lys Pro Gly Leu Glu Gly Tyr Arg Arg Asp Lys
        275                 280

```
<210> SEQ ID NO 29
<211> LENGTH: 275
<212> TYPE: PRT
<213> ORGANISM: Xanthomonas axonopodis
<220> FEATURE:
<223> OTHER INFORMATION: Xanthomonas axonopodis pathovar citri strain
      306 p-hydroxycinnamoyl-CoA hydratase-lyase (HCHL) homolog, lyase,
      fadB gene, locus XAC0883

<400> SEQUENCE: 29
```

Met Asn Glu His Asp Val Val Ser Val Arg Ile Glu Asn Arg Ile Ala
1               5                   10                  15

-continued

```
Trp Val Lys Phe Ala Arg Pro Asp Lys Arg Asn Ala Met Ser Pro Ala
             20                  25                  30

Leu Asn Arg Arg Met Met Asp Val Leu Asp Glu Leu Glu Phe Asp Asp
         35                  40                  45

Asn Val Gly Val Leu Val Leu Gly Gly Glu Gly Thr Ala Trp Ser Ala
 50                  55                  60

Gly Met Asp Leu Lys Glu Tyr Phe Arg Glu Thr Glu Ala Gln Gly Leu
65                  70                  75                  80

Arg Gly Val Arg Arg Ser Gln Arg Glu Ser Tyr Gly Trp Phe Arg Arg
                 85                  90                  95

Leu Arg Trp Tyr Gln Lys Pro Thr Ile Ala Met Val Asn Gly Trp Cys
            100                 105                 110

Phe Gly Gly Gly Phe Gly Pro Leu Phe Ala Cys Asp Leu Ala Ile Ala
        115                 120                 125

Ala Asp Glu Ala Gln Phe Gly Leu Ser Glu Ile Asn Trp Gly Ile Leu
    130                 135                 140

Pro Gly Gly Gly Val Thr Lys Val Ala Val Glu Leu Leu Ser Met Arg
145                 150                 155                 160

Asp Ala Met Trp Met Thr Leu Thr Gly Glu Met Val Asp Gly Lys Lys
                165                 170                 175

Ala Ala Glu Trp Arg Leu Val Asn Glu Ser Val Pro Leu Glu Arg Leu
            180                 185                 190

Glu Ala Arg Thr Arg Glu Val Ala Glu Leu Leu Leu Arg Lys Asn Pro
        195                 200                 205

Val Ala Leu Lys Tyr Ala Lys Asp Ala Val Arg Arg Val Gly Thr Met
    210                 215                 220

Thr Tyr Asp Glu Ala Glu Asp Tyr Leu Val Arg Met Gln Glu Ala Ala
225                 230                 235                 240

Asn Ser Phe Asp Asn Asn Ala Arg Lys Glu Gly Ile Arg Gln Phe Ile
                245                 250                 255

Asp Glu Lys Ser Tyr Lys Pro Gly Leu Gly Glu Tyr Asp Leu Ser Lys
            260                 265                 270

His Ser Ala
        275
```

<210> SEQ ID NO 30
<211> LENGTH: 275
<212> TYPE: PRT
<213> ORGANISM: Xanthomonas campestris
<220> FEATURE:
<223> OTHER INFORMATION: Xanthomonas campestris pathovar campestris
      strain ATCC 33913 p-hydroxycinnamoyl-CoA hydratase-lyase (HCHL) homolog, fadB gene, locus XCC0810

<400> SEQUENCE: 30

Met Asn Glu His Asp Val Val Ser Val His Val Glu Asn Arg Ile Ala
1 5 10 15

Trp Val Lys Phe Ala Arg Pro Asp Lys Arg Asn Ala Met Ser Pro Ala
20 25 30

Leu Asn Arg Arg Met Leu Asp Val Leu Asp Glu Leu Glu Phe Asp Asp
35 40 45

Asn Val Gly Val Leu Val Leu Gly Gly Glu Gly Thr Ala Trp Ser Ala
50 55 60

Gly Met Asp Leu Lys Glu Tyr Phe Arg Glu Thr Glu Ala Gln Gly Leu
65 70 75 80

Arg Gly Val Arg Arg Ser Gln Arg Glu Ser Tyr Gly Trp Phe Arg Arg

```
                     85                  90                  95
Leu Arg Trp Tyr Gln Lys Pro Thr Ile Ala Met Val Asn Gly Trp Cys
            100                 105                 110

Phe Gly Gly Gly Phe Gly Pro Leu Phe Ala Cys Asp Leu Ala Ile Ala
        115                 120                 125

Ala Asp Glu Ala Gln Phe Gly Leu Ser Glu Ile Asn Trp Gly Ile Leu
    130                 135                 140

Pro Gly Gly Gly Val Thr Lys Val Ala Val Glu Leu Leu Ser Met Arg
145                 150                 155                 160

Asp Ala Met Trp Met Thr Leu Thr Gly Glu Leu Val Asp Gly Arg Lys
                165                 170                 175

Ala Ala Glu Trp Arg Leu Val Asn Glu Ser Val Pro Leu Glu Arg Leu
            180                 185                 190

Glu Thr Arg Thr Arg Glu Val Ala Glu Leu Leu Leu Lys Lys Asn Pro
        195                 200                 205

Val Ala Leu Lys Tyr Ala Lys Asp Ala Val Arg Arg Val Gly Thr Met
    210                 215                 220

Thr Tyr Asp Glu Ala Glu Asp Tyr Leu Val Arg Met Gln Glu Ala Ala
225                 230                 235                 240

Asn Ser Phe Asp Asn Asn Ala Arg Lys Glu Gly Ile Arg Gln Phe Ile
                245                 250                 255

Asp Glu Lys Arg Tyr Lys Pro Gly Leu Gly Ala Tyr Glu Pro Asp Ala
            260                 265                 270

Gly Thr Asn
        275

<210> SEQ ID NO 31
<211> LENGTH: 281
<212> TYPE: PRT
<213> ORGANISM: Azospirillum sp.
<220> FEATURE:
<223> OTHER INFORMATION: Azospirillum sp. strain B510 p-
      hydroxycinnamoyl-CoA hydratase-lyase (HCHL) homolog, enoyl-CoA
      hydratase, paaG gene, locus AZL_b03680

<400> SEQUENCE: 31

Met Thr Gln Gln Gln Ala Ala Arg Thr Gly Thr Ala Glu Asp Val
1               5                   10                  15

Val Thr Val Glu Leu Asp Asn Gly Val Ala Trp Val Thr Leu Asn Arg
            20                  25                  30

Pro Asp Lys Arg Asn Ala Met Asn Pro Ala Leu Asn Ala Arg Met His
        35                  40                  45

Gly Val Leu Asp Asp Leu Glu Val Asp Asp Arg Cys Gln Val Leu Val
    50                  55                  60

Leu Thr Gly Ala Gly Glu Ser Phe Ser Ala Gly Met Asp Leu Lys Glu
65                  70                  75                  80

Tyr Phe Arg Glu Thr Glu Ala Lys Gly His Met Ala Thr Arg Arg Ala
                85                  90                  95

Gln Arg Asp Ser Tyr Gly Trp Trp Arg Arg Leu Arg Trp Phe Glu Lys
            100                 105                 110

Pro Ser Ile Ala Met Val Asn Gly Trp Cys Phe Gly Gly Ala Phe Ser
        115                 120                 125

Pro Leu Phe Ala Cys Asp Leu Ala Val Ala Ala Asp Glu Ala Gln Phe
    130                 135                 140

Gly Leu Ser Glu Ile Asn Trp Gly Ile Ile Pro Gly Gly Asn Val Thr
145                 150                 155                 160
```

```
Lys Val Val Ala Asp Leu Met Ser Gln Arg Glu Ala Met Tyr Tyr Ile
                165                 170                 175

Leu Thr Gly Glu Thr Phe Asp Gly Arg Lys Ala Ala Glu Met Lys Leu
            180                 185                 190

Val Asn Phe Ser Val Pro His Ala Glu Leu Arg Ala Lys Val Arg Ala
        195                 200                 205

Ile Ala Asp Asn Leu Leu Glu Lys Asn Pro Gln Thr Leu Lys Ala Ala
    210                 215                 220

Lys Asp Ala Phe Lys Arg Val Val Glu Met Pro Phe Asp Ala Ala Glu
225                 230                 235                 240

Asp Tyr Leu Val Val Arg Gln Glu Ser Leu Asn Tyr Leu Asp Lys Ser
                245                 250                 255

Glu Gly Arg Lys Gln Gly Ile Lys Gln Phe Ile Asp Asp Lys Thr Tyr
            260                 265                 270

Arg Pro Gly Leu Gly Ala Tyr Lys Arg
        275                 280

<210> SEQ ID NO 32
<211> LENGTH: 277
<212> TYPE: PRT
<213> ORGANISM: Agrobacterium vitis
<220> FEATURE:
<223> OTHER INFORMATION: Agrobacterium vitis strain S4 = ATCC BAA-846
      isolate Kecskemet-Hungary p-hydroxycinnamoyl-CoA hydratase-lyase
      (HCHL) homolog, fadB gene, locus Avi_1705

<400> SEQUENCE: 32

Met Thr Val Ala Glu Lys Ser Asp Ala Asp Thr Val Leu Val Asp Ile
1               5                   10                  15

Glu Asp Arg Ile Ala Phe Val Thr Phe Asn Arg Pro Glu Lys Arg Asn
            20                  25                  30

Ala Met Asn Pro Ala Leu Asn Ile Arg Met Ala Glu Val Leu Glu Glu
        35                  40                  45

Leu Glu Ala Asp Asp Arg Cys Gly Val Leu Val Leu Arg Gly Ala Gly
    50                  55                  60

Thr Ser Trp Ser Ala Gly Met Asp Leu Gln Gln Tyr Phe Arg Asp Asn
65                  70                  75                  80

Asp Asp Lys Pro Arg His Ala Thr Leu Lys Ser Arg Arg Gln Ser Gly
                85                  90                  95

Gly Trp Trp Gln Arg Leu Thr Tyr Phe Glu Lys Pro Thr Ile Ala Met
            100                 105                 110

Val Asn Gly Trp Cys Phe Gly Gly Ala Phe Asn Pro Leu Val Ala Cys
        115                 120                 125

Asp Leu Ala Ile Ala Ala Asn Glu Ala Thr Phe Gly Leu Ser Glu Ile
    130                 135                 140

Asn Trp Gly Ile Leu Pro Gly Gly Asn Val Thr Arg Ala Val Ala Glu
145                 150                 155                 160

Val Met Asn His Arg Asp Ser Leu Tyr Tyr Ile Met Thr Gly Glu Pro
                165                 170                 175

Phe Gly Gly Glu Lys Ala Arg Asp Met Gly Leu Val Asn Glu Ser Val
            180                 185                 190

Pro Leu Glu Glu Leu Glu Thr Arg Val Arg Lys Leu Cys Ala Ser Leu
        195                 200                 205

Leu Glu Lys Asn Pro Val Thr Met Lys Ala Ala Lys Asp Thr Phe Lys
    210                 215                 220
```

```
Arg Val Arg Asn Met Pro Trp Glu Leu Ala Asp Asp Tyr Ile Tyr Ala
225                 230                 235                 240

Lys Leu Glu Gln Met Leu Leu Leu Asp Lys Thr Arg Gly Arg Asp Glu
                245                 250                 255

Gly Leu Lys Gln Phe Leu Asp Asp Lys Thr Tyr Arg Pro Gly Leu Gly
                260                 265                 270

Ala Tyr Lys Arg Lys
                275

<210> SEQ ID NO 33
<211> LENGTH: 274
<212> TYPE: PRT
<213> ORGANISM: Rhizobium etli
<220> FEATURE:
<223> OTHER INFORMATION: Rhizobium etli strain CIAT 652 p-
      hydroxycinnamoyl-CoA hydratase-lyase (HCHL) homolog, ech gene,
      locus RHECIAT_PC0000921

<400> SEQUENCE: 33

Met Thr Glu Asn Thr Ser Pro Val Leu Val Glu Phe Asp Gly Gly Ile
1               5                   10                  15

Ala Phe Val Thr Leu Asn Arg Pro Glu Lys Arg Asn Ala Met Asn Pro
                20                  25                  30

Ala Leu Asn Ala Arg Met Leu Glu Val Leu Asp Glu Leu Glu Gly Asp
            35                  40                  45

Glu Arg Cys Gly Val Leu Val Leu Arg Gly Ala Gly Gln Ser Trp Ser
    50                  55                  60

Ala Gly Met Asp Leu Lys Glu Tyr Phe Arg Asp Asn Asp Asp Lys Pro
65                  70                  75                  80

Arg Asp Ala Thr Leu Lys Ala Arg Arg Gln Ser Gly Gly Trp Trp Gly
                85                  90                  95

Arg Leu Met Tyr Phe Glu Lys Pro Thr Ile Ala Met Val Asn Gly Trp
                100                 105                 110

Cys Phe Gly Gly Ala Phe Thr Pro Leu Val Ser Cys Asp Leu Ala Ile
            115                 120                 125

Ala Ala Glu Glu Ala Asn Phe Gly Leu Ser Glu Ile Asn Trp Gly Ile
    130                 135                 140

Leu Pro Gly Gly Asn Val Thr Arg Ala Val Ala Glu Val Met Arg His
145                 150                 155                 160

Arg Asp Ala Leu Tyr Tyr Ile Met Thr Gly Glu Leu Phe Gly Gly Arg
                165                 170                 175

Lys Ala Ala Glu Met Gly Leu Val Asn Glu Ala Val Pro Leu Val Asp
                180                 185                 190

Leu Glu Thr Arg Val Arg Lys Ile Cys Ala Ser Leu Leu Glu Lys Asn
            195                 200                 205

Pro Val Thr Leu Lys Ala Ala Lys Asp Thr Tyr Lys Arg Val Arg Asn
    210                 215                 220

Leu Pro Trp Asp Leu Ala Asp Asp Tyr Ile Tyr Ala Lys Leu Glu Gln
225                 230                 235                 240

Met Leu Phe Leu Asp Lys Thr Lys Gly Arg Asp Glu Gly Leu Lys Gln
                245                 250                 255

Phe Leu Asp Asp Lys Thr Tyr Gln Pro Gly Leu Gly Ala Tyr Lys Arg
                260                 265                 270

Gly Arg

<210> SEQ ID NO 34
```

<211> LENGTH: 274
<212> TYPE: PRT
<213> ORGANISM: Rhizobium leguminosarum
<220> FEATURE:
<223> OTHER INFORMATION: Rhizobium leguminosarum biovar trifolii strain WSM1325 p-hydroxycinnamoyl-CoA hydratase-lyase (HCHL) homolog, locus Rleg_4811

<400> SEQUENCE: 34

```
Met Thr Glu Asp Lys Ser Pro Val Leu Val Glu Phe Asp Ser Gly Ile
1               5                   10                  15

Ala Phe Val Thr Leu Asn Arg Pro Glu Lys Arg Asn Ala Met Asn Pro
            20                  25                  30

Ala Leu Asn Ile Arg Met Leu Glu Val Leu Asp Glu Leu Glu Gly Asp
        35                  40                  45

Glu Arg Cys Gly Val Leu Val Leu Arg Gly Ala Gly Glu Ser Trp Ser
    50                  55                  60

Ala Gly Met Asp Leu Lys Glu Tyr Phe Arg Asp Asn Asp Lys Pro
65                  70                  75                  80

Arg Asp Val Thr Leu Lys Ala Arg Arg Gln Ser Gly Asn Trp Trp Gly
                85                  90                  95

Arg Leu Met Tyr Phe Glu Lys Pro Thr Ile Ala Met Val Asn Gly Trp
            100                 105                 110

Cys Phe Gly Gly Ala Phe Thr Pro Leu Val Ser Cys Asp Leu Ala Ile
        115                 120                 125

Ala Ala Glu Glu Ala Asn Phe Gly Leu Ser Glu Ile Asn Trp Gly Ile
    130                 135                 140

Leu Pro Gly Gly Asn Val Thr Arg Ala Val Ala Glu Val Met Arg His
145                 150                 155                 160

Arg Asp Ala Leu Tyr Tyr Ile Met Thr Gly Glu Leu Phe Gly Gly Arg
                165                 170                 175

Lys Ala Ala Glu Met Gly Leu Val Asn Glu Ala Val Pro Leu Ala Glu
            180                 185                 190

Leu Glu Pro Arg Val Arg Lys Ile Cys Ala Ser Leu Leu Glu Lys Asn
        195                 200                 205

Pro Val Thr Leu Lys Ala Ala Lys Asp Thr Tyr Lys Arg Val Arg Asn
    210                 215                 220

Leu Pro Trp Asp Leu Ala Asp Asp Tyr Ile Tyr Ala Lys Leu Glu Gln
225                 230                 235                 240

Met Leu Phe Leu Asp Lys Thr Lys Gly Arg Asp Glu Gly Leu Lys Gln
                245                 250                 255

Phe Leu Asp Asp Lys Thr Tyr Gln Pro Gly Leu Gly Ala Tyr Lys Arg
            260                 265                 270

Gly Arg
```

<210> SEQ ID NO 35
<211> LENGTH: 1055
<212> TYPE: PRT
<213> ORGANISM: Arabidopsis thaliana
<220> FEATURE:
<223> OTHER INFORMATION: Arabidopsis thaliana secondary cell wall cellulose synthase Cesa4/IRX5

<400> SEQUENCE: 35

```
Met Glu Pro Asn Thr Met Ala Ser Phe Asp Asp Glu His Arg His Ser
1               5                   10                  15

Ser Phe Ser Ala Lys Ile Cys Lys Val Cys Gly Asp Glu Val Lys Asp
            20                  25                  30
```

```
Asp Asp Asn Gly Gln Thr Phe Val Ala Cys His Val Cys Val Tyr Pro
         35                  40                  45

Val Cys Lys Pro Cys Tyr Glu Tyr Glu Arg Ser Asn Gly Asn Lys Cys
 50                  55                  60

Cys Pro Gln Cys Asn Thr Leu Tyr Lys Arg His Lys Gly Ser Pro Lys
 65                  70                  75                  80

Ile Ala Gly Asp Glu Glu Asn Asn Gly Pro Asp Asp Ser Asp Asp Glu
                 85                  90                  95

Leu Asn Ile Lys Tyr Arg Gln Asp Gly Ser Ser Ile His Gln Asn Phe
             100                 105                 110

Ala Tyr Gly Ser Glu Asn Gly Asp Tyr Asn Ser Lys Gln Gln Cys Arg
         115                 120                 125

Pro Asn Gly Arg Ala Phe Ser Ser Thr Gly Ser Val Leu Gly Lys Asp
     130                 135                 140

Phe Glu Ala Glu Arg Asp Gly Tyr Thr Asp Ala Glu Trp Lys Glu Arg
145                 150                 155                 160

Val Asp Lys Trp Lys Ala Arg Gln Glu Lys Arg Gly Leu Val Thr Lys
                 165                 170                 175

Gly Glu Gln Thr Asn Glu Asp Lys Glu Asp Glu Glu Glu Glu Glu Leu
             180                 185                 190

Leu Asp Ala Glu Ala Arg Gln Pro Leu Trp Arg Lys Val Pro Ile Ser
         195                 200                 205

Ser Ser Lys Ile Ser Pro Tyr Arg Ile Val Ile Val Leu Arg Leu Val
     210                 215                 220

Ile Leu Val Phe Phe Phe Arg Phe Arg Ile Leu Thr Pro Ala Lys Asp
225                 230                 235                 240

Ala Tyr Pro Leu Trp Leu Ile Ser Val Ile Cys Glu Ile Trp Phe Ala
                 245                 250                 255

Leu Ser Trp Ile Leu Asp Gln Phe Pro Lys Trp Phe Pro Ile Asn Arg
             260                 265                 270

Glu Thr Tyr Leu Asp Arg Leu Ser Met Arg Phe Glu Arg Asp Gly Glu
         275                 280                 285

Lys Asn Lys Leu Ala Pro Val Asp Val Phe Val Ser Thr Val Asp Pro
     290                 295                 300

Leu Lys Glu Pro Pro Ile Ile Thr Ala Asn Thr Ile Leu Ser Ile Leu
305                 310                 315                 320

Ala Val Asp Tyr Pro Val Asn Lys Val Ser Cys Tyr Val Ser Asp Asp
                 325                 330                 335

Gly Ala Ser Met Leu Leu Phe Asp Thr Leu Ser Glu Thr Ser Glu Phe
             340                 345                 350

Ala Arg Arg Trp Val Pro Phe Cys Lys Lys Tyr Asn Val Glu Pro Arg
         355                 360                 365

Ala Pro Glu Phe Tyr Phe Ser Glu Lys Ile Asp Tyr Leu Lys Asp Lys
     370                 375                 380

Val Gln Thr Thr Phe Val Lys Asp Arg Arg Ala Met Lys Arg Glu Tyr
385                 390                 395                 400

Glu Glu Phe Lys Val Arg Ile Asn Ala Leu Val Ala Lys Ala Gln Lys
                 405                 410                 415

Lys Pro Glu Glu Gly Trp Val Met Gln Asp Gly Thr Pro Trp Pro Gly
             420                 425                 430

Asn Asn Thr Arg Asp His Pro Gly Met Ile Gln Val Tyr Leu Gly Lys
         435                 440                 445
```

Glu Gly Ala Phe Asp Ile Asp Gly Asn Glu Leu Pro Arg Leu Val Tyr
450                 455                 460

Val Ser Arg Glu Lys Arg Pro Gly Tyr Ala His His Lys Lys Ala Gly
465                 470                 475                 480

Ala Met Asn Ala Met Val Arg Val Ser Ala Val Leu Thr Asn Ala Pro
            485                 490                 495

Phe Met Leu Asn Leu Asp Cys Asp His Tyr Ile Asn Asn Ser Lys Ala
        500                 505                 510

Ile Arg Glu Ser Met Cys Phe Leu Met Asp Pro Gln Leu Gly Lys Lys
        515                 520                 525

Leu Cys Tyr Val Gln Phe Pro Gln Arg Phe Asp Gly Ile Asp His Asn
530                 535                 540

Asp Arg Tyr Ala Asn Arg Asn Ile Val Phe Phe Asp Ile Asn Met Arg
545                 550                 555                 560

Gly Leu Asp Gly Ile Gln Gly Pro Val Tyr Val Gly Thr Gly Cys Val
                565                 570                 575

Phe Asn Arg Pro Ala Leu Tyr Gly Tyr Glu Pro Pro Val Ser Glu Lys
            580                 585                 590

Arg Lys Lys Met Thr Cys Asp Cys Trp Pro Ser Trp Ile Cys Cys Cys
        595                 600                 605

Cys Gly Gly Asn Arg Asn His His Lys Ser Lys Ser Ser Asp Ser
        610                 615                 620

Ser Ser Lys Lys Lys Ser Gly Ile Lys Ser Leu Leu Ser Lys Leu Lys
625                 630                 635                 640

Lys Lys Asn Lys Lys Ser Asp Asp Lys Thr Met Ser Ser Tyr Ser
                645                 650                 655

Arg Lys Arg Ser Ala Thr Glu Ala Ile Phe Asp Leu Glu Asp Ile Glu
            660                 665                 670

Glu Gly Leu Glu Gly Tyr Asp Glu Leu Glu Lys Ser Ser Leu Met Ser
        675                 680                 685

Gln Lys Asn Phe Glu Lys Arg Phe Gly Met Ser Pro Val Phe Ile Ala
        690                 695                 700

Ser Thr Leu Met Glu Asn Gly Gly Leu Pro Glu Ala Thr Asn Thr Ser
705                 710                 715                 720

Ser Leu Ile Lys Glu Ala Ile His Val Ile Ser Cys Gly Tyr Glu Glu
            725                 730                 735

Lys Thr Glu Trp Gly Lys Glu Ile Gly Trp Ile Tyr Gly Ser Val Thr
                740                 745                 750

Glu Asp Ile Leu Thr Gly Phe Arg Met His Cys Arg Gly Trp Lys Ser
        755                 760                 765

Val Tyr Cys Met Pro Lys Arg Pro Ala Phe Lys Gly Ser Ala Pro Ile
770                 775                 780

Asn Leu Ser Asp Arg Leu His Gln Val Leu Arg Trp Ala Leu Gly Ser
785                 790                 795                 800

Val Glu Ile Phe Phe Ser Arg His Cys Pro Leu Trp Tyr Ala Trp Gly
            805                 810                 815

Gly Lys Leu Lys Ile Leu Glu Arg Leu Ala Tyr Ile Asn Thr Ile Val
                820                 825                 830

Tyr Pro Phe Thr Ser Ile Pro Leu Leu Ala Tyr Cys Thr Ile Pro Ala
        835                 840                 845

Val Cys Leu Leu Thr Gly Lys Phe Ile Ile Pro Thr Ile Asn Asn Phe
850                 855                 860

Ala Ser Ile Trp Phe Leu Ala Leu Phe Leu Ser Ile Ile Ala Thr Ala

Ile Leu Glu Leu Arg Trp Ser Gly Val Ser Ile Asn Asp Leu Trp Arg
            885                 890                 895

Asn Glu Gln Phe Trp Val Ile Gly Gly Val Ser Ala His Leu Phe Ala
        900                 905                 910

Val Phe Gln Gly Leu Leu Lys Val Leu Phe Gly Val Asp Thr Asn Phe
        915                 920                 925

Thr Val Thr Ser Lys Gly Ala Ser Asp Glu Ala Asp Glu Phe Gly Asp
        930                 935                 940

Leu Tyr Leu Phe Lys Trp Thr Thr Leu Leu Ile Pro Pro Thr Thr Leu
945                 950                 955                 960

Ile Ile Leu Asn Met Val Gly Val Val Ala Gly Val Ser Asp Ala Ile
                965                 970                 975

Asn Asn Gly Tyr Gly Ser Trp Gly Pro Leu Phe Gly Lys Leu Phe Phe
            980                 985                 990

Ala Phe Trp Val Ile Val His Leu Tyr Pro Phe Leu Lys Gly Leu Met
        995                 1000                1005

Gly Arg Gln Asn Arg Thr Pro Thr Ile Val Val Leu Trp Ser Ile Leu
        1010                1015                1020

Leu Ala Ser Ile Phe Ser Leu Val Trp Val Arg Ile Asp Pro Phe Leu
1025                1030                1035                1040

Pro Lys Gln Thr Gly Pro Leu Leu Lys Gln Cys Gly Val Asp Cys
            1045                1050                1055

<210> SEQ ID NO 36
<211> LENGTH: 1953
<212> TYPE: DNA
<213> ORGANISM: Arabidopsis thaliana
<220> FEATURE:
<221> NAME/KEY: promoter
<222> LOCATION: (1)...(1953)
<223> OTHER INFORMATION: Arabidopsis thaliana secondary cell wall-
      specific promoter PATCESA7_PATIRX3

<400> SEQUENCE: 36
tgggaacttt cggtacattt tccaataaaa tctatatact ataagatatt aaatatacac    60
aaatatatct aagtgaatca tacaaattat gtaggcacac aggaagaggc tgctgaggct   120
tatgacattg cagccattaa attcagagga ttaagcgcag tgactaactt cgacatgaac   180
agatacaatg ttaaagcaat cctcgagagc ccgagtctac ctattggtag ttctgcgaaa   240
cgtctcaagg acgttaataa tccggttcca gctatgatga ttagtaataa cgtttcagag   300
agtgcaaata atgttagcgg ttggcaaaac actgcgtttc agcatcatca gggaatggat   360
ttgagcttat tgcagcaaca gcaggagagg tacgttggtt attacaatgg aggaaacttg   420
tctaccgaga gtactagggt tgtttcaaa caagaggagg aacaacaaca cttcttgaga    480
aactcgccga gtcacatgac taatgttgat catcatagct cgacctctga tgattctgtt   540
accgtttgtg gaaatgttgt tagttatggt ggttatcaag gattcgcaat ccctgttgga   600
acatcggtta attacgatcc ctttactgct gctgagattg cttacaacgc aagaaatcat   660
tattactatg ctcagcatca gcaacaacag cagattcagc agtcgccggg aggagatttt   720
ccggtggcga tttcgaataa ccatagctct aacatgtact tcacgggga aggtggtgga    780 gaagggctc caacgttttc agtttggaac gacacttaga aaaataagta aaagatcttt    840
tagttgtttg ctttgtatgt tgcgaacagt ttgattctgt ttttctttt ccttttttg     900 ggtaattttc ttataacttt tttcatagtt tcgattattt ggataaaatt tcagattga    960

```
ggatcatttt atttatttat tagtgtagtc taatttagtt gtataactat aaaattgttg    1020
tttgtttccg aatcataagt ttttttttt tttggttttg tattgatagg tgcaagagac    1080
tcaaaattct ggtttcgatg ttaacagaat tcaagtagct gcccacttga ttcgatttgt    1140
tttgtatttg gaaacaacca tggctggtca aggcccagcc cgttgtgctt ctgaacctgc    1200
ctagtcccat ggactagatc tttatccgca gactccaaaa gaaaaggat tggcgcagag    1260 gaattgtcat ggaaacagaa tgaacaagaa agggtgaaga agatcaaagg catatatgat    1320
ctttacattc tctttagctt atgtatgcag aaaattcacc taattaagga cagggaacgt    1380
aacttggctt gcactcctct caccaaacct taccccctaa ctaattttaa ttcaaaatta    1440
ctagtatttt ggccgatcac tttatataat aagataccag atttattata tttacgaatt    1500
atcagcatgc atatactgta tatagttttt tttttgttaa agggtaaaat aataggatcc    1560
ttttgaataa aatgaacata tataattagt ataatgaaaa cagaaggaaa tgagattagg    1620
acagtaagta aaatgagaga gacctgcaaa ggataaaaaa gagaagctta aggaaaccgc    1680
gacgatgaaa gaaagacatg tcatcagctg atggatgtga gtgatgagtt tgttgcagtt    1740
gtgtagaaat ttttactaaa acagttgttt ttacaaaaaa gaataatat aaaacgaaag    1800 cttagcttga aggcaatgga gactctacaa caaactatgt accatacaga gagagaaact    1860
aaaagctttt cacacataaa aaccaaactt attcgtctct cattgatcac cgttttgttc    1920
tctcaagatc gctgctaatc tccggccgtc cct                                1953

<210> SEQ ID NO 37
<211> LENGTH: 1921
<212> TYPE: DNA
<213> ORGANISM: Arabidopsis thaliana
<220> FEATURE:
<221> NAME/KEY: promoter
<222> LOCATION: (1)...(1921)
<223> OTHER INFORMATION: Arabidopsis thaliana secondary cell wall-
      specific promoter PATCESA8_PATIRX1

<400> SEQUENCE: 37
tttagtgcag tctaggaaga cggatccaaa ggagataaac agagttcaag aagctcttaa     60
ctactataca atcgaatcgt cagccgcgct ttttgtttcg ttcatgatca atttgtttgt    120
aactgcggtt ttcgcgaaag ggttttatgg aaccaaacaa gctgatagta taggactggt    180
taacgcggga tattacctac aagagaaata tggcggtggt gttttcccga tactatacat    240 ttggggggatt ggtttattag ctgctggaca aagcagtact ataaccggga cttatgctgg    300
acagtttata atggaagggt tcttagatct tcaaatggaa caatggctat cagcttttat    360
aacgagaagc tttgctattg tacctactat gtttgttgct attatgttta acacatccga    420
gggctcgctc gatgttttaa acgaatggct taacattctt cagtcgatgc agattccttt    480
cgcggttatt cctctttttga ctatggtttc taatgaacat atcatgggtg tcttcaagat    540
cggaccttcg cttgaggtaa agcaattttt tgtcatctct ctttattgtt atgtgctttt    600
gattgtaacg agttagttgg gatctttgca gaagctagct tggactgtgg cggtgtttgt    660
gatgatgata aatgggtatc ttcttctaga tttcttcatg gctgaagtgg aagggtttct    720
tgttgggttt ctggtttttg gtggagtagt tggatacatc agtttcatca tctatcttgt    780
ttcttataga agctcacaat cttcttcctg gtcgagttta gaaatgtcag agagagttgt    840
ttccacagag acgtagaaac ccataacttt agtattcttc aacccttaca acttatctga    900
gcaaaatcag aaggtcgaat ttgatggatg gttttgctgt atttggtcaa cggttttatt    960
```

```
tgagacagta gaccagagga aactcagatg tgatgatgca aagactgaat tggttaagag    1020
tgtagattga tttgttctaa cattgcaaat gtagagtaga attatgcaaa aaacgttaat    1080
gaacagagaa gtgattaagc agaaacaaaa ttagagaagt gatattatat ctcaaaattt    1140 attttttggta cagctaaagc tcaaattgtt atagagatta gagatattaa accaaatgac    1200
gagtgttttc tttagtagta aacggtgaaa attctcttct gacaaagaca attaaaattt    1260
taggtttaag actttaatat ttgtcacaaa ttgtcattta cctaaataaa aaaaaaacta    1320 aatattttt ttagatacat atgtgtctta taattttaac tataaattt aattttatgt    1380 cttaaataat tgtttacact ataaatttaa atatttaat gctaaaatta atttgattca    1440
aaaaagtgat tttaattctt attttctta tagaaagttg gtgattgaaa agatttactt    1500
aaaaattata caacttcaa tggtgaataa cccgacccga ataaaccgga tataacaact    1560
tcaatgttag cttgatatag aaagtacggt gacgcttagg aggcaagcaa gctagtatct    1620
gccgctggtt agagacaaag aacatgtgtc actcctctca actaaaactt tccttcactt    1680
tcccgcaaaa tcatttcaaa aaagctccaa atttagctta cccatcagct ttctcagaaa    1740
accagtgaaa gaaacttctc aacttccgat ttttcacaat ccaccaaact ttttttaata    1800 acttttttc ctcttattac aaaacctcca ctctcatggc ttctcaaact tgttatccat    1860
ccaaatctca atccctaatt agggttcatt tctctgtttc tccaaacagg ggaattcgaa    1920
g                                                                   1921

<210> SEQ ID NO 38
<211> LENGTH: 2837
<212> TYPE: DNA
<213> ORGANISM: Arabidopsis thaliana
<220> FEATURE:
<221> NAME/KEY: promoter
<222> LOCATION: (1)...(2837)
<223> OTHER INFORMATION: Arabidopsis thaliana secondary cell wall-
      specific promoter PATNST1

<400> SEQUENCE: 38
gtttgtagag ttggatcagc atccagattt aaacccttat ttttgttttt gccaagcatc     60
cagacttaat cctatattag atactgtata tgcatcttga tggaatatag actatataga    120
aagaccaaaa atggaagagt acgaataaaa atgcataata taccttggaa attattcttg    180
gttattgtga aacttaaaac atttcaacga agtcatatac tattatttaa tcattgattt    240
aaaattgcta atcaaatcac gtgttgttgt tatatatgga taaagagtta aactataaca    300
caactgagaa aaaaataaag ttatcaattt tgttaagaat caatgaaggt ttcacaagac    360
tgggaagaaa aaaaaataga tatatggagt acataaaaca ttaaaatttt gctaaatttt    420
acttttgaac tctattgatt cgggttgaca tgatgataat gttacattcg tacaatttca    480
caatgaaaaa aacgagtact aaatattgtc aatcaaacat atgaatgtac aaaaatccat    540
aaactctacc aaaatagaat gaagattctg aaatcaaacc tacttttct ttttaattat    600 aaattcaact atattataaa tttatttatc acaaataata gaggagtgag aatatttag    660 acaacgcaaa tttctttttat ttagttctta tactttattt tttaccaaac gttaattaaa    720
aaaatcacac atacataatt tctaaaaaaa atgtattctt caagtaatat atctttctga    780
gtactagttt atctatttat ctccgtattt aataatcaaa agttacgttt aaaatagaaa    840
caacttttat caaacaaaat atattagaaa acgcatggta ctggctactg gaagaatca    900 tgacctgtaa atttctacag ttttcccgtt ttatatagta cttagaaact ttggattttc    960
```

```
atagcgcaac caataaacac atggacttaa gacacaaaaa aagttgggtg caatgtcatt      1020
aatcaaacta aaaaaataat gattaaaagc atggaattcc gaaaacgcaa caaatgatt      1080 ctgtgtttag acaaatgcag aaaggcctct taactaatct taaataaagt cttagttcca      1140
accacataaa cactccttag ctccattaat tttggttttc ttaattacgt ttctacacaa      1200
gtacacgtac ttacacatac aattccacag tctaaatgat aaaactatgt ggttttttgac     1260 gtcatcgtta cctttctgtc gtctcacctt tatatagtgt ctctaacaga acgtaacaac      1320
caaatgttta aaaaaataaa aacagcaccc cttaattagg ctcattcgtt ttgcactaac      1380
catactacaa atcatctcga acgatcgagc aaagatttga aaaataaata aacgtataac      1440
tctagagatt ttcattagct aagaaaagtg aaatcgattg ttaatcctat ttcagacggg      1500
acaggaacac tcattaccca actctatcat ctctcgaaca ccaaactata tctaccgttt      1560
ggggcattat ttcccacttt ctttcgaaga caatttccca tatataacat atacacatta      1620
ttactaatat atttttataa attttcgtca catcccaaaa aaaaacactc tttgtcacat      1680
caactagttt ttttgtaacg atcaaacctt ttcgtttaaa aaaaaaaaac ttttgtagtg      1740
taaacgttta tttatcgatg aaaaaagcca catcttccgg agggaaactt tttaagacac      1800
cctatttcga ctttattttg taaatacagt gtgcatgtgc atataaagag agatatcatt      1860
tgtataaata tcaagaatta gaagagaaaa agagagaaga agacaatcta ttactattac      1920
gatgtgtggg ttgttaattt gtttaaaggg agcttttcta tagagatttt taaggtcaag      1980
ggtcatcgtt cgatgtgggc ttgcttccta caatctagtt gccttacggg gcctactctt      2040
tttcttttga taactacatc accttttttt tctccgacaa ctatatatca cttttttttat     2100 gttttccttt ttttcttcac aataattctt tactcgttgc aaatgtaaag atacacaaag      2160
ttacttattt tgtttacgat ggttcttagt agtttaaaga attaatgaat aagataaacc      2220
taaactttga aaagactaaa aaaaatgtat aacaacatac attatacgta tttgaaatag      2280
tccaagtgat attatgtcat tgatattagc acaataatt acgatgcctg atattgtcac       2340
atttgatgat tttaagttct tgtaaaagat aagtgtaact aaatcactat agtgaggccc      2400
acgttttaat ttctaaacta attacaatga caataaaata gcaaaactat ttaaaactag      2460
acgccaaaaa aaattgaaac taataattgt gaaaaaagaa caagagaata ataatcatta     2520
ataattgaca agtgaaatta atatattgct cttggagggt tatattttaa ttttcaaact     2580
aaataatgaa tacaaatgga aaagctaatg ataagagttg aattttaata attaagaaaa     2640
acaaaaaaag gtgtacaagg agacacatgc gttttcctca tgcatcttgt ttttatacaa     2700
caatatatat atatatattg agtcattctc tgctagctct ctcatctcca actttcagta     2760
tgatatatag ttacaattaa ataaacctca catgctctat tcttgcttga tttttgagtt     2820
aatcttgaat ctctttg                                                    2837
```

<210> SEQ ID NO 39
<211> LENGTH: 1983
<212> TYPE: DNA
<213> ORGANISM: Arabidopsis thaliana
<220> FEATURE:
<221> NAME/KEY: promoter
<222> LOCATION: (1)...(1983)
<223> OTHER INFORMATION: Arabidopsis thaliana secondary cell wall-
      specific promoter PATCESA4_PATIRX5

<400> SEQUENCE: 39

```
atgaagccat cctctaccctc ggaaaaactt gttgcgagaa gaagacatgc gatggcatgg       60
```

```
atgcttggat ctttgacatt gatgacactc ttctctcaac cattccttac cacaagagca    120
acggttgttt cgggtaaata aactaaactt aaccatatac attagccttg attcggtttt    180
tggtttgatt tatggatatt aaagatccga attatatttg aacaaaaaaa aatgattatg    240
tcacataaaa aaaattggc ttgaattttg gtttagatgg gtttaaatgt ctacctctaa    300
tcatttcatt tgttttctgg ttagctttaa ttcggtttag aatgaaaccg ggattgacat    360
gttacattga tttgaaacag tggtgagcaa ctgaacacga ccaagttcga ggaatggcaa    420
aattcgggca aggcaccagc ggttccacac atggtgaagt tgtaccatga gatcagagag    480
agaggtttca agatcttttt gatctcttct cgtaaagagt atctcagatc tgccaccgtc    540
gaaaatctta ttgaagccgg ttaccacagc tggtctaacc tccttctgag gttcgaatca    600
tatttaataa ccgcattaaa ccgaaattta aattctaatt tcaccaaatc aaaaagtaaa    660
actagaacac ttcagataaa ttttgtcgtt ctgttgactt catttattct ctaaacacaa    720
agaactatag accataatcg aaataaaaac cctaaaaacc aaatttatct atttaaaaca    780
aacattagct atttgagttt cttttaggta agttatttaa ggttttggag actttaagat    840
gttttcagca tttatggttg tgtcattaat ttgtttagtt tagtaaagaa agaaaagata    900
gtaattaaag agttggttgt gaaatcatat ttaaaacatt aataggtatt tatgtctaat    960
ttggggacaa aatagtggaa ttctttatca tatctagcta gttcttatcg agtttgaact   1020
cgggttatga ttatgttaca tgcattggtc catataaatc tatgagcaat caatataatt   1080
cgagcatttt ggtataacat aatgagccaa gtataacaaa agtatcaaac ctatgcaggg   1140
gagaagatga tgaaaagaag agtgtgagcc aatacaaagc agatttgagg acatggctta   1200
caagtcttgg gtacagagtt tggggagtga tgggtgcaca atggaacagc ttctctggtt   1260
gtccagttcc caagagaacc ttcaagctcc ctaactccat ctactatgtc gcctgattaa   1320
atcttattta ctaacaaaac aataagatca gagtttcatt ctgattcttg agtcttttt    1380 ttctctctcc ctcttttcat ttctggttta tataaccaat tcaaatgctt atgatccatg   1440
catgaaccat gatcatcttt gtgtttttt ttccttctgt attaccattt tgggcctttg   1500
tgaaattgat tttgggcttt tgttatataa tctcctcttt ctctttctct acctgattgg   1560
attcaagaac atagccagat ttggtaaagt ttataagata caaaatatta agtaagacta   1620
aagtagaaat acataataac ttgaaagcta ctctaagtta tacaaattct aaagaactca   1680
aaagaataac aaacagtaga agttggaagc tcaagcaatt aaattatata aaaacactaa   1740
ctacactgag ctgtctcctt cttccaccaa atcttgttgc tgtctcttga agctttctta   1800
tgacacaaac cttagaccca atttcactca cagtttggta caacctcagt tttcttcaca   1860
acaaattcaa acatcttacc cttatattac ctctttatct cttcaatcat caaaacacat   1920
agtcacatac atttctctac cccaccttct gctctgcttc cgagagctca gtgtacctcg   1980
cct                                                                  1983
```

<210> SEQ ID NO 40
<211> LENGTH: 1577
<212> TYPE: DNA
<213> ORGANISM: Arabidopsis thaliana
<220> FEATURE:
<221> NAME/KEY: promoter
<222> LOCATION: (1)...(1577)
<223> OTHER INFORMATION: Arabidopsis thaliana secondary cell wall-
      specific promoter PATGAUT8_PATIRX8

<400> SEQUENCE: 40

```
acgagctgac ttgtaccgat gagctggctc ttctgggcga gctggctgat cttgacgagc      60
agacttctcc cgacgagctg acttgtgtcg atgagctggc tcttctgggc gagttggctg     120
atcttgacga gcagacttct cccgacgagc tgacttgtgt cgatgagctg gctcttctgg     180
gcgaactggc tgatcttgac gagcagactt ctcccgacga gctgacttgt gctatccttt     240
ctccaggtct cgaaaaagtc ccctttcccg agactttcta ttccttattt atacccgtcc     300
gtatagtagg gtacgcaagg tgaattctcg agagtgcccc ttttctacgc agccgaactc     360
acatcctgac caggccgggc ttcggcctgg tgggccggct cgagttctaa agtgatggtc     420
ggggctgggt cgttattcct tgaaatgggc cggttgatca ctgaggccca attgatgtat     480
caacatgtgg ttttttataaa aagagtcgtg agaagagttt tctctaaaaa tcccttgtgt     540
ttggtaatca aacttcattc aaccaacgaa ttccaaaaaa acaactaaat tgttcgggta     600
tataaaatga ttggtaatga tatatcccat agaggccgta gacataggcc caaaaagttt     660
ccataactag cagaaattga aacttgcaag ttgcaaatat tattcactg gaaaggcaac      720 aagtcttgaa gtacaaacta caaagacttc ttgtttggat ggggacgact gacgagtttg     780
aataacttaa gagaaagggg tcgcaatcga aattagacaa gaaattagtc ctcaaaaagt     840
aaattctgaa gttgaagctc caatgtcttt gttcaaagac tttatttaga tgtaaagtta     900
tgtcttgtaa ccaccaaaca gctccttttc atctacactc ccaattttttt taacatctat     960 gttttgcatt gcctttgact tgtctttctc tctccaactt ctctccttca acataaagcc    1020
aaatcctaaa tccaaatccc ttaaaccgaa ccgaattaaa ccgaagctgt tgaactatcg    1080
caaaatttca gatcttacta atcataaaca tgtgacgttt aattcatttt aagagtttca    1140
tgatttgcac tgaatggtat tccgagtcca ccggaaaaaa actttttccta caagtagaaa    1200 aaggataacc ccataaatcc aaataaccta accgatcaaa catataccaa tataaaccaa    1260
aacaagattc agattcatcg gtttagtaat cgaagtaatg tactaatgtg taatattgat    1320
tccaccacca gcttagagat tcgaaccaaa aaccgaatag cgcataaccg agaaaaccca    1380
aagcttccta acaaatacat aaaaccgtgg tgtttctaat tctaaccaac acacgttttcc    1440 tttttattca caagaaacat cagagttatg atctgccatt aataacctaa acacaaagca    1500
aggttaggta aatgatatgg acccctaatg aataatcata caatacataa caacgtaaga    1560 tccagttttcc ctcttcg                                                    1577
```

<210> SEQ ID NO 41
<211> LENGTH: 2710
<212> TYPE: DNA
<213> ORGANISM: Arabidopsis thaliana
<220> FEATURE:
<221> NAME/KEY: promoter
<222> LOCATION: (1)...(2710)
<223> OTHER INFORMATION: Arabidopsis thaliana secondary cell wall-
      specific promoter PATNST2

<400> SEQUENCE: 41

```
aacggtggcg tgatggagct tcatcctccc atcttcgccg aattcatcac caacgaattt      60
cccggccatg tcatccacga ctctttaagc ctccgccact catctccacc gcttctccac     120
ggcgaagaac tctttcccgg taacatctac tacctccttc ctctttcttc ttccgcagcc     180
gcgaccgctc aactggattc ctccgaccaa ctatcaacgc cgtacagaat gtctttcggg     240
aagacgccga taatgcggc tttgagtggc ggtggttgtg gagtgtggaa ggtgaggctt     300
gtgataagtc cggagcagtt ggcggaaatt cttgcggagg atgtggaaac ggaagcgttg     360
```

```
gtggaaagtg tgaggacggt ggcgaagtgt ggcggttacg gctgcggcgg aggagttcat    420
tcgagagcga attcagacca gctaagcgtt acgagtagct ttaaagggaa attgtggtaa    480
aatttcgaat tatgaataaa ctacgtttat gttttaatct gtttcacgat ttaagcattt    540
aaattagtat gttgatttcc gtattcattg aagacttgga acgattatat aagtttatca    600
acgtagatat atttgaaata tcattgttat ctctcatgaa acaattaatt tatgaagtcg    660
tagactcgta gttagagatt atttaatctt ccctattcaa tgccaaaagt ctagaagagc    720
aaaacaaaag ggagaaactc ttttatttca ggcccaatga cacaaagctg gccagaaaca    780
gtttaagatt aggctaaagt tataagtccg acaagcacga gtgctaatat atatagttat    840
atgacgtctc accattaagg gtttaataaa ttttgaaaca cctcaaatta agattgcttc    900
ccatgcaaac ttccttcatc ttctagaaaa attacgattt gtaatacttc aattatatca    960
ttttagtttt ttgtcactaa ttatcatcaa tttatcatag ctccgtgccg caacaacgtt   1020
cgttttaatc agattatata ttactctgct ataaactcag aaccatgtta gaaaaatgaa   1080
aaagacattt cagaatattc attaactcaa aattttaatc tcatgattta attttttatt   1140
aacaatgtta tcctatagca catggcaaat ttgaacggcc cttgcgtatt aatctattat   1200
aatctcaaaa ccatgtgtaa gaaaaaggaa attcagaaaa taaccttttg taaataggcc   1260
cccacaaaat ctacaacata cgtagatacc tcctcgctta cagttgtaaa caactgttca   1320
tctagattca tgccgtcatt caagtttaaa ttaatacaat aatttaaaat tttaatttgg   1380
atgaatcgaa tccaccgtcg tttcctgaat accagatagg ttaactttat gattagttcg   1440
agtgaaccac atgcacaata ttcgaatctt agacattcgt tgcaatgtta acttcacata   1500
tatttgataa acgcttcttg aatcagatct taatctcttt ctttctctcc atcttctaag   1560
gaggttgtgg attatcatgt agtatatcat tatcttcgca tcaccttcaa caagaacaag   1620
ctacgagctt taaagtcgta tttaacacaa taatgtataa agtctttctt catcacatca   1680
catacatttt ttgttgccat caccettcat tcactttttt tgttaacact attcgtttct   1740
atataaaata aaaataaaat gaggaatgtc ttgtccatag agattttaa ggtcgagggt   1800 catcggagcg atgtgggctt gcttcctaca ttatagttga tatgtggatc ccgcgtggac   1860 catatttta cccaatagct acgtgcatgg tcccaccgct ctctctcacg cactattccg   1920
aaattgccat aaacaatttc accggacaaa aagagcaaat aatttcgatg tttaataaag   1980
agaccattag tatatttgac ccaaaaaaaa ataaaaaaaa aagagagaca ttactataac   2040
ttttattaga tgaaatattg caacattgta tttataacgg atctaattta ctgaatcata   2100 tttttttct tgttaaaga gatactgaat catgcagaaa aatagataga ttttaaata    2160 ctaggtgaac tcatgacgaa tcaaccatta cgagagattt ctggataaaa gcaaaaacaa   2220
aacaaaacta acatgctaat ctaggcaatt agtagagcga aaagtcggca aaaccaaagg   2280
ccgaagaagc ttgatcgata tactttttt ttttgtttt ggctggatat acttggtatg     2340
aactaagaat taagtaaaaa ctcatagggga gtaattttc gagaagtgca ttcactatga   2400
gtataaaaca gacattttca aattattaaa acaagctctt agaggctcat atgtttaatt   2460
gtaagtggcg gctcatgcga acttataatg aaaacatcaa atattcggaa aaataatact   2520
ccactgttaa aaagaaaact taacaaagga attaaaaata tgagagcaaa agaacacatg   2580
cattttctca tgcatgtact attatttatt ttttgcaga gttgatgtaa aaaatataca    2640
catatatata gacatacttt ggttagttat aaactcgttc tattttcttc tccttttct    2700
```

| | |
|---|---|
| atctttagca | 2710 |

<210> SEQ ID NO 42
<211> LENGTH: 3027
<212> TYPE: DNA
<213> ORGANISM: Arabidopsis thaliana
<220> FEATURE:
<221> NAME/KEY: promoter
<222> LOCATION: (1)...(3027)
<223> OTHER INFORMATION: Arabidopsis thaliana secondary cell wall-
      specific promoter PATNST3

<400> SEQUENCE: 42

| | |
|---|---|
| attctacaca ttcacaaagt ttactacact atatataatt tacccaacaa acacttattt | 60 |
| tactgcatta ttcagtatat tatcttacct ataaatgtgt atcatcatca tcaataacgc | 120 |
| gattatttgt gctgaaggat tatatattca aaatgatcta gttatatatg tcacatgatt | 180 |
| gccgttaaca agacacattt gaagaagcta agcaagaaaa acggacactt ttgcgacttg | 240 |
| ttacataatt taacttatag gtcaaaagaa tttgattagt cattgcaact acgtgtggat | 300 |
| gtcactttct attcaaccaa aactcacaat attatatgat ctagttttgt cgtattactg | 360 |
| atttgtatta taaatgttta tttaatttga attctacgta gatattgctc atgcatgata | 420 |
| gtatgtatct aaactattca ataactaac tacgtggata ttttataatc caagtaaaaa | 480 |
| gcagaaagtg ggtaactacg tcagtatgac tatacttta tcggaattgc ttgcatccaa | 540 |
| aacttttgct atgcttcacc aaccaatgca gtttcactta attattaact attgactatg | 600 |
| tcttattaag ttagcactaa ttcgttaatc attcaaaacg ttatttgatt gaattacata | 660 |
| ttacactctc tttctgcatc accactcaca ccatatgcaa ctataaccaa ctcatcacat | 720 |
| tcaaatgtat taattggatt ttggtgcgag attaaaaatt gaaaggaaac aaaatatgat | 780 |
| aatgggataa aatcttgaac ggaaactcaa actaatcctc ataaggtata acaaaataac | 840 |
| aatttaagct aagcacaaca acatacaagt tcgaccttt cctttgatga tccagcccaa | 900 |
| cagttctctt atatctcaaa ccattcgacc atttgagcca aactagctaa acctgcagga | 960 |
| atcaaaacca acaaagattc agattagcta aaccggtttc atccctttgt cacatgactc | 1020 |
| acatccgtct tctacataac gatttctaat gatgtgagct cttaacttgc tccagcaaga | 1080 |
| tcatcaactt tggagcacct tcaatgattt agttaacatg ttagataaat taaatattct | 1140 |
| tgtttcaata tatatcaact ttagtgtaaa agccttaaca ttctcttgaa tatttaattt | 1200 |
| atttctcctt atttcgattt aatgacaaat gtgaattaat ttttgtgata ttttttgttcg | 1260 |
| aaattagttt tcagttaata acatacatgt gagcatggga cacacatgat ttaacaaaag | 1320 |
| ggaatgacga aatgatatat caaaatatta gtatgggaac aaattacgag gtgaaacttc | 1380 |
| acactcaact caattaaaac tagaataaag aaatggaaaa agtgaaagaa tgagaggtca | 1440 |
| aatgtggtta atcattatgt ggtattagtt aatccatcaa ttgtgtaccc aaaagcatga | 1500 |
| ttaagcatag aatttagaga acaaaaacat cattattaat gttgaaacac aaagatccca | 1560 |
| tcaacagaca aatgataagt acagtgcatg tagggtaaca acttttatgt acatgttata | 1620 |
| tacttatatt atataataag aaaacgatta aagtgtcatt gctccagcct ctatttgtaa | 1680 |
| atcatattat atcagtatgc ttaattccaa taattaagtc cataactaaa atatatacac | 1740 |
| atatatgtat gttaaatggt tgaatatata catatatttt cataaacaaa tattgctaat | 1800 |
| taattcagtt atttgtgtac ataatccaac tatcacctt ttagctggaa gtggatattc | 1860 |
| caacatgtca gtctgtcact cccacattca tactctctat tctttttagc tatttcaata | 1920 |

```
tctacggtta aatattaatg ctatatagc cttacccttc attttagttt ttttttggta      1980
ttcgcataac catcgaatac tcaaacttac tatgtaagat ggtctgaata actatttccg      2040
atttaagatg aatagctaga ttgaaatata catgcactaa ttggacatgc actaaaggca      2100
gaggtgaatt aaatgatgaa atgaagatga agtgtcacac ttgtgcaaaa agcatgtccc      2160
ctgctcttct ccgcttgttt caatttcttt gactttcatc acgttttgt cacttaaata      2220 caccaaaaaa tatagtacaa ttaaacatcg aaaatcgtcc aaaagaaga aaaaaatca      2280 tggaaagttc tttcgttaat gttacacaca ttatcttgat taggtgacac cagatattag      2340
aataaaaatg atagattatg aaagaaaaa aaaattgat gtattttag gatacatcga      2400 aaggaatgaa cataccaaaa acatgggaaa aaatagataa ctaattaaca tggtagaatg      2460
tagatgacgt agatcatgaa acgagtgtgt gatatattaa tgaaaattat tttaatatac      2520
gtagctatat tagaaaataa tttacattta ttttcttcta acaaatcta tactttatat      2580 ttacatacat tagtaaagac caaaacacat ggaattcaaa ttctgcaata agtaattgca      2640
agaaaacaca aagattaatc ccccactaaa cccgtttatt tacgttagta tttttccgtt      2700
ttatacatta cacatgacat gacattacac gtcaaaagaa atatgtctta cgtcagaact      2760
tacgtatgat caaactcgat ttaaacatag aaacatctgt ttactaaatt atactaattt      2820
cataaagaca ctttaatgca tgaacttctt tgtttaaata acaatttccc ccttttgggg      2880
gctatgtctc gtcgagtcct accaccatta taaattatc catcgtttgc tttcttttt      2940 ttaagttgta accatttcca ctcgtaatca tacaacttct ctactcttct agagcaaaaa      3000
cccaaaaata tattgctatc ttcgtta                                           3027

<210> SEQ ID NO 43
<211> LENGTH: 1959
<212> TYPE: DNA
<213> ORGANISM: Arabidopsis thaliana
<220> FEATURE:
<221> NAME/KEY: promoter
<222> LOCATION: (1)...(1959)
<223> OTHER INFORMATION: Arabidopsis thaliana secondary cell wall-
      specific promoter PATFRA8_PATIRX7

<400> SEQUENCE: 43
cttcaaatct cttgtatcat taaatagtaa cgttttaaat attttctgga taagcataag       60
tttctttgaa aactattttg tatatattcc tacttctcca ttttttctaaa ttatttata     120 ttatacatag ttttccaaat tatcaaacat ttttacatgt tttgactaat aaataaacat      180
attactgcga attaattaaa aataaatatt ccacacaata attccttac aagcgaataa      240 acttttacta tgttttcgat gtaaattttt cttacatatt tgtaactgaa atttctaact      300
tgttgtttca taagttttaa aatttattat ctaattatct acttttatgt gttctagagc      360
aaagtgctaa atgtatatat acttagatgt tgtgttgtaa tccaatgtca atataatcaa      420
tgatttagct atttgtaaac atactaaata gtattccacc aaaaaaaaaa catactaaac      480
agtaaacaaa cagcaaaaac aaaatccaca tgtcctaaaa gatagtctga ttttcgttca      540
taatgctctg gttttttgaaa gataataatt gtgttgtatg agtgtatgac aaatattcat      600
tggtttgaga agttaacaaa atttggtggc tacaaatggt ttcctattcg agttgggtcc      660
attatccctt ggcgtgtacg gaaataatac ctacccatca taatctgatc aaagatgagg      720
tagtctttaa ataaattttg cggcttatat caatctttat gtactataaa ctgtgaactt      780
tttgttcttc aggacttcca catcattgcc caatccggtt ataccttcgc tagttaatat      840
```

```
gttaattaac attaaattaa agagctaaca tttcttaggt agtaaaatag aagttttgaa      900
ctactatact actaacatgt gaaaatactt tagtcacaaa tatgacaata tacaaattta      960
ttggaatgca aattcttgaa tttcaattgt ttgaaaatta tatatttcta cataacaatt     1020
ctttataaac taaaaatatt aattttccat ggctatgcgt tatacgtata tgtcaaatat     1080
ttttattatt tatataattt tacgataaat tagtactcca ctttactata ttactcaaca     1140
ctaaaagacc tctttaactc cgcctaacat agatatgttt tcttttgaat gtttcggtta     1200
aacatgacag agatttgttt tcttgctttc gctcaataca tatttgtgct cctttagaaa     1260
agtagtattt cctaacaatc caacattttc atatttatta tatcttttaa atattatcat     1320
ggttcttttt ctttcgtcat gtttggcctc tttaaaataa ttcttgaatt gtatgagcat     1380
taatccaata acgtcctgat cccaaaaaacc tcatattagg tttgagagtc cgaaaatata     1440
cttttcacat aaagcaccta aggtgtcata ctttaacaac ttcacaaaat atgcaaaatt     1500
tgtcattgtc actttgagat gtaagttttt ttttacatgc aaatagattg agtctcttta     1560
cgtgtaaatt catttaataa aattgtatgg aatatctatt tatatcatat atttctaaca     1620
tatatataaa tatctataca aaaatacgac ttttttggcac atgtaattag aaaaatccac     1680
aagaaacaga aaaagaaac accaaataca acgaaatgaa gaaattatta taaatttgaa     1740
tggcttaaca tctcttaaga gtcaacaagg taaaggatta attagtagtc ttcatcaatc     1800
tttctccacc ttcttctatt ccttaatctc cactttatct cccaaacccg aaaactcctc     1860
ttcaccaact taaaccctat taactaatcc caacaatcag atgtttcgaa ttcaacaacc     1920
agctcaggcc ataagattca tcccggagaa acaagaacg                           1959
```

<210> SEQ ID NO 44
<211> LENGTH: 1977
<212> TYPE: DNA
<213> ORGANISM: Arabidopsis thaliana
<220> FEATURE:
<221> NAME/KEY: promoter
<222> LOCATION: (1)...(1977)
<223> OTHER INFORMATION: Arabidopsis thaliana secondary cell wall-
      specific promoter PATIRX9

<400> SEQUENCE: 44

```
cgggttttcg gttcgacccg gactcgaaac gggtctagat gaagaaaacc tcatctcttt       60
ttgtgtctaa ggattttttg gtactgaaac tctcactctt ttttttggtt cctctggtcc      120
ctctctatat gattcagatc gaacactgtg gttttatatt ttttaatgtt ttgttatgtt      180
cacacgttgg gttcagaaaa attgacggcc gagatctttt ctataagagg aaatcggtgg      240
ttctacttag ctaatccttt ttactagaaa agtttaacat tttgtacttt ttgtctgtat      300
gctctctagt tgtttgttga gatctcttgc tgctagattc acttttttggg acacattgct      360 ttgtatttga agctagaaag tttatatcaa catgatctaa aaaagtattt taagagaact      420
acattgaggt agtatttct tttcctaaat tagtcattgg taaattacat cgtgacattt      480
atagaacatt gcagagcata aaagattgaa aaaaaatga gctgagattt gtatgtatat      540
aaagaaaacg tattagcata gctttctttc agatttaacg gtggaaatca tacaaaactt      600
tcttgcagaa caatgagtat atatatgaag gactcgttaa cgaaaatatt agtttaaatc      660
tagatatctt ccagtaaaat atgagtttcg ccttcgtata tgatacggca ataactttgg      720
gaccaactaa tttgcatatc acatgttgat atctctttca gttctactca ttcttttttt      780
ttgaaaacaa caaattattg gctgcaaatg ttttttggtt taactagtgc ttctctaatt      840
```

```
gtcaagtatc ttagtctaga gttaattact taaatactaa aaggctgtcg acaaaatcaa      900
gcttgaatct ccttgtggta tcttcaactc ttcgttgtct gcttacgagt ggtttactca      960
gtaattatct ataatatgtt attttttttc cctcatcttt tagttgttgt ttcattacat     1020
tgaaaagctt gtaatgtctt tatatggtat atatggatct tatgagtgag gcaagatcca     1080
tgatgttttt gatcttagaa tgtatatgat gatcttagaa tgtatttgac cgcccacaaa     1140
ttattgttca ttgggattat atctctagtc caactccaag caatcgaaat gggtcctgct     1200
tttaagaaca acagtatatg tttaagaata ataactttat atattctcga ttttaagatc     1260
ttttgacaaa acctcctttt cgttaggagc gtactaattt ccaagtgttt gattagtggg     1320
gtctccgtaa atttatttag agtttctatc tatttattaa tagctcaatt aattaatcta     1380
tactgtatct aaacatcaat ttatatattt actcttgaga ccaaaactgt caatttataa     1440
cattggatag tttcttaatt cttattatat attttcaaa cacttttcaa gactaatctc      1500
cacattaggt actctctcta gagataaaaa tatttatcaa aaacattttt atttatttat     1560
taagtagtag ataaactact gtggcaaaat cgtaaatgtc taaatgctga tgaatttttt     1620
ttgctgctcc aatctggttt agtgctccat atacatccac ggccaaaatg aatctatggc     1680
ggcattaaga ttcattagta agcaacgatt atattaatat aattgttttt agcaatgatt     1740
ttccgtaatt tcccaaatat gtttcagtta atgtgttcca atcccaacaa ctggttgttg     1800
caaaagacca ccaacgcaag caatcatcaa acatcaaaat aatcttacct tagcgaacaa     1860
acaataacta cacaattctc ataaagctct tatatatcac taacttcaca cattttgttt     1920
tccacaaaaa taaaaacgga actcactcaa gaaaccttct tccttgaaga gagggtt       1977
```

<210> SEQ ID NO 45
<211> LENGTH: 1987
<212> TYPE: DNA
<213> ORGANISM: Arabidopsis thaliana
<220> FEATURE:
<221> NAME/KEY: promoter
<222> LOCATION: (1)...(1987)
<223> OTHER INFORMATION: Arabidopsis thaliana secondary cell wall-
      specific promoter PATGUT1_PATIRX10

<400> SEQUENCE: 45

```
aataacaacc acttaagtta ctgcaagtta ccacaaagaa aaatgatcta gcaaatgagt       60
agcatcatat tgatcaaaga cactgcaaga taaaagtcac cttgctaatg ttcgagataa      120
tgataaagtg tagacttgga gcaagaagcc atttaaacta caacttcct aattgagacc       180 tttcatgtaa cttaatgtca aaatcacaag caactagagg aagaaataaa aatgtaccag      240
gtagcttctt gggcttcctc atgggaacaa atttggcacc aatagccaac gcaataggag      300
ggccaaaaat gaaacctcta gcttcaacac ctgcatttac cacaacatca atttaggcag      360
aaccaaaaat catccaccaa ttcatttcaa cttttcagtt taagctaaag cactcagtat      420
ctaaaaaggc caaagaaac taaatccaca agctgttaat cgattggagt accaaacaga      480
accatacgag ttgttacctg caacaacaga tatgccttta tctttgtatc tatcaacaaa      540
caaagcaata gtatccttaa aggcctcagt gtcgagaaga agcgtcgtta tgtcctgaaa      600
catgattcct gccaagtatc caaattaaaa ccttaagatc ccaacgcaga tcaagactag      660
agacgatatt aatcggtata aatggaaaaa atggagacct ggtttaggga agtcggggat      720
gactctaatg gaagaggcaa tcttagcgat tctgggatct tgcacatctt cagtcgccat      780
ttcactgtcc cgactggctg ctgctttagc aaaatactcg gcgtcagatt tgcaaacaca      840
```

```
                                          -continued gagagaccct aaagactcaa tagagagaca cagtgatgaa aaaatgacca atttatcccg    900
aatggtaacg ctttgacgga attgccccac gcaagcaaaa tatcttttc aaaaggaaac     960 aaaaagttta aagggaaat agaaggtggt ggggtctacc ggcggaggag aagaggcgga    1020
gtgaggtggt tgaacggtgg tttgagaggc ggatcgaagg aggagcacgg tggtggttgt   1080
tgagaagacg gttgcaagga acagcacgag caagacagag acgatgagaa acaagtggag   1140
aaattattat tgtttgcatt gtctttggac tgagagatct taaagagaa tgtaaattac    1200 tttaaacacg gaataatgga caaaagccgt gatcaatgac ttttcaagtc ttaaccaaac   1260
ctataactca tccattgttt gtttttcta catatttctt cacataaaat tggatgattt    1320
agaatctttc agagtgttca cactccaaca gattattatc cacaatgtta tggttacatt   1380
tagagatata taacaatgtt catttcatcg ttgctaatga cataaaacga tcaaaaactg   1440
aatcatagta cttctttac agtgatctca aatatattaa tcgctaatca atgaattatg    1500
tcacctataa ttgtcgtatt accaacaact ataaaacata tatataaaa attgttgtcg    1560 ttaactagtt gttgatagtg gccactctaa aacgatcatg acctactacg gaagttataa   1620
ctagtcaacg ttggacgtta gcaaggccca atggacatta actcagccca taatagcacg   1680
cgccttgtga tgtgcaccag tttccgtctt tggtcgttga attcaaggaa aaaaaaagta   1740
catcacaagc aatttcttac ttatctgtga cttgaagcta tttctccaat ttcgttttcc   1800
atcgacactc tatttcattt tcaccattca cgtcttcctt ctgaataaaa taaaccctaa   1860
aacctaatac cgaagtaaac tcgtcaacca ctgcgcccat gacctcccaa cgatactctt   1920
cccttatatt cttcctcttc cttcttcctt tctgcgatcc aaaccttcaa acacatctcc   1980
ggtagat                                                             1987

<210> SEQ ID NO 46
<211> LENGTH: 1973
<212> TYPE: DNA
<213> ORGANISM: Arabidopsis thaliana
<220> FEATURE:
<221> NAME/KEY: promoter
<222> LOCATION: (1)...(1973)
<223> OTHER INFORMATION: Arabidopsis thaliana secondary cell wall-
      specific promoter PATIRX14

<400> SEQUENCE: 46
acctgcatcg aatttatata aatttaaaac acattatcat catctctaac ttgaactttt     60
aaacaagttt atctttttgt ttcacaaaaa aaaacaagtt tatctttatg tccctcctga    120
gacatataaa acaagattat cttctcttct agtagggata tagcaagtcc ggacgagatc    180
aaaagtagat tgactcttaa gatcttacta agtttgagct tgctttggtt cccacctcta    240
aaaaccagtt ttgcatagtc tgagactcgt gttaaattcg atcaaatctc tctttcaacg    300
acggttaact atggacgtat tcgcaaaaca tcacataaaa acatctctaa agtatttggc    360
tatttgcata aatatttcac tcttacagtc gtcaaaagta tgaatgaact ctacatatcg    420
gcccaatatg aaccaatttg taagaccata atggaaagcc catgtttctc ttgtgcttgt    480
tttagttgca gaatcattag ttcacatatt gaccggatta tattagtttt taaaaacgca    540
tgtatgatgt agtcactgta tcatacccaa gttactgtat tcattaccca gttcaaact    600 cgataaaatg cataaactaa acatacgttc tttagccttt tgttttcact tcaattaact    660 catttgtgc gttgtatatt tttttctctt ccaacagcta cttttctcac gtctatattt    720
tttaccgttt gtgattttg agtctcaaat atatggaatt gttttttta aatggctact     780
```

```
ttccaaagtc ttatattttt taccgttgta aatgttcagt ttcagatata tatggatttc    840
tttttctaat ggctacttct ctaacgtcta tatcttttac cgttgtaaat tttaaattct    900
gaaatatatt accgtttgtg attgagttca cttgacacac cttcgttaaa aattacacaa    960
caaaaagcgt tcacaataag cccaatgggc ctaaaagacc ctaacaatcg aacatacct    1020 tctgaccaac acattttctt aaggagacac tgttggtcca tttactcatt taagtaggat   1080
tcataacact tgtcatggtc gtcatttctt gttcaaatgc cttttttaagt aataacgcaa   1140 tggaagcata tatatacttt aaacccacaa attaataatg catatgtatc tattttttctt   1200 gcatatacta acatgtctaa agtatgatat aaactttgac actttggtgg tgctgagtaa    1260
tcatcatatt tatgctttgt gtgcaagtga aaacgaaccg ataacaatct ttaagacttc    1320
cctaccaaac cggtttaacc ttcacaacaa acaaacctag atcaattatc tctaaaccaa    1380
aacccttcaa accatgtctt ttgtcggacc aaactgtact cttatatatg acatgcagat   1440
acgtcgtttt catgggcctt actaatggcc cattaaaaac attcgtaatc aattattttg   1500
gttagtcttt cccaaattcg tctacattcc tcctcgataa tcacttttaa ttaaaaccat   1560
atgaatttac gaaaaaaaca aaaacacaat tatcattatg caaaacattt aattcaataa   1620
attgagggat gtttaatgtt aacaccaaaa attattacca aaaattgact tcaattagag   1680
acatattaaa acgaccctga ttttactcaa aacttaattg aaagatttaa ttatccaata   1740
ataaaacgac acgtgtacct ccttgtcgct ttcctctgct ttcttcgatg gcgttgcatc   1800
gaagcatcag agagattggt atggtggtgg tggtgagaga gcagcaacaa cagcaagaag   1860
agaaagcgat aatcgaactg attaagatcg tgaaatccaa gtaatctctg ttgcttaatc   1920
tcagatcttt ttgataagga gaaggaagca gaagaaagag gtcaacgaag aag          1973
```

<210> SEQ ID NO 47
<211> LENGTH: 1941
<212> TYPE: DNA
<213> ORGANISM: Arabidopsis thaliana
<220> FEATURE:
<221> NAME/KEY: promoter
<222> LOCATION: (1)...(1941)
<223> OTHER INFORMATION: Arabidopsis thaliana secondary cell wall-
      specific promoter PATMYB46

<400> SEQUENCE: 47

```
gttacactaa cggtttcttg ttagatttag ctgacgtgtc tttatgaata tatatagagt     60
taaattttaa tattttaaga gtagtattac ttcattaaaa gcttagttgt aaaattacta    120
aagattttca tatattataa actatttttt cctggcaaac ttatattata aaatttgttg    180
agcgattgtg tgattctttc atccacaatt agattaaaaa aaatcgcaaa aagtaataca    240
agaaaaaata ataattttac aaattaataa tgattgtttc tttggctaag agttcagatt    300
tgcagagtgt ttttttggtcc ttgggcgata ttacgaaaag tgaattgtaa agatatgtat    360
agattgtgag gaaaatgcga gaataactga gagctagggc tatgcatgag atgattgaaa   420
tatcatgaac caaatggtta gatgagagct tggagtgaga ggtgacactt gtttgagatg    480
gggaatagcg gattaatgtg cttgcatgac cttggttctg aattttcgat tgatgaaatc    540
ttgcatttcg ttattttcaa actttgtcca cgagttttac ataactaggt tcattcaagt   600
tacaacttaa attggttagc tgacgtcttt tttcatgcat atacaagagg ttgcatttgc    660
aagcttcaaa agagattaca ccaaaaacaa tttcccctaa aggttaagat atatctttgg    720
ccttcaattc gacattagga attatgttca agattcaaga ttcagtacta ttctaacttc    780
```

-continued

```
ttttgtactt tatctatgga tgtcttgttt atgattgtat aaaaagtttt gttttttcgg      840
atgggtgggc tattaatatt ataaatcata taatatgagt gttctgtaaa aaaataaaaa      900
tgatatgagt gtaaatcgag aacttaaaaa atcatgacac acgtttatat attaaagaaa      960
aaacgaatat aaaatatatg gataaaagga gtataacatt ttcttcatta caataattag     1020
atttcttcaa gtatacgtgt tggtgcgcga gaggtggttg tgtgaagccg aagcaaaact     1080
tcttgctcgc taagcctcat ataacacaaa aaaagggttc tgtgacacac gtcgatttat     1140
tttatacaat tgaaatatgc ttacatacgt atacaattaa ttaaataaca caacatttgc     1200
ttaccttgaa aatgaagaca tctttgaata gaaatagaca tgctcatgaa tatatatatt     1260
aatgttatat actatcatat atcaatgtta tatatcatat atatacacac gtaaggttaa     1320
cgaattagat atgtctgtaa tgtataccttt gtgaatgaag aaactaatag aaatgagtta     1380
tatattcaaa aagaacaaga aaagaagaaa ataaaattaa gaacaagtga agagcacttc     1440 tcctttttt ctttgatgtt ttgcatatcg ggtcttttttc aaaaccgttt tcgtccatga     1500
ccgatcaact aacgtttctt catttcgtca aattagttat atacaaaaca tacatttgtt     1560
gttggtgtat tttatttat ttaccttaca caatatatgc cgacaaaaaa aatgtgttta     1620
atttgaaaaa gagccagggt tcggatgttt ttcttttatg ttttaaaaca aagcaacact     1680
atattataaa tataatatat acaataaaaa tataattaag gaatagagat taaaaaggaa     1740
gaagtgcaaa tggtttttct tcccagaatt gtaagcaaac catacaacca tcccttctc     1800 atcatcatca ttctcccttc atcaagtctt ctctcttttc tctctctatt ataaaacaaa     1860
cttcactcgt tcacatcaat ggatccttga gaaagacaaa caaattgaag agaaataata     1920
acaattaact caaccaaaaa t                                               1941
```

<210> SEQ ID NO 48
<211> LENGTH: 1956
<212> TYPE: DNA
<213> ORGANISM: Arabidopsis thaliana
<220> FEATURE:
<221> NAME/KEY: promoter
<222> LOCATION: (1)...(1956)
<223> OTHER INFORMATION: Arabidopsis thaliana secondary cell wall-
      specific promoter PATMYB58

<400> SEQUENCE: 48

```
caaagactag agacagaggc gtgccaatag caacacgttt gctttcgtca tgcaaattgg       60
gatatttcaa ctttcttcca ttttttcaac ctagtttact aaacttttct ttttccagtg      120
cgaacctaat tggttctagt taaaataaca ttttcgtaag ttgttcacca aacaaaggaa      180
catatgatta taactttact agagatgcat gcacaataat gctattgtcg aataaatact      240
tatatcttct ccaaaaaagt ttctttatta tgttagaaga tccatcaata tactaattga      300
tttttggtta tatgttttga tttaaagaca aaactataca ggacatgcat gtgagaacaa      360
aaattgttgt tgttgtagtt gctagttgag tttttatttat gttgccaaaa taacaccatg     420
tcaactttaa ttttcgtcat ataatttaac gtaagcatga tgtgtttcgt catatcttgt      480
ttggcatatg gaatataaat catactattg atttggaatc tttaacttaa cttcctatta      540
agtaagcgat tgatgctgat atgtatgttt ctttagattg atgaacgtaa tattaatcag      600
tagtggatat acattgtatc tttagaattt aggttagtat attatggcca aaatgactaa      660
attgagtacc ataaactaaa gttaaagtag tggtaaaagc ttcgatatt gttttataac       720 aattttcaaa aagtaaaaga tatataaatg ttagaggttt tggataacca tattgttcta      780
```

```
taacatttta aacatatgtc atatatgttt cgtttataat atttatgact tgaccaaata    840
atttgtgtat gttatttaaa tccaaatata tatgagaaat atatagacga catgattaaa    900
attatttaaa agagtcatga tgagagggat ggagactaaa aaaagagga gaaaagata     960 gaacgtcgag aaatgttgtg tgtgtataaa gtaaaggaaa gctaatttga tcattgtatt   1020
cgaagaaaac aaaaaagtat acacatgtta cagggttata ggacccattt tctttaaaat   1080
aaatccacta tggactgatg tacatatttt ttcttactgt tcttaagcat gattttatat   1140
gtataatatg gttatagatt agaattttat tcagccttcc acgattctta accctaacca   1200
gtcaattttt tcttccttat aaatatgagt gccaatcgga aggtgatagc atccttacgt   1260
cttgtttggt agattactaa gtcaagtttt attcatgaaa tttccactta tcaaactttc   1320
tcattttgtt aaaatttaaa accgttttc aaaagttggt atagccatag acagaaaaaa    1380
attattacaa tcctatctga tttgactcag acaccctaat tagtcaaatc tcaaaattag   1440
ctaatattaa ctaacgagtt gcgcatttg cagcagtaca acaaaattag tcaaaataat    1500
ttaggataac agcactaatc acaggaacag gtattttttt ttttcctttc ttttgacatc   1560
ataaagatgg attcaactta tagattggtc agaggcaatc tttataggtt tcatgattga   1620
ataaaaaata tgagactcag tatctaagtt tcaaacatgt ttcatctgtg tttagttgat   1680
tacattttca taatagtttta ttaatgacat atagaaatgc gaactataca attataaaaa   1740
agatgtgaat tttgccagat actcatccac aatatagaca agttttaac ctcaacaaat    1800 ctgatgtgac atttgtcaat gtctgtggtt tataacatgt ttctcaatgt caggatcaca   1860
cacaccactt ctcatgtata aatacacata aaagcaattg gatttggtaa gagggaatct   1920
caaaagtgtg tgtctgtgag agaggagaga gagaat                             1956

<210> SEQ ID NO 49
<211> LENGTH: 1868
<212> TYPE: DNA
<213> ORGANISM: Arabidopsis thaliana
<220> FEATURE:
<221> NAME/KEY: promoter
<222> LOCATION: (1)...(1868)
<223> OTHER INFORMATION: Arabidopsis thaliana secondary cell wall-
      specific promoter PATMYB63

<400> SEQUENCE: 49
gttgatatat attaatatgt gtccctatta tgatcacaca aaacatacac atgcagagct     60
ttattccaat agctaaaatc tgaactttaa agtcagtaca ctcgaaattg atattgacgt    120
atgtattact aatagcaaca tgtgttcttt catcataagt ttacataatt ttttaatttt    180
attctactta attaatgtca cagtttccat cgttttgata aggtccatac tccatagga     240 cgttgaaaat ttaatttaat ttttttccact catagttgtc ctttttttct tagtaaagtt   300
tgggaaagtt ttcccactca tacttgtttg ttcaccaacc ttctgattac caagagtcgt    360
ataaaaatgc aaaactaata gatcgtcatt tatatatgtt gctcctatag acttttatcg    420
acaaaatttt ccgaattaat cattttgtaa cttcaataca tatacgtcca gatatttacc    480
ctagtgaaaa atatttcttc ttttttcaaac ctctttttcct ctctattcct cctaagagct   540
tgttaacgta acaaaattgt tgggtttatt aacttcaatt attgtcgata cttagtactt    600 taaaatatttt ggagtaatag atgtagtgat ggctgtgtcg taattgcttg aataattttg    660
gatgggtaca gaggaattaa ttaagtaatg aaggtttggt ggaattaagt aattaacgta    720
gccaagagcc aacaacaaca ccaaacccac caaacattaa aaaagtcaaa aagacgtaag   780
```

```
tctttgacct cttccactct ctttggtctt tagtttggtg agttcgtgca ctatgctcac       840
acacactcct tacgccttttt ggtgttttcg gatgtgatta gaaatgactt tttaacagtt       900
tttttttttt tctgtctctc attttaatgt tatatttaag gattatatat atttctgctt       960
ttttgtatac aaaatatgaa aatattccat ggagtgacgt atggagtgac tgcgtactta      1020
gtaaaacagc attattagtg agagttcatt tttctcgtgt tacactgtat ctacatgatg      1080
atcacgggac tatctattat tcaaaagttg gtaattatac actgagcctg attacagaag      1140
actcgcagac aaaaactaat ataatcaatt cctcctatgt ataccttaag ctaattctta      1200
attaacaagt tgcagattta caatcttatt ttagtcaaaa cactacctaa tattttgcca      1260
ctttataact atatattctt actcctccaa agtatttta ttaagaaata cataaaactc      1320
ttatcattac cgctgtaaat tcctaagacc atttcaatta acactcgtcg acatgtagta      1380
gtttcttaca ttagcgaaat ttatttcaga caatttata agatatgtca aatctgataa      1440 tattttaac acgagatgct agtttccatt attacttgat gtcaaaaaag aagaaaatat      1500
tatttaagga ttttggtttc taaaaacgaa tgtgaaatat tcatgcatcg gtgttagaag      1560
gaaagataag ttgcatgcat cataaggatg ccaaatgaag taaaaatgag aaaatggaat      1620
cataccaaat aatcaaccat accacagaca gacaaccttt tcccactcaa caaatctgat      1680
ttgacattta tcaattcctc tgtttacata ttcatctttt ctcatgtcaa gatcacacac      1740
tcttacctct catatatata aaacagaacc aaattatctt tggtaaaagt gaatctcatc      1800
aggaactgag tgatataaag ttatatatat agaggagaga gggagtgaga gggagtgaga      1860
gagagaga                                                               1868

<210> SEQ ID NO 50
<211> LENGTH: 1928
<212> TYPE: DNA
<213> ORGANISM: Arabidopsis thaliana
<220> FEATURE:
<221> NAME/KEY: promoter
<222> LOCATION: (1)...(1928)
<223> OTHER INFORMATION: Arabidopsis thaliana secondary cell wall-
      specific promoter PATMYB83

<400> SEQUENCE: 50
tttgatacag caacagaaaa aaaataaaaa tacagaagaa cattaagaat gatcttctac        60
catctgagaa tggcaaatcc agaaaggatg agagaagaga tgatcatgat aatagacatt       120
cctgggaaac aagaggctcc tgtctgtgac tctgaatcgt actgtgcgga ggcggtaaag       180
acagaggaga gcgtcattgt ggcgaaaaca gccatcgctg tgtattgatt gtagccagaa       240
gccatgttta ctaaatttga ccctctcaaa accaattatg tcacctttgg ctttggcttt       300
accaatgttg ttgttttata gggaaagaag aagttcgtgg ggacgtgaag agcataaggt       360
taatgctcat ttcataaaac cccactttct gtttgttggt caacgattgt tattgtaatg       420
actaatgacc tatagaacaa aacccatcta acatgaatct tctttttaaat ggatttggtg       480 aaaagaccaa gttttaaaat catcatacgt gcgatgaaag aatacccaat ttgaagcatg       540
agcccaatga tagtttatag gcccaaataa ttttgattta tagtcacaga caggacagga       600
gcctcttgtt ttatgagttg aattgggccg aagatgatac aaatataaagc atgagaccaa       660 tagaggactg accagtttct taccttcgtt cgtcgaagaa tcgaacagtc ccttaattttt      720 tccagattca gattaatagc ctatgtatca tctgtttgga tgtgttaggc tcttttgaat       780
ttcttaaaat tagtctagat tttgatttgt gatatccttg ttatacaaaa tttgaatttt       840
```

```
tcagaaaatt catacttaat ttcatggtag acttgtcgaa cactgtgatt tgtttgggaa      900
aaaaaaggtt tagtttatat tcattacgta cgtgatgcat gatgcttagt atgcattaag      960
atagagtata tgatccgtgc tccatcatta cttgctatta tcgatcgata cttactatta     1020
ttgatcctta aaagctgatt tttgcatgcg cattattttc aatatgctat tttgaaaata     1080 tttttttgatg atgatgattg ttttatttcg gttataagtt ataaacggac tcgttttttgt   1140 gattgaatta tgggcttttg atatcacatc aaatgttatt tatgtggaaa tgaattgaga     1200
aaaaatgatg attttatctt gcacctattc ttaagtttgg ctttgatgtg tttggctttt     1260
gatgctatat ttctgtcaaa gaatcctgaa tttatttatt tatttagatt cggttgattg     1320
tgtcgtaaaa tggaagttac ttcaaaataa gcctccttgc aagagtatat atactatatt     1380
acttttagat agtgaaaatt ggttattagt tgtcgtttag aaagaaggaa attttaagaa     1440
aaaatactga tcgtaaacta taccaatgt atgtattagt actttgat acttcaaaca        1500 cacgtgtgtg gtgcggggat gagacagaga aagaggttgg tcttgttctt gtctttgact     1560
ctaaaccagt cttttcgat acattttct tcactcacaa gtctatcatc atgtttctaa       1620
cgaagacatt tattttattt atattttgta acaaaaaaat gaagacccac ctcttgcttc     1680
ttcttcacat ccccatttca tcttctctct gtctctctct attagagact ctctctactc     1740
tacccatcaa tctcaacaaa cactactttc tatctctttc tctctttgtc atatccatta    1800
cgcatattcg tatcattcca aagcaatccc cacaaatcat atcatcctct ccatctttcc    1860
ttgcttctta caatctctcc aatttcaaat ctgtatactc ttcttcaaaa aggctccacc    1920
agtccaaa                                                              1928

<210> SEQ ID NO 51
<211> LENGTH: 1920
<212> TYPE: DNA
<213> ORGANISM: Arabidopsis thaliana
<220> FEATURE:
<221> NAME/KEY: promoter
<222> LOCATION: (1)...(1920)
<223> OTHER INFORMATION: Arabidopsis thaliana secondary cell wall-
      specific promoter PATMYB85

<400> SEQUENCE: 51
cttagcatac aatctttaat ttttcatgga agattttaa aacatttccg atccgattaa       60
acaaagaagc gagcgagcca cattctgaca ataattaagt agacactatg atacgacgaa     120
gaatattaat ttaatattga agatagatc aatttgtagc aaaaccatga agccaaaatt      180
gcaagtcacc cacaagtcgc aaagattaga acatatatt gatacagtga tctatacgtg     240
tacaccatgt gtcaaatgga tattcgtcta tacttatttt tcgtatcggc gacaaagtat    300
tttgtgcggc aattcattat tgaagctttt aagtttcttc tatgttatgt aaaaaacaaa    360
tcttaccaaa attagagact cgtatataat atacttaata ggtttgttag ggttgccaaa    420
aaaaatggtt tatcgcaatg gactaaagat ctcaattctc aaaacttatc ggattttgcc   480
atagttgaac cggaccaagc caattatttg agattctgaa aagagtatta ttatgggcaa    540
attctgaata ttttatgtaa aatcggtttt gtaaagactg gatcatattt ttattcgtgt   600
ttatttcaca gctgatagcg acaacaatga aaaattcatt ttttttgtgt gtgtcatcaa    660
ctattagagt cggtgattta tatacagttt tggtgacaga ataagtgcct acaacttaaa    720
actacactag ttttagttat caagatcctt agtacttaat gttgaaatta atacattttt    780
taataaataa atacaaagta tatatttatt tgaaacttga gcaagtattt gagtaaaaaa    840
```

```
ggtatgaatc gcacgtgtga ttgcgtacat tcgcacgcat cctatccttt cacattagtt      900
ccaaagtcat tttcaccaac caaatgcgac atctccaata ctcctttcta tgatcctact      960
agcaacagat ttgacaaagt aagacaaatt atatttctta accttaatca tttctgacca     1020
aaaaaaacct gaatcattat ttattagaat aatcttattt tatcagaatt cgtaattctt     1080
tagctgacta actcctaatt aaaatgaacc attcaatata aaaatataaa cgaacgtatt     1140
atgtataaag tcagatacag aagatcttct ttgaaactgt tgtaatttcc ccatcatgac     1200
acctgtatat acatacgtac cttaaaaaaa ttctgatcta tatgtacttt tgtatgaacg     1260
agtaatgcat aattcttatt tagattagac attcttt aat gataaaatag tgaagacggg     1320
tattatacat atattaagtc actattaggg tgattaattg tatttatata ccaagaaatc     1380
tctaagtgac aacattatga gggtgattag tagtccgtac tgttttt cat tctaaccaat     1440 cacataaaag aatactaaaa gcgacaaaaa aaactattat cagcttttta taccatttta     1500
tatgttcgtt atttataccg ttttt aatta tttatatgtt atcaattact tttttcatat     1560
cgacaaaaga tttt ataatt ttttgtgtta ccaatcgaac catgtatata tatataaccg     1620
ttactagtta aaatgctttg ccataatgcc actagaattt ttaataaaag ttactaaaac     1680
aatttcgaaa atattaagat gtaaagttat tttttcctga aaccaattgt gggggaaagg     1740
tgtgagaagg ttatatatag gtgggtgagc tttggtaagc ttttgacata acttgcaagc     1800
tgttgagatt ttccatcctc gataacttta ttcttccata tctcttccat ttcgctctct     1860
atttcacatc cccatataac ataatataca atcacacata tcatttctat atagtattta     1920
```

<210> SEQ ID NO 52
<211> LENGTH: 1975
<212> TYPE: DNA
<213> ORGANISM: Arabidopsis thaliana
<220> FEATURE:
<221> NAME/KEY: promoter
<222> LOCATION: (1)...(1975)
<223> OTHER INFORMATION: Arabidopsis thaliana secondary cell wall-
       specific promoter PATMYB103

<400> SEQUENCE: 52

```
tggtgccctg gtctacagtt ccctagttaa gattctattt tgacaacaaa attgatgatt       60
ccaatcatcc atatttgtta tagggagaaa ttgagcatgc tatatacggt gatatatatg      120
atatttattt aatatattga ataacaaaca cagaactagt gttataggtg caggtatgta      180
aatataatgt gataaacatt ttttatatag attggaaaga atacgagatt gttgttgctc      240
tgttagaacg aacaaacaga actagtgtta taggtgcagg taaggtaaat ataatgtgat      300
aaacattttt tatatagatt ggaacaaata aacattttc tgttagaacg aacaaaggcc      360
tgtcaaaaag aacaaacctg atgtgacata ttacatatat gattataatt gattattgta      420
tatatagtat tgcatgacta tctttacaag atttcaatac gaaaataaat taaaaggaga      480
aaatttataa acgaagcgat ttcattctcg gtaaggtttt ccgatatgtc tcctaactaa      540
atcaaagcct tgtaattgaa acttgtaatg attgttattc tatatatctt tgaagaaagc      600
ttcggtattg gacgtactta atataattgg atttttattta aattacaaaa atcactgtat      660
aattcggcta catgacttaa tcaattattt cacgttgaaa acaatactat atcaacttca      720
aatacactcc ttgtgtatgg attccacaag ttcttttcta tctatagaaa tatagaatcc      780
acaagttcta tctacttttta ttagaatttt ttattgttcg ttgttgttaa cataattata      840
agcaataaat tcaaaaaaaa aaaaatctaa aagacacaaa atttccatct ttgatagggc      900
```

```
ttcggaatca ttaattactt tttacaaaca aaaagaaga agatagggct tcggaaatta      960
ttagaaagat ggaaggatat tgtattaaat ttggcttcat attttccttt ggtttgcggc     1020
catcaagtac tagtactact cagtacccac aggccacagg aaaaaaagta gtactgcttt     1080
attaagtgtg ttacgataaa tggaaagcgt tttagtatgt gattacaaat tgttgtatgt     1140
gatcattaat tagttattgg tccgacttct aagtttaaat attttcagaa ttcagttagt     1200
ttaattatac atgttagacg aaatgactct ttttgagcca atatataatg tatctgaatt     1260
tttcattttg aaaaatcttt ttataaaata ataggtcaac ctcgaattat tataataaaa     1320
taaataattt gcgttactat gaaaattaat ttactgaata cagtatatag agagagatag     1380
aaatagagga aaacagtgga taatacatga ttagttgata ctcatgtgca gcgagtctat     1440
atatattata tactcatgat tagttgatac atatgtgacg attagttcta cgaatcaatc     1500
tctagttttc gtcttaaaat catttggttt tatagaatat aagaaacaaa gaaaacagga     1560
actttcgcgg gagacagaag ggtacgtgaa gagaaaaaca cataaaagtg ataagggctt     1620
aacgtaataa tactacaaca aaacctctct acgtacaacg agtaataaca catgaaaata     1680
gaaagtcgat gagacatcgt tttaaggtta gatcgatgaa gaaatatctc aggccccacc     1740
cctgggaccc gacccgaccc gacccgaccc gacctttgtc tcctctcctt ttaaaaactc     1800
tccattgctt ctttgtcttc tctcttctat aacataactc aagaaattaa agaagataga     1860
tagagagaga gagagagagt aaaaacctaa agggtgatat acttatataa aaattaattt     1920
aagattgtga ttaagtggtt cactatattt aagttacttt gaggagctac taatc          1975
```

<210> SEQ ID NO 53
<211> LENGTH: 1898
<212> TYPE: DNA
<213> ORGANISM: Arabidopsis thaliana
<220> FEATURE:
<221> NAME/KEY: promoter
<222> LOCATION: (1)...(1898)
<223> OTHER INFORMATION: Arabidopsis thaliana secondary cell wall-
      specific promoter PATCADC

<400> SEQUENCE: 53

```
aaagcaaatc gatctgccaa acatatcaca gctcttggag aaaatgcagg tctcttcaga       60
ctctgatatt tcggatctcg atagccttaa attcgatgct ccattgccta gtcatatgca      120
actaagcttt aatttgttga aatctagagt cgaaacttgt gacaaaaatt agatttttt       180 tcttaccgag ctttcttctt tgtgttcatt gaggcccaag tatttgtgta tttggacctg      240
aatattctca tacaaagata aataattata ttaaatgat ttttcgcata taatcattat       300
tgtggtatga ttaacacagt tggtgtgatg actgattgac acaataatca ccgtttggat      360
tcgattcctt taatacttgt cactagagtt gtttgactaa acagctaact tgtcactaga      420
gttattgtgt ttgtattttg atctgttatt aatctgattg ggtataatta cagatagaga      480
gacatctata ttgtaattaa gacaatctta agtgtaaac taaaaagatc tctctgacct       540
ctggaaaacg aaaggtgggt gacacatcac tctagctatg aatatgatga atattcagta      600
cctaaccgaa caaagactgg tttggtattt ttattggaaa aaagagataa ataattgtga      660
atgtgaatta tcctgtctga aaggtaagct gatgacatgg cgttatatga ttggacgagc      720
ttcagaacaa aagagtagcg tcgaatcgaa tctttaccta ctacactttg aactttgaag      780
tacattacct acttcctcct tgatcgaacg tcttttctca aaactatttt atttccccaa      840
ttaaagtagt ggtgataaat tcacaaaaat acaaacactt ttattttga cgtcaaaaac       900
```

```
aaatacttct ttgaacaggc tattacaata tttttaagaa aaaagtaagc aaaatagtcc    960
acaaaccaaa atctgtaaca tattaaacga tttatgtttt ttttttttttt tcttaactag   1020 agaacaattc gggcttttac taaggatgat gagtgtagtt accgaatagt gtattcatat   1080
aatcttttaa tgagcttaag atatgatatt atttcgacta atcagataag agtagttaga   1140
taatttcgta atagagcaac tctttcgcaa ataaaaccat tgtaaacatt accaattagt   1200
ttttcttttt ttttggtcac aaccaattag tttgtttgtt ctattttatg aagtgcgtat   1260
taaagctaac gtgtttacag taacgccaca caaataaaaa taaaaataat tatgtacttt   1320
atggatttat agaaaaaaca agaatagtca ccaaaaattg attgtgtcat atatcttttg   1380
tcaactattt tatcttatttt ttctatggat atgtatgtcc aaaatgttag acaaaaaacc   1440
aaaaaatcat gtccaaaatt tcgttaggct gccgatatct ctgtttccct ttcaacgact   1500
atctatttaa ttaccgtcgt ccacattgtt tttaatatct ttattcgagg ttggtttagt   1560 ttttttttacc aaactcactt tgctacgttt ttgcctttt ggtatggttg tatttgtacc   1620
accgggaaaa aaagataag aggtttggtt ggtcgagctt actgattaaa aaatatacac   1680
gtccaccaaa tattaaaaca atatatccca tttttcctcc tctcttttgg tattacatta   1740
atattttatt atttccccat ttgctctgta tatataaaca tatgtcaata gagtgcctct   1800
acagtcatgt ttccatagac ataatctctc accattgttt ttctctgcaa aactaaagaa   1860
acaaaaaaag aaaaatcgga gaaaccaaga aaaaagaa                           1898
```

<210> SEQ ID NO 54
<211> LENGTH: 1974
<212> TYPE: DNA
<213> ORGANISM: Arabidopsis thaliana
<220> FEATURE:
<221> NAME/KEY: promoter
<222> LOCATION: (1)...(1974)
<223> OTHER INFORMATION: Arabidopsis thaliana secondary cell wall-
      specific promoter PATCADD

<400> SEQUENCE: 54

```
gcttcggtga tgcatttctc cttctcatca atcatcctag caatgttttg aagctgagaa     60
attctccact cgtagctctt cgttctgcca gagttgaagt tgcttctgag ctcatctaca    120
agcaaagctg cttctttttcc actaaagtct gatgcttgct cctttaccac agcagatagt    180
gttgcataac aagtactgat tcaagacacc aaaaccgcaa tgtgagagac tttaagacta    240
aaaatcatgg ataagactaa aaaaacatgg ataagtatca actgttctca cgattattta    300
ttcataccac tgtacttaaa cttaaaaccc actatactaa atagaaaggt aatcatcaaa    360
aaatcagtat gtaaaaacca cttttgtgaa taaaatatgt aaaatgggtg aataaagaaa    420
tgtgcttaca atttcaaccg ataagggata caagcattgc tgcaatatcc accaccaca    480 cgacgagata tccgaaaagg tgaagttgca acatttaatc tgcaacaaaa gaggccattc    540
attaaaatgg tactaattag atctaatcat atcatattga atgaccaaat cattcacaga    600
agcatccatt gctccaatta acattctaga ccaaattcaa cttaaaggta actcttttat    660
acaggaaacc gagaaaccga aacgcaatt cacataaaaa ggaaggcttg tttggagaag    720
cagaatcgaa caagtcaatc tcaaaccctg atgagcaggt ttttcaagtt acctggcagg    780
agaaaaaccc ttggcaaaac aaagggtttg aatatgatta atctctagaa gcttcgtcat    840
gacttgggtt cagttaaaaa tctcaaattg gagacattat tggtgtttat atatttgaga    900
gagagagcca gagaggagac gttgaattga atgaagggtg tggtcggaag agaagacgtg    960
```

| | |
|---|---|
| tagaagagac gagacaagta aatttaagca ttggccccat ttacagccac aagtccgcta | 1020 |
| caacaaatta tttccaagaa actctgagat aacgtcgtga tgaaacggct catgctgctg | 1080 |
| ttgtgattcg tgaattagag gtttatcttt tgggttttg aatgttactt aattggacgg | 1140 |
| tcgattttc aaactgggtg tgaaatgtga atgggtcatt cataatgggc ttttgtttta | 1200 |
| atgtgaagcc attcacacac tctttgtcct tcttttctat tattcataac tgtcactctt | 1260 |
| tgttcttcga aatagtaaag agcaaatcga ttctttgttg atctgggccg taaaatttcc | 1320 |
| atggttgtgg gaagtattct cgcagctgat ctgggccgtc aatgctacag tttcatgtca | 1380 |
| gagagaggtc aagaatcaac acgtggccaa ccatgatttt aaaccaaagc aaacacacga | 1440 |
| ttagacccca cattgtttgt tcaccaaccc ccgtggaccc tcctttagcc gacgtgtcca | 1500 |
| cgtcaatagt ggttttttctt cctttcaaag tacacaaatt ccattctttc tcattttact | 1560 |
| ttttggatta cgttgttgtt ataaactggt aaaatgaatt atgaatgcaa ataaatttca | 1620 |
| tttaagtttt gttggcttct aatatttttt tcacctaaaa ttctaataaa ctacacagcc | 1680 |
| atgagccatc gtatgaaaag aagaagaaaa aaaatgtctt tttctagaag gatctttcaa | 1740 |
| cgactaaaaa agatttttaag cttttgacta attttgtcaa taatatacac aaatttacac | 1800 |
| tcaattatag ccatcaaatg tgtgctatgc agaaacacca attatttcat cacacatacg | 1860 |
| catacgttac gtttccaact ttctctatat atatatatag taatacacac acataaacag | 1920 |
| caaaagcgtg aaagcagcag atcaagataa gaaagaagaa agaatcatca aaaa | 1974 |

<210> SEQ ID NO 55
<211> LENGTH: 1923
<212> TYPE: DNA
<213> ORGANISM: Arabidopsis thaliana
<220> FEATURE:
<221> NAME/KEY: promoter
<222> LOCATION: (1)...(1923)
<223> OTHER INFORMATION: Arabidopsis thaliana secondary cell wall-specific promoter PATPAL1

<400> SEQUENCE: 55

| | |
|---|---|
| ttttcccaat gatacaacta taaatcaaaa agaaaaaatg tactgataaa cgaaactaaa | 60 |
| cgtataaatt aatatatttc ttgacataaa taggaggctt ttgcctgcta gtctgctacg | 120 |
| atggaaggaa aaatgcatgc acacatgaca catgcaaaat gtttcaatga agacgcattg | 180 |
| cccaattaac caacacacca cttcttccat tccaccccata ttatttattt ctaccatttt | 240 |
| ctttaattta ttgttttttc tttgattcat acactgttta tgactattac attttcccctt | 300 |
| tcgactaata ttaacgcgtt taaaccaaag aatggatttg ataatgaaat tttatttat | 360 |
| tagcatatag ataatggatg gcttcatgct tggtttccat gacaaggaat gacacaagat | 420 |
| aattattttg aataaaatca taaatatgat aatactagtt gtaaaaaaac ttgagtgttt | 480 |
| cgtgtgttat ttttcggttt cttgactttt tatatttctc gttttttgtaa ttttaggatg | 540 |
| gattatttag cttgcttttc tctttttatta cttttctaaaa ttttatttat aaactcatttt | 600 |
| ttaatatatt gacaatcaat aaatgagtta tctttaatt aataaaaaat ttgtaaactc | 660 |
| ttgtaaacag atcatagtca ctaaaagcta ttataagtta tttgtagcta tatttttta | 720 |
| tttcatgaac ttaggataag atacgaaaat ggaggttata tttacataaa tgtcaccaca | 780 |
| ttgcctttgt catgcaaacg gcgtgttgcg tcactcgcct cctattggga atcttataat | 840 |
| cgcgtgaata ttattagagt ttgcgatatt tccacgtaat agttatcttt cacaaatttt | 900 |
| atactcaatt acaaaatcaa cgaaaatgta catttgtatc tttaactatt tacgtttttt | 960 |

```
ttacgtatca actttcagtt atatgttttg gataatatat ttttttactt ttgactttc    1020 agtttcacc taatgattgg gatatacata tgcatgcata gttcccatta tttaaatgta     1080
agctaagtgc atatgaactg ttagtcaaaa ttacgaagtt tatttgtaca tatatatagt    1140
tataacaaaa tggtacagta aattaaacag aacatcaaga aagtacaaaa gactgaacac    1200
aataatttac atgaaaacaa aacacttaaa aaatcatccg ataaaatcga aatgatatcc    1260
caaatgacaa aaataacaat atagaaaata caaaaacaaa aacaaaatat gaaagagtgt    1320
tatggtgggg acgttaattg actcaattac gttcatacat tatacacacc tactcccatc    1380
acaatgaaac gctttactcc aaaaaaaaaa aaaaaaccac tcttcaaaaa atctcgtagt    1440
ctcaccaacc gcgaaatgca actatcgtca gccaccagcc acgaccactt ttaccaccgt    1500
gacgttgacg aaaaccaaag aaattcacca ccgtgttaaa atcaaattaa aaataactct    1560 cttttttgcga cttaaaccaa atccacgaat tataatctcc accactaaaa tccatcactc    1620
actctccatc taacggtcat cattaattct caaccaactc cttctttctc actaattttc    1680 atttttcta taatctttat atggaagaaa aaaagaaact agctatctct atacgcttac    1740
ctaccaacaa acactaccac cttatttaaa ccacccttca ttcatctaat tttcctcagg    1800
aacaaataca attccttaac caacaatatt acaaataagc tcctatcttc tttctttctt    1860
ttagagatct tgtaatctcc tcttagttaa tcttctattg taaaactaag atcaaagtc    1920 taa                                                                  1923

<210> SEQ ID NO 56
<211> LENGTH: 1941
<212> TYPE: DNA
<213> ORGANISM: Arabidopsis thaliana
<220> FEATURE:
<221> NAME/KEY: promoter
<222> LOCATION: (1)...(1941)
<223> OTHER INFORMATION: Arabidopsis thaliana secondary cell wall-
      specific promoter PATPAL2

<400> SEQUENCE: 56
tttccctgtt ttttttcccc tctttctgtt tcccatttga aagtaaaaga tcatttaagc    60
acctaactca atttattttt atttttaaaca cctaatgtca tgctccttgg ctccttgtaa    120
ttagttgatc gtttcaattt agaccagcaa acatttttag tatgttcgta aatattgcgt    180
acatgccatt tcgtttgtca tgcaaacggt gtgtgtttct ttacttagct tctagttggt    240
gtatattgcg tcgcattaat atcggtttac cttcctcctg tctacgtaat gatatattct    300
ccaccacaaa tttaaattct tattgaaatt tcctaatttt ttaggtagct caaggtctca    360
agtatactac gtaccctatt tttttgaata tctatctata ttataacaag agttttttctg    420 agctagttaa tgagatgaca atattctaca taaataaatg accctcgaaa gtttcaagta    480 cttaggatc tgaccaaatc ggggtaaaac attttgaaac taattacgtt cacatctacc    540
atcgatgatt gacaagctta ttgtcacctt ttatgttaaa gtgacatggt cttgacgtta    600
atttgcatgt tattctacat ctatagtcca aagatagcaa accaaagaaa aaaattgtca    660
cagagggttc aatgttactt agatagaaat ggttctttac aataaataat ttatgttcca    720
ttcttcatgg accgatggta tatatatgac tatatatatg ttacaagaaa aacaaaaact    780 tatatttct aaatatgtct tcatccatgt cactagctca ttgtgtatac atttacttgc     840 ttcttttgt tctatttcat ttcctctaac aaattattcc ttatatttg tgatgtactg      900 aattattatg aaaaaaaacc tttacacttg atagagaagc atatttggaa acgtatataa    960
```

```
tttgtttaat tggagtcacc aaaattatac aaatcttgta atatcattaa cataatagca   1020
aactaattaa atatatgttt tgaggtcaaa tgttcggttt agtgttgaaa ctgaaaaaaa   1080
ttattggtta ataaaatttc aaataaaagg acaggtcttt ctcaccaaaa caaatttcaa   1140
gtatagataa gaaaaatata ataagataaa caattcatgc tggtttggtt cgacttcaac   1200
tagttagttg tataagaata tatttttta  atacatttt  ttagcaactt tgttttga    1260 tacatataaa caaatattca caataaaacc aaactacaaa tagcaactaa aataatttt   1320 tgaaaacgaa attagtgggg acgaccttga attgactgaa ctacattcct acgttccaca   1380
actactccca tttcattccc aaaccataat caatcactcg tataaacatt tttgtctcca   1440
aaaagtctca ccaaccgcaa aacgcttatt agttattacc ttctcaattc ctcagccacc   1500
agccacgact acctttttcga tgcttgaggt tgatatttga cggaacacac aaatttaacc   1560
aaaccaaacc aaaaccaaac gcgttttaaa tctaaaaact aattgacaaa ctctttttgc   1620
gactcaaacc aaattcacgt tttccattat ccaccattag atcaccaatc ttcatccaac   1680
ggtcatcatt aaactctcac ccaccccctca tacttcactt tttttctcca aaaaatcaaa   1740
acttgtgttc tctcttctct cttctcttgt ccttacctaa caacaacact aacattgtcc   1800
ttcttattta aacgtctctt ctctcttctt cctcctcaga aaaccaaaaa ccaccaacaa   1860
ttcaaactct ctctttctcc tttcaccaaa caatacaaga gatctgatct cattcaccta   1920
aacacaactt cttgaaaacc a                                             1941
```

<210> SEQ ID NO 57
<211> LENGTH: 2589
<212> TYPE: DNA
<213> ORGANISM: Arabidopsis thaliana
<220> FEATURE:
<221> NAME/KEY: promoter
<222> LOCATION: (1)...(2589)
<223> OTHER INFORMATION: Arabidopsis thaliana secondary cell wall-
       specific promoter PATC3H

<400> SEQUENCE: 57

```
atcgtaagtt ttttgtgtg  tgtgttaaca atgtactcac tactcactgt tccatatttt    60
tgatgtacgt atatcgaaaa cattctgcca acaaatgcaa acataacaaa agtcaaaaac   120
aataacataa ccgggaatta aaccaaaatg taattgcttt ttattagtgt caggccttct   180
gcttaaaaat attctcggcc cagagcccat taacacctat ctcaattcat attgaagaaa   240
atgactatat tacttgacaa aaactttagt cagaaaaata tggaatctct ttcggtactg   300
ctaagtgcta accttaaata gtatagaatt cttagttcat tctcaaaaac atagctatat   360
gtagattata aaagttcgat attatttcct gcaaagatg ttataatgtt acaacttaca   420
agaaaatgat gtatatgtag attttataaa ctggtaccgt aattcataaa agatggtggt   480
gggtatgtat cagtaacgga acttacatat gcgtgtgtat tactatgtct atatggtgta   540
ttcctttgtg tggaacaatg cacgtcagag ttgtttattt tcttatagaa tttaaggaat   600
caattattgg atttctcaag gtgaaagtgg acttctttgc acgcaaggtc tagttgccga   660
cttgccgttg catgtaacat gattgttgaa ataaagtgaa ttgagagaag tttggccaga   720
catttaaaat ttaacccaaa aaaagtaggg cctaacacaa aatataaccct ctctttgttc   780 aaaggaaata acacctacgt cttataattg aaccaaacat tgaatcattg aactcaccta   840
taataattat aataacacga attcacaaga cacctaaaag aaaaagttca caaaaacaaa   900
taaaaattta cctctcacca aacacactca cctacccgtc tggtcccact gacccccaaca   960
```

-continued

```
tacaacaccg actctctccc acaccaattt ttttttttgg cgttttaaaa caaataaact    1020 atctatttt  ttttcttacc aactgattaa ttcgtgaata atctattatc ttcttctttt    1080
ttttgtgacg gatgattagt gcgtggggaa atcaaaattt acaaaatttg ggatgattcc    1140 gattttttgcc attcgattaa ttttggttaa aagatatact attcattcac caagttttca    1200
gatgagtcta aaagataata tcatttcact agtcacttaa aaaaagggtt aaaagaacat    1260
caataatatc actggtttcc ttaggtgacc caaaaaaaga agaaaaagtc actagtttct    1320
ttttggaaat tttactgggc atatagacga agttgtaatg agtgagttta aatttatcta    1380
tggcacgcag ctacgtctgg tcggactata ccaagttacc aactctctct acttcatgtg    1440
attgccaata aaaggtgacg tctctctctc tctcaccaac cccaaaccac tttccccact    1500
cgctctcaaa acgcttgcca cccaaatcta tggcttacgg ggacatgtat taacatatat    1560
cactgagtga aaagaagggt ttattaccgt tggaccagtg atcaaacgtg ttttataaaa    1620
atttggaatt gaaaacatga tttgacattt ttaatgatgg cagcagacga aaccaacaac    1680
actaagttta acgttcgtgg agtatacttt tctattttcg aagaagacat ataactaagc    1740
tgattgttat tcttcataga tttcttttca ctgcgaataa aagtttgtga acatgtcacc    1800
gtttgaacac tcaacaatca taagcgtttt acctttgtgg ggtggagaag atgacaatga    1860
gaaagtcgtc gtacatataa tttaagaaaa tactattctg actctggaac gtgtaaataa    1920
ttatctaaac agattgcgaa tgttctctac ttttttttg tttacattaa aaatgcaaat    1980
tttataacat tttacatcgc gtaaatattc ctgttttatc tataattaat gaaagctact    2040
gaaaaaaaac atccaggtca ggtacatgta tttcacctca acttagtaaa taaccagtaa    2100
aatccaaagt aattaccttt tctctggaaa ttttcctcag tagtttatac cagtcaaatt    2160
aaaacctcaa atctgaatgt tgaaaatttg atatccaaga aatttctca ttggaataaa    2220 agttcaatct gaaatagat atttctctac ctctgttttt ttttttctcc accaactttc    2280
ccctacttat cactatcaat aatcgacatt atccatcttt tttattgtct gaactttgc    2340 aatttaattg catactagtt tcttgttttta cataaaagaa gtttggtggt agcaaatata    2400
tatgtctgaa attgattatt taaaaacaaa aaaagataaa tcggttcacc aaccccctcc    2460
ctaatataaa tcaaagtctc caccacatat atctagaaga attctacaag tgaattcgat    2520
ttacactttt ttttgtccct tttttattaat aaatcactga cccgaaaata aaaatagaag    2580
caaaacttc                                                             2589
```

<210> SEQ ID NO 58
<211> LENGTH: 1894
<212> TYPE: DNA
<213> ORGANISM: Arabidopsis thaliana
<220> FEATURE:
<221> NAME/KEY: promoter
<222> LOCATION: (1)...(1894)
<223> OTHER INFORMATION: Arabidopsis thaliana secondary cell wall-
      specific promoter PATCCR1_PATIRX4

<400> SEQUENCE: 58

```
aaaattgtgt ctaagaatgt ggaaccgagt agttctccag aagtcaggta tgaaagtata      60
taagaattct agttttagtt gtttgaaagt ttgatccgtg agtgaattag ttcacaatta     120
tggatgtaga tcctctatgc aaacaatgaa gaagaaagac tctgtaacag actccattaa     180
gcaaacaaaa agaaccaaag gtgcactgaa ggctgtaagc aatgaaccag aaagcactac     240
agggaaaaat cttaaatcct tgaaaaagct gaatggtgaa cctgataaaa caagaggcag     300
```

```
aactggcaaa aagcagaagg tgactcaagc tatgcaccgg aaaatcgaaa aagattgtga      360
tgagcaggaa gacctcgaaa ccaaagatga agaagacagt ctgaaattgg ggaaagaatc      420
agatgcagag cctgatcgta tggaagatca ccaagaattg cctgaaaatc acaatgtaga      480
aaccaaaact gatggagaag agcaggaggc agcgaaagag ccaacggcag agtctaaaac      540
taatggagag gagccaaatg cagaacccga aactgatgga aaagagcata atcattgaa       600
ggagccaaat gcagagccca aatctgatgg agaagagcag gaggcagcaa aagagccaaa      660
tgctgagctc aaaactgatg gagaaaatca ggaggcagca aaagagctaa ctgcagaacg      720
caaaactgat gaggaagagc acaaggtagc tgatgaggta gagcaaaagt cacagaaaga      780
gacaaatgta gaaccggaag ctgagggaga agagcaaaag tcagtggaag agccaaatgc      840
agaacccaag accaaggtag aagagaaaga gtcagcaaaa gagcaaactg cagacacaaa      900
attgattgag aaggaggata tgtctaagac aaagggagaa gagattgata agaaacata      960
ttcaagcatc cctgagactg gtaaagtagg aaacgaagct gaagaagatg atcagagagt     1020
gattaaggaa ctggaagaag agtctgacaa ggcagaagtc agtactacgg tgcttgaggt     1080
tgatccatga atgaaggatt gttaggtaaa tgttaatcca ggaaaaaaag attggttctt     1140
gtggtttagg taacttatgt attaagtgaa gctgcttgtt tagagactaa tggtgtgttt     1200
tatgagtaga ttcttctgac ctatgtctcg ttatggaact agtttgatct tatgtcacct     1260
tgctagcagc agatattgat atttatatat ttaagacca tgcgcatgag aatgagggta     1320
tggaaaagtc catatcagat gacacaaaca atgatcgtat gtgtagtcac ttgtgcattt     1380
ccagttttgg acataaaatt ctgatattgc atagaaatgt tttaaataa cactaatcca     1440
aacctaaata aaatatctct atacatcatc tagaaatgta tggcttgatc aagaattgta     1500
gataataata ccctgagtta aatgattgta ggtattattt cagttttcaa aattgtccaa     1560
atttatgagc tatattaaag ataatatttt caataaggtg tgtagttcta aatgtttctt     1620
cttcttccac caaccctct ttctatatgt atgttctttt ttctaaaata attgtttgtt     1680
cttttttaga tatatcaaat taaatataaa aaatattgac aaaacttatt taccattgtt     1740
aggtgaactt ggcaagtgtg taaatataaa gataacattc cttttcgttc tttatatata     1800
cgaaacgtac cacaaatttc taactaaagc attcatagtc tctcgaaagc ctctttcag     1860
aaccgaagct ctttactttc gtccaccggg aaat                                 1894
```

<210> SEQ ID NO 59
<211> LENGTH: 1981
<212> TYPE: DNA
<213> ORGANISM: Arabidopsis thaliana
<220> FEATURE:
<221> NAME/KEY: promoter
<222> LOCATION: (1)...(1981)
<223> OTHER INFORMATION: Arabidopsis thaliana secondary cell wall-
      specific promoter PATF5H

<400> SEQUENCE: 59

```
aaatttttgt atgaaatatt tctttaacga aaataaatta ataaaatttt aaaatttata      60
tttggagttc tatttttaat ttagagtttt tattgttacc acattttttg aattattcta     120
atattaattt gtgatattat tacaaaaagt aaaaaatatga tattttagaa tactattatc     180
gatatttgat attattgacc ttagctttgt ttgggtggag acatgtgatt atcttattac     240
cttttttattc catgaaacta cagagttcgc caggtaccat acatgcacac ccctcgtga     300
aacgagcgtg acttaatatg atctagaact taaatagtac tactaattgt gtcatttgaa     360
```

| | |
|---|---|
| ctttctccta tgtcggtttc acttcatgta tcgcagaaca ggtggaatac agtgtccttg | 420 |
| agtttcaccc aaatcggtcc aatttttgtga tatatattgc gatacagaca tacagcctac | 480 |
| agagttttgt cttagcccac tggttggcaa acgaaattgt ctttatttt ttatgttttg | 540 |
| ttgtcaatgt gtctttgttt ttaactagat tgaggtttaa ttttaataca tttgttagtt | 600 |
| tacagattat gcagtgtaat ctgataatgt aagttgaact gcgttggtca aagtcttgtg | 660 |
| taacgcactg tatctaaatt gtgagtaacg acaaaataat taaaattaaa gggaccttca | 720 |
| agtattatta gtatctctgt ctaagatgca caggtattca gtaatagtaa taaataatta | 780 |
| cttgtataat taatatctaa ttagtaaacc ttgtgtctaa acctaaatga cataaatcc | 840 |
| aaaagcaaaa atctaaacct aactgaaaaa gtcattacga aaaaagaaa aaaaaagag | 900 |
| aaaaaactac ctgaaaagtc atgcacaacg ttcatcttgg ctaaatttat ttagtttatt | 960 |
| aaatacaaaa atggcgagtt tctggagttt gttgaaaata tatttgttta gccactttag | 1020 |
| aatttcttgt tttaatttgt tattaagata tatcgagata atgcgtttat atcaccaata | 1080 |
| tttttgccaa actagtccta tacagtcatt tttcaacagc tatgttcact aatttaaaac | 1140 |
| ccactgaaag tcaatcatga ttcgtcatat ttatatgctc gaattcagta aaatccgttt | 1200 |
| ggtatactat ttatttcgta taagtatgta attccactag atttccttaa actaaattat | 1260 |
| atatttacat aattgttttc tttaaaagtc tacaacagtt attaagttat aggaaattat | 1320 |
| ttcttttatt tttttttttt tttaggaaat tatttctttt gcaacacatt tgtcgtttgc | 1380 |
| aaacttttaa aagaaaataa atgattgtta taattgatta catttcagtt tatgacagat | 1440 |
| ttttttatc taacctttaa tgtttgtttc ctgtttttag gaaaatcata ccaaaatata | 1500 |
| tttgtgatca cagtaaatca cggaatagtt atgaccaaga ttttcaaagt aatacttaga | 1560 |
| atcctattaa ataaacgaaa ttttaggaag aaataatcaa gattttagga aacgatttga | 1620 |
| gcaaggattt agaagatttg aatctttaat taaatatttt cattcctaaa taattaatgc | 1680 |
| tagtggcata atattgtaaa taagttcaag tacatgatta atttgttaaa atggttgaaa | 1740 |
| aatatatata tgtagatttt tcaaaaggt atactaatta ttttcatatt ttcaagaaaa | 1800 |
| tataagaaat ggtgtgtaca tatatggatg aagaaattta agtagataat acaaaaatgt | 1860 |
| caaaaaaagg gaccacacaa tttgattata aaacctacct ctctaatcac atcccaaaat | 1920 |
| ggagaacttt gcctcctgac aacatttcag aaaataatcg aatccaaaaa aaacactcaa | 1980 |
| t | 1981 |

<210> SEQ ID NO 60
<211> LENGTH: 1899
<212> TYPE: DNA
<213> ORGANISM: Arabidopsis thaliana
<220> FEATURE:
<221> NAME/KEY: promoter
<222> LOCATION: (1)...(1899)
<223> OTHER INFORMATION: Arabidopsis thaliana secondary cell wall-
    specific promoter PATLAC4

<400> SEQUENCE: 60

| | |
|---|---|
| caattatatt tggtttcgat tgaaattcaa tctaatgtgg ttagatgagt cctatattac | 60 |
| catgtcattg ttaataccca ttgccaaaaa taaagtgaa gcagaaggag aaattgtttt | 120 |
| tgtatacccg aaggaattaa gatgtacgat cttaaaatag acatttcggc catctatcaa | 180 |
| aataaatgtc taaagttttt gtggtcgtct taaatactac ttcgagttca gacgtatacg | 240 |
| tctcaccaaa gtaatgcaca tacttgatgt taagtttatc tctttttact atttcaaatt | 300 |

-continued

```
tcgcgtttga caacactttta agtctacatt atccatagag aatataacat aaagatcatg    360
aacttctcat gaatgtataa gacaaatcaa gcttatatat gagatctatt tagtaatttg    420
atatgtatgt aatatatgat aaatctttga tgcaatattt tattatgatt attagatata    480
cactagtcaa cttttaacttt agaagattaa tcattccgtc gcaaaccata ccataaatta    540
gcaagggatc gacttaatat ctccgatccg ctatatattt aagaagcatt tagattgttt    600
ataatacatg tcatgatttt ataattatgt atatataaat actaattgat gtatgaagta    660
cgtagataat gttacgatct attaatctat ttacattaac ttttaattag tgttgagtag    720
ggaaaattaa catataaacc tttagcagtt ggttgtatta ttaaaaataa tttgaactta    780
aaatccacct tcgaaaagat aaatcaaaca agtataaaaa atgctataaa tccagaatat    840
ttacctaagg tttttattct tctacttaat aatgtaagat aaaaccggca caatacttgt    900
tacgtatgca tggtaggtac cgcaattgtg taagcaaatc ggcacaatac taaggttaca    960
tatactaact aaataaaaca atctgatttc agtgacaccg tatatctaac ctttattcaa   1020
atccaaggga acatgacttg acttcttctg ttggaactaa ctcgatccct caaccatctc   1080
cagggataga agagttagta aaatcaaact tgaagtgagg aagtaagcag tttaacgact   1140
ccatatgact acagttatat acaaagttgg gcacaaagta caagtactaa atactcaaag   1200
tcagataata attttaataa gtacaaacta tatatatgca gtacaattat tgagtatata   1260
taaacgagac tggtgatttg gggcattgtc caccagggtg ttatatccca attgaaattt   1320
gaaaatttaa gtgtgtgagt gttacgacaa aaaaagtgt gtgaattgta ggcgcggtga    1380
aaaggtaaat taagattgga actagaaaaa tagttgaata tcctttacta aaagttgtca   1440
attccggttt tagtaaaaaa aaattttaaa atagaaattt tatccaaaag acttcaaaca   1500
cacatattcg catatataac ataagatatc attttttgta aacagttaaa aagaaaaaca   1560
catgtttttt tttttaattt agaaaaaaac atgttattat acaaaacaga gttttgccca   1620
cttttaatat gttatgaaaa gaaaatgat tttcttgggt ttggtcagag agattggttg    1680
tggtaagaat gggaatctta attacaaaga attggatttt gggtcgacct accacctaaa   1740
acgacgtcgc ctccatctct ggtttccaaa tctctttctc ctctcccttt ataagcttgc   1800
gttggccagt cgctcatctc gaaaacagag agaaaaagac taaaaacaca gtttaagaag   1860
aaggagagat agagagagaa gagaaagata gagagggag                         1899
```

<210> SEQ ID NO 61
<211> LENGTH: 1911
<212> TYPE: DNA
<213> ORGANISM: Arabidopsis thaliana
<220> FEATURE:
<221> NAME/KEY: promoter
<222> LOCATION: (1)...(1911)
<223> OTHER INFORMATION: Arabidopsis thaliana secondary cell wall-
      specific promoter PATLAC17

<400> SEQUENCE: 61

```
taagtttaag tccaataatt tcattttact agtaaagatc acaatgtcat ttaccgcatt     60
cacttaataa ttgctgaatt cacatagtgc ctgtaaatta agactaattt taggtttcaa    120
ataatttttc ttttttacat aacttacgat cgatattttta aatggtattg gtaagtttaa    180
ggtatataga tagtgtgtct aaactagagt tcgttgaaat tggtctgagg tataaatacc    240
taaaaggtta tatatgtttt tagtttaatg taattcgata aatttttagtc gaaaccgtta    300 agagatatca gaatttcgtt ttcaaataat atgggatata attacccggg attaaccgta    360
```

```
cctgataaaa tatagctctc gtacgtgtca catgcctaat gcctagttaa acttaaaacg      420
aatatctata tttactgtta ttgattgtga gttaccaact aaaatattgt taaaagacat      480
tgtaaaacta caaatggttc gaactgtata ctaatgatgt aaactcgtgt tcatcgtta       540 tgtccgatat ttttttcatt caaccattat tcaatttcaa gatttcttta ttgtcttttt      600
ttctttctag aaagcctata tatttaatta cccactttgc atattcagag gataagttga     660
tacgtacttg ttagcaacct gtctagatca tcttttgatt gtagatttga ctttaaattt     720
ctcacaatta taaatatgaa aaataacaag caaagaattt acaaatgtat ataattatat    780
acacgcattg atgaataaac atatttagaa aataatgtgt tctaaggaaa ttttgtggca    840 tttttttaaaa aataattaaa caaataagaa tagtgtaaag ttgtttaaat atgtatgtat    900
aagtggcatg cctttgagga tacgaactta aaagggagtt aggtaacttg cttgggaaat     960
aaaatagcca accttaattt gaggtttcct caatgttctt atcaaaaaga ataaaaattt    1020
cggaaattcc cttcatggat tttgatatct aaccctaatc gtgaccttct ttgatagcta    1080
caatctccct ctctttgctt attccccaag caatttagc ttacgaatgt tttgactaac    1140
tccacatcgg tttatctctt aagttcccca cctacaaata tacaaaaaaa gaagtaaaat    1200
aaaaataatt attaacaaac cgatgaagta cttatcattt ataaacatgc ttatgaaatg   1260
tattttctaa aacataaccg ctaaccagag aagtttccta gagttctgct tcagactctt    1320
ttggtcgatc aagaagtctc caagagttgt ttttgttggg tctaaacaaa acttggccag   1380
ggaacaaatc aaactatatt attaatcttc tacatctggt cctaagttcc ttactatctc    1440
atgttaaaat ttgaagtcta atatactcaa agctgtcaaa gaagcagaac atggaagagg   1500
aactgtcata tctgagaaac caaaattggc aatcttgcat ttcatattta gaatctacgc    1560
catagtattg agatggaaac aaagagtttt cgaagagggt caaagagttt gacttatctt    1620
tgacaccact catacattag ctgttcatat aatctaacaa ctagtcaata tcaagtgtct    1680
ccaaattacg gagagtactt ctctaccaat tatctttttg ttttttcataa acatttttact    1740 aattgttttt tctatatctc ctgctcaagc aaacacctaa ctctccttc ctatatatac      1800 actaaaggtt gaaaacaatg aatccacaat ctacagcaaa acataagcga ggcagagtct   1860
tcagaaaact tacctgctct aaacaacgcc tccgtgtcca agctcacttc a             1911
```

<210> SEQ ID NO 62
<211> LENGTH: 267
<212> TYPE: PRT
<213> ORGANISM: Rhizobium etli
<220> FEATURE:
<223> OTHER INFORMATION: Rhizobium etli Brasil 5 p-hydroxycinnamoyl-CoA
      hydratase-lyase (HCHL) homolog (partial)

<400> SEQUENCE: 62

Val Leu Val Glu Phe Asp Gly Gly Ile Ala Phe Val Thr Leu Asn Arg
1               5                   10                  15

Pro Glu Lys Arg Asn Ala Met Asn Pro Ala Leu Asn Ala Arg Met Leu
            20                  25                  30

Glu Val Leu Asp Glu Leu Glu Gly Asp Glu Arg Cys Gly Val Leu Val
        35                  40                  45

Leu Arg Gly Ala Gly Gln Ser Trp Ser Ala Gly Met Asp Leu Lys Glu
    50                  55                  60

Tyr Phe Arg Asp Asn Asp Asp Lys Pro Arg Asp Ala Thr Leu Lys Ala
65                  70                  75                  80

Arg Arg Gln Ser Gly Gly Trp Trp Gly Arg Leu Met Tyr Phe Glu Lys

```
                    85                  90                  95
Pro Thr Ile Ala Met Val Asn Gly Trp Cys Phe Gly Gly Ala Phe Thr
                100                 105                 110

Pro Leu Val Ser Cys Asp Leu Ala Ile Ala Ala Glu Glu Ala Asn Phe
                115                 120                 125

Gly Leu Ser Glu Ile Asn Trp Gly Ile Leu Pro Gly Gly Asn Val Thr
            130                 135                 140

Arg Ala Val Ala Glu Val Met Arg His Arg Asp Ala Leu Tyr Tyr Ile
145                 150                 155                 160

Met Thr Gly Glu Leu Phe Gly Gly Arg Lys Ala Ala Glu Met Gly Leu
                165                 170                 175

Val Asn Glu Ala Val Pro Leu Val Asp Leu Glu Thr Arg Val Arg Lys
                180                 185                 190

Ile Cys Ala Ser Leu Leu Glu Lys Asn Pro Val Thr Leu Lys Ala Ala
                195                 200                 205

Lys Asp Thr Tyr Lys Arg Val Arg Asn Leu Pro Trp Asp Leu Ala Asp
            210                 215                 220

Asp Tyr Ile Tyr Ala Lys Leu Glu Gln Met Leu Phe Leu Asp Lys Thr
225                 230                 235                 240

Lys Gly Arg Asp Glu Gly Leu Lys Gln Phe Leu Asp Asp Lys Thr Tyr
                245                 250                 255

Gln Pro Gly Leu Gly Ala Tyr Lys Arg Gly Arg
            260                 265
```

<210> SEQ ID NO 63
<211> LENGTH: 296
<212> TYPE: PRT
<213> ORGANISM: Artificial Sequence
<220> FEATURE:
<223> OTHER INFORMATION: synthetic p-hydroxycinnamoyl-CoA hydratase-
      lyase (HCHL) homolog majority sequence
<220> FEATURE:
<221> NAME/KEY: VARIANT
<222> LOCATION: (1)...(296)
<223> OTHER INFORMATION: Xaa = any amino acid

<400> SEQUENCE: 63

```
Xaa Xaa Xaa Xaa Xaa Xaa Xaa Xaa Met Ser Lys Tyr Xaa Xaa Xaa Xaa
1               5                   10                  15

Glu Gly Arg Trp Xaa Gln Thr Val Lys Val Glu Val Glu Ala Xaa Gly
                20                  25                  30

Ile Ala Trp Val Thr Leu Asn Arg Pro Glu Lys Arg Asn Ala Met Ser
            35                  40                  45

Pro Thr Leu Asn Arg Glu Met Ile Asp Val Leu Glu Ala Leu Glu Leu
        50                  55                  60

Asp Asp Asp Ala Gly Val Leu Val Leu Thr Gly Ala Gly Glu Ala Trp
65                  70                  75                  80

Thr Ala Gly Met Asp Leu Lys Glu Tyr Phe Arg Glu Val Asp Ala Gly
                85                  90                  95

Pro Glu Xaa Ile Leu Gln Glu Lys Ile Arg Arg Asp Ala Ser Arg Trp
                100                 105                 110

Gln Trp Arg Leu Leu Arg Met Tyr Ala Lys Pro Thr Ile Ala Met Val
            115                 120                 125

Asn Gly Trp Cys Phe Gly Gly Phe Ser Pro Leu Val Ala Cys Asp
        130                 135                 140

Leu Ala Ile Ala Ala Asp Glu Ala Val Phe Gly Leu Ser Glu Ile Asn
145                 150                 155                 160
```

```
Trp Gly Ile Pro Pro Gly Asn Leu Val Ser Lys Ala Met Ala Asp Thr
            165                 170                 175

Val Gly His Arg Gln Ala Leu Tyr Tyr Ile Met Thr Gly Glu Thr Phe
        180                 185                 190

Thr Gly Arg Glu Ala Ala Glu Met Gly Leu Val Asn Glu Ser Val Pro
    195                 200                 205

Leu Ala Gln Leu Arg Glu Ala Thr Arg Ala Leu Ala Ala Lys Leu Leu
210                 215                 220

Xaa Lys Asn Pro Val Val Leu Arg Ala Ala Lys His Gly Phe Lys Arg
225                 230                 235                 240

Cys Arg Glu Leu Thr Trp Glu Gln Asn Glu Asp Tyr Leu Tyr Ala Lys
            245                 250                 255

Leu Asp Gln Ala Gln Leu Arg Asp Pro Glu Gly Gly Arg Glu Gln Gly
        260                 265                 270

Leu Lys Gln Phe Leu Asp Asp Lys Ser Ile Lys Pro Gly Leu Gln Ala
    275                 280                 285

Tyr Lys Arg Xaa Xaa Xaa Xaa Xaa
    290                 295

<210> SEQ ID NO 64
<211> LENGTH: 37
<212> TYPE: DNA
<213> ORGANISM: Artificial Sequence
<220> FEATURE:
<223> OTHER INFORMATION: synthetic PCR amplification oligonucleotide for
      Arabidopsis IRX5 promoter

<400> SEQUENCE: 64
cccggcggcc gcatgaagcc atcctctacc tcggaaa                              37

<210> SEQ ID NO 65
<211> LENGTH: 35
<212> TYPE: DNA
<213> ORGANISM: Artificial Sequence
<220> FEATURE:
<223> OTHER INFORMATION: synthetic PCR amplification oligonucleotide for
      Arabidopsis IRX5 promoter

<400> SEQUENCE: 65
cccggctagc ggcgaggtac actgagctct cggaa                                35

<210> SEQ ID NO 66
<211> LENGTH: 55
<212> TYPE: DNA
<213> ORGANISM: Artificial Sequence
<220> FEATURE:
<223> OTHER INFORMATION: synthetic PCR amplification oligonucleotide for
      Pseudomonas fluorescens AN103 HCHL codon-optimized
      for expression in Arabidopsis

<400> SEQUENCE: 66
ggggacaagt ttgtacaaaa aagcaggctt catgtctact tacgagggaa gatgg          55

<210> SEQ ID NO 67
<211> LENGTH: 51
<212> TYPE: DNA
<213> ORGANISM: Artificial Sequence
<220> FEATURE:
<223> OTHER INFORMATION: synthetic PCR amplification oligonucleotide for
      Pseudomonas fluorescens AN103 HCHL codon-optimized
      for expression in Arabidopsis

<400> SEQUENCE: 67
```

```
ggggaccact ttgtacaaga aagctgggtc tctcttgtaa gcctggagtc c              51

<210> SEQ ID NO 68
<211> LENGTH: 21
<212> TYPE: DNA
<213> ORGANISM: Artificial Sequence
<220> FEATURE:
<223> OTHER INFORMATION: synthetic tub8-specific oligonucleotide for
      cDNA PCR quality control

<400> SEQUENCE: 68
gggctaaagg acactacact g                                              21

<210> SEQ ID NO 69
<211> LENGTH: 25
<212> TYPE: DNA
<213> ORGANISM: Artificial Sequence
<220> FEATURE:
<223> OTHER INFORMATION: synthetic tub8-specific oligonucleotide for
      cDNA PCR quality control

<400> SEQUENCE: 69
cctcctgcac ttccacttcg tcttc                                          25

<210> SEQ ID NO 70
<211> LENGTH: 24
<212> TYPE: DNA
<213> ORGANISM: Artificial Sequence
<220> FEATURE:
<223> OTHER INFORMATION: synthetic oligonucleotide for detection of HCHL
      expression by PCR

<400> SEQUENCE: 70
atgtctactt acgagggaag atgg                                           24

<210> SEQ ID NO 71
<211> LENGTH: 21
<212> TYPE: DNA
<213> ORGANISM: Artificial Sequence
<220> FEATURE:
<223> OTHER INFORMATION: synthetic oligonucleotide for detection of HCHL
      expression by PCR

<400> SEQUENCE: 71
tctcttgtaa gcctggagtc c                                              21
```